US009200055B2

(12) United States Patent
Rohlff et al.

(10) Patent No.: US 9,200,055 B2
(45) Date of Patent: Dec. 1, 2015

(54) PROTEIN

(75) Inventors: Christian Rohlff, Abingdon (GB); Alasdair Stamps, Abingdon (GB)

(73) Assignee: Oxford BioTherapeutics, Ltd., Abingdon (GB)

(*) Notice: Subject to any disclaimer, the term of this patent is extended or adjusted under 35 U.S.C. 154(b) by 270 days.

(21) Appl. No.: 12/547,736

(22) Filed: Aug. 26, 2009

(65) Prior Publication Data

US 2010/0098626 A1 Apr. 22, 2010

Related U.S. Application Data

(63) Continuation of application No. PCT/GB2008/050127, filed on Feb. 26, 2008.

(60) Provisional application No. 60/903,509, filed on Feb. 26, 2007, provisional application No. 60/903,510, filed on Feb. 26, 2007.

(30) Foreign Application Priority Data

Feb. 25, 2008 (WO) ............... PCT/GB2008/050124

(51) Int. Cl.
G01N 33/00 (2006.01)
C07K 14/705 (2006.01)
G01N 33/574 (2006.01)

(52) U.S. Cl.
CPC ........ *C07K 14/705* (2013.01); *G01N 33/57407* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 6,432,666 B1 | 8/2002 | Hart | |
| 6,900,016 B1 | 5/2005 | Venter et al. | |
| 7,608,413 B1 * | 10/2009 | Joseloff et al. | 435/7.23 |
| 7,842,466 B1 * | 11/2010 | Kim et al. | 435/7.1 |
| 7,998,689 B2 | 8/2011 | Joseloff et al. | |
| 8,147,835 B2 | 4/2012 | Ledbetter et al. | |
| 8,168,586 B1 | 5/2012 | Fang et al. | |
| 8,236,318 B2 | 8/2012 | Keler et al. | |
| 2004/0157307 A1 | 8/2004 | Harris | |
| 2006/0281672 A1 | 12/2006 | Hart | |
| 2009/0087445 A1 | 4/2009 | Freund et al. | |

FOREIGN PATENT DOCUMENTS

| | | |
|---|---|---|
| EP | 2159291 | 3/2010 |
| EP | 2444409 | 4/2012 |
| EP | 2520935 | 11/2012 |
| WO | 9745449 | 12/1997 |
| WO | 0157251 | 8/2001 |
| WO | 02102235 | 12/2002 |
| WO | 03042661 | 5/2003 |
| WO | 03080640 | 10/2003 |
| WO | 03083069 | 10/2003 |
| WO | 2004019978 | 3/2004 |
| WO | 2004/053138 A | 6/2004 |
| WO | WO2004053138 * | 6/2004 |
| WO | 2005/016952 A | 2/2005 |
| WO | 2005016962 | 2/2005 |
| WO | 2005017148 | 2/2005 |
| WO | 2005/019258 A | 3/2005 |
| WO | 2005037989 | 4/2005 |
| WO | 2005067667 | 7/2005 |
| WO | 2006/093524 A | 9/2006 |
| WO | 2007/030531 A | 3/2007 |
| WO | 2007141280 | 12/2007 |
| WO | 2008016356 | 2/2008 |
| WO | 2008104804 | 9/2008 |
| WO | 2008104806 | 9/2008 |
| WO | 2009/061996 A | 5/2009 |
| WO | 2011011677 | 1/2011 |

OTHER PUBLICATIONS

Tubuly et al, Int. J. Cancer, 71:605-611, 1997.*
Lectins, 2011.*
Classification of lymphoma/lymphocyte leukemia/Hodgkin , Lymphoma Research Foundation 2012.*
AL-Tubuly et al, Bri J Can 74:1005-1011 1996.*
Charalambous A, et al., "Dendritic cell targeting of survivin protein in a xenogeneic form elicits strong CD4+ T cell immunity to mouse survivin.", J. Immunol., 2006, pp. 8410-8421, vol. 177, No. 12.
Guo M, et al., "A Monoclonal Antibody to the DEC-205 Endocytosis Receptor on Human Dendritic Cells.", Hum. Immunol., 2000, pp. 729-738, vol. 61, No. 8.
Kato M, et al., "Expression of human DEC-205 (CD205) multilectin receptor on leukocytes.", Int. Immunol., 2006, pp. 857-869, vol. 18, No. 6.
Nchinda G, et al., "The efficacy of DNA vaccination is enhanced in mice by targeting the encoded protein to dendritic cells.", J. Clin. Invest., 2008, pp. 1427-1436, vol. 118, No. 4.
Johnson et al., "Inhibition of melanoma growth by targeting of antigen to dendritic cells via an anti-DEC-205 single-chain fragment variable molecule", Clin Cancer Res, 2008, 14, 8169-8177.
Birkholz et al., "Targeting of DEC-205 on human dendritic cells results in efficient MHC class II-restricted antigen presentation", Blood, 2010, 116, 2277-2285.
Mahnke et al., "Targeting of antigens to activated dendritic cells in vivo cures metastatic melanoma in mice", Cancer Res, 2005, 65, 7007-7012.
Giridhar et al., "Interleukin-6 receptor enhances early colonization of the murine omentum by upregulation of a mannose family receptor, LY75, in ovarian tumor cells", Clin Exp Metastasis, 2011, 28, 887-897.
Kuppers, "Hodgkin lymphoma", Atlas of Genetics and Cytogenetics in Oncology and Haematology, 2011, 15, 527-528.
Reddy, "Chronic lymphocytic leukaemia (CLL)", Atlas of Genetics and Cytogenetics in Oncology and Haematology, 2005, 9, 238-240.

* cited by examiner

*Primary Examiner* — Lei Yao
(74) *Attorney, Agent, or Firm* — Klauber & Jackson LLC

(57) ABSTRACT

The present invention provides methods and compositions for screening, diagnosis and prognosis of colorectal cancer, kidney cancer, liver cancer, lung cancer, lymphoid leukaemia (particularly chronic lymphocytic leukaemia), ovarian cancer or pancreatic cancer, for monitoring the effectiveness of colorectal cancer, kidney cancer, liver cancer, lung cancer, lymphoid leukaemia (particularly chronic lymphocytic leukaemia), ovarian cancer or pancreatic cancer treatment, and for drug development.

8 Claims, 31 Drawing Sheets

Figure 1

OGTA076

Peptide Source: iTRAQ Colorectal cancer

```
OGTA076b (SEQ ID No: 2)    MRTGWATPRRPAGLLMLLFWFFDLAEPSGRAANDPFTIVHGNTGKCIKPVYGWIVADDCD  60
OGTA076c (SEQ ID No: 3)    MRTGWATPRRPAGLLMLLFWFFDLAEPSGRAANDPFTIVHGNTGKCIKPVYGWIVADDCD  60
OGTA076a (SEQ ID No: 1)    MRTGWATPRRPAGLLMLLFWFFDLAEPSGRAANDPFTIVHGNTGKCIKPVYGWIVADDCD  60
                           ************************************************************

OGTA076b (SEQ ID No: 2)    ETEDKLWKWVSQHRLFHLHSQKCLGLDITKSVNELRMFSCDSSAMLWWKCEHHSLYGAAR  120
OGTA076c (SEQ ID No: 3)    ETEDKLWKWVSQHRLFHLHSQKCLGLDITKSVNELRMFSCDSSAMLWWKCEHHSLYGAAR  120
OGTA076a (SEQ ID No: 1)    ETEDKLWKWVSQHRLFHLHSQKCLGLDITKSVNELRMFSCDSSAMLWWKCEHHSLYGAAR  120
                           ************************************************************

OGTA076b (SEQ ID No: 2)    YRLALKDGHGTAISNASDVWKKGGSEESLCDQPYHEIYTRDGNSYGRPCEFPFLIDGTWH  180
OGTA076c (SEQ ID No: 3)    YRLALKDGHGTAISNASDVWKKGGSEESLCDQPYHEIYTRDGNSYGRPCEFPFLIDGTWH  180
OGTA076a (SEQ ID No: 1)    YRLALKDGHGTAISNASDVWKKGGSEESLCDQPYHEIYTRDGNSYGRPCEFPFLIDGTWH  180
                           ************************************************************

OGTA076b (SEQ ID No: 2)    HDCILDEDHSGPWCATTLNYEYDRKWGICLKPENGCEDNWEKNEQFGSCYQFNTQTALSW  240
OGTA076c (SEQ ID No: 3)    HDCILDEDHSGPWCATTLNYEYDRKWGICLKPENGCEDNWEKNEQFGSCYQFNTQTALSW  240
OGTA076a (SEQ ID No: 1)    HDCILDEDHSGPWCATTLNYEYDRKWGICLKPENGCEDNWEKNEQFGSCYQFNTQTALSW  240
                           ************************************************************

OGTA076b (SEQ ID No: 2)    KEAYVSCQNQGADLLSINSAAELTYLKEKEGIAKIFWIGLNQLYSARGWEWSDEKPLNFL  300
OGTA076c (SEQ ID No: 3)    KEAYVSCQNQGADLLSINSAAELTYLKEKEGIAKIFWIGLNQLYSARGWEWSDEKPLNFL  300
OGTA076a (SEQ ID No: 1)    KEAYVSCQNQGADLLSINSAAELTYLKEKEGIAKIFWIGLNQLYSARGWEWSDEKPLNFL  300
                           ************************************************************

OGTA076b (SEQ ID No: 2)    NWDPDRPSAPTIGGSSCARMDAESGLWQSFSCEAQLPYVCRKPLNNTVELTDVWTYSDTR  360
OGTA076c (SEQ ID No: 3)    NWDPDRPSAPTIGGSSCARMDAESGLWQSFSCEAQLPYVCRKPLNNTVELTDVWTYSDTR  360
OGTA076a (SEQ ID No: 1)    NWDPDRPSAPTIGGSSCARMDAESGLWQSFSCEAQLPYVCRKPLNNTVELTDVWTYSDTR  360
                           ************************************************************

OGTA076b (SEQ ID No: 2)    CDAGWLPNNGFCYLLVNESNSWDKAHAKCKAFSSDLISIHSLADVEVVVTKLHNEDIKEE  420
OGTA076c (SEQ ID No: 3)    CDAGWLPNNGFCYLLVNESNSWDKAHAKCKAFSSDLISIHSLADVEVVVTKLHNEDIKEE  420
OGTA076a (SEQ ID No: 1)    CDAGWLPNNGFCYLLVNESNSWDKAHAKCKAFSSDLISIHSLADVEVVVTKLHNEDIKEE  420
                           ************************************************************

OGTA076b (SEQ ID No: 2)    VWIGLKNINIPTLFQWSDGTEVTLTYWDENEPNVPYNKTPNCVSYLGELGQWKVQSCEEK  480
OGTA076c (SEQ ID No: 3)    VWIGLKNINIPTLFQWSDGTEVTLTYWDENEPNVPYNKTPNCVSYLGELGQWKVQSCEEK  480
OGTA076a (SEQ ID No: 1)    VWIGLKNINIPTLFQWSDGTEVTLTYWDENEPNVPYNKTPNCVSYLGELGQWKVQSCEEK  480
                           ************************************************************

OGTA076b (SEQ ID No: 2)    LKYVCKRKGEKLNDASSDKMCPPDEGWKRHGETCYKIYEDEVPFGTNCNLTITSRFEQEY  540
OGTA076c (SEQ ID No: 3)    LKYVCKRKGEKLNDASSDKMCPPDEGWKRHGETCYKIYEDEVPFGTNCNLTITSRFEQEY  540
OGTA076a (SEQ ID No: 1)    LKYVCKRKGEKLNDASSDKMCPPDEGWKRHGETCYKIYEDEVPFGTNCNLTITSRFEQEY  540
                           ************************************************************

OGTA076b (SEQ ID No: 2)    LNDLMKKYDKSLRKYFWTGLRDVDSCGEYNWATVGGRRRAVTFSNWNFLEPASPGGCVAM  600
OGTA076c (SEQ ID No: 3)    LNDLMKKYDKSLRKYFWTGLRDVDSCGEYNWATVGGRRRAVTFSNWNFLEPASPGGCVAM  600
OGTA076a (SEQ ID No: 1)    LNDLMKKYDKSLRKYFWTGLRDVDSCGEYNWATVGGRRRAVTFSNWNFLEPASPGGCVAM  600
                           ************************************************************

OGTA076b (SEQ ID No: 2)    STGKSVGKWEVKDCRSFKALSICKKMSGPLGPEEASPKPDDPCPEGWQSFPASLSCYKVF  660
OGTA076c (SEQ ID No: 3)    STGKSVGKWEVKDCRSFKALSICKKMSGPLGPEEASPKPDDPCPEGWQSFPASLSCYKVF  660
OGTA076a (SEQ ID No: 1)    STGKSVGKWEVKDCRSFKALSICKKMSGPLGPEEASPKPDDPCPEGWQSFPASLSCYKVF  660
                           ************************************************************

OGTA076b (SEQ ID No: 2)    HAERIVRKRNWEEAERFCQALGAHLSSFSHVDEIKEFLHFLTDQFSGQHWLWIGLNKRSP  720
OGTA076c (SEQ ID No: 3)    HAERIVRKRNWEEAERFCQALGAHLSSFSHVDEIKEFLHFLTDQFSGQHWLWIGLNKRSP  720
OGTA076a (SEQ ID No: 1)    HAERIVRKRNWEEAERFCQALGAHLSSFSHVDEIKEFLHFLTDQFSGQHWLWIGLNKRSP  720
                           ************************************************************

OGTA076b (SEQ ID No: 2)    DLQGSWQWSDRTPVSTIIMPNEFQQDYDIRDCAAVKVFHRPWRRGWHFYDDREFIYLRPF  780
OGTA076c (SEQ ID No: 3)    DLQGSWQWSDRTPVSTIIMPNEFQQDYDIRDCAAVKVFHRPWRRGWHFYDDREFIYLRPF  780
OGTA076a (SEQ ID No: 1)    DLQGSWQWSDRTPVSTIIMPNEFQQDYDIRDCAAVKVFHRPWRRGWHFYDDREFIYLRPF  780
                           ************************************************************

OGTA076b (SEQ ID No: 2)    ACDTKLEWVCQIPKGRTPKTPDWYNPDRAGIHGPPLIIEGSEYWFVADLHLNYEEAVLYC  840
OGTA076c (SEQ ID No: 3)    ACDTKLEWVCQIPKGRTPKTPDWYNPDRAGIHGPPLIIEGSEYWFVADLHLNYEEAVLYC  840
OGTA076a (SEQ ID No: 1)    ACDTKLEWVCQIPKGRTPKTPDWYNPDRAGIHGPPLIIEGSEYWFVADLHLNYEEAVLYC  840
```

Figure 1 (cont)

```
                          ************************************************************
OGTA076b (SEQ ID No: 2)   ASNHSPLATITSFVGLKAIKNKIANISGDGQKWWIRISEWPIDDHFTYSRYPWHRFPVTF 900
OGTA076c (SEQ ID No: 3)   ASNHSPLATITSFVGLKAIKNKIANISGDGQKWWIRISEWPIDDHFTYSRYPWHRFPVTF 900
OGTA076a (SEQ ID No: 1)   ASNHSPLATITSFVGLKAIKNKIANISGDGQKWWIRISEWPIDDHFTYSRYPWHRFPVTF 900
                          ************************************************************

OGTA076b (SEQ ID No: 2)   GEECLYMSAKTWLIDLGKPTDCSTKLPFICEKYNVSSLEKYSPDSAAKVQCSEQWIPFQN 960
OGTA076c (SEQ ID No: 3)   GEECLYMSAKTWLIDLGKPTDCSTKLPFICEKYNVSSLEKYSPDSAAKVQCSEQWIPFQN 960
OGTA076a (SEQ ID No: 1)   GEECLYMSAKTWLIDLGKPTDCSTKLPFICEKYNVSSLEKYSPDSAAKVQCSEQWIPFQN 960
                          ************************************************************

OGTA076b (SEQ ID No: 2)   KCFLKIKPVSLTFSQASDTCHSYGGTLPSVLSQIEQDFITSLLPDMEATLWIGLRWTAYE 1020
OGTA076c (SEQ ID No: 3)   KCFLKIKPVSLTFSQASDTCHSYGGTLPSVLSQIEQDFITSLLPDMEATLWIGLRWTAYE 1020
OGTA076a (SEQ ID No: 1)   KCFLKIKPVSLTFSQASDTCHSYGGTLPSVLSQIEQDFITSLLPDMEATLWIGLRWTAYE 1020
                          ************************************************************

OGTA076b (SEQ ID No: 2)   KINKWTDNRELTYSNFHPLLVSGRLRIPENFFEEESRYHCALILNLQKSPFTGTWNFTSC 1080
OGTA076c (SEQ ID No: 3)   KINKWTDNRELTYSNFHPLLVSGRLRIPENFFEEESRYHCALILNLQKSPFTGTWNFTSC 1080
OGTA076a (SEQ ID No: 1)   KINKWTDNRELTYSNFHPLLVSGRLRIPENFFEEESRYHCALILNLQKSPFTGTWNFTSC 1080
                          ************************************************************

OGTA076b (SEQ ID No: 2)   SERHFVSLCQKYSEVKSRQTLQNASETVKYLNNLYKIIPKTLTWHSAKRECLKSNMQLVS 1140
OGTA076c (SEQ ID No: 3)   SERHFVSLCQKYSEVKSRQTLQNASETVKYLNNLYKIIPKTLTWHSAKRECLKSNMQLVS 1140
OGTA076a (SEQ ID No: 1)   SERHFVSLCQKYSEVKSRQTLQNASETVKYLNNLYKIIPKTLTWHSAKRECLKSNMQLVS 1140
                          ************************************************************

OGTA076b (SEQ ID No: 2)   ITDPYQQAFLSVQALLHNSSLWIGLFSQDDELNFGWSDGKRLHFSRWAETNGQLEDCVVL 1200
OGTA076c (SEQ ID No: 3)   ITDPYQQAFLSVQALLHNSSLWIGLFSQDDELNFGWSDGKRLHFSRWAETNGQLEDCVVL 1200
OGTA076a (SEQ ID No: 1)   ITDPYQQAFLSVQALLHNSSLWIGLFSQDDELNFGWSDGKRLHFSRWAETNGQLEDCVVL 1200
                          ************************************************************

OGTA076b (SEQ ID No: 2)   DTDGFWKTVDCNDNQPGAICYYSGNETEKEVKPVDSVKCPSPVLNTPWIPFQNCCYNFII 1260
OGTA076c (SEQ ID No: 3)   DTDGFWKTVDCNDNQPGAICYYSGNETEKEVKPVDSVKCPSPVLNTPWIPFQNCCYNFII 1260
OGTA076a (SEQ ID No: 1)   DTDGFWKTVDCNDNQPGAICYYSGNETEKEVKPVDSVKCPSPVLNTPWIPFQNCCYNFII 1260
                          ************************************************************

OGTA076b (SEQ ID No: 2)   TKNRHMATTQDEVHTKCQKLNPKSHILSIRDEKENNFVLEQLLYFNYMASWVMLGITYRN 1320
OGTA076c (SEQ ID No: 3)   TKNRHMATTQDEVHTKCQKLNPKSHILSIRDEKENNFVLEQLLYFNYMASWVMLGITYRN 1320
OGTA076a (SEQ ID No: 1)   TKNRHMATTQDEVHTKCQKLNPKSHILSIRDEKENNFVLEQLLYFNYMASWVMLGITYRN 1320
                          ************************************************************

OGTA076b (SEQ ID No: 2)   NSLMWFDKTPLSYTHWRAGRPTIKNEKFLAGLSTDGFWDIQTFKVIEEAVYFHQHSILAC 1380
OGTA076c (SEQ ID No: 3)   NSLMWFDKTPLSYTHWRAGRPTIKNEKFLAGLSTDGFWDIQTFKVIEEAVYFHQHSILAC 1380
OGTA076a (SEQ ID No: 1)   NSLMWFDKTPLSYTHWRAGRPTIKNEKFLAGLSTDGFWDIQTFKVIEEAVYFHQHSILAC 1380
                          ************************************************************

OGTA076b (SEQ ID No: 2)   KIEMVDYKEEHNTTLPQFMPYEDGIYSVIQKKVTWYEALNMCSQSGGHLASVHNQNGQLF 1440
OGTA076c (SEQ ID No: 3)   KIEMVDYKEEHNTTLPQFMPYEDGIYSVIQKKVTWYEALNMCSQSGGHLASVHNQNGQLF 1440
OGTA076a (SEQ ID No: 1)   KIEMVDYKEEHNTTLPQFMPYEDGIYSVIQKKVTWYEALNMCSQSGGHLASVHNQNGQLF 1440
                          ************************************************************

OGTA076b (SEQ ID No: 2)   LEDIVKRDGFPLWVGLSSHDGSESSFEWSDGSTFDYIPWKGQTSPGNCVLLDPKGTWKHE 1500
OGTA076c (SEQ ID No: 3)   LEDIVKRDGFPLWVGLSSHDGSESSFEWSDGSTFDYIPWKGQTSPGNCVLLDPKGTWKHE 1500
OGTA076a (SEQ ID No: 1)   LEDIVKRDGFPLWVGLSSHDGSESSFEWSDGSTFDYIPWKGQTSPGNCVLLDPKGTWKHE 1500
                          ************************************************************

OGTA076b (SEQ ID No: 2)   KCNSVKDGAICYKPTKSKKLSRLTYSSRCPAAKENGSRWIQYKGHCYKSDQALHSFSEAK 1560
OGTA076c (SEQ ID No: 3)   KCNSVKDGAICYKPTKSKKLSRLTYSSRCPAAKENGSRWIQYKGHCYKSDQALHSFSEAK 1560
OGTA076a (SEQ ID No: 1)   KCNSVKDGAICYKPTKSKKLSRLTYSSRCPAAKENGSRWIQYKGHCYKSDQALHSFSEAK 1560
                          ************************************************************

OGTA076b (SEQ ID No: 2)   KLCSKHDHSATIVSIKDEDENKFVSRLMRFNNNITMRVWLGLSQHSVDQSWSWLDGSEVT 1620
OGTA076c (SEQ ID No: 3)   KLCSKHDHSATIVSIKDEDENKFVSRLMRENNNITMRVWLGLSQHSVD------------ 1608
OGTA076a (SEQ ID No: 1)   KLCSKHDHSATIVSIKDEDENKFVSRLMRENNNITMRVWLGLSQHSVDQSWSWLDGSEVT 1608
                          ************************************************************

OGTA076b (SEQ ID No: 2)   FVKWENKSKSGVGRCSMLIASNETWKKVECEHGFGRVVCKVPLDCPSSTWIQFQDSCYIF 1680
OGTA076c (SEQ ID No: 3)   ------------------------------------------CPSSTWIQFQDSCYIF 1624
OGTA076a (SEQ ID No: 1)   FVKWENKSKSGVGRCSMLIASNETWKKVECEHGFGRVVCKVPLGPDYTAIAIIVATLSIL

OGTA076b (SEQ ID No: 2)   LQEAIKVESIEDVRNQCTDHGADMISIHNEEENAFILDTLKKQWKGPDDILLGMFYDTDD 1740
OGTA076c (SEQ ID No: 3)   LQEAIKVESIEDVRNQCTDHGADMISIHNEEENAFILDTLKKQWKGPDDILLGMFYDTDD 1684
OGTA076a (SEQ ID No: 1)   VLMGGLIWFLFQRHRLHLAGFSSVRYAQGVNEDEIMLPSFHD------------------
```

Figure 1 (cont)

```
OGTA076b (SEQ ID No: 2)    ASFKWFDNSNMTFDKWTDQDDDEDLVDTCAFLHIKTGEWKKGNCEVSSVEGTLCKTAIPY 1800
OGTA076c (SEQ ID No: 3)    ASFKWFDNSNMTFDKWTDQDDDEDLVDTCAFLHIKTGEWKKGNCEVSSVEGTLCKTAIPY 1744
OGTA076a (SEQ ID No: 1)    ------------------------------------------------------------

OGTA076b (SEQ ID No: 2)    KRKYLSDNHILISALVIASTVILTVLGAIIWFLYKKHSDSRFTTVFSTAPQSPYNEDCVL 1860
OGTA076c (SEQ ID No: 3)    KRKYLSDNHILISALVIASTVILTVLGAIIWFLYKKHSDSRFTTVFSTAPQSPYNEDCVL 1804
OGTA076a (SEQ ID No: 1)    ------------------------------------------------------------

OGTA076b (SEQ ID No: 2)    VVGEENEYPVQFD 1873
OGTA076c (SEQ ID No: 3)    VVGEENEYPVQFD 1817
OGTA076a (SEQ ID No: 1)    -------------
```

Mass Match Peptides (bold):
EGIAK [SEQ ID NO: 14]
IIPK [SEQ ID NO: 28]
LALK [SEQ ID NO: 35]
LNPK [SEQ ID NO: 40]

Tandem Peptides (underline):
EGIAK [SEQ ID NO: 14]
IIPK [SEQ ID NO: 28]
LALK [SEQ ID NO: 35]
LNPK [SEQ ID NO: 40]

Peptide Source: iTRAQ Kidney cancer

```
OGTA076b (SEQ ID No: 2)    MRTGWATPRRPAGLLMLLFWFFDLAEPSGRAANDPFTIVHGNTGKCIKPVYGWIVADDCD 60
OGTA076c (SEQ ID No: 3)    MRTGWATPRRPAGLLMLLFWFFDLAEPSGRAANDPFTIVHGNTGKCIKPVYGWIVADDCD 60
OGTA076a (SEQ ID No: 1)    MRTGWATPRRPAGLLMLLFWFFDLAEPSGRAANDPFTIVHGNTGKCIKPVYGWIVADDCD 60
                           ************************************************************

OGTA076b (SEQ ID No: 2)    ETEDKLWKWVSQHRLFHLHSQKCLGLDITKSVNELRMFSCDSSAMLWWKCEHHSLYGAAR 120
OGTA076c (SEQ ID No: 3)    ETEDKLWKWVSQHRLFHLHSQKCLGLDITKSVNELRMFSCDSSAMLWWKCEHHSLYGAAR 120
OGTA076a (SEQ ID No: 1)    ETEDKLWKWVSQHRLFHLHSQKCLGLDITKSVNELRMFSCDSSAMLWWKCEHHSLYGAAR 120
                           ************************************************************

OGTA076b (SEQ ID No: 2)    YRLALKDGHGTAISNASDVWKKGGSEESLCDQPYHEIYTRDGNSYGRPCEFPFLIDGTWH 180
OGTA076c (SEQ ID No: 3)    YRLALKDGHGTAISNASDVWKKGGSEESLCDQPYHEIYTRDGNSYGRPCEFPFLIDGTWH 180
OGTA076a (SEQ ID No: 1)    YRLALKDGHGTAISNASDVWKKGGSEESLCDQPYHEIYTRDGNSYGRPCEFPFLIDGTWH 180
                           ************************************************************

OGTA076b (SEQ ID No: 2)    HDCILDEDHSGPWCATTLNYEYDRKWGICLKPENGCEDNWEKNEQFGSCYQFNTQTALSW 240
OGTA076c (SEQ ID No: 3)    HDCILDEDHSGPWCATTLNYEYDRKWGICLKPENGCEDNWEKNEQFGSCYQFNTQTALSW 240
OGTA076a (SEQ ID No: 1)    HDCILDEDHSGPWCATTLNYEYDRKWGICLKPENGCEDNWEKNEQFGSCYQFNTQTALSW 240
                           ************************************************************

OGTA076b (SEQ ID No: 2)    KEAYVSCQNQGADLLSINSAAELTYLKEKEGIAKIFWIGLNQLYSARGWEWSDHKPLNFL 300
OGTA076c (SEQ ID No: 3)    KEAYVSCQNQGADLLSINSAAELTYLKEKEGIAKIFWIGLNQLYSARGWEWSDHKPLNFL 300
OGTA076a (SEQ ID No: 1)    KEAYVSCQNQGADLLSINSAAELTYLKEKEGIAKIFWIGLNQLYSARGWEWSDHKPLNFL 300
                           ************************************************************

OGTA076b (SEQ ID No: 2)    NWDPDRPSAPTIGGSSCARMDAESGLWQSFSCEAQLPYVCRKPLNNTVELTDVWTYSDTR 360
OGTA076c (SEQ ID No: 3)    NWDPDRPSAPTIGGSSCARMDAESGLWQSFSCEAQLPYVCRKPLNNTVELTDVWTYSDTR 360
OGTA076a (SEQ ID No: 1)    NWDPDRPSAPTIGGSSCARMDAESGLWQSFSCEAQLPYVCRKPLNNTVELTDVWTYSDTR 360
                           ************************************************************

OGTA076b (SEQ ID No: 2)    CDAGWLPNNGFCYLLVNESNSWDKAHAKCKAFSSDLISIHSLADVEVVVTKLHNEDIKEE 420
OGTA076c (SEQ ID No: 3)    CDAGWLPNNGFCYLLVNESNSWDKAHAKCKAFSSDLISIHSLADVEVVVTKLHNEDIKEE 420
OGTA076a (SEQ ID No: 1)    CDAGWLPNNGFCYLLVNESNSWDKAHAKCKAFSSDLISIHSLADVEVVVTKLHNEDIKEE 420
                           ************************************************************

OGTA076b (SEQ ID No: 2)    VWIGLKNINIPTLFQWSDGTEVTLTYWDENEPNVPYNKTPNCVSYLGELGQWKVQSCEEK 480
OGTA076c (SEQ ID No: 3)    VWIGLKNINIPTLFQWSDGTEVTLTYWDENEPNVPYNKTPNCVSYLGELGQWKVQSCEEK 480
OGTA076a (SEQ ID No: 1)    VWIGLKNINIPTLFQWSDGTEVTLTYWDENEPNVPYNKTPNCVSYLGELGQWKVQSCEEK 480
                           ************************************************************

OGTA076b (SEQ ID No: 2)    LKYVCKRKGEKLNDASSDKMCPPDEGWKRHGETCYKIYEDEVPFGTNCNLTITSRFEQEY 540
OGTA076c (SEQ ID No: 3)    LKYVCKRKGEKLNDASSDKMCPPDEGWKRHGETCYKIYEDEVPFGTNCNLTITSRFEQEY 540
```

Figure 1 (cont)

```
OGTA076a (SEQ ID No: 1)   LKYVCKRKCEKLNDASSEKMCPPDECWKRHGETCYKIYEDEVPFGTNCNLTITSRFEQEY  540
                          ************************************************************

OGTA076b (SEQ ID No: 2)   LNDLMKKYDKSLRKYFWTGLRDVDSCGEYNWATVGGRRRAVTFSNWNFLEPASPGGCVAM  600
OGTA076c (SEQ ID No: 3)   LNDLMKKYDKSLRKYFWTGLRDVDSCGEYNWATVGGRRRAVTFSNWNFLEPASPGGCVAM  600
OGTA076a (SEQ ID No: 1)   LNDLMKKYDKSLRKYFWTGLRDVDSCGEYNWATVGGRRRAVTFSNWNFLEPASPGGCVAM  600
                          ************************************************************

OGTA076b (SEQ ID No: 2)   STGKSVGKWEVKDCRSFKALSICKKMSGPLGPEEASPKPDDPCPEGWQSFPASLSCYKVF  660
OGTA076c (SEQ ID No: 3)   STGKSVGKWEVKDCRSFKALSICKKMSGPLGPEEASPKPDDPCPEGWQSFPASLSCYKVF  660
OGTA076a (SEQ ID No: 1)   STGKSVGKWEVKDCRSFKALSICKKMSGPLGPEEASPKPDDPCPEGWQSFPASLSCYKVF  660
                          ************************************************************

OGTA076b (SEQ ID No: 2)   HAERIVRKRNWEEAERFCQALGAHLSSFSHVDEIKEFLHFLTDQFSGQHWLWIGLNKRSP  720
OGTA076c (SEQ ID No: 3)   HAERIVRKRNWEEAERFCQALGAHLSSFSHVDEIKEFLHFLTDQFSGQHWLWIGLNKRSP  720
OGTA076a (SEQ ID No: 1)   HAERIVRKRNWEEAERFCQALGAHLSSFSHVDEIKEFLHFLTDQFSGQHWLWIGLNKRSP  720
                          ************************************************************

OGTA076b (SEQ ID No: 2)   DLQGSWQWSDRTPVSTIIMPNEFQQDYDIRDCAAVKVFHRFWRRGWHFYDDREFIYLRPF  780
OGTA076c (SEQ ID No: 3)   DLQGSWQWSDRTPVSTIIMPNEFQQDYDIRDCAAVKVFHRFWRRGWHFYDDREFIYLRPF  780
OGTA076a (SEQ ID No: 1)   DLQGSWQWSDRTPVSTIIMPNEFQQDYDIRDCAAVKVFHRFWRRGWHFYDDREFIYLRPF  780
                          ************************************************************

OGTA076b (SEQ ID No: 2)   ACDTKLEWVCQIPKGRTPKTPDWYNPDRAGIHGPPLIIEGSEYWFVADLHLNYEEAVLYC  840
OGTA076c (SEQ ID No: 3)   ACDTKLEWVCQIPKGRTPKTPDWYNPDRAGIHGPPLIIEGSEYWFVADLHLNYEEAVLYC  840
OGTA076a (SEQ ID No: 1)   ACDTKLEWVCQIPKGRTPKTPDWYNPDRAGIHGPPLIIEGSEYWFVADLHLNYEEAVLYC  840
                          ************************************************************

OGTA076b (SEQ ID No: 2)   ASNHSFLATITSFVGLKAIKNKIANISGDGQKWWIRISEWPIDDHFTYSRYPWHRFPVTF  900
OGTA076c (SEQ ID No: 3)   ASNHSFLATITSFVGLKAIKNKIANISGDGQKWWIRISEWPIDDHFTYSRYPWHRFPVTF  900
OGTA076a (SEQ ID No: 1)   ASNHSFLATITSFVGLKAIKNKIANISGDGQKWWIRISEWPIDDHFTYSRYPWHRFPVTF  900
                          ************************************************************

OGTA076b (SEQ ID No: 2)   GEECLYMSAKTWLIDLGKPTDCSTKLPFICEKYNVSSLEKYSPDSAAKVQCSFQWIPFQN  960
OGTA076c (SEQ ID No: 3)   GEECLYMSAKTWLIDLGKPTDCSTKLPFICEKYNVSSLEKYSPDSAAKVQCSFQWIPFQN  960
OGTA076a (SEQ ID No: 1)   GEECLYMSAKTWLIDLGKPTDCSTKLPFICEKYNVSSLEKYSPDSAAKVQCSFQWIPFQN  960
                          ************************************************************

OGTA076b (SEQ ID No: 2)   KCFLKIKPVSLTFSQASDTCHSYGGTLPSVLSQIEQDFITSLLPDMEATLWICLRWTAYE  1020
OGTA076c (SEQ ID No: 3)   KCFLKIKPVSLTFSQASDTCHSYGGTLPSVLSQIEQDFITSLLPDMEATLWICLRWTAYE  1020
OGTA076a (SEQ ID No: 1)   KCFLKIKPVSLTFSQASDTCHSYGGTLPSVLSQIEQDFITSLLPDMEATLWICLRWTAYE  1020
                          ************************************************************

OGTA076b (SEQ ID No: 2)   KINKWTDNRELTYSNFHPLLVSGRLRIPENFFEEESRYHCALILNLQKSPFTGTWNFTSC  1080
OGTA076c (SEQ ID No: 3)   KINKWTDNRELTYSNFHPLLVSGRLRIPENFFEEESRYHCALILNLQKSPFTGTWNFTSC  1080
OGTA076a (SEQ ID No: 1)   KINKWTDNRELTYSNFHPLLVSGRLRIPENFFEEESRYHCALILNLQKSPFTGTWNFTSC  1080
                          ************************************************************

OGTA076b (SEQ ID No: 2)   SERHFVSLCQKYSEVKSRQTLQNASETVKYLNNLYKIIPKTLTWHSAKRECLKSNMQLVS  1140
OGTA076c (SEQ ID No: 3)   SERHFVSLCQKYSEVKSRQTLQNASETVKYLNNLYKIIPKTLTWHSAKRECLKSNMQLVS  1140
OGTA076a (SEQ ID No: 1)   SERHFVSLCQKYSEVKSRQTLQNASETVKYLNNLYKIIPKTLTWHSAKRECLKSNMQLVS  1140
                          ************************************************************

OGTA076b (SEQ ID No: 2)   ITDPYQQAFLSVQALLHNSSLWIGLFSQDDELNFGWSDGKRLHFSRWAETNGQLEDCVVL  1200
OGTA076c (SEQ ID No: 3)   ITDPYQQAFLSVQALLHNSSLWIGLFSQDDELNFGWSDGKRLHFSRWAETNGQLEDCVVL  1200
OGTA076a (SEQ ID No: 1)   ITDPYQQAFLSVQALLHNSSLWIGLFSQDDELNFGWSDGKRLHFSRWAETNGQLEDCVVL  1200
                          ************************************************************

OGTA076b (SEQ ID No: 2)   DTDGFWKTVDCNDNQPGAICYYSGNETEKEVKPVDSVKCPSPVLNTPWIPFQNCCYNFII  1260
OGTA076c (SEQ ID No: 3)   DTDGFWKTVDCNDNQPGAICYYSGNETEKEVKPVDSVKCPSPVLNTPWIPFQNCCYNFII  1260
OGTA076a (SEQ ID No: 1)   DTDGFWKTVDCNDNQPGAICYYSGNETEKEVKPVDSVKCPSPVLNTPWIPFQNCCYNFII  1260
                          ************************************************************

OGTA076b (SEQ ID No: 2)   TKNRHMATTQDEVHTKCQKLNPKSHILSIRDEKENNFVLEQLLYFNYMASWVMLGITYRN  1320
OGTA076c (SEQ ID No: 3)   TKNRHMATTQDEVHTKCQKLNPKSHILSIRDEKENNFVLEQLLYFNYMASWVMLGITYRN  1320
OGTA076a (SEQ ID No: 1)   TKNRHMATTQDEVHTKCQKLNPKSHILSIRDEKENNFVLEQLLYFNYMASWVMLGITYRN  1320
                          ************************************************************

OGTA076b (SEQ ID No: 2)   NSLMWFDKTPLSYTHWRAGRPTIKNEKFLAGLSTDGFWDIQTFKVIEEAVYFHQHSILAC  1380
OGTA076c (SEQ ID No: 3)   NSLMWFDKTPLSYTHWRAGRPTIKNEKFLAGLSTDGFWDIQTFKVIEEAVYFHQHSILAC  1380
OGTA076a (SEQ ID No: 1)   NSLMWFDKTPLSYTHWRAGRPTIKNEKFLAGLSTDGFWDIQTFKVIEEAVYFHQHSILAC  1380
                          ************************************************************

OGTA076b (SEQ ID No: 2)   KIEMVDYKEEHNTTLPQFMPYEDGIYSVIQKKVTWYEALNMCSQSGGHLASVHNQNGQLF  1440
OGTA076c (SEQ ID No: 3)   KIEMVDYKEEHNTTLPQFMPYEDGIYSVIQKKVTWYEALNMCSQSGGHLASVHNQNGQLF  1440
OGTA076a (SEQ ID No: 1)   KIEMVDYKEEHNTTLPQFMPYEDGIYSVIQKKVTWYEALNMCSQSGGHLASVHNQNGQLF  1440
                          ************************************************************
```

Figure 1 (cont)

```
OGTA076b (SEQ ID No: 2)    LEDIVKRDGFPLWVGLSSHDGSESSFEWSDGSTFDYIPWKGQTSPGNCVLLDPKGTWKHE 1500
OGTA076c (SEQ ID No: 3)    LEDIVKRDGFPLWVGLSSHDGSESSFEWSDGSTFDYIPWKGQTSPGNCVLLDPKGTWKHE 1500
OGTA076a (SEQ ID No: 1)    LEDIVKRDGFPLWVGLSSHDGSESSFEWSDGSTFDYIPWKGQTSPGNCVLLDPKGTWKHE 1500
                           ************************************************************

OGTA076b (SEQ ID No: 2)    KCNSVKDGAICYKPTKSKKLSRLTYSSRCPAAKENGSRWIQYKGHCYKSDQALHSFSEAK 1560
OGTA076c (SEQ ID No: 3)    KCNSVKDGAICYKPTKSKKLSRLTYSSRCPAAKENGSRWIQYKGHCYKSDQALHSFSEAK 1560
OGTA076a (SEQ ID No: 1)    KCNSVKDGAICYKPTKSKKLSRLTYSSRCPAAKENGSRWIQYKGHCYKSDQALHSFSEAK 1560
                           ************************************************************

OGTA076b (SEQ ID No: 2)    KLCSKHDHSATIVSIKDEDENKFVSRLMRENNNITMRVWLGLSQHSVDQSWSWLDGSEVT 1620
OGTA076b (SEQ ID No: 2)    KLCSKHDHSATIVSIKDEDENKFVSRLMRENNNITMRVWLGLSQHSVDQSWSWLDGSEVT 1620
OGTA076c (SEQ ID No: 3)    KLCSKHDHSATIVSIKDEDENKFVSRLMRENNNITMRVWLGLSQHSVD------------ 1608
OGTA076a (SEQ ID No: 1)    KLCSKHDHSATIVSIKDEDENKFVSRLMRENNNITMRVWLGLSQHSVDQSWSWLDGSEVT 1608
                           ************************************************

OGTA076b (SEQ ID No: 2)    FVKWENKSKSGVGRCSMLIASNETWKKVECEHGFGRVVCKVPLDCPSSTWIQFQDSCYIF 1680
OGTA076c (SEQ ID No: 3)    ----------------------------------------CPSSTWIQFQDSCYIF 1624
OGTA076a (SEQ ID No: 1)    FVKWENKSKSGVGRCSMLIASNETWKKVECEHGFGRVVCKVPLGPDYTAIAIIVAFLSIL

OGTA076b (SEQ ID No: 2)    LQEAIKVESIEDVRNQCTDHGADMISIHNEEENAFILDTLKKQWKGPDDILLGMFYDTDD 1740
OGTA076c (SEQ ID No: 3)    LQEAIKVESIEDVRNQCTDHGADMISIHNEEENAFILDTLKKQWKGPDDILLGMFYDTDD 1684
OGTA076a (SEQ ID No: 1)    VLMGGLIWFLFQRHRLHLAGFSSVRYAQGVNEDEIMLPSFHD------------------

OGTA076b (SEQ ID No: 2)    ASFKWFDNSNMFDKWTDQDDDEDLVDTCAFLHIKTGEWKKGNCEVSSVEGTLCKTAIPY 1800
OGTA076c (SEQ ID No: 3)    ASFKWFDNSNMFDKWTDQDDDEDLVDTCAFLHIKTGEWKKGNCEVSSVEGTLCKTAIPY 1744
OGTA076a (SEQ ID No: 1)    ----------------------------------------------------------

OGTA076b (SEQ ID No: 2)    KRKYLSDNHILISALVIASTVILTVLCAIIWFLYKKHSDSRFTTVFSTAPQSPYNEDCVL 1860
OGTA076c (SEQ ID No: 3)    KRKYLSDNHILISALVIASTVILTVLCAIIWFLYKKHSDSRFTTVFSTAPQSPYNEDCVL 1804
OGTA076a (SEQ ID No: 1)    ----------------------------------------------------------

OGTA076b (SEQ ID No: 2)    VVGEENEYPVQFD 1873
OGTA076c (SEQ ID No: 3)    VVGEENEYPVQFD 1817
OGTA076a (SEQ ID No: 1)    -------------
```

Mass Match Peptides (bold):
EGIAK [SEQ ID NO: 14]
LALK [SEQ ID NO: 35]
LNPK [SEQ ID NO: 40]
YLNNLYK [SEQ ID NO: 66]

Tandem Peptides (underline):
EGIAK [SEQ ID NO: 14]
LALK [SEQ ID NO: 35]
LNPK [SEQ ID NO: 40]
YLNNLYK [SEQ ID NO: 66]

Peptide Source: iTRAQ Liver cancer

```
OGTA076b (SEQ ID No: 2)    MRTGWATPRRPAGLLMLLFWFFDLAEPSGRAANDPFTIVHGNTGKCIKPVYGWIVADDCD 60
OGTA076c (SEQ ID No: 3)    MRTGWATPRRPAGLLMLLFWFFDLAEPSGRAANDPFTIVHGNTGKCIKPVYGWIVADDCD 60
OGTA076a (SEQ ID No: 1)    MRTGWATPRRPAGLLMLLFWFFDLAEPSGRAANDPFTIVHGNTGKCIKPVYGWIVADDCD 60
                           ************************************************************

OGTA076b (SEQ ID No: 2)    ETEDKLWKWVSQHRLFHLHSQKCLGLDITKSVNELRMFSCDSSAMLWWKCEHHSLYGAAR 120
OGTA076c (SEQ ID No: 3)    ETEDKLWKWVSQHRLFHLHSQKCLGLDITKSVNELRMFSCDSSAMLWWKCEHHSLYGAAR 120
OGTA076a (SEQ ID No: 1)    ETEDKLWKWVSQHRLFHLHSQKCLGLDITKSVNELRMFSCDSSAMLWWKCEHHSLYGAAR 120
                           ************************************************************

OGTA076b (SEQ ID No: 2)    YRLALKDGHGTAISNASDVWKKGGSEESLCDQPYHEIYTRDGNSYGRPCEFPFLIDGTWH 180
OGTA076c (SEQ ID No: 3)    YRLALKDGHGTAISNASDVWKKGGSEESLCDQPYHEIYTRDGNSYGRPCEFPFLIDGTWH 180
OGTA076a (SEQ ID No: 1)    YRLALKDGHGTAISNASDVWKKGGSEESLCDQPYHEIYTRDGNSYGRPCEFPFLIDGTWH 180
                           ************************************************************

OGTA076b (SEQ ID No: 2)    HDCILDEDHSGPWCATTLNYEYDRKWGICLKPENGCEDNWEKNEQFGSCYQFNTQFALSW 240
```

Figure 1 (cont)

```
OGTA076c (SEQ ID No: 3)    HDCILDEDHSGPWCATTLNYEYDRKWCICLKPENGCEDNWEKNEQFGSCYQFNTQTALSW 240
OGTA076a (SEQ ID No: 1)    HDCILDEDHSGPWCATTLNYEYDRKWCICLKPENGCEDNWEKNEQFGSCYQFNTQTALSW 240
                           ************************************************************

OGTA076b (SEQ ID No: 2)    KEAYVSCQNQGADLLSINSAAELTYLKEKEGIAKIFWIGLNQLYSARGWEWSDHKPLNFL 300
OGTA076c (SEQ ID No: 3)    KEAYVSCQNQGADLLSINSAAELTYLKEKEGIAKIFWIGLNQLYSARGWEWSDHKPLNFL 300
OGTA076a (SEQ ID No: 1)    KEAYVSCQNQGADLLSINSAAELTYLKEKEGIAKIFWIGLNQLYSARGWEWSDHKPLNFL 300
                           ************************************************************

OGTA076b (SEQ ID No: 2)    NWDPDRPSAPTIGGSSCARMDAESGLWQSFSCEAQLPYVCRKPLNNTVELTDVWTYSDTR 360
OGTA076c (SEQ ID No: 3)    NWDPDRPSAPTIGGSSCARMDAESGLWQSFSCEAQLPYVCRKPLNNTVELTDVWTYSDTR 360
OGTA076a (SEQ ID No: 1)    NWDPDRPSAPTIGGSSCARMDAESGLWQSFSCEAQLPYVCRKPLNNTVELTDVWTYSDTR 360
                           ************************************************************

OGTA076b (SEQ ID No: 2)    CDAGWLPNNGFCYLLVNESNSWDKAHAKCKAFSSDLISIHSLADVEVVVTKLINEDIKEE 420
OGTA076c (SEQ ID No: 3)    CDAGWLPNNGFCYLLVNESNSWDKAHAKCKAFSSDLISIHSLADVEVVVTKLINEDIKEE 420
OGTA076a (SEQ ID No: 1)    CDAGWLPNNGFCYLLVNESNSWDKAHAKCKAFSSDLISIHSLADVEVVVTKLINEDIKEE 420
                           ************************************************************

OGTA076b (SEQ ID No: 2)    VWIGLKNINIPTLFQWSDGTEVTLTYWDENEPNVPYNKTPNCVSYLGELGQWKVQSCEEK 480
OGTA076c (SEQ ID No: 3)    VWIGLKNINIPTLFQWSDGTEVTLTYWDENEPNVPYNKTPNCVSYLGELGQWKVQSCEEK 480
OGTA076a (SEQ ID No: 1)    VWIGLKNINIPTLFQWSDGTEVTLTYWDENEPNVPYNKTPNCVSYLGELGQWKVQSCEEK 480
                           ************************************************************

OGTA076b (SEQ ID No: 2)    LKYVCKRKGEKLNDASSDKMCPPDEGWKRHGETCYKIYEDEVPFGTNCNLTITSRFEQEY 540
OGTA076c (SEQ ID No: 3)    LKYVCKRKGEKLNDASSDKMCPPDEGWKRHGETCYKIYEDEVPFGTNCNLTITSRFEQEY 540
OGTA076a (SEQ ID No: 1)    LKYVCKRKGEKLNDASSDKMCPPDEGWKRHGETCYKIYEDEVPFGTNCNLTITSRFEQEY 540
                           ************************************************************

OGTA076b (SEQ ID No: 2)    LNDLMKKYDKSLRKYFWTGLRDVDSCGEYNWATVGGRRRAVTFSNWNFLEPASPGGCVAM 600
OGTA076c (SEQ ID No: 3)    LNDLMKKYDKSLRKYFWTGLRDVDSCGEYNWATVGGRRRAVTFSNWNFLEPASPGGCVAM 600
OGTA076a (SEQ ID No: 1)    LNDLMKKYDKSLRKYFWTGLRDVDSCGEYNWATVGGRRRAVTFSNWNFLEPASPGGCVAM 600
                           ************************************************************

OGTA076b (SEQ ID No: 2)    STGKSVGKWEVKDCRSFKALSICKKMSGPLGPEEASPKPDDPCPEGWQSFPASLSCYKVF 660
OGTA076c (SEQ ID No: 3)    STGKSVGKWEVKDCRSFKALSICKKMSGPLGPEEASPKPDDPCPEGWQSFPASLSCYKVF 660
OGTA076a (SEQ ID No: 1)    STGKSVGKWEVKDCRSFKALSICKKMSGPLGPEEASPKPDDPCPEGWQSFPASLSCYKVF 660
                           ************************************************************

OGTA076b (SEQ ID No: 2)    HAERIVRKRNWEEAERFCQALGAHLSSFSHVDEIKEFLHFLTDQFSGQHWLWIGLNKRSP 720
OGTA076c (SEQ ID No: 3)    HAERIVRKRNWEEAERFCQALGAHLSSFSHVDEIKEFLHFLTDQFSGQHWLWIGLNKRSP 720
OGTA076a (SEQ ID No: 1)    HAERIVRKRNWEEAERFCQALGAHLSSFSHVDEIKEFLHFLTDQFSGQHWLWIGLNKRSP 720
                           ************************************************************

OGTA076b (SEQ ID No: 2)    DLQGSWQWSDRTPVSTIIMPNEFQQDYDIRDCAAVKVFHRPWRRGWHFYDDREFIYLRPF 780
OGTA076c (SEQ ID No: 3)    DLQGSWQWSDRTPVSTIIMPNEFQQDYDIRDCAAVKVFHRPWRRGWHFYDDREFIYLRPF 780
OGTA076a (SEQ ID No: 1)    DLQGSWQWSDRTPVSTIIMPNEFQQDYDIRDCAAVKVFHRPWRRGWHFYDDREFIYLRPF 780
                           ************************************************************

OGTA076b (SEQ ID No: 2)    ACDTKLEWVCQIPKGRTPKTPDWYNPDRAGIHGPPLIIEGSEYWFVADLHLNYEEAVLYC 840
OGTA076c (SEQ ID No: 3)    ACDTKLEWVCQIPKGRTPKTPDWYNPDRAGIHGPPLIIEGSEYWFVADLHLNYEEAVLYC 840
OGTA076a (SEQ ID No: 1)    ACDTKLEWVCQIPKGRTPKTPDWYNPDRAGIHGPPLIIEGSEYWFVADLHLNYEEAVLYC 840
                           ************************************************************

OGTA076b (SEQ ID No: 2)    ASNHSFLATITSFVGLKAIKNKIANISGDGQKWWIRISEWPIDDHFTYSRYPWHRFPVTF 900
OGTA076c (SEQ ID No: 3)    ASNHSFLATITSFVGLKAIKNKIANISGDGQKWWIRISEWPIDDHFTYSRYPWHRFPVTF 900
OGTA076a (SEQ ID No: 1)    ASNHSFLATITSFVGLKAIKNKIANISGDGQKWWIRISEWPIDDHFTYSRYPWHRFPVTF 900
                           ************************************************************

OGTA076b (SEQ ID No: 2)    GEECLYMSAKTWLIDLGKPTDCSTKLPFICEKYNVSSLEKYSPDSAAKVQCSEQWIPFQN 960
OGTA076c (SEQ ID No: 3)    GEECLYMSAKTWLIDLGKPTDCSTKLPFICEKYNVSSLEKYSPDSAAKVQCSEQWIPFQN 960
OGTA076a (SEQ ID No: 1)    GEECLYMSAKTWLIDLGKPTDCSTKLPFICEKYNVSSLEKYSPDSAAKVQCSEQWIPFQN 960
                           ************************************************************

OGTA076b (SEQ ID No: 2)    KCFLKIKPVSLTFSQASDTCHSYGGTLPSVLSQIEQDFITSLLPDMEATLWIGLRWTAYE 1020
OGTA076c (SEQ ID No: 3)    KCFLKIKPVSLTFSQASDTCHSYGGTLPSVLSQIEQDFITSLLPDMEATLWIGLRWTAYE 1020
OGTA076a (SEQ ID No: 1)    KCFLKIKPVSLTFSQASDTCHSYGGTLPSVLSQIEQDFITSLLPDMEATLWIGLRWTAYE 1020
                           ************************************************************

OGTA076b (SEQ ID No: 2)    KINKWTDNRELTYSNFHPLLVSGRLRIPENFFEEESRYHCALILNLQKSPFTGTWNFTSC 1080
OGTA076c (SEQ ID No: 3)    KINKWTDNRELTYSNFHPLLVSGRLRIPENFFEEESRYHCALILNLQKSPFTGTWNFTSC 1080
OGTA076a (SEQ ID No: 1)    KINKWTDNRELTYSNFHPLLVSGRLRIPENFFEEESRYHCALILNLQKSPFTGTWNFTSC 1080
                           ************************************************************

OGTA076b (SEQ ID No: 2)    SERHFVSLCQKYSEVKSRQTLQNASETVKYLNNLYKIIPKTLTWHSAKRECLKSNMQLVS 1140
OGTA076c (SEQ ID No: 3)    SERHFVSLCQKYSEVKSRQTLQNASETVKYLNNLYKIIPKTLTWHSAKRECLKSNMQLVS 1140
OGTA076a (SEQ ID No: 1)    SERHFVSLCQKYSEVKSRQTLQNASETVKYLNNLYKIIPKTLTWHSAKRECLKSNMQLVS 1140
                           ************************************************************
```

Figure 1 (cont)

```
                      ************************************************************
OGTA076b (SEQ ID No: 2)   ITDPYQQAFLSVQALLHNSSLWIGLFSQDDELNFGWSDGKRLHFSRWAETNGQLEDCVVL 1200
OGTA076c (SEQ ID No: 3)   ITDPYQQAFLSVQALLHNSSLWIGLFSQDDELNFGWSDCKRLHFSRWAETNGQLEDCVVL 1200
OGTA076a (SEQ ID No: 1)   ITDPYQQAFLSVQALLHNSSLWIGLFSQDDELNFGWSDGKRLHFSRWAETNGQLEDCVVL 1200
                      ************************************************************

OGTA076b (SEQ ID No: 2)   DTDGFWKTVDCNDNQPGAICYYSGNETEKEVKPVDSVKCPSPVLNTPWIPFQNCCYNFII 1260
OGTA076c (SEQ ID No: 3)   DTDGFWKTVDCNDNQPGAICYYSGNETEKEVKPVDSVKCPSPVLNTPWIPFQNCCYNFII 1260
OGTA076a (SEQ ID No: 1)   DTDGFWKTVDCNDNQPGAICYYSGNETEKEVKPVDSVKCPSPVLNTPWIPFQNCCYNFII 1260
                      ************************************************************

OGTA076b (SEQ ID No: 2)   TKNRHMATTQDEVHTKCQKLNPKSHILSIRDEKENNFVLEQLLYFNYMASWVMLGITYRN 1320
OGTA076c (SEQ ID No: 3)   TKNRHMATTQDEVHTKCQKLNPKSHILSIRDEKENNFVLEQLLYFNYMASWVMLGITYRN 1320
OGTA076a (SEQ ID No: 1)   TKNRHMATTQDEVHTKCQKLNPKSHILSIRDEKENNFVLEQLLYFNYMASWVMLGITYRN 1320
                      ************************************************************

OGTA076b (SEQ ID No: 2)   NSLMWFDKTPLSYTHWRAGRPTIKNEKFLAGLSTDGFWDIQTFKVIEEAVYFHQHSILAC 1380
OGTA076c (SEQ ID No: 3)   NSLMWFDKTPLSYTHWRAGRPTIKNEKFLAGLSTDGFWDIQTFKVIEEAVYFHQHSILAC 1380
OGTA076a (SEQ ID No: 1)   NSLMWFDKTPLSYTHWRAGRPTIKNEKFLAGLSTDGFWDIQTFKVIEEAVYFHQHSILAC 1380
                      ************************************************************

OGTA076b (SEQ ID No: 2)   KIEMVDYKEEHNTTLPQFMPYEDGIYSVIQKKVTWYEALNMCSQSGGHLASVHNQNGQLF 1440
OGTA076c (SEQ ID No: 3)   KIEMVDYKEEHNTTLPQFMPYEDGIYSVIQKKVTWYEALNMCSQSGGHLASVHNQNGQLF 1440
OGTA076a (SEQ ID No: 1)   KIEMVDYKEEHNTTLPQFMPYEDGIYSVIQKKVTWYEALNMCSQSGGHLASVHNQNGQLF 1440
                      ************************************************************

OGTA076b (SEQ ID No: 2)   LEDIVKRDGFPLWVGLSSHDGSESSFEWSDGSTFDYIPWKGQTSPGNCVLLDPKGTWKHE 1500
OGTA076c (SEQ ID No: 3)   LEDIVKRDGFPLWVGLSSHDGSESSFEWSDGSTFDYIPWKGQTSPGNCVLLDPKGTWKHE 1500
OGTA076a (SEQ ID No: 1)   LEDIVKRDGFPLWVGLSSHDGSESSFEWSDGSTFDYIPWKGQTSPGNCVLLDPKGTWKHE 1500
                      ************************************************************

OGTA076b (SEQ ID No: 2)   KCNSVKDGAICYKPTKSKKLSRLTYSSRCPAAKENGSRWIQYKGHCYKSDQALHSFSEAK 1560
OGTA076c (SEQ ID No: 3)   KCNSVKDGAICYKPTKSKKLSRLTYSSRCPAAKENGSRWIQYKGHCYKSDQALHSFSEAK 1560
OGTA076a (SEQ ID No: 1)   KCNSVKDGAICYKPTKSKKLSRLTYSSRCPAAKENGSRWIQYKGHCYKSDQALHSFSEAK 1560
                      ************************************************************

OGTA076b (SEQ ID No: 2)   KLCSKHDHSATIVSIKDEDENKFVSRLMRENNNITMRVWLGLSQHSVDQSWSWLDGSEVT 1620
OGTA076c (SEQ ID No: 3)   KLCSKHDHSATIVSIKDEDENKFVSRLMRENNNITMRVWLGLSQHSVD------------ 1608
OGTA076a (SEQ ID No: 1)   KLCSKHDHSATIVSIKDEDENKFVSRLMRENNNITMRVWLGLSQHSVDQSWSWLDGSEVT 1608
                      ************************************************

OGTA076b (SEQ ID No: 2)   FVKWENKSKSGVGRCSMLIASNETWKKVECEHGFGRVVCKVPLDCPSSTWIQFQDSCYIF 1680
OGTA076c (SEQ ID No: 3)   ----------------------------------------CPSSTWIQFQDSCYIF 1624
OGTA076a (SEQ ID No: 1)   FVKWENKSKSGVGRCSMLIASNETWKKVECEHGFGRVVCKVPLGPDYTAIAIIVATLSIL

OGTA076b (SEQ ID No: 2)   LQEAIKVESIEDVRNQCTDHGADMISIHNEEENAFILDTLKKQWKGPDDILLGMFYDTDD 1740
OGTA076c (SEQ ID No: 3)   LQEAIKVESIEDVRNQCTDHGADMISIHNEEENAFILDTLKKQWKGPDDILLGMFYDTDD 1684
OGTA076a (SEQ ID No: 1)   VLMGGLIWFLFQRHRLHLAGFSSVRYAQGVNEDEIMLPSFHD------------------

OGTA076b (SEQ ID No: 2)   ASFKWFDNSNMTFDKWTDQDDDEDLVDTCAFLHIKTGEWKKGNCEVSSVEGTLCKTAIPY 1800
OGTA076c (SEQ ID No: 3)   ASFKWFDNSNMTFDKWTDQDDDEDLVDTCAFLHIKTGEWKKGNCEVSSVEGTLCKTAIPY 1744
OGTA076a (SEQ ID No: 1)   ------------------------------------------------------------

OGTA076b (SEQ ID No: 2)   KRKYLSDNHILISALVIASTVILTVLGAIIWFLYKKHSDSRFTTVFSTAPQSPYNEDCVL 1860
OGTA076c (SEQ ID No: 3)   KRKYLSDNHILISALVIASTVILTVLGAIIWFLYKKHSDSRFTTVFSTAPQSPYNEDCVL 1804
OGTA076a (SEQ ID No: 1)   ------------------------------------------------------------

OGTA076b (SEQ ID No: 2)   VVGEENEYPVQFD 1873
OGTA076c (SEQ ID No: 3)   VVGEENEYPVQFD 1817
OGTA076a (SEQ ID No: 1)   -------------
```

Mass Match Peptides (bold):
YLNNLYK [SEQ ID NO: 66]

Tandem Peptides (underline):
YLNNLYK [SEQ ID NO: 66]

Figure 1 (cont)

Peptide Source: iTRAQ Non-small cell lung cancer

```
CGTA076b (SEQ ID No: 2)    MRTGWATPRRPAGLLMLLFWFFDLAEPSGRAANDPFTIVHGNTGKCIKPVYGWIVADDCD 60
CGTA076c (SEQ ID No: 3)    MRTGWATPRRPAGLLMLLFWFFDLAEPSGRAANDPFTIVHGNTGKCIKPVYGWIVADDCD 60
CGTA076a (SEQ ID No: 1)    MRTGWATPRRPAGLLMLLFWFFDLAEPSGRAANDPFTIVHGNTGKCIKPVYGWIVADDCD 60
                           ************************************************************

CGTA076b (SEQ ID No: 2)    ETEDKLWKWVSQHRLFHLHSQKCLGLDITKSVNELRMFSCDSSAMLWWKCEHHSLYGAAR 120
CGTA076c (SEQ ID No: 3)    ETEDKLWKWVSQHRLFHLHSQKCLGLDITKSVNELRMFSCDSSAMLWWKCEHHSLYGAAR 120
CGTA076a (SEQ ID No: 1)    ETEDKLWKWVSQHRLFHLHSQKCLGLDITKSVNELRMFSCDSSAMLWWKCEHHSLYGAAR 120
                           ************************************************************

CGTA076b (SEQ ID No: 2)    YRLALKDGHGTAISNASDVWKKGGSEESLCDQPYHEIYTRDGNSYGRPCEFPFLIDGTWH 180
CGTA076c (SEQ ID No: 3)    YRLALKDGHGTAISNASDVWKKGGSEESLCDQPYHEIYTRDGNSYGRPCEFPFLIDGTWH 180
CGTA076a (SEQ ID No: 1)    YRLALKDGHGTAISNASDVWKKGGSEESLCDQPYHEIYTRDGNSYGRPCEFPFLIDGTWH 180
                           ************************************************************

CGTA076b (SEQ ID No: 2)    EDCILDEDHSGPWCATTLNYEYDRKWGICLKPENGCEDNWEKNEQFGSCYQFNTQTALSW 240
CGTA076c (SEQ ID No: 3)    EDCILDEDHSGPWCATTLNYEYDRKWGICLKPENGCEDNWEKNEQFGSCYQFNTQTALSW 240
CGTA076a (SEQ ID No: 1)    EDCILDEDHSGPWCATTLNYEYDRKWGICLKPENGCEDNWEKNEQFGSCYQFNTQTALSW 240
                           ************************************************************

CGTA076b (SEQ ID No: 2)    KEAYVSCQNQGADLLSINSAAELTYLKEKEGIAKIFWICLNQLYSARCWEWSDHKPLNFL 300
CGTA076c (SEQ ID No: 3)    KEAYVSCQNQGADLLSINSAAELTYLKEKEGIAKIFWIGLNQLYSARGWEWSDHKPLNFL 300
CGTA076a (SEQ ID No: 1)    KEAYVSCQNQGADLLSINSAAELTYLKEKEGIAKIFWIGLNQLYSARGWEWSDHKPLNFL 300
                           ************************************************************

CGTA076b (SEQ ID No: 2)    NWDPDRPSAPTIGGSSCARMDAESGLWQSFSCEAQLPYVCRKPLNNTVELTDVWTYSDTR 360
CGTA076c (SEQ ID No: 3)    NWDPDRPSAPTIGGSSCARMDAESGLWQSFSCEAQLPYVCRKPLNNTVELTDVWTYSDTR 360
CGTA076a (SEQ ID No: 1)    NWDPDRPSAPTIGGSSCARMDAESGLWQSFSCEAQLPYVCRKPLNNTVELTDVWTYSDTR 360
                           ************************************************************

CGTA076b (SEQ ID No: 2)    CDAGWLPNNGFCYLLVNFSNSWDKAHAKCKAFSSDLISIHSLADVEVVVTKLHNEDIKEE 420
CGTA076c (SEQ ID No: 3)    CDAGWLPNNGFCYLLVNFSNSWDKAHAKCKAFSSDLISIHSLADVEVVVTKLHNEDIKEE 420
CGTA076a (SEQ ID No: 1)    CDAGWLPNNGFCYLLVNFSNSWDKAHAKCKAFSSDLISIHSLADVEVVVTKLHNEDIKEE 420
                           ************************************************************

CGTA076b (SEQ ID No: 2)    VWIGLKNINIPTLFQWSDGTEVTLTYWDENEPNVPYNKTPNCVSYLGELGQWKVQSCEEK 480
CGTA076c (SEQ ID No: 3)    VWIGLKNINIPTLFQWSDGTEVTLTYWDENEPNVPYNKTPNCVSYLGELGQWKVQSCEEK 480
CGTA076a (SEQ ID No: 1)    VWIGLKNINIPTLFQWSDGTEVTLTYWDENEPNVPYNKTPNCVSYLGELGQWKVQSCEEK 480
                           ************************************************************

CGTA076b (SEQ ID No: 2)    LKYVCKRKGEKLNDASSDKMCPPDEGWKRHGETCYKIYEDEVPFGTNCNLTITSRFEQEY 540
CGTA076c (SEQ ID No: 3)    LKYVCKRKGEKLNDASSDKMCPPDEGWKRHGETCYKIYEDEVPFGTNCNLTITSRFEQEY 540
CGTA076a (SEQ ID No: 1)    LKYVCKRKGEKLNDASSDKMCPPDEGWKRHGETCYKIYEDEVPFGTNCNLTITSRFEQEY 540
                           ************************************************************

CGTA076b (SEQ ID No: 2)    LNDLMKKYDKSLRKYFWTGLRDVDSCGEYNWATVGGRRRAVTFSNWNFLEPASPGGCVAM 600
CGTA076c (SEQ ID No: 3)    LNDLMKKYDKSLRKYFWTGLRDVDSCGEYNWATVGGRRRAVTFSNWNFLEPASPGGCVAM 600
CGTA076a (SEQ ID No: 1)    LNDLMKKYDKSLRKYFWTGLRDVDSCGEYNWATVGGRRRAVTFSNWNFLEPASPGGCVAM 600
                           ************************************************************

CGTA076b (SEQ ID No: 2)    STGKSVGKWEVKDCRSFKALSICKKMSGPLGPEEASPKPDDPCPEGWQSFPASLSCYKVF 660
CGTA076c (SEQ ID No: 3)    STGKSVGKWEVKDCRSFKALSICKKMSGPLGPEEASPKPDDPCPEGWQSFPASLSCYKVF 660
CGTA076a (SEQ ID No: 1)    STGKSVGKWEVKDCRSFKALSICKKMSGPLGPEEASPKPDDPCPEGWQSFPASLSCYKVF 660
                           ************************************************************

CGTA076b (SEQ ID No: 2)    HAERIVRKRNWEEAERFCQALGAHLSSFSHVDEIKEFLHFLTDQFSGQHWLWIGLNKRSP 720
CGTA076c (SEQ ID No: 3)    HAERIVRKRNWEEAERFCQALGAHLSSFSHVDEIKEFLHFLTDQFSGQHWLWIGLNKRSP 720
CGTA076a (SEQ ID No: 1)    HAERIVRKRNWEEAERFCQALGAHLSSFSHVDEIKEFLHFLTDQFSGQHWLWIGLNKRSP 720
                           ************************************************************

CGTA076b (SEQ ID No: 2)    DLQGSWQWSDRTPVSTIIMPNEFQQDYDIRDCAAVKVFHRPWRRGWHFYDDREFIYLRPF 780
CGTA076c (SEQ ID No: 3)    DLQGSWQWSDRTPVSTIIMPNEFQQDYDIRDCAAVKVFHRPWRRGWHFYDDREFIYLRPF 780
CGTA076a (SEQ ID No: 1)    DLQGSWQWSDRTPVSTIIMPNEFQQDYDIRDCAAVKVFHRPWRRGWHFYDDREFIYLRPF 780
                           ************************************************************

CGTA076b (SEQ ID No: 2)    ACDTKLEWVCQIPKGRTPKTPDWYNPDRAGIHGPPLIIEGSEYWFVADLHLNYEEAVLYC 840
CGTA076c (SEQ ID No: 3)    ACDTKLEWVCQIPKGRTPKTPDWYNPDRAGIHGPPLIIEGSEYWFVADLHLNYEEAVLYC 840
CGTA076a (SEQ ID No: 1)    ACDTKLEWVCQIPKGRTPKTPDWYNPDRAGIHGPPLIIEGSEYWFVADLHLNYEEAVLYC 840
                           ************************************************************

CGTA076b (SEQ ID No: 2)    ASNHSFLATITSFVGLKAIKNKIANISGDGQKWWIRISEWPIDDHFTYSRYPWHRFPVTF 900
CGTA076c (SEQ ID No: 3)    ASNHSFLATITSFVGLKAIKNKIANISGDGQKWWIRISEWPIDDHFTYSRYPWHRFPVTF 900
CGTA076a (SEQ ID No: 1)    ASNHSFLATITSFVGLKAIKNKIANISGDGQKWWIRISEWPIDDHFTYSRYPWHRFPVTF 900
```

Figure 1 (cont)

```
                                  ****************************************************
OGTA076b (SEQ ID No: 2)    GEECLYMSAKTWLIDLGKPTDCSTKLPFICEKYNVSSLEKYSPDSAAKVQCSEQWIPFQN 960
OGTA076c (SEQ ID No: 3)    GEECLYMSAKTWLIDLGKPTDCSTKLPFICEKYNVSSLEKYSPDSAAKVQCSEQWIPFQN 960
OGTA076a (SEQ ID No: 1)    GEECLYMSAKTWLIDLGKPTDCSTKLPFICEKYNVSSLEKYSPDSAAKVQCSEQWIPFQN 960
                           ************************************************************

OGTA076b (SEQ ID No: 2)    KCFLKIKPVSLTFSQASDTCHSYGGTLPSVLSQIEQDFITSLLPDMEATLWIGLRWTAYE 1020
OGTA076c (SEQ ID No: 3)    KCFLKIKPVSLTFSQASDTCHSYGGTLPSVLSQIEQDFITSLLPDMEATLWIGLRWTAYE 1020
OGTA076a (SEQ ID No: 1)    KCFLKIKPVSLTFSQASDTCHSYGGTLPSVLSQIEQDFITSLLPDMEATLWIGLRWTAYE 1020
                           ************************************************************

OGTA076b (SEQ ID No: 2)    KINKWTDNREIYYSNFHPLAVSGRLRIPENFFEEESRYHCALILNLQKSPFTGTWNFTSC 1080
OGTA076c (SEQ ID No: 3)    KINKWTDNREIYYSNFHPLAVSGRLRIPENFFEEESRYHCALILNLQKSPFTGTWNFTSC 1080
OGTA076a (SEQ ID No: 1)    KINKWTDNREIYYSNFHPLAVSGRLRIPENFFEEESRYHCALILNLQKSPFTGTWNFTSC 1080
                           ************************************************************

OGTA076b (SEQ ID No: 2)    SERHFVSLCQKYSEVKSRQTLQNASETVKYLNNLYKIIPKTLTWHSAKRECLKSNMQLVS 1140
OGTA076c (SEQ ID No: 3)    SERHFVSLCQKYSEVKSRQTLQNASETVKYLNNLYKIIPKTLTWHSAKRECLKSNMQLVS 1140
OGTA076a (SEQ ID No: 1)    SERHFVSLCQKYSEVKSRQTLQNASETVKYLNNLYKIIPKTLTWHSAKRECLKSNMQLVS 1140
                           ************************************************************

OGTA076b (SEQ ID No: 2)    ITDPYQQAFLSVQALLHNSSLWIGLFSQDDELNFGWSDGKRLHFSRWAETNGQLEDCVVL 1200
OGTA076c (SEQ ID No: 3)    ITDPYQQAFLSVQALLHNSSLWIGLFSQDDELNFGWSDGKRLHFSRWAETNGQLEDCVVL 1200
OGTA076a (SEQ ID No: 1)    ITDPYQQAFLSVQALLHNSSLWIGLFSQDDELNFGWSDGKRLHFSRWAETNGQLEDCVVL 1200
                           ************************************************************

OGTA076b (SEQ ID No: 2)    DTDGFWKTVDCNDNQPGAICYYSGNETEKEVKPVDSVKCPSPVLNTPWIPFQNCCYNFII 1260
OGTA076c (SEQ ID No: 3)    DTDGFWKTVDCNDNQPGAICYYSGNETEKEVKPVDSVKCPSPVLNTPWIPFQNCCYNFII 1260
OGTA076a (SEQ ID No: 1)    DTDGFWKTVDCNDNQPGAICYYSGNETEKEVKPVDSVKCPSPVLNTPWIPFQNCCYNFII 1260
                           ************************************************************

OGTA076b (SEQ ID No: 2)    TKNRHMATTQDEVETKCQKLNPKSHILSIRDEKENNFVLEQLLYFNYMASWVMLGITYRN 1320
OGTA076c (SEQ ID No: 3)    TKNRHMATTQDEVETKCQKLNPKSHILSIRDEKENNFVLEQLLYFNYMASWVMLGITYRN 1320
OGTA076a (SEQ ID No: 1)    TKNRHMATTQDEVETKCQKLNPKSHILSIRDEKENNFVLEQLLYFNYMASWVMLGITYRN 1320
                           ************************************************************

OGTA076b (SEQ ID No: 2)    NSLMWFDKTPLSYTHWRAGRPTIKNEKFLAGLSTDGFWDIQTFKVIEEAVYFHQHSILAC 1380
OGTA076c (SEQ ID No: 3)    NSLMWFDKTPLSYTHWRAGRPTIKNEKFLAGLSTDGFWDIQTFKVIEEAVYFHQHSILAC 1380
OGTA076a (SEQ ID No: 1)    NSLMWFDKTPLSYTHWRAGRPTIKNEKFLAGLSTDGFWDIQTFKVIEEAVYFHQHSILAC 1380
                           ************************************************************

OGTA076b (SEQ ID No: 2)    KIEMVDYKEEHNTTLPQFMPYEDGIYSVIQKKVTWYEALNMCSQSGGHLASVHNQNGQLF 1440
OGTA076c (SEQ ID No: 3)    KIEMVDYKEEHNTTLPQFMPYEDGIYSVIQKKVTWYEALNMCSQSGGHLASVHNQNGQLF 1440
OGTA076a (SEQ ID No: 1)    KIEMVDYKEEHNTTLPQFMPYEDGIYSVIQKKVTWYEALNMCSQSGGHLASVHNQNGQLF 1440
                           ************************************************************

OGTA076b (SEQ ID No: 2)    LEDIVKRDGFPLWVGLSSHDGSESSFEWSDGSTFDYIPWKGQTSPGNCVLLDPKGTWKHE 1500
OGTA076c (SEQ ID No: 3)    LEDIVKRDGFPLWVGLSSHDGSESSFEWSDGSTFDYIPWKGQTSPGNCVLLDPKGTWKHE 1500
OGTA076a (SEQ ID No: 1)    LEDIVKRDGFPLWVGLSSHDGSESSFEWSDGSTFDYIPWKGQTSPGNCVLLDPKGTWKHE 1500
                           ************************************************************

OGTA076b (SEQ ID No: 2)    KCNSVKDGAICYKPTKSKKLSRLTYSSRCPAAKENGSRWIQYKGHCYKSDQALHSFSEAK 1560
OGTA076c (SEQ ID No: 3)    KCNSVKDGAICYKPTKSKKLSRLTYSSRCPAAKENGSRWIQYKGHCYKSDQALHSFSEAK 1560
OGTA076a (SEQ ID No: 1)    KCNSVKDGAICYKPTKSKKLSRLTYSSRCPAAKENGSRWIQYKGHCYKSDQALHSFSEAK 1560
                           ************************************************************

OGTA076b (SEQ ID No: 2)    KLCSKHDHSATIVSIKDEDENKFVSRLMRENNNITMRVWLGLSQHSVDQSWSWLDGSEVT 1620
OGTA076c (SEQ ID No: 3)    KLCSKHDHSATIVSIKDEDENKFVSRLMRENNNITMRVWLGLSQHSVD------------ 1608
OGTA076a (SEQ ID No: 1)    KLCSKHDHSATIVSIKDEDENKFVSRLMRENNNITMRVWLGLSQHSVDQSWSWLDGSEVT 1608
                           ************************************************

OGTA076b (SEQ ID No: 2)    FVKWENKSKSGVGRCSMLIASNETWKKVECEHGFGRVVCKVPLDCPSSTWIQFQDSCYIF 1680
OGTA076c (SEQ ID No: 3)    --------------------------------------CPSSTWIQFQDSCYIF 1624
OGTA076a (SEQ ID No: 1)    FVKWENKSKSGVGRCSMLIASNETWKKVECEHGFGRVVCKVPLGPDYTAIAIIVATLSIL

OGTA076b (SEQ ID No: 2)    LQEAIKVESIEDVRNQCTDHGADMISIHNEEENAFILDTLKKQWKGPDDILLGMFYDTDD 1740
OGTA076c (SEQ ID No: 3)    LQEAIKVESIEDVRNQCTDHGADMISIHNEEENAFILDTLKKQWKGPDDILLGMFYDTDD 1684
OGTA076a (SEQ ID No: 1)    VLMGGIIWFLFQREREHLAGFSSVRYAQGVNEDEIMLPSFED-----------------

OGTA076b (SEQ ID No: 2)    ASFKWFDNSNMTFDKWTDQDDDEDLVDTCAFLHIKTGEWKKGNCEVSSVEGTLCKTAIPY 1800
OGTA076c (SEQ ID No: 3)    ASFKWFDNSNMTFDKWTDQDDDEDLVDTCAFLHIKTGEWKKGNCEVSSVEGTLCKTAIPY 1744
OGTA076a (SEQ ID No: 1)    ------------------------------------------------------------
```

Figure 1 (cont)

```
OGTA076b (SEQ ID No: 2)    KRKYLSDNHILISALVIASTVILTVLGAIIWFLYKKHSDSRFTTVFSTAPQSPYNEDCVL 1860
OGTA076c (SEQ ID No: 3)    KRKYLSDNHILISALVIASTVILTVLGAIIWFLYKKHSDSRFTTVFSTAPQSPYNEDCVL 1804
OGTA076a (SEQ ID No: 1)    ------------------------------------------------------------

OGTA076b (SEQ ID No: 2)    VVGEENEYPVQFD 1873
OGTA076c (SEQ ID No: 3)    VVGEENEYPVQFD 1817
OGTA076a (SEQ ID No: 1)    -------------
```

Mass Match Peptides (bold):
IIPK [SEQ ID NO: 28]
LALK [SEQ ID NO: 35]
YLNNLYK [SEQ ID NO: 66]

Tandem Peptides (underline):
IIPK [SEQ ID NO: 28]
LALK [SEQ ID NO: 35]
YLNNLYK [SEQ ID NO: 66]

Peptide Source: iTRAQ Small cell lung cancer

```
OGTA076b (SEQ ID No: 2)    MRTGWATPRRPAGLLMLLFWFFDLAEPSCRAANDPFTIVHGNTGKCIKPVYGWIVADDCD 60
OGTA076c (SEQ ID No: 3)    MRTGWATPRRPAGLLMLLFWFFDLAEPSCRAANDPFTIVHGNTGKCIKPVYGWIVADDCD 60
OGTA076a (SEQ ID No: 1)    MRTGWATPRRPAGLLMLLFWFFDLAEPSCRAANDPFTIVHGNTGKCIKPVYGWIVADDCD 60
                           ************************************************************

OGTA076b (SEQ ID No: 2)    ETEDKLWKWVSQHRLFHLHSQKCLGLDITKSVNELRMFSCDSSAMLWWKCEHHSLYGAAR 120
OGTA076c (SEQ ID No: 3)    ETEDKLWKWVSQHRLFHLHSQKCLGLDITKSVNELRMFSCDSSAMLWWKCEHHSLYGAAR 120
OGTA076a (SEQ ID No: 1)    ETEDKLWKWVSQHRLFHLHSQKCLGLDITKSVNELRMFSCDSSAMLWWKCEHHSLYGAAR 120
                           ************************************************************

OGTA076b (SEQ ID No: 2)    YRLALKDGHGTAISNASDVWKKGGSEESLCDQPYHEIYTRDGNSYGRPCEFPFLIDGTWH 180
OGTA076c (SEQ ID No: 3)    YRLALKDGHGTAISNASDVWKKGGSEESLCDQPYHEIYTRDGNSYGRPCEFPFLIDGTWH 180
OGTA076a (SEQ ID No: 1)    YRLALKDGHGTAISNASDVWKKGGSEESLCDQPYHEIYTRDGNSYGRPCEFPFLIDGTWH 180
                           ************************************************************

OGTA076b (SEQ ID No: 2)    HDCILDEDHSGPWCATTLNYEYDRKWGICLKPENGCEDNWEKNEQFGSCYQFNTQTALSW 240
OGTA076c (SEQ ID No: 3)    HDCILDEDHSGPWCATTLNYEYDRKWGICLKPENGCEDNWEKNEQFGSCYQFNTQTALSW 240
OGTA076a (SEQ ID No: 1)    HDCILDEDHSGPWCATTLNYEYDRKWGICLKPENGCEDNWEKNEQFGSCYQFNTQTALSW 240
                           ************************************************************

OGTA076b (SEQ ID No: 2)    KEAYVSCQNQGADLLSINSAAELTYLKEKEGIAKIFWIGLNQLYSARGWEWSDHKPLNFL 300
OGTA076c (SEQ ID No: 3)    KEAYVSCQNQGADLLSINSAAELTYLKEKEGIAKIFWIGLNQLYSARGWEWSDHKPLNFL 300
OGTA076a (SEQ ID No: 1)    KEAYVSCQNQGADLLSINSAAELTYLKEKEGIAKIFWIGLNQLYSARGWEWSDHKPLNFL 300
                           ************************************************************

OGTA076b (SEQ ID No: 2)    NWDPDRPSAPTIGGSSCARMDAESGLWQSFSCEAQLPYVCRKPLNNTVELTDVWTYSDTR 360
OGTA076c (SEQ ID No: 3)    NWDPDRPSAPTIGGSSCARMDAESGLWQSFSCEAQLPYVCRKPLNNTVELTDVWTYSDTR 360
OGTA076a (SEQ ID No: 1)    NWDPDRPSAPTIGGSSCARMDAESGLWQSFSCEAQLPYVCRKPLNNTVELTDVWTYSDTR 360
                           ************************************************************

OGTA076b (SEQ ID No: 2)    CDAGWLPNNGFCYLLVNESNSWDKAHAKCKAFSSDLISIHSLADVEVVVTKLHNEDIKEE 420
OGTA076c (SEQ ID No: 3)    CDAGWLPNNGFCYLLVNESNSWDKAHAKCKAFSSDLISIHSLADVEVVVTKLHNEDIKEE 420
OGTA076a (SEQ ID No: 1)    CDAGWLPNNGFCYLLVNESNSWDKAHAKCKAFSSDLISIHSLADVEVVVTKLHNEDIKEE 420
                           ************************************************************

OGTA076b (SEQ ID No: 2)    VWIGLKNINIPTLFQWSDGTEVTLTYWDENEPNVPYNKTPNCVSYLGELGQWKVQSCEEK 480
OGTA076c (SEQ ID No: 3)    VWIGLKNINIPTLFQWSDGTEVTLTYWDENEPNVPYNKTPNCVSYLGELGQWKVQSCEEK 480
OGTA076a (SEQ ID No: 1)    VWIGLKNINIPTLFQWSDGTEVTLTYWDENEPNVPYNKTPNCVSYLGELGQWKVQSCEEK 480
                           ************************************************************

OGTA076b (SEQ ID No: 2)    LKYVCKRKGEKLNDASSDKMCPPDEGWKRHGETCYKIYEDEVPFGTNCNLTITSRFEQEY 540
OGTA076c (SEQ ID No: 3)    LKYVCKRKGEKLNDASSDKMCPPDEGWKRHGETCYKIYEDEVPFGTNCNLTITSRFEQEY 540
OGTA076a (SEQ ID No: 1)    LKYVCKRKGEKLNDASSDKMCPPDEGWKRHGETCYKIYEDEVPFGTNCNLTITSRFEQEY 540
                           ************************************************************

OGTA076b (SEQ ID No: 2)    LNDLMKKYDKSLRKYFWTGLRDVDSCGEYNWATVGGRRRAVTFSNWNFLEPASPGGCVAM 600
OGTA076c (SEQ ID No: 3)    LNDLMKKYDKSLRKYFWTGLRDVDSCGEYNWATVGGRRRAVTFSNWNFLEPASPGGCVAM 600
OGTA076a (SEQ ID No: 1)    LNDLMKKYDKSLRKYFWTGLRDVDSCGEYNWATVGGRRRAVTFSNWNFLEPASPGGCVAM 600
                           ************************************************************
```

Figure 1 (cont)

```
OGTA076b  (SEQ ID No: 2)   STGKSVGKWEVKDCRSFKALSICKKMSGPLGPEEASPKPDDPCPEGWQSFPASLSCYKVF  660
OGTA076c  (SEQ ID No: 3)   STGKSVGKWEVKDCRSFKALSICKKMSGPLGPEEASPKPDDPCPEGWQSFPASLSCYKVF  660
OGTA076a  (SEQ ID No: 1)   STGKSVGKWEVKDCRSFKALSICKKMSGPLGPEEASPKPDDPCPEGWQSFPASLSCYKVF  660
                           ************************************************************

OGTA076b  (SEQ ID No: 2)   HAFRIVRKRNWEEAERFCQALGAHLSSFSEVDETKEFLEFLTDQFSGQIWLWTGLNKRSP  720
OGTA076c  (SEQ ID No: 3)   HAFRIVRKRNWEEAERFCQALGAHLSSFSEVDETKEFLEFLTDQFSGQIWLWTGLNKRSP  720
OGTA076a  (SEQ ID No: 1)   HAFRIVRKRNWEEAERFCQALGAHLSSFSEVDETKEFLEFLTDQFSGQIWLWTGLNKRSP  720
                           ************************************************************

OGTA076b  (SEQ ID No: 2)   DLQGSWQWSDRTPVSTIIMPNEFQQDYDIRDCAAVKVFERPWRRGWEFYDDREFIYLRPF  780
OGTA076c  (SEQ ID No: 3)   DLQGSWQWSDRTPVSTIIMPNEFQQDYDIRDCAAVKVFERPWRRGWEFYDDREFIYLRPF  780
OGTA076a  (SEQ ID No: 1)   DLQGSWQWSDRTPVSTIIMPNEFQQDYDIRDCAAVKVFERPWRRGWEFYDDREFIYLRPF  780
                           ************************************************************

OGTA076b  (SEQ ID No: 2)   ACDTKLFWVCQIPKGRTPKTPDWYNPDRAGIHGPPLIIEGSEYWFVADLHLNYEEAVLYC  840
OGTA076c  (SEQ ID No: 3)   ACDTKLFWVCQIPKGRTPKTPDWYNPDRAGIHGPPLIIEGSEYWFVADLHLNYEEAVLYC  840
OGTA076a  (SEQ ID No: 1)   ACDTKLFWVCQIPKGRTPKTPDWYNPDRAGIHGPPLIIEGSEYWFVADLHLNYEEAVLYC  840
                           ************************************************************

OGTA076b  (SEQ ID No: 2)   ASNESFLATITSFVGLKAIKNKIANISGDGQKWWIRISEWPIDDHFTYSRYPWHRFPVTF  900
OGTA076c  (SEQ ID No: 3)   ASNESFLATITSFVGLKAIKNKIANISGDGQKWWIRISEWPIDDHFTYSRYPWHRFPVTF  900
OGTA076a  (SEQ ID No: 1)   ASNESFLATITSFVGLKAIKNKIANISGDGQKWWIRISEWPIDDHFTYSRYPWHRFPVTF  900
                           ************************************************************

OGTA076b  (SEQ ID No: 2)   GEECLYMSAKTWLIDLGKPTDCSTKLPFICEKYNVSSLEKYSPDSAAKVQCSEQWIPFQN  960
OGTA076c  (SEQ ID No: 3)   GEECLYMSAKTWLIDLGKPTDCSTKLPFICEKYNVSSLEKYSPDSAAKVQCSEQWIPFQN  960
OGTA076a  (SEQ ID No: 1)   GEECLYMSAKTWLIDLGKPTDCSTKLPFICEKYNVSSLEKYSPDSAAKVQCSEQWIPFQN  960
                           ************************************************************

OGTA076b  (SEQ ID No: 2)   KCFLKIKPVSLTFSQASDTCHSYGGTLFSVLSQIEQDFITSLLPDMEATLWIGLRWTAYE  1020
OGTA076c  (SEQ ID No: 3)   KCFLKIKPVSLTFSQASDTCHSYGGTLFSVLSQIEQDFITSLLPDMEATLWIGLRWTAYE  1020
OGTA076a  (SEQ ID No: 1)   KCFLKIKPVSLTFSQASDTCHSYGGTLFSVLSQIEQDFITSLLPDMEATLWIGLRWTAYE  1020
                           ************************************************************

OGTA076b  (SEQ ID No: 2)   KINKWTDNRELTYSNFHPLLVSGRLRIPENFFEEESRYHCALILNLQKSPFTGTWNFTSC  1080
OGTA076c  (SEQ ID No: 3)   KINKWTDNRELTYSNFHPLLVSGRLRIPENFFEEESRYHCALILNLQKSPFTGTWNFTSC  1080
OGTA076a  (SEQ ID No: 1)   KINKWTDNRELTYSNFHPLLVSGRLRIPENFFEEESRYHCALILNLQKSPFTGTWNFTSC  1080
                           ************************************************************

OGTA076b  (SEQ ID No: 2)   SERHFVSLCQKYSEVKSRQTLQNASETVKYLNNLYKIIPKTLTWHSAKRECLKSNMQLVS  1140
OGTA076c  (SEQ ID No: 3)   SERHFVSLCQKYSEVKSRQTLQNASETVKYLNNLYKIIPKTLTWHSAKRECLKSNMQLVS  1140
OGTA076a  (SEQ ID No: 1)   SERHFVSLCQKYSEVKSRQTLQNASETVKYLNNLYKIIPKTLTWHSAKRECLKSNMQLVS  1140
                           ************************************************************

OGTA076b  (SEQ ID No: 2)   ITDPYQQAFLSVQALLHNSSLWIGLFSQDDELNFGWSDGKRLHFSRWAETNGQLEDCVVL  1200
OGTA076c  (SEQ ID No: 3)   ITDPYQQAFLSVQALLHNSSLWIGLFSQDDELNFGWSDGKRLHFSRWAETNGQLEDCVVL  1200
OGTA076a  (SEQ ID No: 1)   ITDPYQQAFLSVQALLHNSSLWIGLFSQDDELNFGWSDGKRLHFSRWAETNGQLEDCVVL  1200
                           ************************************************************

OGTA076b  (SEQ ID No: 2)   DTDGFWKTVDCNDNQPGAICYYSGNETEKEVKPVDSVKCPSPVLNTPWIPFQNCCYNFII  1260
OGTA076c  (SEQ ID No: 3)   DTDGFWKTVDCNDNQPGAICYYSGNETEKEVKPVDSVKCPSPVLNTPWIPFQNCCYNFII  1260
OGTA076a  (SEQ ID No: 1)   DTDGFWKTVDCNDNQPGAICYYSGNETEKEVKPVDSVKCPSPVLNTPWIPFQNCCYNFII  1260
                           ************************************************************

OGTA076b  (SEQ ID No: 2)   TKNRHMATTQDEVHTKCQKLNPKSHILSIRDEKENNFVLEQLLYFNYMASWVMLGITYRN  1320
OGTA076c  (SEQ ID No: 3)   TKNRHMATTQDEVHTKCQKLNPKSHILSIRDEKENNFVLEQLLYFNYMASWVMLGITYRN  1320
OGTA076a  (SEQ ID No: 1)   TKNRHMATTQDEVHTKCQKLNPKSHILSIRDEKENNFVLEQLLYFNYMASWVMLGITYRN  1320
                           ************************************************************

OGTA076b  (SEQ ID No: 2)   NSLMWFDKTPLSYTHWRAGRPTIKNEKFLAGLSTDGFWDIQTFKVIEEAVYFHQHSILAC  1380
OGTA076c  (SEQ ID No: 3)   NSLMWFDKTPLSYTHWRAGRPTIKNEKFLAGLSTDGFWDIQTFKVIEEAVYFHQHSILAC  1380
OGTA076a  (SEQ ID No: 1)   NSLMWFDKTPLSYTHWRAGRPTIKNEKFLAGLSTDGFWDIQTFKVIEEAVYFHQHSILAC  1380
                           ************************************************************

OGTA076b  (SEQ ID No: 2)   KIEMVDYKEEHNTTLPQFMPYEDGIYSVIQKKVTWYEALNMCSQSGGHLASVHNQNGQLF  1440
OGTA076c  (SEQ ID No: 3)   KIEMVDYKEEHNTTLPQFMPYEDGIYSVIQKKVTWYEALNMCSQSGGHLASVHNQNGQLF  1440
OGTA076a  (SEQ ID No: 1)   KIEMVDYKEEHNTTLPQFMPYEDGIYSVIQKKVTWYEALNMCSQSGGHLASVHNQNGQLF  1440
                           ************************************************************

OGTA076b  (SEQ ID No: 2)   LEDIVKRDGFPLWVGLSSHDGSESSFEWSDGSTFDYIPWKGQTSPGNCVLLDPKGTWKHE  1500
OGTA076c  (SEQ ID No: 3)   LEDIVKRDGFPLWVGLSSHDGSESSFEWSDGSTFDYIPWKGQTSPGNCVLLDPKGTWKHE  1500
OGTA076a  (SEQ ID No: 1)   LEDIVKRDGFPLWVGLSSHDGSESSFEWSDGSTFDYIPWKGQTSPGNCVLLDPKGTWKHE  1500
                           ************************************************************

OGTA076b  (SEQ ID No: 2)   KCNSVKDGAICYKPTKSKKLSRLTYSSRCPAAKENGSRWIQYKGHCYKSDQALHSFSEAK  1560
```

Figure 1 (cont)

```
OGTA076c (SEQ ID No: 3)  KCNSVKDGAICYKPTKSKKLSRLTYSSRCPAAKENGSRWIQYKGHCYKSDQALHSFSEAK 1560
OGTA076a (SEQ ID No: 1)  KCNSVKDGAICYKPTKSKKLSRLTYSSRCPAAKENGSRWIQYKGHCYKSDQALHSFSEAK 1560
                         ************************************************************

OGTA076b (SEQ ID No: 2)  KLCSKHDESATIVSIKDEDENKFVSRLMRENNNITMRVWLGLSQHSVDQSWSWLDGSEVT 1620
OGTA076c (SEQ ID No: 3)  KLCSKHDESATIVSIKDEDENKFVSRLMRENNNITMRVWLGLSQHSVD------------ 1608
OGTA076a (SEQ ID No: 1)  KLCSKHDESATIVSIKDEDENKFVSRLMRENNNITMRVWLGLSQHSVDQSWSWLDGSEVT 1608
                         ***********************************************

OGTA076b (SEQ ID No: 2)  FVKWENKSKSGVGRCSMLIASNETWKKVECEHGFGRVVCKVPLDCPSSTWIQFQDSCYIF 1680
OGTA076c (SEQ ID No: 3)  ------------------------------------------CPSSTWIQFQDSCYIF 1624
OGTA076a (SEQ ID No: 1)  FVKWENKSKSGVGRCSMLIASNETWKKVECEHGFGRVVCKVPLGPDYTAIAIIVATLSIL 1668

OGTA076b (SEQ ID No: 2)  LQEAIKVESIEDVRNQCTDHGADMISIENEEENAFILDTLKKQWKGPDDILLGMFYDTDD 1740
OGTA076c (SEQ ID No: 3)  LQEAIKVESIEDVRNQCTDHGADMISIENEEENAFILDTLKKQWKGPDDILLGMFYDTDD 1684
OGTA076a (SEQ ID No: 1)  VLMGGLIWFLFQRHRLHLAGFSSVRYAQGVNEDEIMLPSFHD------------------

OGTA076b (SEQ ID No: 2)  ASFKWFDNSNMTFDKWTDQDDDEDLVDTCAFLHIKTGEWKKGNCEVSSVEGTLCKTAIPY 1800
OGTA076c (SEQ ID No: 3)  ASFKWFDNSNMTFDKWTDQDDDEDLVDTCAFLHIKTGEWKKGNCEVSSVEGTLCKTAIPY 1744
OGTA076a (SEQ ID No: 1)  ------------------------------------------------------------

OGTA076b (SEQ ID No: 2)  KRKYLSDNHILISALVIASTVILTVLGAIIWFLYKKHSDSRFTTVFSTAPQSPYNEDCVL 1860
OGTA076c (SEQ ID No: 3)  KRKYLSDNHILISALVIASTVILTVLGAIIWFLYKKHSDSRFTTVFSTAPQSPYNEDCVL 1804
OGTA076a (SEQ ID No: 1)  ------------------------------------------------------------

OGTA076b (SEQ ID No: 2)  VVGEENEYPVQFD 1873
OGTA076c (SEQ ID No: 3)  VVGEENEYPVQFD 1817
OGTA076a (SEQ ID No: 1)  -------------
```

Mass Match Peptides (bold):
EGIAK [SEQ ID NO: 14]

Tandem Peptides (underline):
EGIAK [SEQ ID NO: 14]

Peptide Source: iTRAQ Ovarian cancer

```
OGTA076b (SEQ ID No: 2)  MRTGWATPRRPAGLLMLLFWFFDLAEPSGRAANDPFTIVHGNTGKCIKPVYGWIVADDCD 60
OGTA076c (SEQ ID No: 3)  MRTGWATPRRPAGLLMLLFWFFDLAEPSGRAANDPFTIVHGNTGKCIKPVYGWIVADDCD 60
OGTA076a (SEQ ID No: 1)  MRTGWATPRRPAGLLMLLFWFFDLAEPSGRAANDPFTIVHGNTGKCIKPVYGWIVADDCD 60
                         ************************************************************

OGTA076b (SEQ ID No: 2)  ETEDKLWKWVSQERLFHLHSQKCLGLDITKSVNELRMFSCDSSAMLWWKCEHHSLYGAAR 120
OGTA076c (SEQ ID No: 3)  ETEDKLWKWVSQERLFHLHSQKCLGLDITKSVNELRMFSCDSSAMLWWKCEHHSLYGAAR 120
OGTA076a (SEQ ID No: 1)  ETEDKLWKWVSQERLFHLHSQKCLGLDITKSVNELRMFSCDSSAMLWWKCEHHSLYGAAR 120
                         ************************************************************

OGTA076b (SEQ ID No: 2)  YRLALKDGHGTAISNASDVWKKGGSEESLCDQPYHEIYTRDGNSYGRPCEFPFLIDGTWH 180
OGTA076c (SEQ ID No: 3)  YRLALKDGHGTAISNASDVWKKGGSEESLCDQPYHEIYTRDGNSYGRPCEFPFLIDGTWH 180
OGTA076a (SEQ ID No: 1)  YRLALKDGHGTAISNASDVWKKGGSEESLCDQPYHEIYTRDGNSYGRPCEFPFLIDGTWH 180
                         ************************************************************

OGTA076b (SEQ ID No: 2)  HDCILDEDHSGPWCATTLNYEYDRKWGICLKPENGCEDNWEKNEQFGSCYQFNTQTALSW 240
OGTA076c (SEQ ID No: 3)  HDCILDEDHSGPWCATTLNYEYDRKWGICLKPENGCEDNWEKNEQFGSCYQFNTQTALSW 240
OGTA076a (SEQ ID No: 1)  HDCILDEDHSGPWCATTLNYEYDRKWGICLKPENGCEDNWEKNEQFGSCYQFNTQTALSW 240
                         ************************************************************

OGTA076b (SEQ ID No: 2)  KEAYVSCQNQGADLLSINSAAELTYLKEKEGIAKIFWIGLNQLYSARGWEWSDHKPLNFL 300
OGTA076c (SEQ ID No: 3)  KEAYVSCQNQGADLLSINSAAELTYLKEKEGIAKIFWIGLNQLYSARGWEWSDHKPLNFL 300
OGTA076a (SEQ ID No: 1)  KEAYVSCQNQGADLLSINSAAELTYLKEKEGIAKIFWIGLNQLYSARGWEWSDHKPLNFL 300
                         ************************************************************

OGTA076b (SEQ ID No: 2)  NWDPDRPSAPTIGGSSCARMDAESGLWQSFSCEAQLPYVCRKPLNNTVELTDVWTYSDTR 360
OGTA076c (SEQ ID No: 3)  NWDPDRPSAPTIGGSSCARMDAESGLWQSFSCEAQLPYVCRKPLNNTVELTDVWTYSDTR 360
OGTA076a (SEQ ID No: 1)  NWDPDRPSAPTIGGSSCARMDAESGLWQSFSCEAQLPYVCRKPLNNTVELTDVWTYSDTR 360
                         ************************************************************
```

Figure 1 (cont)

```
OGTA076b (SEQ ID No: 2)    CDAGWLPNNGFCYLLVNESNSWDKAHAKCKAFSSDLISIHSLADVEVVVTKLHNEDIKEE  420
OGTA076c (SEQ ID No: 3)    CDAGWLPNNGFCYLLVNESNSWDKAHAKCKAFSSDLISIHSLADVEVVVTKLHNEDIKEE  420
OGTA076a (SEQ ID No: 1)    CDAGWLPNNGFCYLLVNESNSWDKAHAKCKAFSSDLISIHSLADVEVVVTKLHNEDIKEE  420
                           ************************************************************

OGTA076b (SEQ ID No: 2)    VWIGLKNINIPTLFQWSDGTEVTLTYWDENEPNVPYNKTPNCVSYLGELGQWKVQSCEEK  480
OGTA076c (SEQ ID No: 3)    VWIGLKNINIPTLFQWSDGTEVTLTYWDENEPNVPYNKTPNCVSYLGELGQWKVQSCEEK  480
OGTA076a (SEQ ID No: 1)    VWIGLKNINIPTLFQWSDGTEVTLTYWDENEPNVPYNKTPNCVSYLGELGQWKVQSCEEK  480
                           ************************************************************

OGTA076b (SEQ ID No: 2)    LKYVCKRKGEKLNDASSDKMCPPDEGWKRHGETCYKIYEDEVPFGTNCNLTITSRFEQEY  540
OGTA076c (SEQ ID No: 3)    LKYVCKRKGEKLNDASSDKMCPPDEGWKRHGETCYKIYEDEVPFGTNCNLTITSRFEQEY  540
OGTA076a (SEQ ID No: 1)    LKYVCKRKGEKLNDASSDKMCPPDEGWKRHGETCYKIYEDEVPFGTNCNLTITSRFEQEY  540
                           ************************************************************

OGTA076b (SEQ ID No: 2)    LNDLMKKYDKSLRKYFWTGLRDVDSCGEYNWATVGGRRAVTFSNWNFLEPASPGGCVAM   600
OGTA076c (SEQ ID No: 3)    LNDLMKKYDKSLRKYFWTGLRDVDSCGEYNWATVGGRRAVTFSNWNFLEPASPGGCVAM   600
OGTA076a (SEQ ID No: 1)    LNDLMKKYDKSLRKYFWTGLRDVDSCGEYNWATVGGRRAVTFSNWNFLEPASPGGCVAM   600
                           ************************************************************

OGTA076b (SEQ ID No: 2)    STGKSVGKWEVKDCRSFKALSICKKMSGPLGPEEASPKPDDPCPEGWQSFPASLSCYKVF  660
OGTA076c (SEQ ID No: 3)    STGKSVGKWEVKDCRSFKALSICKKMSGPLGPEEASPKPDDPCPEGWQSFPASLSCYKVF  660
OGTA076a (SEQ ID No: 1)    STGKSVGKWEVKDCRSFKALSICKKMSGPLGPEEASPKPDDPCPEGWQSFPASLSCYKVF  660
                           ************************************************************

OGTA076b (SEQ ID No: 2)    HAERIVRKRNWEEAERFCQALGAHLSSFSHVDEIKEFLHFLTDQFSGQHWLWIGLNKRSP  720
OGTA076c (SEQ ID No: 3)    HAERIVRKRNWEEAERFCQALGAHLSSFSHVDEIKEFLHFLTDQFSGQHWLWIGLNKRSP  720
OGTA076a (SEQ ID No: 1)    HAERIVRKRNWEEAERFCQALGAHLSSFSHVDEIKEFLHFLTDQFSGQHWLWIGLNKRSP  720
                           ************************************************************

OGTA076b (SEQ ID No: 2)    DLQGSWQWSDRTPVSTIIMPNEFQQDYDIRDCAAVKVFHRPWRRGWHFYDDREFIYLRPF  780
OGTA076c (SEQ ID No: 3)    DLQGSWQWSDRTPVSTIIMPNEFQQDYDIRDCAAVKVFHRPWRRGWHFYDDREFIYLRPF  780
OGTA076a (SEQ ID No: 1)    DLQGSWQWSDRTPVSTIIMPNEFQQDYDIRDCAAVKVFHRPWRRGWHFYDDREFIYLRPF  780
                           ************************************************************

OGTA076b (SEQ ID No: 2)    ACDTKLEWVCQIPKGRTPKTPDWYNPDRAGIHGPPLIIEGSEYWFVADLHLNYEEAVLYC  840
OGTA076c (SEQ ID No: 3)    ACDTKLEWVCQIPKGRTPKTPDWYNPDRAGIHGPPLIIEGSEYWFVADLHLNYEEAVLYC  840
OGTA076a (SEQ ID No: 1)    ACDTKLEWVCQIPKGRTPKTPDWYNPDRAGIHGPPLIIEGSEYWFVADLHLNYEEAVLYC  840
                           ************************************************************

OGTA076b (SEQ ID No: 2)    ASNHSFLATITSFVGLKAIKNKIANISGDGCQKWWIRISEWPIDDHFTYSRYPWERFPVTF 900
OGTA076c (SEQ ID No: 3)    ASNHSFLATITSFVGLKAIKNKIANISGDGCQKWWIRISEWPIDDHFTYSRYPWERFPVTF 900
OGTA076a (SEQ ID No: 1)    ASNHSFLATITSFVGLKAIKNKIANISGDGCQKWWIRISEWPIDDHFTYSRYPWERFPVTF 900
                           ************************************************************

OGTA076b (SEQ ID No: 2)    GEECLYMSAKTWLIDLGKPTDCSTKLPFICEKYNVSSLEKYSPDSAAKVQCSEQWIPFQN  960
OGTA076c (SEQ ID No: 3)    GEECLYMSAKTWLIDLGKPTDCSTKLPFICEKYNVSSLEKYSPDSAAKVQCSEQWIPFQN  960
OGTA076a (SEQ ID No: 1)    GEECLYMSAKTWLIDLGKPTDCSTKLPFICEKYNVSSLEKYSPDSAAKVQCSEQWIPFQN  960
                           ************************************************************

OGTA076b (SEQ ID No: 2)    KCFLKIKPVSLTFSQASDTCHSYGGTLPSVLSQIEQDFITSLLPDMEATLWIGLRWTAYE  1020
OGTA076c (SEQ ID No: 3)    KCFLKIKPVSLTFSQASDTCHSYGGTLPSVLSQIEQDFITSLLPDMEATLWIGLRWTAYE  1020
OGTA076a (SEQ ID No: 1)    KCFLKIKPVSLTFSQASDTCHSYGGTLPSVLSQIEQDFITSLLPDMEATLWIGLRWTAYE  1020
                           ************************************************************

OGTA076b (SEQ ID No: 2)    KINKWTDNRELTYSNFHPLLVSGRLRIPENFFEEESRYHCALILNLQKSPFTGTWNFTSC  1080
OGTA076c (SEQ ID No: 3)    KINKWTDNRELTYSNFHPLLVSGRLRIPENFFEEESRYHCALILNLQKSPFTGTWNFTSC  1080
OGTA076a (SEQ ID No: 1)    KINKWTDNRELTYSNFHPLLVSGRLRIPENFFEEESRYHCALILNLQKSPFTGTWNFTSC  1080
                           ************************************************************

OGTA076b (SEQ ID No: 2)    SERHFVSLCQKYSEVKSRQTLQNASETVKYLNNLYKIIPKTLTWHSAKRECLKSNMQLVS  1140
OGTA076c (SEQ ID No: 3)    SERHFVSLCQKYSEVKSRQTLQNASETVKYLNNLYKIIPKTLTWHSAKRECLKSNMQLVS  1140
OGTA076a (SEQ ID No: 1)    SERHFVSLCQKYSEVKSRQTLQNASETVKYLNNLYKIIPKTLTWHSAKRECLKSNMQLVS  1140
                           ************************************************************

OGTA076b (SEQ ID No: 2)    ITDPYQQAFLSVQALLHNSSLWIGLFSQDDELNFGWSDGKRLHFSRWAETNGQLEDCVVL  1200
OGTA076c (SEQ ID No: 3)    ITDPYQQAFLSVQALLHNSSLWIGLFSQDDELNFGWSDGKRLHFSRWAETNGQLEDCVVL  1200
OGTA076a (SEQ ID No: 1)    ITDPYQQAFLSVQALLHNSSLWIGLFSQDDELNFGWSDGKRLHFSRWAETNGQLEDCVVL  1200
                           ************************************************************

OGTA076b (SEQ ID No: 2)    DTDGFWKTVDCNDNQPGAICYYSGNETEKEVKPVDSVKCPSPVLNTPWIPFQNCCYNFII  1260
OGTA076c (SEQ ID No: 3)    DTDGFWKTVDCNDNQPGAICYYSGNETEKEVKPVDSVKCPSPVLNTPWIPFQNCCYNFII  1260
OGTA076a (SEQ ID No: 1)    DTDGFWKTVDCNDNQPGAICYYSGNETEKEVKPVDSVKCPSPVLNTPWIPFQNCCYNFII  1260
                           ************************************************************

OGTA076b (SEQ ID No: 2)    TKNRHMATTQDEVHTKCQKLNPKSHILSIRDEKENNFVLEQLLYFNYMASWVMLGITYRN  1320
OGTA076c (SEQ ID No: 3)    TKNRHMATTQDEVHTKCQKLNPKSHILSIRDEKENNFVLEQLLYFNYMASWVMLGITYRN  1320
```

Figure 1 (cont)

```
OGTA076a (SEQ ID No: 1)      TKNRHMATTQDEVHTKCQKLNPKSHILSIRDEKENNFVLEQLLYFNYMASWVMLGITYRN 1320
                             ************************************************************

OGTA076b (SEQ ID No: 2)      NSLMWFDKTPLSYTHWRAGRPTIKNEKFLAGLSTDGFWDIQTFKVIEEAVYFHQHSILAC 1380
OGTA076c (SEQ ID No: 3)      NSLMWFDKTPLSYTHWRAGRPTIKNEKFLAGLSTDGFWDIQTFKVIEEAVYFHQHSILAC 1380
OGTA076a (SEQ ID No: 1)      NSLMWFDKTPLSYTHWRAGRPTIKNEKFLAGLSTDGFWDIQTFKVIEEAVYFHQHSILAC 1380
                             ************************************************************

OGTA076b (SEQ ID No: 2)      KIEMVDYKEEHNTTLPQFMPYEDGIYSVIQKKVTWYEALNMCSQSGGHLASVHNQNGQLF 1440
OGTA076c (SEQ ID No: 3)      KIEMVDYKEEHNTTLPQFMPYEDGIYSVIQKKVTWYEALNMCSQSGGHLASVHNQNGQLF 1440
OGTA076a (SEQ ID No: 1)      KIEMVDYKEEHNTTLPQFMPYEDGIYSVIQKKVTWYEALNMCSQSGGHLASVHNQNGQLF 1440
                             ************************************************************

OGTA076b (SEQ ID No: 2)      LEDIVKRDGFPLWVGLSSHDGSESSFEWSDGSTFDYIPWKGQTSPGNCVLLDPKGTWKHE 1500
OGTA076c (SEQ ID No: 3)      LEDIVKRDGFPLWVGLSSHDGSESSFEWSDGSTFDYIPWKGQTSPGNCVLLDPKGTWKHE 1500
OGTA076a (SEQ ID No: 1)      LEDIVKRDGFPLWVGLSSHDGSESSFEWSDGSTFDYIPWKGQTSPGNCVLLDPKGTWKHE 1500
                             ************************************************************

OGTA076b (SEQ ID No: 2)      KCNSVKDGAICYKPTKSKKLSRLTYSSRCPAAKENGSRWIQYKGHCYKSDQALHSFSEAK 1560
OGTA076c (SEQ ID No: 3)      KCNSVKDGAICYKPTKSKKLSRLTYSSRCPAAKENGSRWIQYKGHCYKSDQALHSFSEAK 1560
OGTA076a (SEQ ID No: 1)      KCNSVKDGAICYKPTKSKKLSRLTYSSRCPAAKENGSRWIQYKGHCYKSDQALHSFSEAK 1560
                             ************************************************************

OGTA076b (SEQ ID No: 2)      KLCSKHDHSATIVSIKDEDENKFVSRLMRENNNITMRVWLGLSQHSVDQSWSWLDGSEVT 1620
OGTA076c (SEQ ID No: 3)      KLCSKHDHSATIVSIKDEDENKFVSRLMRENNNITMRVWLGLSQHSVD------------ 1608
OGTA076a (SEQ ID No: 1)      KLCSKHDHSATIVSIKDEDENKFVSRLMRENNNITMRVWLGLSQHSVDQSWSWLDGSEVT 1608
                             ************************************************************

OGTA076b (SEQ ID No: 2)      FVKWENKSKSGVGRCSMLIASNETWKKVECEHGFGRVVCKVPLDCPSSTWIQFQDSCYIF 1680
OGTA076c (SEQ ID No: 3)      --------------------------------------------CPSSTWIQFQDSCYIF 1624
OGTA076a (SEQ ID No: 1)      FVKWENKSKSGVGRCSMLIASNETWKKVECEHGFGRVVCKVPLGPDYTAIAIIVATLSIL

OGTA076b (SEQ ID No: 2)      LQEAIKVESIEDVRNQCTDHGADMISIHNEEENAFILDTLKKQWKGPDDILLGMFYDTDD 1740
OGTA076c (SEQ ID No: 3)      LQEAIKVESIEDVRNQCTDHGADMISIHNEEENAFILDTLKKQWKGPDDILLGMFYDTDD 1684
OGTA076a (SEQ ID No: 1)      VLMGGLIWFLFQRHRLHLAGFSSVRYAQGVNEDEIMLPSFHC------------------

OGTA076b (SEQ ID No: 2)      ASFKWFDNSMTFDKWTDQDDDEDLVDTCAFLHIKTGEWKKGNCEVSSVEGTLCKTAIPY 1800
OGTA076c (SEQ ID No: 3)      ASFKWFDNSMTFDKWTDQDDDEDLVDTCAFLHIKTGEWKKGNCEVSSVEGTLCKTAIPY 1744
OGTA076a (SEQ ID No: 1)      -----------------------------------------------------------

OGTA076b (SEQ ID No: 2)      KRKYLSDNHILISALVIASTVILTVLGAIIWFLYKKHSDSRFTTVFSTAPQSPYNEDCVL 1860
OGTA076c (SEQ ID No: 3)      KRKYLSDNHILISALVIASTVILTVLGAIIWFLYKKHSDSRFTTVFSTAPQSPYNEDCVL 1804
OGTA076a (SEQ ID No: 1)      -----------------------------------------------------------

OGTA076b (SEQ ID No: 2)      VVGEENEYPVQFD 1873
OGTA076c (SEQ ID No: 3)      VVGEENEYPVQFD 1817
OGTA076a (SEQ ID No: 1)      -------------
```

Mass Match Peptides (bold):
LALK [SEQ ID NO: 35]
YLNNLYK [SEQ ID NO: 66]

Tandem Peptides (underline):
LALK [SEQ ID NO: 35]
YLNNLYK [SEQ ID NO: 66]

Peptide Source: 1D GE Chronic lymphocytic leukaemia

```
OGTA076b (SEQ ID No: 2)      MRTGWATPRRPAGLLMLLFWFFDLAEPSGRAANDPFTIVHGNTGKCIKPVYGWIVADDCD 60
OGTA076c (SEQ ID No: 3)      MRTGWATPRRPAGLLMLLFWFFDLAEPSGRAANDPFTIVHGNTGKCIKPVYGWIVADDCD 60
OGTA076a (SEQ ID No: 1)      MRTGWATPRRPAGLLMLLFWFFDLAEPSGRAANDPFTIVHGNTGKCIKPVYGWIVADDCD 60
                             ************************************************************

OGTA076b (SEQ ID No: 2)      ETEDKLWKWVSQHRLFHLHSQKCLGLDITKSVNELRMFSCDSSAMLWWKCEHHSLYGAAR 120
OGTA076c (SEQ ID No: 3)      ETEDKLWKWVSQHRLFHLHSQKCLGLDITKSVNELRMFSCDSSAMLWWKCEHHSLYGAAR 120
OGTA076a (SEQ ID No: 1)      ETEDKLWKWVSQHRLFHLHSQKCLGLDITKSVNELRMFSCDSSAMLWWKCEHHSLYGAAR 120
                             ************************************************************
```

Figure 1 (cont)

```
OGTA076b (SEQ ID No: 2)    YRLALKDGHGTAISNASDVWKKGGSEESLCDQPYHEIYTRDGNSYGRPCEFPFLIDGTWH 180
OGTA076c (SEQ ID No: 3)    YRLALKDGHGTAISNASDVWKKGGSEESLCDQPYHEIYTRDGNSYGRPCEFPFLIDGTWH 180
OGTA076a (SEQ ID No: 1)    YRLALKDGHGTAISNASDVWKKGGSEESLCDQPYHEIYTRDGNSYGRPCEFPFLIDGTWH 180
                           ************************************************************

OGTA076b (SEQ ID No: 2)    HDCILDEDHSGPWCATTLNYEYDRKWGICLKPENGCEDNWEKNEQFGSCYQFNTQTALSW 240
OGTA076c (SEQ ID No: 3)    HDCILDEDHSGPWCATTLNYEYDRKWGICLKPENGCEDNWEKNEQFGSCYQFNTQTALSW 240
OGTA076a (SEQ ID No: 1)    HDCILDEDHSGPWCATTLNYEYDRKWGICLKPENGCEDNWEKNEQFGSCYQFNTQTALSW 240
                           ************************************************************

OGTA076b (SEQ ID No: 2)    KEAYVSCQNQGADLLSINSAAELTYLKEKEGIAKIFWIGLNQLYSARGWEWSDHKPLNFL 300
OGTA076c (SEQ ID No: 3)    KEAYVSCQNQGADLLSINSAAELTYLKEKEGIAKIFWIGLNQLYSARGWEWSDHKPLNFL 300
OGTA076a (SEQ ID No: 1)    KEAYVSCQNQGADLLSINSAAELTYLKEKEGIAKIFWIGLNQLYSARGWEWSDHKPLNFL 300
                           ************************************************************

OGTA076b (SEQ ID No: 2)    NWDPDRPSAPTIGGSSCARMDAESGLWQSFSCEAQLPYVCRKPLNNTVELTDVWTYSDTR 360
OGTA076c (SEQ ID No: 3)    NWDPDRPSAPTIGGSSCARMDAESGLWQSFSCEAQLPYVCRKPLNNTVELTDVWTYSDTR 360
OGTA076a (SEQ ID No: 1)    NWDPDRPSAPTIGGSSCARMDAESGLWQSFSCEAQLPYVCRKPLNNTVELTDVWTYSDTR 360
                           ************************************************************

OGTA076b (SEQ ID No: 2)    CDAGWLPNNGFCYLLVNESNSWDKAHAKCKAFSSDLISIHSLADVEVVVTKLHNEDIKEE 420
OGTA076c (SEQ ID No: 3)    CDAGWLPNNGFCYLLVNESNSWDKAHAKCKAFSSDLISIHSLADVEVVVTKLHNEDIKEE 420
OGTA076a (SEQ ID No: 1)    CDAGWLPNNGFCYLLVNESNSWDKAHAKCKAFSSDLISIHSLADVEVVVTKLHNEDIKEE 420
                           ************************************************************

OGTA076b (SEQ ID No: 2)    VWIGLKNINIPTLFQWSDGTEVTLTYWDENEPNVPYNKTPNCVSYLGELGQWKVQSCEEK 480
OGTA076c (SEQ ID No: 3)    VWIGLKNINIPTLFQWSDGTEVTLTYWDENEPNVPYNKTPNCVSYLGELGQWKVQSCEEK 480
OGTA076a (SEQ ID No: 1)    VWIGLKNINIPTLFQWSDGTEVTLTYWDENEPNVPYNKTPNCVSYLGELGQWKVQSCEEK 480
                           ************************************************************

OGTA076b (SEQ ID No: 2)    LKYVCKRKGEKLNDASSDKMCPPDEGWKRHGETCYKIYEDEVPFGTNCNLTITSRFEQEY 540
OGTA076c (SEQ ID No: 3)    LKYVCKRKGEKLNDASSDKMCPPDEGWKRHGETCYKIYEDEVPFGTNCNLTITSRFEQEY 540
OGTA076a (SEQ ID No: 1)    LKYVCKRKGEKLNDASSDKMCPPDEGWKRHGETCYKIYEDEVPFGTNCNLTITSRFEQEY 540
                           ************************************************************

OGTA076b (SEQ ID No: 2)    LNDLMKKYDKSLRKYFWTGLRDVDSCGEYNWATVGGRRRAVTFSNWNFLEPASPGGCVAM 600
OGTA076c (SEQ ID No: 3)    LNDLMKKYDKSLRKYFWTGLRDVDSCGEYNWATVGGRRRAVTFSNWNFLEPASPGGCVAM 600
OGTA076a (SEQ ID No: 1)    LNDLMKKYDKSLRKYFWTGLRDVDSCGEYNWATVGGRRRAVTFSNWNFLEPASPGGCVAM 600
                           ************************************************************

OGTA076b (SEQ ID No: 2)    STGKSVGKWEVKDCRSFKALSICKKMSGPLGPEEASPKPDDPCPEGWQSFPASLSCYKVF 660
OGTA076c (SEQ ID No: 3)    STGKSVGKWEVKDCRSFKALSICKKMSGPLGPEEASPKPDDPCPEGWQSFPASLSCYKVF 660
OGTA076a (SEQ ID No: 1)    STGKSVGKWEVKDCRSFKALSICKKMSGPLGPEEASPKPDDPCPEGWQSFPASLSCYKVF 660
                           ************************************************************

OGTA076b (SEQ ID No: 2)    HAERIVRKRNWEEAERFCQALGAHLSSFSHVDEIKEFLHFLTDQFSCQHWLWICLNKRSP 720
OGTA076c (SEQ ID No: 3)    HAERIVRKRNWEEAERFCQALGAHLSSFSHVDEIKEFLHFLTDQFSCQHWLWICLNKRSP 720
OGTA076a (SEQ ID No: 1)    HAERIVRKRNWEEAERFCQALGAHLSSFSHVDEIKEFLHFLTDQFSCQHWLWICLNKRSP 720
                           ************************************************************

OGTA076b (SEQ ID No: 2)    DLQGSWQWSDRTPVSTIIMPNEFQQDYDIRDCAAVKVFHRPWRRGWHFYDDREFIYLRPF 780
OGTA076c (SEQ ID No: 3)    DLQGSWQWSDRTPVSTIIMPNEFQQDYDIRDCAAVKVFHRPWRRGWHFYDDREFIYLRPF 780
OGTA076a (SEQ ID No: 1)    DLQGSWQWSDRTPVSTIIMPNEFQQDYDIRDCAAVKVFHRPWRRGWHFYDDREFIYLRPF 780
                           ************************************************************

OGTA076b (SEQ ID No: 2)    ACDTKLEWVCQIPKGRTPKTPDWYNPDRAGIHGPPLIIEGSEYWFVADLHLNYEEAVLYC 840
OGTA076c (SEQ ID No: 3)    ACDTKLEWVCQIPKGRTPKTPDWYNPDRAGIHGPPLIIEGSEYWFVADLHLNYEEAVLYC 840
OGTA076a (SEQ ID No: 1)    ACDTKLEWVCQIPKGRTPKTPDWYNPDRAGIHGPPLIIEGSEYWFVADLHLNYEEAVLYC 840
                           ************************************************************

OGTA076b (SEQ ID No: 2)    ASNHSFLATITSFVGLKAIKNKIANISGDGQKWWIRISEWPIDDHFTYSRYPWHRFPVTF 900
OGTA076c (SEQ ID No: 3)    ASNHSFLATITSFVGLKAIKNKIANISGDGQKWWIRISEWPIDDHFTYSRYPWHRFPVTF 900
OGTA076a (SEQ ID No: 1)    ASNHSFLATITSFVGLKAIKNKIANISGDGQKWWIRISEWPIDDHFTYSRYPWHRFPVTF 900
                           ************************************************************

OGTA076b (SEQ ID No: 2)    GEECLYMSAKTWLIDLGKPTDCSTKLPFICEKYNVSSLEKYSPDSAAKVQCSEQWIPFQN 960
OGTA076c (SEQ ID No: 3)    GEECLYMSAKTWLIDLGKPTDCSTKLPFICEKYNVSSLEKYSPDSAAKVQCSEQWIPFQN 960
OGTA076a (SEQ ID No: 1)    GEECLYMSAKTWLIDLGKPTDCSTKLPFICEKYNVSSLEKYSPDSAAKVQCSEQWIPFQN 960
                           ************************************************************

OGTA076b (SEQ ID No: 2)    KCFLKIKPVSLTFSQASDTCHSYGGTLPSVLSQIEQDFITSLLPDMEATLWIGLRWTAYE 1020
OGTA076c (SEQ ID No: 3)    KCFLKIKPVSLTFSQASDTCHSYGGTLPSVLSQIEQDFITSLLPDMEATLWIGLRWTAYE 1020
OGTA076a (SEQ ID No: 1)    KCFLKIKPVSLTFSQASDTCHSYGGTLPSVLSQIEQDFITSLLPDMEATLWIGLRWTAYE 1020
                           ************************************************************

OGTA076b (SEQ ID No: 2)    KINKWTDNRELTYSNFHPLLVSGRLRIPENFFEEESRYHCALILNLQKSPFTGTWNFTSC 1080
```

Figure 1 (cont)

```
OGTA076c (SEQ ID No: 3)  KINKWTDNRELTYSNFHPLLVSGRLRIPENFFEEESRYECALILNLQKSPFTGTWNFTSC 1080
OGTA076a (SEQ ID No: 1)  KINKWTDNRELTYSNFHPLLVSGRLRIPENFFEEESRYECALILNLQKSPFTGTWNFTSC 1080
                         ************************************************************

OGTA076b (SEQ ID No: 2)  SERHFVSLCQKYSEVKSRQTLQNASETVKYLNNLYKIIPKTLTWHSAKRECLKSNMQLVS 1140
OGTA076c (SEQ ID No: 3)  SERHFVSLCQKYSEVKSRQTLQNASETVKYLNNLYKIIPKTLTWHSAKRECLKSNMQLVS 1140
OGTA076a (SEQ ID No: 1)  SERHFVSLCQKYSEVKSRQTLQNASETVKYLNNLYKIIPKTLTWHSAKRECLKSNMQLVS 1140
                         ************************************************************

OGTA076b (SEQ ID No: 2)  ITDPYQQAFLSVQALLHNSSLWIGLFSQDDELNFGWSDGKRLHFSRWAETNGQLEDCVVL 1200
OGTA076c (SEQ ID No: 3)  ITDPYQQAFLSVQALLHNSSLWIGLFSQDDELNFGWSDGKRLHFSRWAETNGQLEDCVVL 1200
OGTA076a (SEQ ID No: 1)  ITDPYQQAFLSVQALLHNSSLWIGLFSQDDELNFGWSDGKRLHFSRWAETNGQLEDCVVL 1200
                         ************************************************************

OGTA076b (SEQ ID No: 2)  DTDGFWKTVDCNDNQPGAICYYSGNETEKEVKPVDSVKCPSPVLNTPWIPFQNCCYNFII 1260
OGTA076c (SEQ ID No: 3)  DTDGFWKTVDCNDNQPGAICYYSGNETEKEVKPVDSVKCPSPVLNTPWIPFQNCCYNFII 1260
OGTA076a (SEQ ID No: 1)  DTDGFWKTVDCNDNQPGAICYYSGNETEKEVKPVDSVKCPSPVLNTPWIPFQNCCYNFII 1260
                         ************************************************************

OGTA076b (SEQ ID No: 2)  TKNRHMATTQDEVHTKCQKLNPKSHILSIRDEKENNFVLEQLLYFNYMASWVMLGITYRN 1320
OGTA076c (SEQ ID No: 3)  TKNRHMATTQDEVHTKCQKLNPKSHILSIRDEKENNFVLEQLLYFNYMASWVMLGITYRN 1320
OGTA076a (SEQ ID No: 1)  TKNRHMATTQDEVHTKCQKLNPKSHILSIRDEKENNFVLEQLLYFNYMASWVMLGITYRN 1320
                         ************************************************************

OGTA076b (SEQ ID No: 2)  NSLMWFDKTPLSYTHWRAGRPTIKNEKFLAGLSTDGFWDIQTFKVIEEAVYFHQHSILAC 1380
OGTA076c (SEQ ID No: 3)  NSLMWFDKTPLSYTHWRAGRPTIKNEKFLAGLSTDGFWDIQTFKVIEEAVYFHQHSILAC 1380
OGTA076a (SEQ ID No: 1)  NSLMWFDKTPLSYTHWRAGRPTIKNEKFLAGLSTDGFWDIQTFKVIEEAVYFHQHSILAC 1380
                         ************************************************************

OGTA076b (SEQ ID No: 2)  KIEMVDYKEEIINTTLPQFMPYEDGIYSVIQKKVTWYEALNMCSQSGGHLASVHNQNGQLF 1440
OGTA076c (SEQ ID No: 3)  KIEMVDYKEEIINTTLPQFMPYEDGIYSVIQKKVTWYEALNMCSQSGGHLASVHNQNGQLF 1440
OGTA076a (SEQ ID No: 1)  KIEMVDYKEEIINTTLPQFMPYEDGIYSVIQKKVTWYEALNMCSQSGGHLASVHNQNGQLF 1440
                         ************************************************************

OGTA076b (SEQ ID No: 2)  LEDIVKRDGFPLWVGLSSEDGSESSPEWSDGSTFDYIPWKGQTSPGNCVLLDPKGTWKHE 1500
OGTA076c (SEQ ID No: 3)  LEDIVKRDGFPLWVGLSSEDGSESSPEWSDGSTFDYIPWKGQTSPGNCVLLDPKGTWKHE 1500
OGTA076a (SEQ ID No: 1)  LEDIVKRDGFPLWVGLSSEDGSESSPEWSDGSTFDYIPWKGQTSPGNCVLLDPKGTWKHE 1500
                         ************************************************************

OGTA076b (SEQ ID No: 2)  KCNSVKDGAICYKPTKSKKLSRLTYSSRCPAAKENGSRWIQYKGHCYKSDQALHSFSEAK 1560
OGTA076c (SEQ ID No: 3)  KCNSVKDGAICYKPTKSKKLSRLTYSSRCPAAKENGSRWIQYKGHCYKSDQALHSFSEAK 1560
OGTA076a (SEQ ID No: 1)  KCNSVKDGAICYKPTKSKKLSRLTYSSRCPAAKENGSRWIQYKGHCYKSDQALHSFSEAK 1560
                         ************************************************************

OGTA076b (SEQ ID No: 2)  KLCSKHDHSATIVSIKDEDENKFVSRLMRENNNITMRVWLGLSQHSVDQSWSWLDGSEVT 1620
OGTA076c (SEQ ID No: 3)  KLCSKHDHSATIVSIKDEDENKFVSRLMRENNNITMRVWLGLSQHSVD------------ 1608
OGTA076a (SEQ ID No: 1)  KLCSKHDHSATIVSIKDEDENKFVSRLMRENNNITMRVWLGLSQHSVDQSWSWLDGSEVT 1608
                         ************************************************

OGTA076b (SEQ ID No: 2)  FVKWENKSKSGVGRCSMLIASNETWKKVECEHGFGRVVCKVPLDCPSSTWIQFQDSCYIF 1680
OGTA076c (SEQ ID No: 3)  --------------------------------------------CPSSTWIQFQDSCYIF 1624
OGTA076a (SEQ ID No: 1)  FVKWENKSKSGVGRCSMLIASNETWKKVECEHGFGRVVCKVPLGPDYTAIAIIVATLSIL

OGTA076b (SEQ ID No: 2)  LQEAIKVESIEDVRNQCTDHGADMISIHNEEENAFILDTLKKQWKGPDDILLGMFYDTDD 1740
OGTA076c (SEQ ID No: 3)  LQEAIKVESIEDVRNQCTDHGADMISIHNEEENAFILDTLKKQWKGPDDILLGMFYDTDD 1684
OGTA076a (SEQ ID No: 1)  VIMGGLIWFLFQRERLHLAGFSSVRYAQGVNEDEIMLPSFHD------------------

OGTA076b (SEQ ID No: 2)  ASFKWFDNSNMTFDKWTDQDDDEDLVDTCAFLHIKTGEWKKGNCEVSSVEGTLCKTAIPY 1800
OGTA076c (SEQ ID No: 3)  ASFKWFDNSNMTFDKWTDQDDDEDLVDTCAFLHIKTGEWKKGNCEVSSVEGTLCKTAIPY 1744
OGTA076a (SEQ ID No: 1)  ------------------------------------------------------------

OGTA076b (SEQ ID No: 2)  KRKYLSDNHILISALVIASTVILTVLGAIIWFLYKKHSDSRFTTVFSTAPQSPYNEDCVL 1860
OGTA076c (SEQ ID No: 3)  KRKYLSDNHILISALVIASTVILTVLGAIIWFLYKKHSDSRFTTVFSTAPQSPYNEDCVL 1804
OGTA076a (SEQ ID No: 1)  ------------------------------------------------------------

OGTA076b (SEQ ID No: 2)  VVGEENEYPVQFD 1873
OGTA076c (SEQ ID No: 3)  VVGEENEYPVQFD 1817
OGTA076a (SEQ ID No: 1)  -------------
```

Mass Match Peptides (bold):
AANDPFTIVHGNTGK [SEQ ID NO: 4]

Figure 1 (cont)

```
CEHHSLYGAAR [SEQ ID NO: 6]
CLGLDITK [SEQ ID NO: 7]
CSMLIASNETWKK [SEQ ID NO: 8]
DGAICYKPTK [SEQ ID NO: 9]
ELTYSNFHPLLVSGR [SEQ ID NO: 15]
FEQEYLNDLMK [SEQ ID NO: 18]
GWHFYDDR [SEQ ID NO: 21]
HDHSATIVSIK [SEQ ID NO: 22]
HFVSLCQK [SEQ ID NO: 23]
HMATTQDEVHTK [SEQ ID NO: 25]
IEMVDYK [SEQ ID NO: 27]
IPENFFEEESR [SEQ ID NO: 29]
ISEWPIDDHFTYSR [SEQ ID NO: 30]
KGNCEVSSVEGTLCK [SEQ ID NO: 31]
KVECEHGFGR [SEQ ID NO: 33]
KYFWTGLR [SEQ ID NO: 34]
LFHLHSQK [SEQ ID NO: 36]
LHNEDIK [SEQ ID NO: 38]
NWEEAER [SEQ ID NO: 46]
RGWHFYDDR [SEQ ID NO: 48]
RLHFSR [SEQ ID NO: 50]
RNWEEAER [SEQ ID NO: 51]
SDQALHSFSEAK [SEQ ID NO: 52]
SHILSIR [SEQ ID NO: 53]
SPDLQGSWQWSDR [SEQ ID NO: 55]
TPLSYTHWR [SEQ ID NO: 58]
TPVSTIIMPNEFQQDYDIR [SEQ ID NO: 59]
VECEHGFGR [SEQ ID NO: 60]
VFHRPWR [SEQ ID NO: 61]
VQCSEQWIPFQNK [SEQ ID NO: 63]
WVSQHR [SEQ ID NO: 64]
YFWTGLR [SEQ ID NO: 65]
YLNNLYK [SEQ ID NO: 66]
```

Tandem Peptides (underline):
```
DGAICYKPTK [SEQ ID NO: 9]
IPENFFEEESR [SEQ ID NO: 29]
ISEWPIDDHFTYSR [SEQ ID NO: 30]
SDQALHSFSEAK [SEQ ID NO: 52]
SNFHPLLVSGR [SEQ ID NO: 54]
SPDLQGSWQWSDR [SEQ ID NO: 55]
TPLSYTHWR [SEQ ID NO: 58]
```

Peptide Source: 1D GE Colorectal cancer

```
OGTA076b (SEQ ID No: 2)    MRTGWATPRRPAGLLMLLFWFFDLAEPSGRAANDPFTIVHGNTGKCIKPVYGWIVADDCD 60
OGTA076c (SEQ ID No: 3)    MRTGWATPRRPAGLLMLLFWFFDLAEPSGRAANDPFTIVHGNTGKCIKPVYGWIVADDCD 60
OGTA076a (SEQ ID No: 1)    MRTGWATPRRPAGLLMLLFWFFDLAEPSGRAANDPFTIVHGNTGKCIKPVYGWIVADDCD 60
                           ************************************************************

OGTA076b (SEQ ID No: 2)    ETEDKLWKWVSQHRLFHLHSQKCLGLDITKSVNELRMFSCDSSAMLWWKCEHHSLYGAAR 120
OGTA076c (SEQ ID No: 3)    ETEDKLWKWVSQHRLFHLHSQKCLGLDITKSVNELRMFSCDSSAMLWWKCEHHSLYGAAR 120
OGTA076a (SEQ ID No: 1)    ETEDKLWKWVSQHRLFHLHSQKCLGLDITKSVNELRMFSCDSSAMLWWKCEHHSLYGAAR 120
                           ************************************************************

OGTA076b (SEQ ID No: 2)    YRLALKDGHGTAISNASDVWKKGGSEESLCDQPYHEIYTRDGNSYGRPCEFPFLIDGTWH 180
OGTA076c (SEQ ID No: 3)    YRLALKDGHGTAISNASDVWKKGGSEESLCDQPYHEIYTRDGNSYGRPCEFPFLIDGTWH 180
OGTA076a (SEQ ID No: 1)    YRLALKDGHGTAISNASDVWKKGGSEESLCDQPYHEIYTRDGNSYGRPCEFPFLIDGTWH 180
                           ************************************************************

OGTA076b (SEQ ID No: 2)    HDCILDEDHSGPWCATTLNYEYDRKWGICLKPENGCEDNWEKNEQFGSCYQFNTQTALSW 240
OGTA076c (SEQ ID No: 3)    HDCILDEDHSGPWCATTLNYEYDRKWGICLKPENGCEDNWEKNEQFGSCYQFNTQTALSW 240
OGTA076a (SEQ ID No: 1)    HDCILDEDHSGPWCATTLNYEYDRKWGICLKPENGCEDNWEKNEQFGSCYQFNTQTALSW 240
```

Figure 1 (cont)

```
OGTA076b (SEQ ID No: 2)    KEAYVSCQNQGADLLSINSAAELTYLKEKEGIAKIFWIGLNQLYSARGWEWSDHKPLNFL 300
OGTA076c (SEQ ID No: 3)    KEAYVSCQNQGADLLSINSAAELTYLKEKEGIAKIFWIGLNQLYSARGWEWSDHKPLNFL 300
OGTA076a (SEQ ID No: 1)    KEAYVSCQNQGADLLSINSAAELTYLKEKEGIAKIFWIGLNQLYSARGWEWSDHKPLNFL 300
                           ************************************************************

OGTA076b (SEQ ID No: 2)    NWDPDRPSAPTIGGSSCARMDAESGLWQSFSCEAQLPYVCRKPLNNTVELTDVWTYSDTR 360
OGTA076c (SEQ ID No: 3)    NWDPDRPSAPTIGGSSCARMDAESGLWQSFSCEAQLPYVCRKPLNNTVELTDVWTYSDTR 360
OGTA076a (SEQ ID No: 1)    NWDPDRPSAPTIGGSSCARMDAESGLWQSFSCEAQLPYVCRKPLNNTVELTDVWTYSDTR 360
                           ************************************************************

OGTA076b (SEQ ID No: 2)    CDAGWLPNNGFCYLLVNESNSWDKAHAKCKAFSSDLISIHSLADVEVVVTKLHNEDIKEE 420
OGTA076c (SEQ ID No: 3)    CDAGWLPNNGFCYLLVNESNSWDKAHAKCKAFSSDLISIHSLADVEVVVTKLHNEDIKEE 420
OGTA076a (SEQ ID No: 1)    CDAGWLPNNGFCYLLVNESNSWDKAHAKCKAFSSDLISIHSLADVEVVVTKLHNEDIKEE 420
                           ************************************************************

OGTA076b (SEQ ID No: 2)    VWIGLKNINIPTLFQWSDGTEVTLTYWDENEPNVPYNKTPNCVSYLGELGQWKVQSCEEK 480
OGTA076c (SEQ ID No: 3)    VWIGLKNINIPTLFQWSDGTEVTLTYWDENEPNVPYNKTPNCVSYLGELGQWKVQSCEEK 480
OGTA076a (SEQ ID No: 1)    VWIGLKNINIPTLFQWSDGTEVTLTYWDENEPNVPYNKTPNCVSYLGELGQWKVQSCEEK 480
                           ************************************************************

OGTA076b (SEQ ID No: 2)    LKYVCKRKGEKLNDASSDKMCPPDEGWKRHGETCYKIYEDEVPFGTNCNLTITSRFEQEY 540
OGTA076c (SEQ ID No: 3)    LKYVCKRKGEKLNDASSDKMCPPDEGWKRHGETCYKIYEDEVPFGTNCNLTITSRFEQEY 540
OGTA076a (SEQ ID No: 1)    LKYVCKRKGEKLNDASSDKMCPPDEGWKRHGETCYKIYEDEVPFGTNCNLTITSRFEQEY 540
                           ************************************************************

OGTA076b (SEQ ID No: 2)    LNDLMKKYDKSLRKYFWTGLRDVDSCGEYNWATVGGRRRAVTFSNWNFLEPASPGGCVAM 600
OGTA076c (SEQ ID No: 3)    LNDLMKKYDKSLRKYFWTGLRDVDSCGEYNWATVGGRRRAVTFSNWNFLEPASPGGCVAM 600
OGTA076a (SEQ ID No: 1)    LNDLMKKYDKSLRKYFWTGLRDVDSCGEYNWATVGGRRRAVTFSNWNFLEPASPGGCVAM 600
                           ************************************************************

OGTA076b (SEQ ID No: 2)    STGKSVGKWEVKDCRSFKALSICKKMSGPLGPEEASPKPDDPCPEGWQSFPASLSCYKVF 660
OGTA076c (SEQ ID No: 3)    STGKSVGKWEVKDCRSFKALSICKKMSGPLGPEEASPKPDDPCPEGWQSFPASLSCYKVF 660
OGTA076a (SEQ ID No: 1)    STGKSVGKWEVKDCRSFKALSICKKMSGPLGPEEASPKPDDPCPEGWQSFPASLSCYKVF 660
                           ************************************************************

OGTA076b (SEQ ID No: 2)    HAERIVRKRNWEEAERFCQALGAHLSSFSHVDEIKEFLHFLTDQFSGQEWLWIGLNKRSP 720
OGTA076c (SEQ ID No: 3)    HAERIVRKRNWEEAERFCQALGAHLSSFSHVDEIKEFLHFLTDQFSGQEWLWIGLNKRSP 720
OGTA076a (SEQ ID No: 1)    HAERIVRKRNWEEAERFCQALGAHLSSFSHVDEIKEFLHFLTDQFSGQEWLWIGLNKRSP 720
                           ************************************************************

OGTA076b (SEQ ID No: 2)    DLQGSWQWSDRTPVSTIIMPNEFQQDYDIRDCAAVKVFHRPWRRGWHFYDDREFIYLRPF 780
OGTA076c (SEQ ID No: 3)    DLQGSWQWSDRTPVSTIIMPNEFQQDYDIRDCAAVKVFHRPWRRGWHFYDDREFIYLRPF 780
OGTA076a (SEQ ID No: 1)    DLQGSWQWSDRTPVSTIIMPNEFQQDYDIRDCAAVKVFHRPWRRGWHFYDDREFIYLRPF 780
                           ************************************************************

OGTA076b (SEQ ID No: 2)    ACDTKLEWVCQIPKGRTPKTPDWYNPDRAGIHGPPLIIEGSEYWFVADLHLNYEEAVLYC 840
OGTA076c (SEQ ID No: 3)    ACDTKLEWVCQIPKGRTPKTPDWYNPDRAGIHGPPLIIEGSEYWFVADLHLNYEEAVLYC 840
OGTA076a (SEQ ID No: 1)    ACDTKLEWVCQIPKGRTPKTPDWYNPDRAGIHGPPLIIEGSEYWFVADLHLNYEEAVLYC 840
                           ************************************************************

OGTA076b (SEQ ID No: 2)    ASNHSFLATITSFVGLKAIKNKIANISGDGQKWWIRISEWPIDDHFTYSRYPWHRFPVTF 900
OGTA076c (SEQ ID No: 3)    ASNHSFLATITSFVGLKAIKNKIANISGDGQKWWIRISEWPIDDHFTYSRYPWHRFPVTF 900
OGTA076a (SEQ ID No: 1)    ASNHSFLATITSFVGLKAIKNKIANISGDGQKWWIRISEWPIDDHFTYSRYPWHRFPVTF 900
                           ************************************************************

OGTA076b (SEQ ID No: 2)    CEECLYMSAKTWLIDLGKPTDCSTKLPFICEKYNVSSLEKYSPDSAAKVQCSEQWIPFQN 960
OGTA076c (SEQ ID No: 3)    CEECLYMSAKTWLIDLGKPTDCSTKLPFICEKYNVSSLEKYSPDSAAKVQCSEQWIPFQN 960
OGTA076a (SEQ ID No: 1)    CEECLYMSAKTWLIDLGKPTDCSTKLPFICEKYNVSSLEKYSPDSAAKVQCSEQWIPFQN 960
                           ************************************************************

OGTA076b (SEQ ID No: 2)    KCFLKIKPVSLTFSQASDTCHSYGGTLPSVLSQIEQDFITSLLPDMEATLWIGLRWTAYE 1020
OGTA076c (SEQ ID No: 3)    KCFLKIKPVSLTFSQASDTCHSYGGTLPSVLSQIEQDFITSLLPDMEATLWIGLRWTAYE 1020
OGTA076a (SEQ ID No: 1)    KCFLKIKPVSLTFSQASDTCHSYGGTLPSVLSQIEQDFITSLLPDMEATLWIGLRWTAYE 1020
                           ************************************************************

OGTA076b (SEQ ID No: 2)    KINKWTDNRELTYSNFHPLLVSGRLRIPENFFEEESRYHCALILNLQKSPFTGTWNFTSC 1080
OGTA076c (SEQ ID No: 3)    KINKWTDNRELTYSNFHPLLVSGRLRIPENFFEEESRYHCALILNLQKSPFTGTWNFTSC 1080
OGTA076a (SEQ ID No: 1)    KINKWTDNRELTYSNFHPLLVSGRLRIPENFFEEESRYHCALILNLQKSPFTGTWNFTSC 1080
                           ************************************************************

OGTA076b (SEQ ID No: 2)    SERHFVSLCQKYSEVKSRQTLQNASETVKYLNNLYKIIPKTLTWHSAKRECLKSNMQLVS 1140
OGTA076c (SEQ ID No: 3)    SERHFVSLCQKYSEVKSRQTLQNASETVKYLNNLYKIIPKTLTWHSAKRECLKSNMQLVS 1140
OGTA076a (SEQ ID No: 1)    SERHFVSLCQKYSEVKSRQTLQNASETVKYLNNLYKIIPKTLTWHSAKRECLKSNMQLVS 1140
                           ************************************************************
```

Figure 1 (cont)

```
OGTA076b (SEQ ID No: 2)    ITDPYQQAFLSVQALLHNSSLWICLFSQDDELNFCWSDGKRLHFSRWAETNGQLEDCVVL 1200
OGTA076c (SEQ ID No: 3)    ITDPYQQAFLSVQALLHNSSLWICLFSQDDELNFCWSDGKRLHFSRWAETNGQLEDCVVL 1200
OGTA076a (SEQ ID No: 1)    ITDPYQQAFLSVQALLHNSSLWIGLFSQDDELNFGWSDGKRLHFSRWAETNGQLEDCVVL 1200
                           ************************************************************

OGTA076b (SEQ ID No: 2)    DTDGFWKTVDCNDNQPGAICYYSGNETEKEVKPVDSVKCPSPVLNTPWIPFQNCCYNFII 1260
OGTA076c (SEQ ID No: 3)    DTDGFWKTVDCNDNQPGAICYYSGNETEKEVKPVDSVKCPSPVLNTPWIPFQNCCYNFII 1260
OGTA076a (SEQ ID No: 1)    DTDGFWKTVDCNDNQPGAICYYSGNETEKEVKPVDSVKCPSPVLNTPWIPFQNCCYNFII 1260
                           ************************************************************

OGTA076b (SEQ ID No: 2)    TKNRHMATTQDEVETKCQKLNPKSHILSIRDEKENNFVLEQLLYFNYMASWVMLGITYRN 1320
OGTA076c (SEQ ID No: 3)    TKNRHMATTQDEVETKCQKLNPKSHILSIRDEKENNFVLEQLLYFNYMASWVMLGITYRN 1320
OGTA076a (SEQ ID No: 1)    TKNRHMATTQDEVETKCQKLNPKSHILSIRDEKENNFVLEQLLYFNYMASWVMLGITYRN 1320
                           ************************************************************

OGTA076b (SEQ ID No: 2)    NSLMWFDKTPLSYTHWRAGRPTIKNEKFLAGLSTDGFWDIQTFKVIEEAVYFHQHSILAC 1380
OGTA076c (SEQ ID No: 3)    NSLMWFDKTPLSYTHWRAGRPTIKNEKFLAGLSTDGFWDIQTFKVIEEAVYFHQHSILAC 1380
OGTA076a (SEQ ID No: 1)    NSLMWFDKTPLSYTHWRAGRPTIKNEKFLAGLSTDGFWDIQTFKVIEEAVYFHQHSILAC 1380
                           ************************************************************

OGTA076b (SEQ ID No: 2)    KIEMVDYKEEHNTTLPQFMPYEDGIYSVIQKKVTWYEALNMCSQSGGHLASVHNQNGQLF 1440
OGTA076c (SEQ ID No: 3)    KIEMVDYKEEHNTTLPQFMPYEDGIYSVIQKKVTWYEALNMCSQSGGHLASVHNQNGQLF 1440
OGTA076a (SEQ ID No: 1)    KIEMVDYKEEHNTTLPQFMPYEDGIYSVIQKKVTWYEALNMCSQSGGHLASVHNQNGQLF 1440
                           ************************************************************

OGTA076b (SEQ ID No: 2)    LEDIVKRDGFPLWVGLSSHDGSESSFEWSDGSTFDYIPWKGQTSPGNCVLLDPKGTWKEE 1500
OGTA076c (SEQ ID No: 3)    LEDIVKRDGFPLWVGLSSHDGSESSFEWSDGSTFDYIPWKGQTSPGNCVLLDPKGTWKEE 1500
OGTA076a (SEQ ID No: 1)    LEDIVKRDGFPLWVGLSSHDGSESSFEWSDGSTFDYIPWKGQTSPGNCVLLDPKGTWKEE 1500
                           ************************************************************

OGTA076b (SEQ ID No: 2)    KCNSVKDGAICYKPTKSKKLSRLTYSSRCPAAKENGSRWIQYKGHCYKSDQALHSFSEAK 1560
OGTA076c (SEQ ID No: 3)    KCNSVKDGAICYKPTKSKKLSRLTYSSRCPAAKENGSRWIQYKGHCYKSDQALHSFSEAK 1560
OGTA076a (SEQ ID No: 1)    KCNSVKDGAICYKPTKSKKLSRLTYSSRCPAAKENGSRWIQYKGHCYKSDQALHSFSEAK 1560
                           ************************************************************

OGTA076b (SEQ ID No: 2)    KLCSKHDHSATIVSIKDEDENKFVSRLMRENNNITMRVWLGLSQHSVDQSWSWLDGSEVT 1620
OGTA076c (SEQ ID No: 3)    KLCSKHDHSATIVSIKDEDENKFVSRLMRENNNITMRVWLGLSQHSVD----------- 1608
OGTA076a (SEQ ID No: 1)    KLCSKHDHSATIVSIKDEDENKFVSRLMRENNNITMRVWLGLSQHSVDQSWSWLDGSEVT 1608
                           ************************************************************

OGTA076b (SEQ ID No: 2)    FVKWENKSKSGVGRCSMLIASNETWKKVECEHGFGRVVCKVPLDCPSSTWIQFQDSCYIF 1680
OGTA076c (SEQ ID No: 3)    ----------------------------------------CPSSTWIQFQDSCYIF 1624
OGTA076a (SEQ ID No: 1)    FVKWENKSKSGVGRCSMLIASNETWKKVECEHGFGRVVCKVPLGPDYTAIAIIVATLSIL

OGTA076b (SEQ ID No: 2)    LQEAIKVESIEDVRNQCTDHGADMISIHNEEENAFILDTLKKQWKGPDDILLGMFYDTDD 1740
OGTA076c (SEQ ID No: 3)    LQEAIKVESIEDVRNQCTDHGADMISIHNEEENAFILDTLKKQWKGPDDILLGMFYDTDD 1684
OGTA076a (SEQ ID No: 1)    VLMGGLIWFLFQRERLHLAGFSSVRYAQGVNEDEIMLPSFHD------------------

OGTA076b (SEQ ID No: 2)    ASFKWFDNSNMTFDKWTDQDDDEDLVDTCAFLHIKTGEWKKGNCEVSSVEGTLCKTAIPY 1800
OGTA076c (SEQ ID No: 3)    ASFKWFDNSNMTFDKWTDQDDDEDLVDTCAFLHIKTGEWKKGNCEVSSVEGTLCKTAIPY 1744
OGTA076a (SEQ ID No: 1)    ------------------------------------------------------------

OGTA076b (SEQ ID No: 2)    KRKYLSDNHILISALVIASTVILTVLGAIIWFLYKKHSDSRFTTVFSTAPQSPYNEDCVL 1860
OGTA076c (SEQ ID No: 3)    KRKYLSDNHILISALVIASTVILTVLGAIIWFLYKKHSDSRFTTVFSTAPQSPYNEDCVL 1804
OGTA076a (SEQ ID No: 1)    ------------------------------------------------------------

OGTA076b (SEQ ID No: 2)    VVGEENEYPVQFD 1873
OGTA076c (SEQ ID No: 3)    VVGEENEYPVQFD 1817
OGTA076a (SEQ ID No: 1)    -------------
```

Mass Match Peptides (bold):
CLGLDITK [SEQ ID NO: 7]
DGAICYKPTK [SEQ ID NO: 9]
DVDSCGEYNWATVGGRRR [SEQ ID NO: 11]
EEVWIGLK [SEQ ID NO: 12]
ENNNITMR [SEQ ID NO: 16]
EVKPVDSVK [SEQ ID NO: 17]
GWHFYDDR [SEQ ID NO: 21]
HDHSATIVSIK [SEQ ID NO: 22]

Figure 1 (cont)

HFVSLCQK [SEQ ID NO: 23]
HGETCYK [SEQ ID NO: 24]
IPENFFEEESR [SEQ ID NO: 29]
KYFWTGLR [SEQ ID NO: 34]
LNDASSDK [SEQ ID NO: 39]
LPFICEK [SEQ ID NO: 41]
MCPPDEGWKR [SEQ ID NO: 42]
MFSCDSSAMLWWK [SEQ ID NO: 43]
NNSLMWFDK [SEQ ID NO: 45]
QTLQNASETVK [SEQ ID NO: 47]
RHGETCYK [SEQ ID NO: 49]
TLTWHSAK [SEQ ID NO: 56]
TPDWYNPDR [SEQ ID NO: 57]

Tandem Peptides (underline):
IPENFFEEESR [SEQ ID NO: 29]

Peptide Source: 1D GE Pancreatic cancer

```
OGTA076b (SEQ ID No: 2)    MRTGWATPRRPAGLLMLLFWFFDLAEPSGRAANDPFTIVHGNTGKCIKPVYGWIVADDCD  60
OGTA076c (SEQ ID No: 3)    MRTGWATPRRPAGLLMLLFWFFDLAEPSGRAANDPFTIVHGNTGKCIKPVYGWIVADDCD  60
OGTA076a (SEQ ID No: 1)    MRTGWATPRRPAGLLMLLFWFFDLAEPSGRAANDPFTIVHGNTGKCIKPVYGWIVADDCD  60
                           ************************************************************

OGTA076b (SEQ ID No: 2)    ETEDKLWKWVSQHRLFHLHSQKCLGLDITKSVNELRMFSCDSSAMLWWKCEHHSLYGAAR  120
OGTA076c (SEQ ID No: 3)    ETEDKLWKWVSQHRLFHLHSQKCLGLDITKSVNELRMFSCDSSAMLWWKCEHHSLYGAAR  120
OGTA076a (SEQ ID No: 1)    ETEDKLWKWVSQHRLFHLHSQKCLGLDITKSVNELRMFSCDSSAMLWWKCEHHSLYGAAR  120
                           ************************************************************

OGTA076b (SEQ ID No: 2)    YRLALKDGHGTAISNASDVWKKGGSEESLCDQPYEEIYTRDGNSYGRPCEFPFLIDGTWH  180
OGTA076c (SEQ ID No: 3)    YRLALKDGHGTAISNASDVWKKGGSEESLCDQPYEEIYTRDGNSYGRPCEFPFLIDGTWH  180
OGTA076a (SEQ ID No: 1)    YRLALKDGHGTAISNASDVWKKGGSEESLCDQPYEEIYTRDGNSYGRPCEFPFLIDGTWH  180
                           ************************************************************

OGTA076b (SEQ ID No: 2)    EDCILDEDESGPWCATTLNYEYDRKWGICLKPENGCEDNWEKNEQFGSCYQFNTQTALSW  240
OGTA076c (SEQ ID No: 3)    EDCILDEDESGPWCATTLNYEYDRKWGICLKPENGCEDNWEKNEQFGSCYQFNTQTALSW  240
OGTA076a (SEQ ID No: 1)    EDCILDEDESGPWCATTLNYEYDRKWGICLKPENGCEDNWEKNEQFGSCYQFNTQTALSW  240
                           ************************************************************

OGTA076b (SEQ ID No: 2)    KEAYVSCQNQGADLLSINSAAELTYLKEKEGIAKIFWIGLNQLYSARGWEWSDHKPLNFL  300
OGTA076c (SEQ ID No: 3)    KEAYVSCQNQGADLLSINSAAELTYLKEKEGIAKIFWIGLNQLYSARGWEWSDHKPLNFL  300
OGTA076a (SEQ ID No: 1)    KEAYVSCQNQGADLLSINSAAELTYLKEKEGIAKIFWIGLNQLYSARGWEWSDHKPLNFL  300
                           ************************************************************

OGTA076b (SEQ ID No: 2)    NWDPDRPSAPTIGGSSCARMDAESGLWQSFSCEAQLPYVCRKFLNNTVELTDVWTYSDTR  360
OGTA076c (SEQ ID No: 3)    NWDPDRPSAPTIGGSSCARMDAESGLWQSFSCEAQLPYVCRKFLNNTVELTDVWTYSDTR  360
OGTA076a (SEQ ID No: 1)    NWDPDRPSAPTIGGSSCARMDAESGLWQSFSCEAQLPYVCRKFLNNTVELTDVWTYSDTR  360
                           ************************************************************

OGTA076b (SEQ ID No: 2)    CDAGWLPNNGFCYLLVNESNSWDKAHAKCKAFSSDLISIHSLADVEVVVTKLHNEDIKEE  420
OGTA076c (SEQ ID No: 3)    CDAGWLPNNGFCYLLVNESNSWDKAHAKCKAFSSDLISIHSLADVEVVVTKLHNEDIKEE  420
OGTA076a (SEQ ID No: 1)    CDAGWLPNNGFCYLLVNESNSWDKAHAKCKAFSSDLISIHSLADVEVVVTKLHNEDIKEE  420
                           ************************************************************

OGTA076b (SEQ ID No: 2)    VWIGLKNINIPTLFQWSDCTEVTLTYWDENEPNVPYNKTPNCVSYLGELGQWKVQSCEEK  480
OGTA076c (SEQ ID No: 3)    VWIGLKNINIPTLFQWSDCTEVTLTYWDENEPNVPYNKTPNCVSYLGELGQWKVQSCEEK  480
OGTA076a (SEQ ID No: 1)    VWIGLKNINIPTLFQWSDCTEVTLTYWDENEPNVPYNKTPNCVSYLGELGQWKVQSCEEK  480
                           ************************************************************

OGTA076b (SEQ ID No: 2)    LKYVCKRKGEKLNDASSDKMCPPDEGWKRHGETCYKIYEDEVPFGTNCNLTITSRFEQEY  540
OGTA076c (SEQ ID No: 3)    LKYVCKRKGEKLNDASSDKMCPPDEGWKRHGETCYKIYEDEVPFGTNCNLTITSRFEQEY  540
OGTA076a (SEQ ID No: 1)    LKYVCKRKGEKLNDASSDKMCPPDEGWKRHGETCYKIYEDEVPFGTNCNLTITSRFEQEY  540
                           ************************************************************

OGTA076b (SEQ ID No: 2)    LNDLMKKYDKSLRKYFWTGLRDVDSCGEYNWATVGGRRRAVTFSNWNFLEPASPGGCVAM  600
OGTA076c (SEQ ID No: 3)    LNDLMKKYDKSLRKYFWTGLRDVDSCGEYNWATVGGRRRAVTFSNWNFLEPASPGGCVAM  600
OGTA076a (SEQ ID No: 1)    LNDLMKKYDKSLRKYFWTGLRDVDSCGEYNWATVGGRRRAVTFSNWNFLEPASPGGCVAM  600
                           ************************************************************

OGTA076b (SEQ ID No: 2)    STGKSVGKWEVKDCRSFKALSICKKMSGPLGPEEASPKPDDPCPEGWQSFPASLSCYKVF  660
```

Figure 1 (cont)

```
OGTA076c (SEQ ID No: 3)   STGKSVGKWEVKDCRSFKALSICKKMSGPLGPEEASPKPDDPCPEGWQSFPASLSCYKVF 660
OGTA076a (SEQ ID No: 1)   STGKSVGKWEVKDCRSFKALSICKKMSGPLGPEEASPKPDDPCPEGWQSFPASLSCYKVF 660
                          ************************************************************

OGTA076b (SEQ ID No: 2)   HAERIVRKRNWEEAERFCQALGAHLSSFSHVDEIKEFLHFLTDQFSGQHWLWIGLNKRSP 720
OGTA076c (SEQ ID No: 3)   HAERIVRKRNWEEAERFCQALGAHLSSFSHVDEIKEFLHFLTDQFSGQHWLWIGLNKRSP 720
OGTA076a (SEQ ID No: 1)   HAERIVRKRNWEEAERFCQALGAHLSSFSHVDEIKEFLHFLTDQFSGQHWLWIGLNKRSP 720
                          ************************************************************

OGTA076b (SEQ ID No: 2)   DLQGSWQWSDRTPVSTIIMPNEFQQDYDIRDCAAVKVFHRPWRRGWHFYDDREFIYLRPF 780
OGTA076c (SEQ ID No: 3)   DLQGSWQWSDRTPVSTIIMPNEFQQDYDIRDCAAVKVFHRPWRRGWHFYDDREFIYLRPF 780
OGTA076a (SEQ ID No: 1)   DLQGSWQWSDRTPVSTIIMPNEFQQDYDIRDCAAVKVFHRPWRRGWHFYDDREFIYLRPF 780
                          ************************************************************

OGTA076b (SEQ ID No: 2)   ACDTKLEWVCQIPKGRTPKTPDWYNPDRAGIHGPPLIIEGSEYWFVADLHLNYEEAVLYC 840
OGTA076c (SEQ ID No: 3)   ACDTKLEWVCQIPKGRTPKTPDWYNPDRAGIHGPPLIIEGSEYWFVADLHLNYEEAVLYC 840
OGTA076a (SEQ ID No: 1)   ACDTKLEWVCQIPKGRTPKTPDWYNPDRAGIHGPPLIIEGSEYWFVADLHLNYEEAVLYC 840
                          ************************************************************

OGTA076b (SEQ ID No: 2)   ASNHSFLATITSFVGLKAIKNKIANISGDGQKWWIRISEWPIDDHFTYSRYPWHRFPVTF 900
OGTA076c (SEQ ID No: 3)   ASNHSFLATITSFVGLKAIKNKIANISGDGQKWWIRISEWPIDDHFTYSRYPWHRFPVTF 900
OGTA076a (SEQ ID No: 1)   ASNHSFLATITSFVGLKAIKNKIANISGDGQKWWIRISEWPIDDHFTYSRYPWHRFPVTF 900
                          ************************************************************

OGTA076b (SEQ ID No: 2)   GEECLYMSAKTWLIDLGKPTDCSTKLPFICEKYNVSSLEKYSPDSAAKVQCSEQWIPFQN 960
OGTA076c (SEQ ID No: 3)   GEECLYMSAKTWLIDLGKPTDCSTKLPFICEKYNVSSLEKYSPDSAAKVQCSEQWIPFQN 960
OGTA076a (SEQ ID No: 1)   GEECLYMSAKTWLIDLGKPTDCSTKLPFICEKYNVSSLEKYSPDSAAKVQCSEQWIPFQN 960
                          ************************************************************

OGTA076b (SEQ ID No: 2)   KCFLKIKPVSLTFSQASDTCHSYGGTLPSVLSQIEQDFITSLLPDMEATLWIGLRWTAYE 1020
OGTA076c (SEQ ID No: 3)   KCFLKIKPVSLTFSQASDTCHSYGGTLPSVLSQIEQDFITSLLPDMEATLWIGLRWTAYE 1020
OGTA076a (SEQ ID No: 1)   KCFLKIKPVSLTFSQASDTCHSYGGTLPSVLSQIEQDFITSLLPDMEATLWIGLRWTAYE 1020
                          ************************************************************

OGTA076b (SEQ ID No: 2)   KINKWTDNRELTYSNFHPLLVSGRLRIPENFFEEESRYHCALILNLQKSPFTGTWNFTSC 1080
OGTA076c (SEQ ID No: 3)   KINKWTDNRELTYSNFHPLLVSGRLRIPENFFEEESRYHCALILNLQKSPFTGTWNFTSC 1080
OGTA076a (SEQ ID No: 1)   KINKWTDNRELTYSNFHPLLVSGRLRIPENFFEEESRYHCALILNLQKSPFTGTWNFTSC 1080
                          ************************************************************

OGTA076b (SEQ ID No: 2)   SERHFVSLCQKYSEVKSRQTLQNASETVKYLNNLYKIIPKTLTWHSAKRECLKSNMQLVS 1140
OGTA076c (SEQ ID No: 3)   SERHFVSLCQKYSEVKSRQTLQNASETVKYLNNLYKIIPKTLTWHSAKRECLKSNMQLVS 1140
OGTA076a (SEQ ID No: 1)   SERHFVSLCQKYSEVKSRQTLQNASETVKYLNNLYKIIPKTLTWHSAKRECLKSNMQLVS 1140
                          ************************************************************

OGTA076b (SEQ ID No: 2)   ITDPYQQAFLSVQALLHNSSLWIGLFSQDDELNFGWSDGKRLHFSRWAETNGQLEDCVVL 1200
OGTA076c (SEQ ID No: 3)   ITDPYQQAFLSVQALLHNSSLWIGLFSQDDELNFGWSDGKRLHFSRWAETNGQLEDCVVL 1200
OGTA076a (SEQ ID No: 1)   ITDPYQQAFLSVQALLHNSSLWIGLFSQDDELNFGWSDGKRLHFSRWAETNGQLEDCVVL 1200
                          ************************************************************

OGTA076b (SEQ ID No: 2)   DTDGFWKTVDCNDNQPGAICYYSGNETEKEVKPVDSVKCPSPVLNTPWIPFQNCCYNFII 1260
OGTA076c (SEQ ID No: 3)   DTDGFWKTVDCNDNQPGAICYYSGNETEKEVKPVDSVKCPSPVLNTPWIPFQNCCYNFII 1260
OGTA076a (SEQ ID No: 1)   DTDGFWKTVDCNDNQPGAICYYSGNETEKEVKPVDSVKCPSPVLNTPWIPFQNCCYNFII 1260
                          ************************************************************

OGTA076b (SEQ ID No: 2)   TKNRHMATTQDEVHTKCQKLNPKSHILSIRDEKENNFVLEQLLYFNYMASWVMLGITYRN 1320
OGTA076c (SEQ ID No: 3)   TKNRHMATTQDEVHTKCQKLNPKSHILSIRDEKENNFVLEQLLYFNYMASWVMLGITYRN 1320
OGTA076a (SEQ ID No: 1)   TKNRHMATTQDEVHTKCQKLNPKSHILSIRDEKENNFVLEQLLYFNYMASWVMLGITYRN 1320
                          ************************************************************

OGTA076b (SEQ ID No: 2)   NSLMWFDKTPLSYTHWRAGRPTIKNEKFLAGLSTDGFWDIQTFKVIEEAVYFHQESILAC 1380
OGTA076c (SEQ ID No: 3)   NSLMWFDKTPLSYTHWRAGRPTIKNEKFLAGLSTDGFWDIQTFKVIEEAVYFHQESILAC 1380
OGTA076a (SEQ ID No: 1)   NSLMWFDKTPLSYTHWRAGRPTIKNEKFLAGLSTDGFWDIQTFKVIEEAVYFHQESILAC 1380
                          ************************************************************

OGTA076b (SEQ ID No: 2)   KIEMVDYKEEHNTTLPQFMPYEDGIYSVIQKKVTWYEALNMCSQSGGHLASVHNQNGQLF 1440
OGTA076c (SEQ ID No: 3)   KIEMVDYKEEHNTTLPQFMPYEDGIYSVIQKKVTWYEALNMCSQSGGHLASVHNQNGQLF 1440
OGTA076a (SEQ ID No: 1)   KIEMVDYKEEHNTTLPQFMPYEDGIYSVIQKKVTWYEALNMCSQSGGHLASVHNQNGQLF 1440
                          ************************************************************

OGTA076b (SEQ ID No: 2)   LEDIVKRDGFPLWVGLSSHDGSESSFEWSDGSTFDYIPWKGQTSPGNCVLLDPKGTWKHE 1500
OGTA076c (SEQ ID No: 3)   LEDIVKRDGFPLWVGLSSHDGSESSFEWSDGSTFDYIPWKGQTSPGNCVLLDPKGTWKHE 1500
OGTA076a (SEQ ID No: 1)   LEDIVKRDGFPLWVGLSSHDGSESSFEWSDGSTFDYIPWKGQTSPGNCVLLDPKGTWKHE 1500
                          ************************************************************

OGTA076b (SEQ ID No: 2)   KCNSVKDGAICYKPTKSKKLSRLTYSSRCPAAKENCSRWIQYKGHCYKSDQALHSFSEAK 1560
OGTA076c (SEQ ID No: 3)   KCNSVKDGAICYKPTKSKKLSRLTYSSRCPAAKENGSRWIQYKGHCYKSDQALHSFSEAK 1560
OGTA076a (SEQ ID No: 1)   KCNSVKDGAICYKPTKSKKLSRLTYSSRCPAAKENGSRWIQYKGHCYKSDQALHSFSEAK 1560
```

Figure 1 (cont)

```
****************************************************************
OGTA076b (SEQ ID No: 2)    KLCSKHDHSATIVSIKDEDENKFVSRLMRENNNITMRVWLGLSQHSVDQSWSWLDGSEVT 1620
OGTA076c (SEQ ID No: 3)    KLCSKHDHSATIVSIKDEDENKFVSRLMRENNNITMRVWLGLSQHSVD----------- 1608
OGTA076a (SEQ ID No: 1)    KLCSKHDHSATIVSIKDEDENKFVSRLMRENNNITMRVWLGLSQHSVDQSWSWLDGSEVT 1608
                           *******************************************

OGTA076b (SEQ ID No: 2)    FVKWENKSKSGVGRCSMLIASNETWKKVECEHGFGRVVCKVPLDCPSSTWIQFQDSCYIF 1680
OGTA076c (SEQ ID No: 3)    -------------------------------------------CPSSTWIQFQDSCYIF 1624
OGTA076a (SEQ ID No: 1)    FVKWENKSKSGVGRCSMLIASNETWKKVECEHGFGRVVCKVPLGPDYTAIAIIVATLSIL

OGTA076b (SEQ ID No: 2)    LQEAIKVESIEDVRNQCTDHGADMISIHNEEENAFILDTLKKQWKGPDDILLGMFYDTDD 1740
OGTA076c (SEQ ID No: 3)    LQEAIKVESIEDVRNQCTDHGADMISIHNEEENAFILDTLKKQWKGPDDILLGMFYDTDD 1684
OGTA076a (SEQ ID No: 1)    VLMCGLIWFLFQRHRLHLAGFSSVRYAQCVNEDEIMLPSFHD-----------------

OGTA076b (SEQ ID No: 2)    ASFKWFDNSNMTFDKWTDQDDDEDLVDTCAFLHIKTGEWKKGNCEVSSVEGTLCKTAIPY 1800
OGTA076c (SEQ ID No: 3)    ASFKWFDNSNMTFDKWTDQDDDEDLVDTCAFLHIKTGEWKKGNCEVSSVEGTLCKTAIPY 1744
OGTA076a (SEQ ID No: 1)    ------------------------------------------------------------

OGTA076b (SEQ ID No: 2)    KRKYLSDNHILISALVIASTVILTVLCAIIWFLYKKHSDSRFTTVFSTAPQSPYNEDCVL 1860
OGTA076c (SEQ ID No: 3)    KRKYLSDNHILISALVIASTVILTVLCAIIWFLYKKHSDSRFTTVFSTAPQSPYNEDCVL 1804
OGTA076a (SEQ ID No: 1)    ------------------------------------------------------------

OGTA076b (SEQ ID No: 2)    VVGEENEYPVQFD 1873
OGTA076c (SEQ ID No: 3)    VVGEENEYPVQFD 1817
OGTA076a (SEQ ID No: 1)    -------------
```

Mass Match Peptides (bold):
AFSSDLISIHSLADVEVVVTK [SEQ ID NO: 5]
CLGLDITK [SEQ ID NO: 7]
DGAICYKPTK [SEQ ID NO: 9]
DGHGTAISNASDVWKK [SEQ ID NO: 10]
DVDSCGEYNWATVGGRRR [SEQ ID NO: 11]
EEVWIGLK [SEQ ID NO: 12]
EFIYLRPFACDTK [SEQ ID NO: 13]
FEQEYLNDLMK [SEQ ID NO: 18]
FPVTFGEECLYMSAK [SEQ ID NO: 19]
GNCEVSSVEGTLCK [SEQ ID NO: 20]
GWHFYDDR [SEQ ID NO: 21]
HFVSLCQK [SEQ ID NO: 23]
HMATTQDEVHTK [SEQ ID NO: 25]
IANISGDGQK [SEQ ID NO: 26]
IPENFFEEESR [SEQ ID NO: 29]
ISEWPIDDHFTYSR [SEQ ID NO: 30]
KRNWEEAER [SEQ ID NO: 32]
KYFWTGLR [SEQ ID NO: 34]
LHLAGFSSVR [SEQ ID NO: 37]
NNSLMWFDK [SEQ ID NO: 45]
RGWHFYDDR [SEQ ID NO: 48]
RHGETCYK [SEQ ID NO: 49]
RNWEEAER [SEQ ID NO: 51]
SDQALHSFSEAK [SEQ ID NO: 52]
SHILSIR [SEQ ID NO: 53]
SPDLQGSWQWSDR [SEQ ID NO: 55]
TLTWHSAK [SEQ ID NO: 56]
TPDWYNPDR [SEQ ID NO: 57]
TPLSYTHWR [SEQ ID NO: 58]
TPVSTIIMPNEFQQDYDIR [SEQ ID NO: 59]
VECEHGFGR [SEQ ID NO: 60]
VFHRPWR [SEQ ID NO: 61]
VQCSEQWIPFQNK [SEQ ID NO: 63]
WVSQHR [SEQ ID NO: 64]

Figure 1 (cont)

```
YFWTGLR [SEQ ID NO: 65]
```
Tandem Peptides (underline):
```
FEQEYLNDLMK [SEQ ID NO: 18]
IPENFFEEESR [SEQ ID NO: 29]
MSGPLGPEEASPK [SEQ ID NO: 44]
SNFHPLLVSGR [SEQ ID NO: 54]
SPDLQGSWQWSDR [SEQ ID NO: 55]
VIEEAVYFHQH [SEQ ID NO: 62]
```

Whole Cell

PROTEIN

RELATED APPLICATIONS

The present application is a Continuation of PCT Application No. PCT/GB2008/050127 filed Feb. 26, 2008, which in turn, claims priority from PCT Application No. PCT/GB2008/050124 filed Feb. 25, 2008 and U.S. Provisional Application Ser. Nos. 60/903,509 and 60/903,510, both filed Feb. 26, 2007. Applicants claim the benefits of 35 U.S.C. §120 as to the first-referenced PCT application and priority under 35 U.S.C. §119 as to the second-referenced PCT application, and the said U.S. Provisional applications, and the entire disclosures of all applications are incorporated herein by reference in their entireties.

INTRODUCTION

The present invention relates to the identification of membrane protein associated with colorectal cancer, kidney cancer, liver cancer, lung cancer, lymphoid leukaemia (particularly chronic lymphocytic leukaemia), ovarian cancer and pancreatic cancer which has utility as a marker for colorectal cancer, kidney cancer, liver cancer, lung cancer, ovarian cancer and pancreatic cancer metastases and which also forms a biological target against which therapeutic antibodies (or other affinity reagents) or other pharmaceutical agents can be made.

BACKGROUND OF THE INVENTION

Chronic Lymphocytic Leukaemia

Chronic lymphocytic leukaemia (CLL) is the most common adult leukaemia in the Western Hemisphere, and is generally fatal once the disease progresses. There are probably two different kinds of CLL. One is very slow growing and rarely needs to be treated. People with this kind of CLL survive on average 13 to 15 years. The other kind of CLL is faster growing and is a more serious disease. People with this form of CLL survive only about 6 to 8 years. About 9,800 new cases of CLL are diagnosed each year in the USA, with about 4,600 deaths. CLL affects only adults. The average age of patients is about 70 and it is rarely seen in people under the age of 40.

Chronic Lymphocytic Leukaemia Diagnosis

Diagnostic tests for chronic lymphocytic leukaemia carried out include blood cell count, bone marrow aspiration, bone marrow biopsy, excisional lymph node biopsy, blood chemistry tests and lumbar puncture. Other lab tests include routine microscopic exam, cytochemistry, flow cytometry, immunocytochemistry, cytogenetics, molecular genetic studies, and fluorescent in situ hybridization (FISH). Imaging tests may also be carried out including chest x-rays, computed tomography (CT) scans, magnetic resonance imaging (MRI) and ultrasound.

Chronic Lymphocytic Leukaemia Staging

The prognosis of a patient with leukaemia depends on the leukaemia's type or subtype, cellular features determined by lab tests, and results of imaging studies.

There are 2 different systems for staging CLL. The Rai classification is used more often in the USA, whereas the Binet system is used more widely in Europe.

The 5 Rai system stages can be separated into low-, intermediate-, and high-risk categories. Stage 0 is considered low risk, stages I and II are considered intermediate risk, and stages III and IV are considered high risk.

The Binet staging system uses the letters A (least severe), B, and C (most severe) to define the stages. CLL is classified according to the number of affected lymphoid tissue groups and the presence of anemia or thrombocytopenia.

Other markers such as chromosome changes, mutational status, ZAP-70 and CD38 status are also used to distinguish between the two different types of CLL.

Chronic Lymphocytic Leukaemia Treatment

The prognosis for patients with low-risk CLL is very good. Treatment is only considered if there are signs that the leukaemia is progressing. When indicated, initial treatment is usually chemotherapy. Chlorambucil (Leukeran) and fludarabine (Fludara) are the chemotherapy drugs most commonly used to treat CLL.

Patients with intermediate- and high-risk CLL who do not have any symptoms may not need treatment right away. Some with very high-risk disease may best be treated with early stem cell transplantation. No specific treatment has been shown to improve survival. In general, chemotherapy is used as treatment. Monoclonal antibodies such as rituximab can be used alongside chemotherapy. Alemtuzumab (Campath) is used in patients with CLL who are no longer responding to standard chemotherapy treatments.

Colorectal Cancer

Colorectal cancer (CRC) is one of the leading causes of cancer-related morbidity and mortality, responsible for an estimated half a million deaths per year, mostly in Western, well developed countries. In these territories, CRC is the third most common malignancy (estimated number of new cases per annum in USA and EU is approximately 350,000 per year). Estimated healthcare costs related to treatment for colorectal cancer in the United States are more than $8 billion.

Colorectal Cancer Diagnosis

Today, the fecal occult blood test and colonoscopy, a highly invasive procedure, are the most frequently used screening and diagnostic methods for colorectal cancer. Other diagnostic tools include Flexible Sigmoidoscopy (allowing the observation of only about half of the colon) and Double Contrast Barium Enema (DCBE, to obtain X-ray images).

Colorectal Cancer Staging

CRC has four distinct stages: patients with stage I disease have a five-year survival rate of >90%, while those with metastatic stage IV disease have a <5% survival rate according to the US National Institutes of Health (NIH).

Colorectal Cancer Treatment

Once CRC has been diagnosed, the correct treatment needs to be selected. Surgery is usually the main treatment for rectal cancer, although radiation and chemotherapy will often be given before surgery. Possible side effects of surgery include bleeding from the surgery, deep vein thrombosis and damage to nearby organs during the operation.

Currently, 60 percent of colorectal cancer patients receive chemotherapy to treat their disease; however, this form of treatment only benefits a few percent of the population, while carrying with it high risks of toxicity, thus demonstrating a need to better define the patient selection criteria.

Colorectal cancer has a 30 to 40 percent recurrence rate within an average of 18 months after primary diagnosis. As with all cancers, the earlier it is detected the more likely it can be cured, especially as pathologists have recognised that the majority of CRC tumours develop in a series of well-defined stages from benign adenomas.

Colon Cancer Survival by Stage

| Stage | Survival Rate |
|---|---|
| I | 93% |
| IIA | 85% |
| IIB | 72% |
| IIIA | 83% |
| IIIB | 64% |
| IIIC | 44% |
| IV | 8% |

Kidney Cancer

Kidney cancer accounts for about 1.9% of cancer cases globally and 1.5% of deaths. Global incidence of kidney cancer is around 208,000 cases, with over 100,000 deaths. The incidence of kidney cancer is much higher in developed countries, being the sixth most common form of cancer in Western Europe. Around 38,900 new cases of kidney cancer are diagnosed in the USA each year, with around 12,800 deaths. It is very uncommon under age 45, and its incidence is highest between the ages of 55 and 84. The rate of people developing kidney cancer has been increasing at about 1.5% per year but the death rate has not been increasing. Renal cell carcinoma accounts for more than 90% of malignant kidney tumours. It has been estimated that approximately US $1.9 billion is spent in the USA each year on treating kidney cancer.

Kidney Cancer Diagnosis

Many renal cell cancers are found at a late stage; they can become quite large without causing any pain or discomfort and there are no simple tests that can detect renal cell cancer early. About 25% of patients with renal cell carcinoma will already have metastatic spread of their cancer when they are diagnosed.

Renal cell cancer can often be diagnosed without the need for a biopsy using a CT scan, MRI, ultrasound, positron emission tomography (PET) scan, intravenous pyelogram (IVP) and/or angiography. Fine needle aspiration biopsy may however be valuable when imaging results are not conclusive enough to warrant removing a kidney.

Kidney Cancer Staging

Renal cell cancers are usually graded on a scale of 1-4. Renal cell cancer is also staged using the American Joint Committee on Cancer (AJCC) TNM system—stage I-IV. The University of California Los Angeles Integrated Staging System can also be used, which divides patients without any tumour spread into three groups—low risk, intermediate risk and high risk. The 5-year cancer-specific survival for the low-risk group is 91%, for the intermediate-risk group is 80%, and for the high-risk group is 55%. Patients with tumour spread are also divided into three groups—low, intermediate and high risk. The 5-year cancer-specific survival for the low-risk group is 32%, for the intermediate-risk group 20% and for the high-risk group 0%.

Kidney Cancer Treatment

Surgery by radical nephrectomy (and sometimes regional lymphadenectomy), partial nephrectomy or laparoscopic nephrectomy is the main treatment for renal cell carcinoma. Renal cell carcinomas are not very sensitive to radiation so using radiation therapy before or after removing the cancer is not routinely recommended because studies have shown no improvement in survival rates.

Renal cell cancers are very resistant to present forms of chemotherapy. Some drugs, such as vinblastine, floxuridine, and 5-fluorouracil (5-FU) are mildly effective. A combination of 5-FU and gemcitabine has benefited some patients. A 5-FU-like drug, capecitabine, may also have some benefit.

Cytokines (interleukin-2 (IL-2) and interferon-alpha) have become one of the standard treatments for metastatic renal cell carcinoma. These cause the cancers to shrink to less than half their original size in about 10% to 20% of patients. Patients who respond to IL-2 tend to have lasting responses. Recent research with a combination of IL-2, interferon, and chemotherapy (using 5-fluorouracil) is also promising and may offer a better chance of partial or complete remission. Cytokine therapy does have severe side affects however.

Sorafenib (Nexavar), Sunitinib (Sutent) and Bevacizumab (Avastin) are other drugs which may also be effective against renal cell cancer.

Kidney Cancer Survival by Stage

| T stage cancer | 5/10-year cancer-specific survival |
|---|---|
| T1 | 95%/91% |
| T2 | 80%/70% |
| T3a | 66%/53% |
| T3b | 52%/43% |
| T3c | 43%/42% |

Liver Cancer

Around 80% of all cases of liver cancer are hepatocellular carcinoma, which arises from the main cells of the liver (the hepatocytes). Hepatocellular carcinoma is usually confined to the liver and is associated with cirrhosis in 50% to 80% of patients. Hepatocellular carcinoma is about 3 times more common in males than in females. Chronic infection with hepatitis B virus (HBV) or hepatitis C virus (HCV) is a major cause of HCC and is responsible for making liver cancer the most common cancer in many parts of the world. In the United States, hepatitis C infection is responsible for about 50% to 60% of all liver cancers and hepatitis B is responsible for another 20%. Exposure to Aflatoxins is also a cause of HCC, mostly in warmer and tropical countries. Liver cancer accounts for about 5.8% of all cancer cases globally (about 626,000 cases) and 8.9% of deaths per year (about 598,000). It is the 3rd most common cause of cancer-related death in both men and women worldwide. HCC is predominantly found in Asia and Africa, which account for 80% of cases. In the USA, there are approximately 18,500 new cases of HCC and 16,000 deaths per year. About 85% of people diagnosed with liver cancer are between 45 and 85 years of age. About 4% are between 35 and 44 years of age and only 2.4% are younger than 35.

Liver Cancer Diagnosis

Since symptoms of liver cancer often do not appear until the disease is advanced, only a small number of liver cancers are found in the early stages and can be removed with surgery. Many signs and symptoms of liver cancer are relatively non-specific—that is, they can be caused by other cancers or by non-cancerous diseases. Imaging tests such as ultrasound, computed tomography (CT), magnetic resonance imaging (MRI) and angiography are commonly used to diagnose HCC. Other diagnostic tools include laparoscopy, biopsy, alpha-fetoprotein (AFP) blood test, liver function tests (LFTs), prothrombin time (PT) and tests for hepatitis B and C.

Liver Cancer Staging

HCC has four stages, stage I to stage IV according to the American Joint Committee on Cancer (AJCC) TNM system. HCC can be classified as localized resectable, localized unresectable or advanced. The overall 5-year relative survival rate for liver cancer is about 9%. One reason for this low survival rate is that most patients with liver cancer also have cirrhosis of the liver, which itself can be fatal (people with liver cancer and class C cirrhosis are generally too sick for any treatment and usually die in a few months). The 5 year survival for localized resectable HCC following surgery is between 40% and 70%. For advanced HCC there is no standard treatment and the 5 year survival rate is less than 5%. Survival continues to drop after diagnosis and treatment so that by 10 years it is less than 2.5%.

Liver Cancer Treatment

Treatment of liver cancer depends on the size of the tumour and whether the patient has cirrhosis. At this time, surgery, either by resection or liver transplantation, offers the only chance to cure a liver cancer. People without cirrhosis can do well with surgical removal of the tumour. However, in many cases, it might not be possible to safely remove a localized liver cancer. Less than 30% of the patients having explorative surgery are able to have their cancer completely removed by surgery. Partial hepatectomy results in a 5-year survival of 30% to 40%. If there is cirrhosis, or a very large tumour, most experts recommend liver transplantation as the main treatment. The 5-year survival for liver transplantation patients is around 70% but the opportunities for liver transplantation are limited.

Other treatments include radiofrequency ablation (RFA), ethanol ablation, cryosurgery, hepatic artery embolization, chemoembolization or three-dimensional conformal radiation therapy (3DCRT). Chemotherapy can also be used but shrinks fewer than 1 in 5 tumours. This may be improved by hepatic artery infusion (HAI). Chemotherapeutic agents used include Adriamycin, VP-16, Cisplatinum, Mitomycin, 5-FU and Leucovorin.

The prognosis for any treated primary liver cancer patient with progressing, recurring, or relapsing disease is poor. Treatment of liver cancer that returns after initial therapy depends on many factors, including the site of the recurrence, the type of initial treatment, and the functioning of the liver. Patients with localized resectable disease that recurs in the same spot may be eligible for further surgery.

Lung Cancer

Lung cancer is the most common form of cancer worldwide (accounting for about 12% of cancer cases) and the main cause of death from cancer (accounting for about 18% of deaths). Global incidence of lung cancer is over 1,300,000 per year, with the number of deaths over 1,100,000. In the USA, there are about 170,000 new cases per year (about 13% of all cancers), with about 160,000 deaths (about 28% of cancer deaths). Lung cancer is much more prevalent among men than women. Nearly 70% of people diagnosed with lung cancer are older than 65; fewer than 3% of all cases are found in people under the age of 45. Around 15% of all lung cancers are small cell type (SCLC), which tend to spread widely through the body, while the remaining 85% are non-small cell (NSCLC). It has been estimated that approximately US $9.6 billion is spent in the USA each year on treating lung cancer.

Lung Cancer Diagnosis

Lung cancer is a life-threatening disease because it often metastasises even before it can be detected on a chest x-ray. Usually symptoms of lung cancer do not appear until the disease is in an advanced stage. So far, there is no screening test that has been shown to improve a person's chance for a cure. Imaging tests such as a chest x-ray, CT scan, MRI scan or PET scan may be used to detect lung cancer. Tests to confirm the diagnosis are then performed and include sputum cytology, needle biopsy, bronchoscopy, endobronchial ultrasound and complete blood count (CBC).

Lung Cancer Staging

Nearly 60% of people diagnosed with lung cancer die within one year of diagnosis; 75% die within 2 years. The 5-year survival rate for people diagnosed with NSCLC is about 15%; for SCLC the 5-year survival rate is about 6%. NSCLC is staged using the American Joint Committee on Cancer (AJCC) TNM system—Stage 0-Stage IV. The 5-year survival rates by stage are as follows: stage I: 47%; stage II; 26%; stage III: 8% and stage IV: 2%. SCLC has a 2-stage system—limited stage and extensive stage. About two thirds of SCLC patients have extensive disease at diagnosis. If SCLC is found very early and is localised to the lung alone, the 5-year survival rate is around 21%, but only 6% of patients fall into this category. Where the cancer has spread, the 5-year survival is around 11%. For patients with extensive disease, the 5-year survival is just 2%.

Lung Cancer Treatment

Surgery is the only reliable method to cure NSCLC. Types of surgery include lobectomy, pneumonectomy, segmentectomy and video-assisted thoracic surgery (for small tumours). External beam radiation therapy is sometimes used as the primary treatment, especially if the patient's health is too poor to undergo surgery. Radiation therapy can also be used after surgery. Chemotherapy may be given as the primary treatment or as an adjuvant to surgery. Targeted therapy using epidermal growth factor receptor (EGFR) antagonists such as gefitinib or erlotinib can also be given after other treatments have failed. Antiangiogenic drugs, such as bevacizumab, have been found to prolong survival of patients with advanced lung cancer. Photodynamic therapy is also being researched as a treatment for lung cancer.

The main treatment for SCLC is chemotherapy, either alone or in combination with external beam radiation therapy and very rarely, surgery.

Chemotherapeutic agents used for NSCLC and SCLC include cisplatin, carboplatin, mitomycin C, ifosfamide, vinblastine, gemcitabine, etoposide, vinorelbine, paclitaxel, docetaxel and irinotecan.

Ovarian Cancer

Ovarian cancer accounts for about 1.9% of cancer cases globally and around 1.8% of deaths. Global incidence of ovarian cancer is around 205,000, predominantly in postmenopausal women in developed countries, with around 125,000 deaths. About 85% to 90% of ovarian cancers are epithelial ovarian carcinomas. About 5% of ovarian cancers are germ cell tumours and a smaller percentage are stromal tumours. Ovarian cancer is the eighth most common cancer among women. In the USA, about 20,200 new cases of ovarian cancer are diagnosed each year and it accounts for about 3% of all cancers in women. The risk of developing and dying from ovarian cancer is higher for white women than black women. Around two-thirds of women with ovarian cancer are 55 or older. Ovarian cancer ranks fifth in cancer deaths among women in the USA, accounting for more deaths than any other cancer of the female reproductive system. There are around 15,300 deaths in the USA from ovarian cancer each year. It has been estimated that approximately US $2.2 billion is spent in the USA each year on treating ovarian cancer.

Ovarian Cancer Diagnosis

It is currently difficult to diagnose ovarian cancer at an early stage. Imaging tests such as ultrasound, computed tomography and magnetic resonance imaging can confirm whether a pelvic mass is present. Blood tests, including a CA-125 test and a laparoscopy are performed. Ovarian cancer is then confirmed by biopsy.

Ovarian Cancer Staging

Ovarian cancer is staged using the American Joint Committee on Cancer (AJCC) TNM system—stage I-IV. The FIGO (International Federation of Gynecology and Obstetrics) system is also used. Ovarian cancers are also given a grade from 1-3. About 76% of women with ovarian cancer survive 1 year after diagnosis, and 45% survive longer than 5 years after diagnosis. If diagnosed and treated while the cancer has not spread outside the ovary, the 5-year survival rate is 94%. However, only 19% of all ovarian cancers are found at this early stage.

Ovarian Cancer Treatment Surgery for ovarian cancer includes hysterectomy, bilateral salpingectomy, bilateral oophorectomy and omentectomy. Debulking is performed in women in whom the cancer has spread widely throughout their abdomen.

Intraperitoneal (IP) chemotherapy using a combination therapy using a platinum compound, such as cisplatin or carboplatin, and a taxane, such as paclitaxel or docetaxel, is the standard approach. Tumour recurrence is sometimes treated with additional cycles of a platinum compound and/or a taxane. In other cases, recurrence is treated with other drugs, such as topotecan, anthracyclines such as doxorubicin (Adriamycin) and liposomal doxorubicin (Doxil), gemcitabine, cyclophosphamide, vinorelbine (Navelbine), hexamethylmelamine, ifosfamide, and etoposide. Resistance to currently-available chemotherapeutic agents is a major problem. Although complete clinical response is achieved in 75% of patients after initial treatment, most will develop recurrent disease and require re-treatment.

External beam radiation therapy can also sometimes be used.

Ovarian Cancer Survival by Stage

| Stage | Relative 5-Years Survival Rate |
|---|---|
| IA | 92.7% |
| IB | 85.4% |
| IC | 84.7% |
| IIA | 78.6% |
| IIB | 72.4% |
| IIC | 64.4% |
| IIIA | 50.8% |
| IIIB | 42.4% |
| IIIC | 31.5% |
| IV | 17.5% |

Pancreatic Cancer

Pancreatic cancer is a very difficult cancer to detect and the prognosis for patients is usually very poor. The number of new cases and deaths per year is almost equal. Global incidence of pancreatic cancer is approximately 230,000 cases (about 2% of all cancer cases), with about 225,000 deaths (3.4% of cancer deaths) per year. It is much more prevalent in the developed world. In the USA, there are about 34,000 new cases per year, with about 32,000 deaths. It has been estimated that approximately US $1.5 billion is spent in the USA each year on treating pancreatic cancer.

Pancreatic Cancer Diagnosis

Pancreatic cancer is very difficult to detect and very few pancreatic cancers are found early. Patients usually have no symptoms until the cancer has spread to other organs. There are currently no blood tests or easily available screening tests that can accurately detect early cancers of the pancreas. An endoscopic ultrasound followed by a biopsy is the best way to diagnose pancreatic cancer. Other detection methods include CT, CT-guided needle biopsy, PET, ultrasonography and MRI. Blood levels of CA 19-9 and carcinoembryonic antigen (CEA) may be elevated but by the time blood levels are high enough to be detected, the cancer is no longer in its early stages.

Pancreatic Cancer Staging

Pancreatic cancer has four stages, stage I to stage IV according to the American Joint Committee on Cancer (AJCC) TNM system. Pancreatic cancer is also divided into resectable, locally advanced (unresectable) and metastatic cancer. For patients with advanced cancers, the overall survival rate is <1% at 5 years with most patients dying within 1 year.

Pancreatic Cancer Treatment

Surgery is the only method of curing pancreatic cancer. About 10% of pancreatic cancers are contained entirely within the pancreas at the time of diagnosis and attempts to remove the entire cancer by surgery may be successful in some of these patients. The 5-year survival for those undergoing surgery with the intent of completely removing the cancer is about 20%. Potentially curative surgery, usually by pancreaticoduodenectomy (Whipple procedure), is used when it may be possible to remove all of the cancer. Palliative surgery may be performed if the tumour is too widespread to be completely removed. Removing only part of the cancer does not allow patients to live longer. Pancreatic cancer surgery is difficult to perform with a high likelihood of complications.

External beam radiation therapy combined with chemotherapy can be given before or after surgery and can also be given to patients whose tumours are too widespread to be removed by surgery. The main chemotherapeutic agents which are used are gemcitabine and 5-fluorouracil. Targeted therapy using drugs such as erlotinib and cetuximab may be of benefit to patients with advanced pancreatic cancer.

Therapeutic Challenges

The major challenges in treatment of colorectal cancer, kidney cancer, liver cancer, lung cancer, lymphoid leukaemia (particularly chronic lymphocytic leukaemia), ovarian cancer and pancreatic cancer are to improve early detection rates, to find new non-invasive markers that can be used to follow disease progression and identify relapse, and to find improved and less toxic therapies, especially for more advanced disease where 5 year survival is still poor. There is a great need to identify targets which are more specific to the cancer cells, e.g. ones which are expressed on the surface of the tumour cells so that they can be attacked by promising new approaches like immunotherapeutics and targeted toxins.

SUMMARY OF THE INVENTION

The present invention provides methods and compositions for screening, diagnosis, prognosis and therapy of colorectal cancer, kidney cancer, liver cancer, lung cancer, lymphoid leukaemia (particularly chronic lymphocytic leukaemia), ovarian cancer or pancreatic cancer, for colorectal cancer, kidney cancer, liver cancer, lung cancer, lymphoid leukaemia (particularly chronic lymphocytic leukaemia), ovarian cancer or pancreatic cancer patients' stratification, for monitoring the effectiveness of colorectal cancer, kidney cancer, liver cancer, lung cancer, lymphoid leukaemia (particularly chronic lymphocytic leukaemia), ovarian cancer or pancreatic cancer treatment, and for drug development for treatment of colorectal cancer, kidney cancer, liver cancer, lung cancer, lymphoid leukaemia (particularly chronic lymphocytic leukaemia), ovarian cancer or pancreatic cancer.

We have used mass spectrometry to identify peptides generated by gel electrophoresis or tagging with iTRAQ reagents and tryptic digest of membrane proteins extracted from colorectal cancer, kidney cancer, liver cancer, lung cancer, lymphoid leukaemia (particularly chronic lymphocytic leukaemia), ovarian cancer or pancreatic cancer tissue samples. Peptide sequences were compared to existing protein and cDNA databases and the corresponding gene sequences identified. The protein of the invention has not been previously reported to originate from colorectal cancer, kidney cancer, liver cancer, lung cancer, lymphoid leukaemia (particularly chronic lymphocytic leukaemia), ovarian cancer or pancreatic cancer cell membranes and represents a protein of new diagnostic and therapeutic value.

Thus according to a first aspect of the invention we provide a method of detecting, diagnosing and/or screening for or monitoring the progression of colorectal cancer, kidney cancer, liver cancer, lung cancer, lymphoid leukaemia (particularly chronic lymphocytic leukaemia), ovarian cancer or pancreatic cancer or of monitoring the effect of an anti-colorectal cancer, anti-kidney cancer, anti-liver cancer, anti-lung cancer, anti-lymphoid leukaemia (particularly chronic lymphocytic leukaemia), anti-ovarian cancer or anti-pancreatic cancer drug or therapy in a subject which comprises detecting the presence or level of OGTA076, or one or more fragments thereof, or the presence or level of nucleic acid encoding OGTA076 or the presence or level of the activity of OGTA076 or which comprises detecting a change in the level thereof in said subject.

According to a second aspect of the invention we provide a method of detecting, diagnosing and/or screening for colorectal cancer, kidney cancer, liver cancer, lung cancer, lymphoid leukaemia (particularly chronic lymphocytic leukaemia), ovarian cancer or pancreatic cancer in a candidate subject which comprises detecting the presence of OGTA076, or one or more fragments thereof, or the presence of nucleic acid encoding OGTA076 or the presence of the activity of OGTA076 in said candidate subject, in which either (a) the presence of an elevated level of OGTA076 or said one or more fragments thereof or an elevated level of nucleic acid encoding OGTA076 or the presence of an elevated level of OGTA076 activity in the candidate subject as compared with the level in a healthy subject or (b) the presence of a detectable level of OGTA076 or said one or more fragments thereof or a detectable level of nucleic acid encoding OGTA076 or the presence of a detectable level of OGTA076 activity in the candidate subject as compared with a corresponding undetectable level in a healthy subject indicates the presence of colorectal cancer, kidney cancer, liver cancer, lung cancer, lymphoid leukaemia (particularly chronic lymphocytic leukaemia), ovarian cancer or pancreatic cancer in said subject.

According to a third aspect of the invention we provide a method of monitoring the progression of colorectal cancer, kidney cancer, liver cancer, lung cancer, lymphoid leukaemia (particularly chronic lymphocytic leukaemia), ovarian cancer or pancreatic cancer in a subject or of monitoring the effect of an anti-colorectal cancer, anti-kidney cancer, anti-liver cancer, anti-lung cancer, anti-lymphoid leukaemia (particularly chronic lymphocytic leukaemia), anti-ovarian cancer or anti-pancreatic cancer drug or therapy which comprises detecting the presence of OGTA076, or one or more fragments thereof, or the presence of nucleic acid encoding OGTA076 or the presence of the activity of OGTA076 in said candidate subject at a first time point and at a later time point, the presence of an elevated or lowered level of OGTA076 or said one or more fragments thereof or an elevated or lowered level of nucleic acid encoding OGTA076 or the presence of an elevated or lowered level of OGTA076 activity in the subject at the later time point as compared with the level in the subject at said first time point, indicating the progression or regression of colorectal cancer, kidney cancer, liver cancer, lung cancer, lymphoid leukaemia (particularly chronic lymphocytic leukaemia), ovarian cancer or pancreatic cancer or indicating the effect or non-effect of an anti-colorectal cancer, anti-kidney cancer, anti-liver cancer, anti-lung cancer, anti-lymphoid leukaemia (particularly chronic lymphocytic leukaemia), anti-ovarian cancer or anti-pancreatic cancer drug or therapy in said subject.

The presence of OGTA076, or one or more fragments thereof, or the presence of nucleic acid encoding OGTA076 or the presence of the activity of OGTA076 may, for example, be detected by analysis of a biological sample obtained from said subject.

The method of invention may typically include the step of obtaining a biological sample for analysis from said subject. However, in one or more aspects the method according to the invention does not include the step of obtaining the biological sample.

The biological sample used can be from any source such as a serum sample or a tissue sample e.g. colorectal, kidney, liver, lung, lymphoid, ovarian or pancreatic tissue. For instance, when looking for evidence of metastatic colorectal cancer, kidney cancer, liver cancer, lung cancer, ovarian cancer or pancreatic cancer, one would look at major sites of colorectal cancer, kidney cancer, liver cancer, lung cancer, ovarian cancer or pancreatic cancer metastasis, e.g. the liver, the peritoneal cavity, the pelvis, the retroperitoneum and the lungs for colorectal cancer; the bones, the lungs and the liver for kidney cancer; the lungs and bones for liver cancer; the brain, the liver, the bones and adrenal glands for lung cancer; the abdomen for ovarian cancer and the liver for pancreatic cancer.

Alternatively the presence of OGTA076, or one or more fragments thereof, or the presence of nucleic acid encoding OGTA076 or the presence of the activity of OGTA076 may be detected by analysis in situ.

In certain embodiments, methods of diagnosis described herein may be at least partly, or wholly, performed in vitro.

Suitably the presence of OGTA076, or one or more fragments thereof, or the presence of nucleic acid encoding OGTA076 or the presence of the activity of OGTA076 is detected quantitatively.

For example, quantitatively detecting may comprise:
(a) contacting a biological sample with an affinity reagent that is specific for OGTA076, said affinity reagent optionally being conjugated to a detectable label; and
(b) detecting whether binding has occurred between the affinity reagent and at least one species in the sample, said detection being performed either directly or indirectly.

Alternatively the presence of OGTA076, or one or more fragments thereof, or the presence of nucleic acid encoding OGTA076 or the presence of the activity of OGTA076 may be detected quantitatively by means involving use of an imaging technology.

In another embodiment, the method of the invention involves use of immunohistochemistry on tissue sections in order to determine the presence of OGTA076, or one or more fragments thereof, or the presence of nucleic acid encoding OGTA076 or the presence of the activity of OGTA076, and thereby to localise colorectal cancer, kidney cancer, liver cancer, lung cancer, lymphoid leukaemia (particularly chronic lymphocytic leukaemia), ovarian cancer or pancreatic cancer cells.

In one embodiment the presence of OGTA076 or one or more epitope-containing fragments thereof is detected, for example using an affinity reagent capable of specific binding to OGTA076 or one or more fragments thereof, such as an antibody.

In another embodiment the activity of OGTA076 is detected.

According to another aspect of the invention there is provided a method of detecting, diagnosing and/or screening for or monitoring the progression of colorectal cancer, kidney cancer, liver cancer, lung cancer, lymphoid leukaemia (particularly chronic lymphocytic leukaemia), ovarian cancer or pancreatic cancer or of monitoring the effect of an anti-colorectal cancer, anti-kidney cancer, anti-liver cancer, anti-lung cancer, anti-lymphoid leukaemia (particularly chronic lymphocytic leukaemia), anti-ovarian cancer or anti-pancreatic cancer drug or therapy in a subject which comprises detecting the presence or level of antibodies capable of immunospecific binding to OGTA076, or one or more epitope-containing fragments thereof or which comprises detecting a change in the level thereof in said subject.

According to another aspect of the invention there is also provided a method of detecting, diagnosing and/or screening for colorectal cancer, kidney cancer, liver cancer, lung cancer, lymphoid leukaemia (particularly chronic lymphocytic leukaemia), ovarian cancer or pancreatic cancer in a subject which comprises detecting the presence of antibodies capable of immunospecific binding to OGTA076, or one or more epitope-containing fragments thereof in said subject, in which (a) the presence of an elevated level of antibodies capable of immunospecific binding to OGTA076 or said one or more epitope-containing fragments thereof in said subject as compared with the level in a healthy subject or (b) the presence of a detectable level of antibodies capable of immunospecific binding to OGTA076 or said one or more epitope-containing fragments thereof in said subject as compared with a corresponding undetectable level in a healthy subject indicates the presence of colorectal cancer, kidney cancer, liver cancer, lung cancer, lymphoid leukaemia (particularly chronic lymphocytic leukaemia), ovarian cancer or pancreatic cancer in said subject.

One particular a method of detecting, diagnosing and/or screening for colorectal cancer, kidney cancer, liver cancer, lung cancer, lymphoid leukaemia (particularly chronic lymphocytic leukaemia), ovarian cancer or pancreatic cancer comprises:
(a) bringing into contact with a biological sample to be tested OGTA076, or one or more epitope-containing fragments thereof; and
(b) detecting the presence of antibodies in the subject capable of immunospecific binding to OGTA076, or one or more epitope-containing fragments thereof.

According to another aspect of the invention there is provided a method of monitoring the progression of colorectal cancer, kidney cancer, liver cancer, lung cancer, lymphoid leukaemia (particularly chronic lymphocytic leukaemia), ovarian cancer or pancreatic cancer or of monitoring the effect of an anti-colorectal cancer, anti-kidney cancer, anti-liver cancer, anti-lung cancer, anti-lymphoid leukaemia (particularly chronic lymphocytic leukaemia), anti-ovarian cancer or anti-pancreatic cancer drug or therapy in a subject which comprises detecting the presence of antibodies capable of immunospecific binding to OGTA076, or one or more epitope-containing fragments thereof in said subject at a first time point and at a later time point, the presence of an elevated or lowered level of antibodies capable of immunospecific binding to OGTA076, or one or more epitope-containing fragments thereof in said subject at the later time point as compared with the level in said subject at said first time point, indicating the progression or regression of colorectal cancer, kidney cancer, liver cancer, lung cancer, lymphoid leukaemia (particularly chronic lymphocytic leukaemia), ovarian cancer or pancreatic cancer or the effect or non-effect of an anti-colorectal cancer, anti-kidney cancer, anti-liver cancer, anti-lung cancer, anti-lymphoid leukaemia (particularly chronic lymphocytic leukaemia), anti-ovarian cancer or anti-pancreatic cancer drug or therapy in said subject.

The presence of antibodies capable of immunospecific binding to OGTA076, or one or more epitope-containing fragments thereof is typically detected by analysis of a biological sample obtained from said subject (exemplary biological samples are mentioned above, e.g. the sample is a sample of colorectal, kidney, liver, lung, lymphoid, ovarian or pancreatic tissue, or else a sample of blood or saliva).

The method may include the step of obtaining said biological sample for analysis from said subject.

The antibodies that may be detected include IgA, IgM and IgG antibodies.

In any of the above methods, the level that may be detected in the candidate subject who has colorectal cancer, kidney cancer, liver cancer, lung cancer, lymphoid leukaemia (particularly chronic lymphocytic leukaemia), ovarian cancer or pancreatic cancer is 2 or more fold higher than the level in the healthy subject.

Another aspect of the invention is an agent capable of specific binding to OGTA076, or a fragment thereof, or a hybridising agent capable of hybridizing to nucleic acid encoding OGTA076 or an agent capable of detecting the activity of OGTA076 for use in screening for, detecting and/or diagnosing disease, such as cancer, and especially colorectal cancer, kidney cancer, liver cancer, lung cancer, lymphoid leukaemia (particularly chronic lymphocytic leukaemia), ovarian cancer or pancreatic cancer.

Another aspect of the invention is OGTA076, or a fragment thereof for use in screening for, detecting and/or diagnosing disease such as cancer, and especially colorectal cancer, kidney cancer, liver cancer, lung cancer, lymphoid leukaemia (particularly chronic lymphocytic leukaemia), ovarian cancer or pancreatic cancer.

Another aspect of the invention is an affinity reagent capable of specific binding to OGTA076 or a fragment thereof, for example an affinity reagent which contains or is conjugated to a detectable label or contains or is conjugated to a therapeutic moiety such as a cytotoxic moiety. The affinity reagent may, for example, be an antibody.

Another aspect of the invention is a hybridizing agent capable of hybridizing to nucleic acid encoding OGTA076, for example, a hybridizing agent which contains or is conjugated to a detectable label. One example of a hybridizing agent is an inhibitory RNA (RNAi). Other examples include anti-sense oligonucleotides and ribozymes.

The invention also provides a kit containing OGTA076 and/or one or more fragments thereof or containing one or more aforementioned affinity reagents and/or hybridizing agents or containing one or more agents capable of detecting the activity of OGTA076 together with instructions for their use in an aforementioned method. The kit may further contain reagents capable of detecting and reporting the binding of said affinity reagents and/or hybridizing agents to their binding partners.

Another aspect of the invention is a pharmaceutical composition comprising a therapeutically effective amount of an affinity reagent capable of specific binding to OGTA076 or a fragment thereof.

Another aspect of the invention is a pharmaceutically acceptable diluent or carrier and a pharmaceutical composition comprising one or more affinity reagents or hybridizing reagents as aforesaid and a pharmaceutically acceptable diluent or carrier.

In one embodiment the cancer to be detected, prevented or treated is colorectal cancer.

In another embodiment the cancer to be detected, prevented or treated is kidney cancer.

In another embodiment the cancer to be detected, prevented or treated is liver cancer.

In another embodiment the cancer to be detected, prevented or treated is lung cancer.

In another embodiment the cancer to be detected, prevented or treated is lymphoid leukaemia (particularly chronic lymphocytic leukaemia).

In another embodiment the cancer to be detected, prevented or treated is ovarian cancer.

In another embodiment the cancer to be detected, prevented or treated is pancreatic cancer.

Other aspects of the present invention are set out below and in the claims herein.

BRIEF DESCRIPTION OF THE FIGURES

FIG. 1 shows the amino acid sequences of the three isoforms of the protein of the invention. The tryptic peptides detected experimentally by mass spectrometry are highlighted—mass match peptides are shown in bold, tandem peptides are underlined.

DETAILED DESCRIPTION OF THE INVENTION

Figure 2:
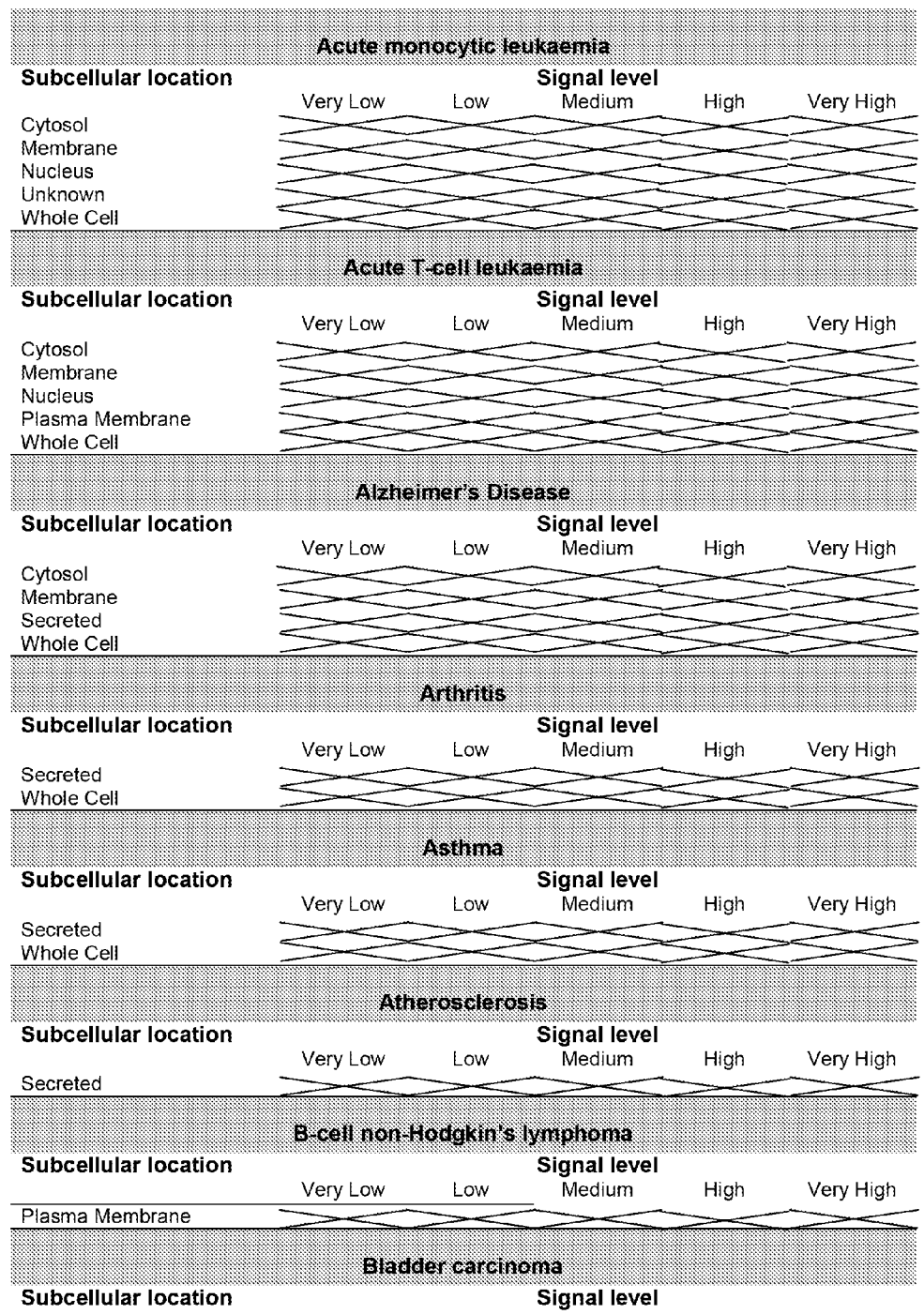
FIG. 2 shows the Protein Index for the protein of the invention.
Figure 2:
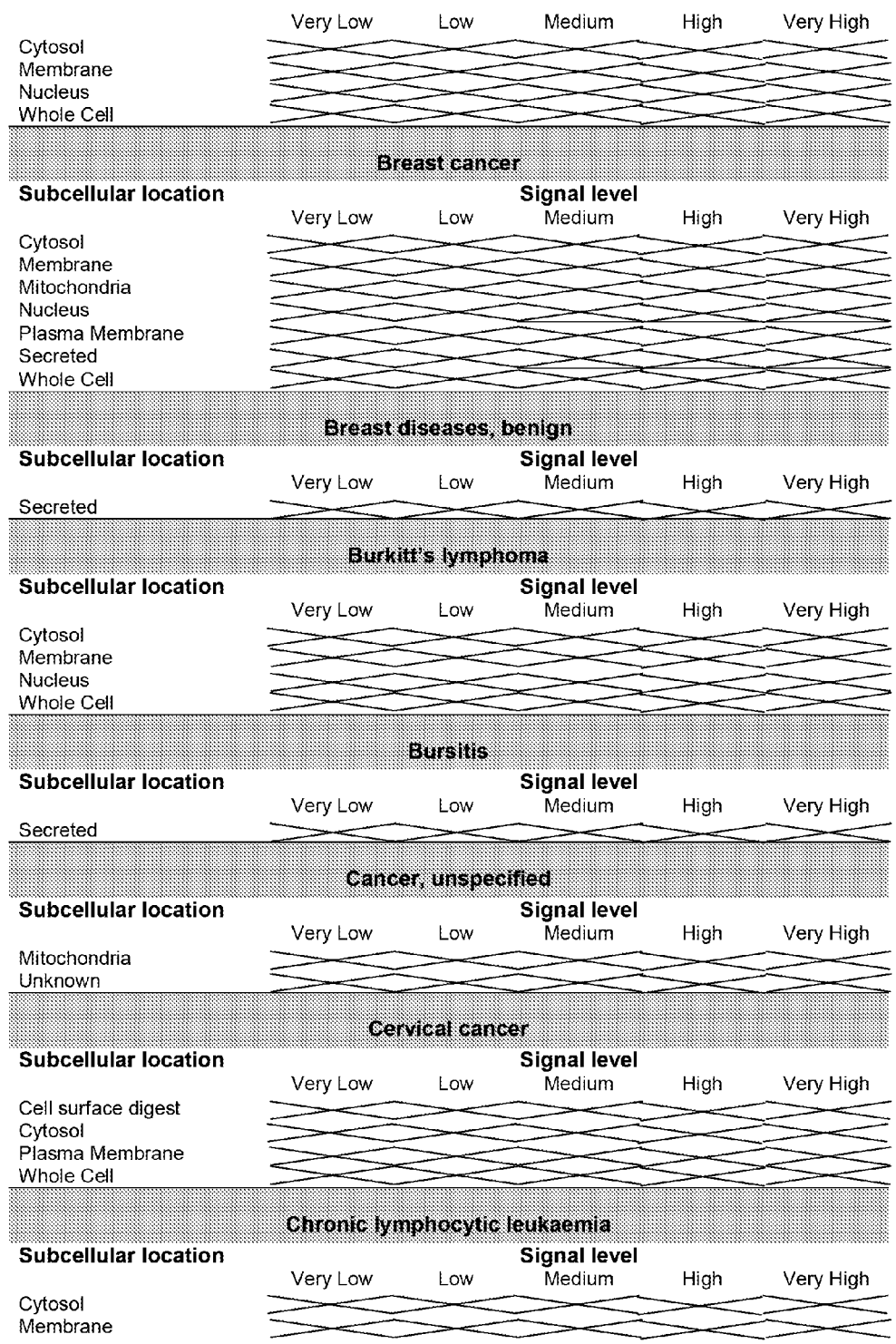
Figure 2:
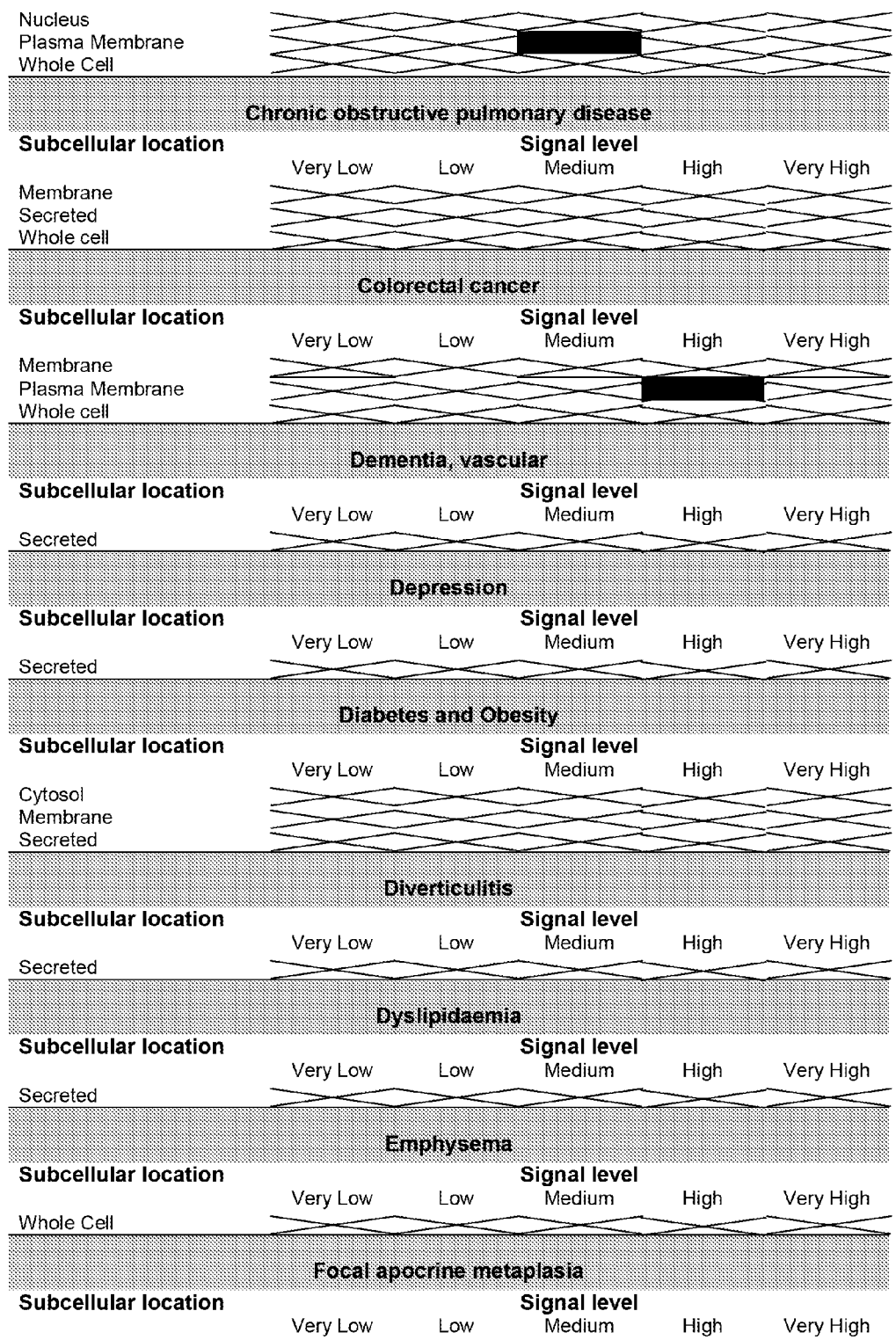
Figure 2:
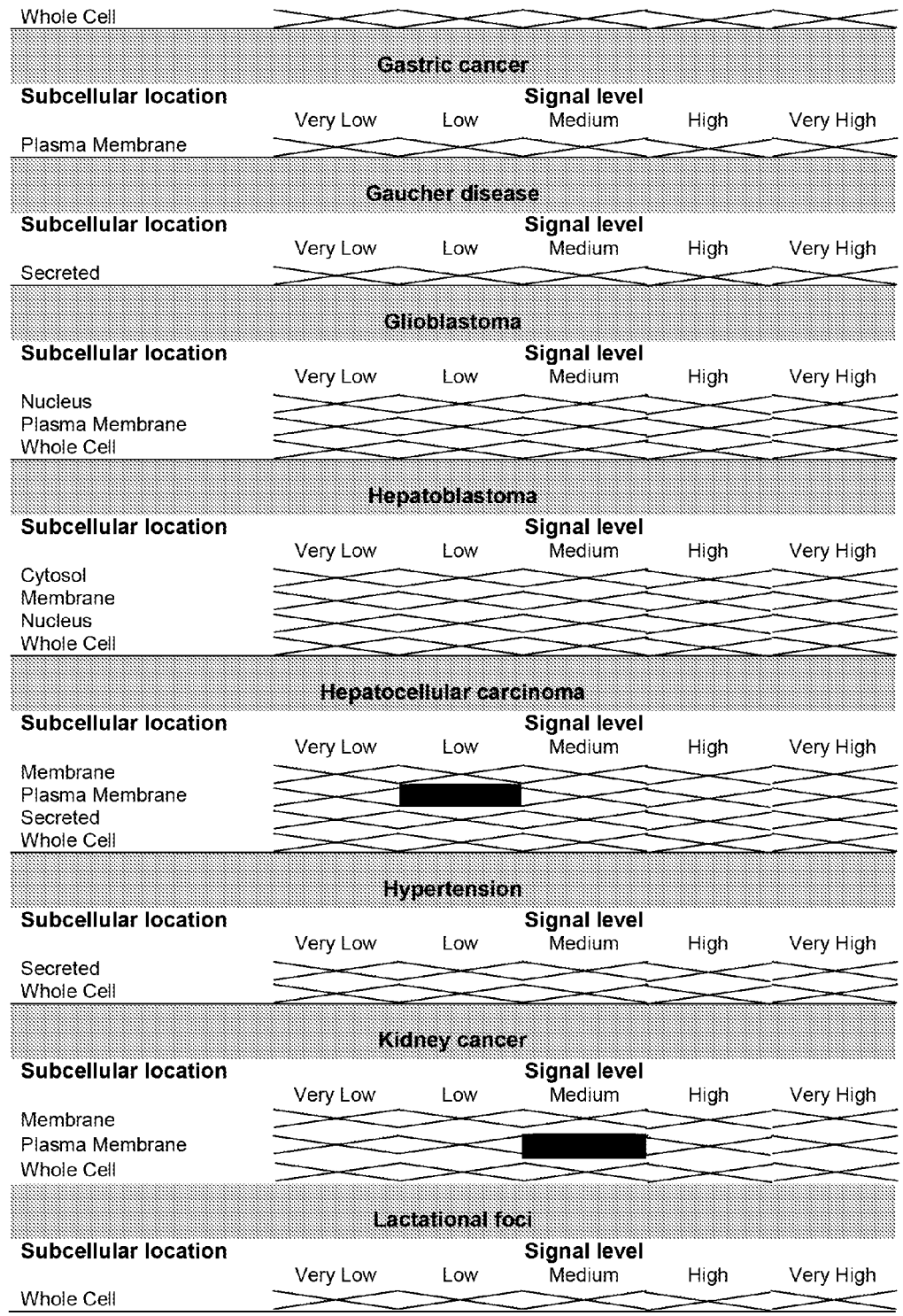
Figure 2:
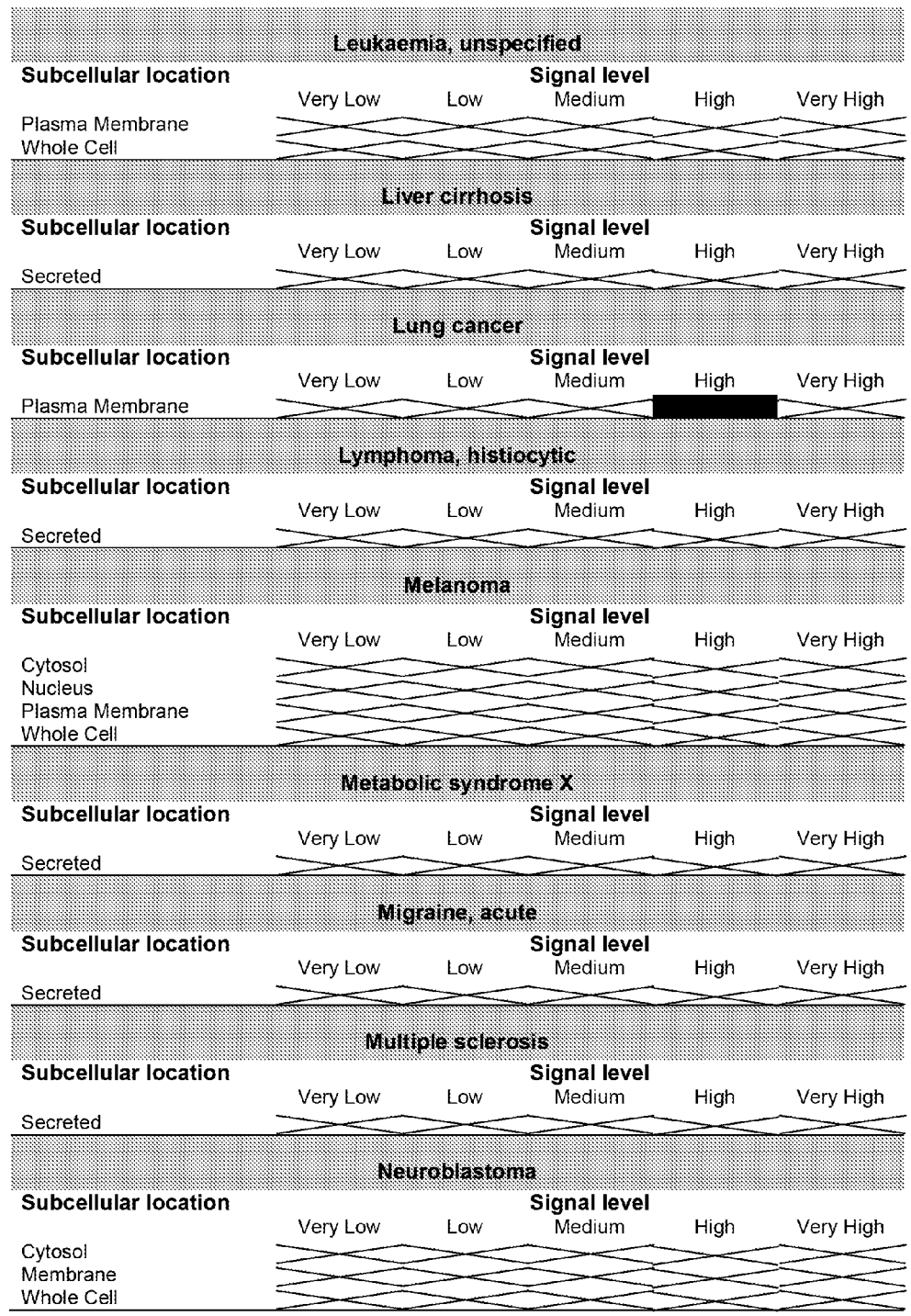
Figure 2:
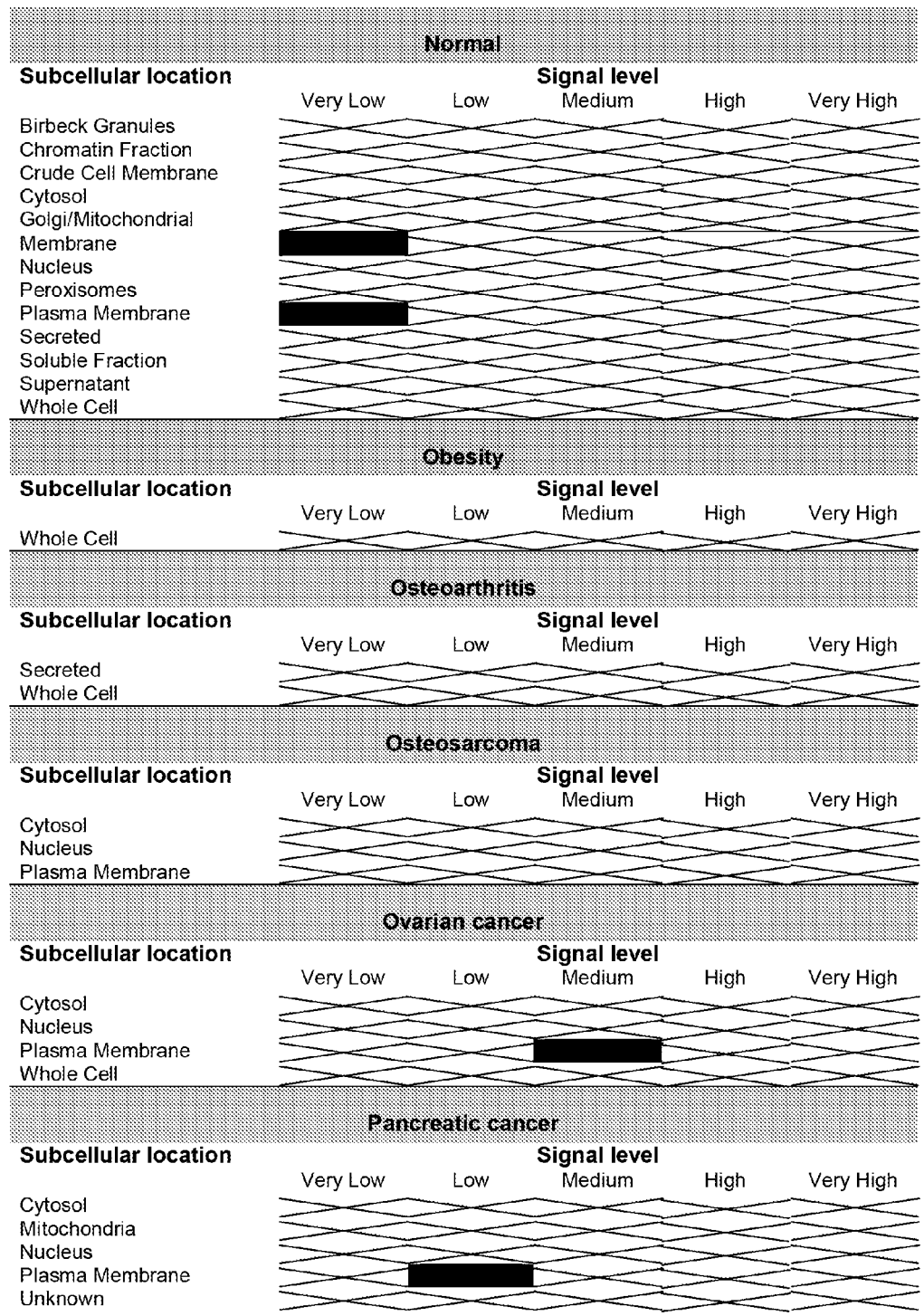
Figure 2:
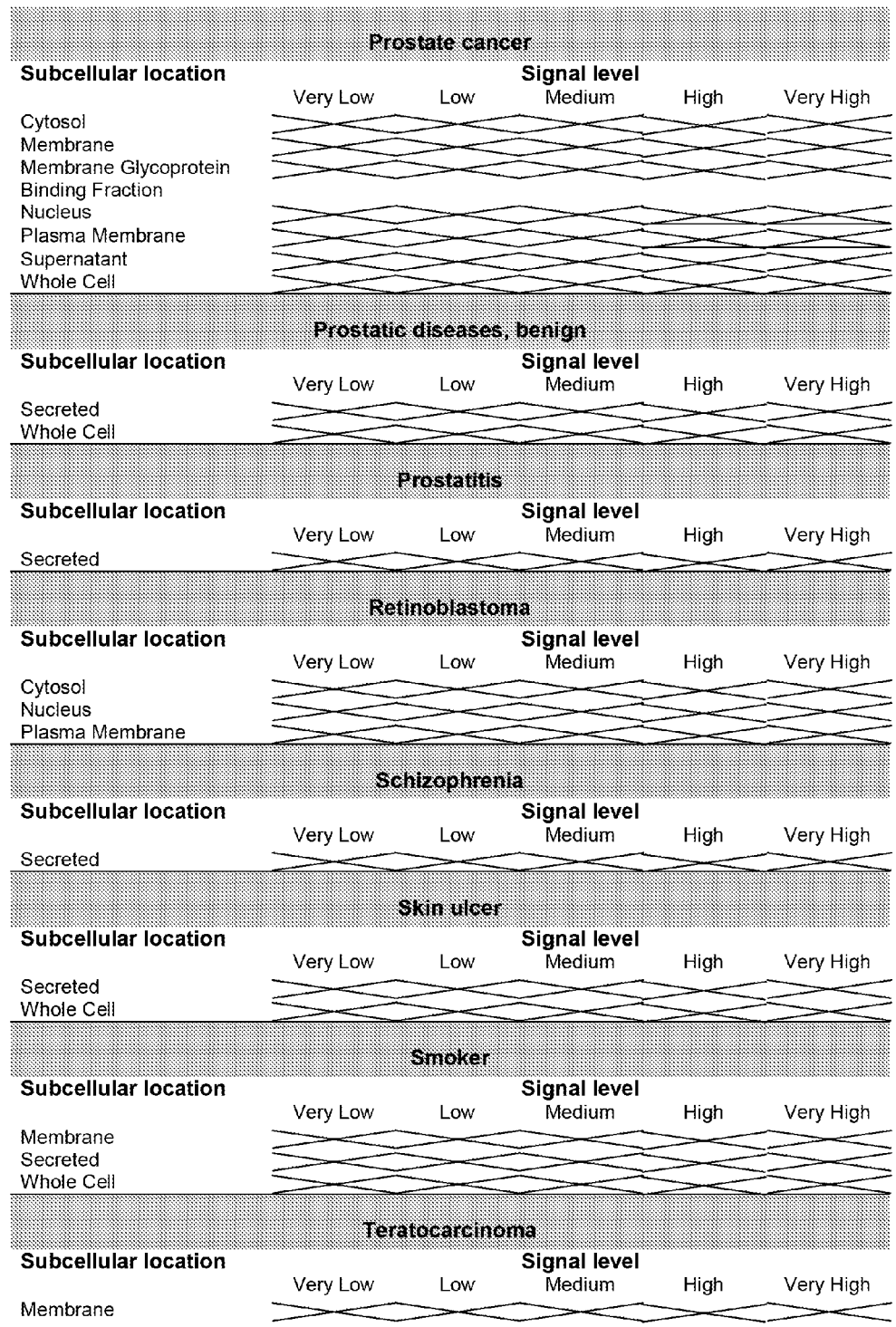
Figure 2:

The invention described in detail below provides methods and compositions for clinical screening, diagnosis and prognosis of colorectal cancer, kidney cancer, liver cancer, lung cancer, lymphoid leukaemia (particularly chronic lymphocytic leukaemia), ovarian cancer or pancreatic cancer in a mammalian subject for identifying patients most likely to respond to a particular therapeutic treatment, for monitoring the results of colorectal cancer, kidney cancer, liver cancer, lung cancer, lymphoid leukaemia (particularly chronic lymphocytic leukaemia), ovarian cancer or pancreatic cancer therapy, for drug screening and drug development. The invention also encompasses the administration of therapeutic compositions to a mammalian subject to treat or prevent colorectal cancer, kidney cancer, liver cancer, lung cancer, lymphoid leukaemia (particularly chronic lymphocytic leukaemia), ovarian cancer or pancreatic cancer. The mammalian subject may be a non-human mammal, for example a human, such as a human adult, i.e. a human subject at least 21 (for example at least 35, at least 50, at least 60, at least 70, or at least 80) years old. For clarity of disclosure, and not by way of limitation, the invention will be described with respect to the analysis of colorectal, kidney, liver, lung, lymphoid, ovarian or pancreatic tissue. However, as one skilled in the art will appreciate, the assays and techniques described below can be applied to other types of patient samples, including body fluids (e.g. blood, urine or saliva), a tissue sample from a patient at risk of having colorectal cancer, kidney cancer, liver cancer, lung cancer, lymphoid leukaemia (particularly chronic lymphocytic leukaemia), ovarian cancer or pancreatic cancer (e.g. a biopsy such as a colorectal, kidney, liver, lung, bone marrow, ovarian or pancreatic biopsy) or homogenate thereof. The methods and compositions of the present invention are specially suited for screening, diagnosis and prognosis of a living subject, but may also be used for postmortem diagnosis in a subject, for example, to identify family members at risk of developing the same disease.

OGTA076

In one aspect of the invention, one-dimensional electrophoresis or isobaric tags for relative and absolute quantification (iTRAQ) or other appropriate methods are used to analyze colorectal cancer, kidney cancer, liver cancer, lung cancer, lymphoid leukaemia (particularly chronic lymphocytic leukaemia), ovarian cancer or pancreatic cancer tissue samples from a subject, preferably a living subject, in order to measure the expression of the protein of the invention for screening or diagnosis of colorectal cancer, kidney cancer, liver cancer, lung cancer, lymphoid leukaemia (particularly chronic lymphocytic leukaemia), ovarian cancer or pancreatic cancer, to determine the prognosis of a colorectal cancer, kidney cancer, liver cancer, lung cancer, lymphoid leukaemia (particularly chronic lymphocytic leukaemia), ovarian cancer or pancreatic cancer patient, to monitor the effectiveness of colorectal cancer, kidney cancer, liver cancer, lung cancer, lymphoid leukaemia (particularly chronic lymphocytic leukaemia), ovarian cancer or pancreatic cancer therapy, or for drug development.

As used herein, the term "Protein of the invention", or "OGTA076", refers to the protein illustrated in FIG. 1 in all its isoforms, in particular in its three different isoforms detected experimentally by 1D gel electrophoresis and iTRAQ analysis of colorectal cancer, kidney cancer, liver cancer, lung cancer, lymphoid leukaemia (particularly chronic lymphocytic leukaemia), ovarian cancer and pancreatic cancer tissue samples (OGTA076a [SEQ ID No: 1]; OGTA076b [SEQ ID No: 2] and OGTA076c [SEQ ID No: 3]). Protein derivatives of these sequences may also be useful for the same purposes as described herein.

This protein has been identified in membrane protein extracts of colorectal cancer, kidney cancer, liver cancer, lung cancer, lymphoid leukaemia (particularly chronic lymphocytic leukaemia), ovarian cancer and pancreatic cancer tissue samples from colorectal cancer, kidney cancer, liver cancer, lung cancer, lymphoid leukaemia (particularly chronic lymphocytic leukaemia), ovarian cancer and pancreatic cancer patients, through the methods and apparatus of the Preferred Technologies (1D gel electrophoresis or iTRAQ together with tryptic digest of membrane protein extracts). Peptide sequences were compared to the SWISS-PROT and trEMBL databases (held by the Swiss Institute of Bioinformatics (SIB) and the European Bioinformatics Institute (EBI) which are available at worldwide web expasy.com), and the following entry: O60449, Lymphocyte antigen 75, was identified.

According to SWISS-PROT, Lymphocyte antigen 75 is expressed in spleen, thymus, colon and peripheral blood lymphocytes. It has been detected in myeloid and B lymphoid cell lines. Isoforms OGTA076b and OGTA076c are expressed in malignant Hodgkin's lymphoma cells called Hodgkin's and Reed-Sternberg (HRS) cells. Lymphocyte antigen 75 acts as an endocytic receptor to direct captured antigens from the extracellular space to a specialized antigen-processing compartment. It causes reduced proliferation of B-lymphocytes.

The protein of the invention is useful as are fragments particularly epitope containing fragments e.g. antigenic or immunogenic fragments thereof and derivatives thereof. Epitope containing fragments including antigenic or immunogenic fragments will typically be of length 12 amino acids or more e.g. 20 amino acids or more e.g. 50 or 100 amino acids or more. Fragments may be 95% or more of the length of the full protein e.g. 90% or more e.g. 75% or 50% or 25% or 10% or more of the length of the full protein.

Epitope containing fragments including antigenic or immunogenic fragments will be capable of eliciting a relevant immune response in a patient, for example when presented to the immune system in an appropriate form such as in a formulation containing one or more adjuvants. DNA encoding the protein of the invention is also useful as are fragments thereof e.g. DNA encoding fragments of the protein of the invention such as immunogenic fragments thereof. Fragments of nucleic acid (e.g. DNA) encoding the protein of the invention may be 95% or more of the length of the full coding region e.g. 90% or more e.g. 75% or 50% or 25% or 10% or more of the length of the full coding region. Fragments of nucleic acid (e.g. DNA) may be 36 nucleotides or more e.g. 60 nucleotides or more e.g. 150 or 300 nucleotides or more in length.

Derivatives of the protein of the invention include variants on the sequence in which one or more (e.g. 1-20 such as 15 amino acids, or up to 20% such as up to 10% or 5% or 1% by number of amino acids based on the total length of the protein) deletions, insertions or substitutions have been made. Substitutions may typically be conservative substitutions. Derivatives will typically have essentially the same biological function as the protein from which they are derived. Derivatives will typically be comparably antigenic or immunogenic to the protein from which they are derived. Derivatives will typically have either the ligand-binding activity, or the active receptor-complex forming ability, or preferably both, of the protein from which they are derived.

Tables 1a-1f below illustrates the different occurrences of OGTA076 as detected by iTRAQ and mass spectrometry of membrane protein extracts of colorectal, kidney, liver, lung and ovarian tissue samples from colorectal cancer, kidney cancer, liver cancer, non-small cell lung cancer, small cell lung cancer and ovarian cancer patients respectively. The first column provides the samples batch number, the second column gives the iTRAQ experiment number for those samples and the last column provides a list of the sequences observed by mass spectrometry and the corresponding SEQ ID Nos.

Table 2a-2c below illustrates the different occurrences of OGTA076 as detected by 1D gel electrophoresis and mass spectrometry of membrane protein extracts of colorectal, lymphoid and pancreatic tissue samples from colorectal cancer, chronic lymphocytic leukaemia and pancreatic cancer patients respectively. The first column provides the molecular weight, the second column gives information on the subfractionation protocol used, if any (see Example 1 below), and the last column provides a list of the sequences observed by mass spectrometry and the corresponding SEQ ID Nos.

TABLE 1a

Colorectal cancer iTRAQ

| Samples batch no. | Experiment no. | Tryptics identified [SEQ ID No] |
|---|---|---|
| Samples 1 | Experiment 1 | EGIAK [14], IIPK [28], LALK [35], LNPK [40] |
| Samples 1 | Experiment 2 | EGIAK [14], LALK [35] |
| Samples 1 | Experiment 3 | EGIAK [14], IIPK [28], LALK [35] |
| Samples 1 | Experiment 4 | LNPK [40] |

TABLE 1b

Kidney cancer iTRAQ

| Sample no. | Experiment no. | Tryptics identified [SEQ ID No] |
|---|---|---|
| Samples 1 | Experiment 1 | EGIAK [14], LALK [35], LNPK [40], YLNNLYK [66] |
| Samples 1 | Experiment 2 | LALK [35] |

TABLE 1c

Liver cancer iTRAQ

| Sample no. | Experiment no. | Tryptics identified [SEQ ID No] |
|---|---|---|
| Samples 1 | Experiment 1 | YLNNLYK [66] |

TABLE 1d

Non-small cell lung cancer iTRAQ

| Sample no. | Experiment no. | Tryptics identified [SEQ ID No] |
|---|---|---|
| Samples 1 | Experiment 1 | YLNNLYK [66] |
| Samples 1 | Experiment 2 | LALK [35] |
| Samples 2 | Experiment 1 | IIPK [28], LALK [35], YLNNLYK [66] |
| Samples 2 | Experiment 2 | YLNNLYK [66] |

TABLE 1e

Small cell lung cancer iTRAQ

| Sample no. | Experiment no. | Tryptics identified [SEQ ID No] |
|---|---|---|
| Samples 1 | Experiment 1 | EGIAK [14] |
| Samples 1 | Experiment 2 | EGIAK [14] |

TABLE 1f

Ovarian cancer iTRAQ

| Sample no. | Experiment no. | Tryptics identified [SEQ ID No] |
|---|---|---|
| Samples 1 | Experiment 1 | LALK [35] |
| Samples 1 | Experiment 2 | LALK [35], YLNNLYK [66] |
| Samples 1 | Experiment 3 | LALK [35] |

TABLE 2a

Colorectal cancer 1D gel

| MW (Da) | Subfractionation | Tryptics identified [SEQ ID No] |
|---|---|---|
| 167535 | | CLGLDITK [7], DGAICYKPTK [9], DVDSCGEYNWATVGGRRR [11], EEVWIGLK [12], ENNNITMR [16], EVKPVDSVK [17], GWHFYDDR [21], HDHSATIVSIK [22], HFVSLCQK [23], HGETCYK [24], IPENFFEEESR [29], KYFWTGLR [34], LNDASSDK [39], LPFICEK [41], MCPPDEGWKR [42], MFSCDSSAMLWWK [43], NNSLMWFDK [45], QTLQNASETVK [47], RHGETCYK [49], TLTWHSAK [56], TPDWYNPDR [57] |

TABLE 2b

Chronic lymphocytic leukaemia 1D gel

| MW (Da) | Subfractionation | Tryptics identified [SEQ ID No] |
|---|---|---|
| 198008 | | AANDPFTIVHGNTGK [4], CSMLIASNETWKK [8], DGAICYKPTK [9], ELTYSNFHPLLVSGR [15], FEQEYLNDLMK [18], GWHFYDDR [21], HDHSATIVSIK [22], HMATTQDEVHTK [25], IPENFFEEESR [29], ISEWPIDDHFTYSR [30], KYFWTGLR [34], LFHLHSQK [36], NWEEAER [46], RGWHFYDDR [48], SHILSIR [53], SPDLQGSWQWSDR [55], TPLSYTHWR [58], TPVSTIIMPNEFQQDYDIR [59], VFHRPWR [61], VQCSEQWIPFQNK [63], WVSQHR [64], YFWTGLR [65] |
| 223568 | | AANDPFTIVHGNTGK [4], DGAICYKPTK [9], GWHFYDDR [21], HDHSATIVSIK [22], HFVSLCQK [23], HMATTQDEVHTK [25], IPENFFEEESR [29], KVECEHGFGR [33], LFHLHSQK [36], LHNEDIK [38], NWEEAER [46], SDQALHSFSEAK [52], SHILSIR [53], SNFHPLLVSGR [54], TPLSYTHWR [58], VFHRPWR [61], VQCSEQWIPFQNK [63], WVSQHR [64], YLNNLYK [66] |
| 238644 | | CEHHSLYGAAR [6], CLGLDITK [7], IEMVDYK [27], IPENFFEEESR [29], KGNCEVSSVEGTLCK [31], KVECEHGFGR [33], LFHLHSQK [36], LHNEDIK [38], RGWHFYDDR [48], RLHFSR [50], RNWEEAER [51], SDQALHSFSEAK [52], SHILSIR [53], TPLSYTHWR [58], VECEHGFGR [60], YFWTGLR [65], YLNNLYK [66] |

TABLE 2c

Pancreatic cancer 1D gel

| MW (Da) | Subfractionation | Tryptics identified [SEQ ID No] |
|---|---|---|
| 161314 | | DGAICYKPTK [9], EFIYLRPFACDTK [13], FPVTFGEECLYMSAK [19], GWHFYDDR [21], HFVSLCQK [23], IPENFFEEESR [29], ISEWPIDDHFTYSR [30], KRNWEEAER [32], NNSLMWFDK [45], RGWHFYDDR [48], RHGETCYK [49], SNFHPLLVSGR [54], SPDLQGSWQWSDR [55], TLTWHSAK [56], TPDWYNPDR [57], TPLSYTHWR [58], VQCSEQWIPFQNK [63], WVSQHR [64] |
| 168430 | | DGAICYKPTK [9], EEVWIGLK [12], EFIYLRPFACDTK [13], FEQEYLNDLMK [18], FPVTFGEECLYMSAK [19], GWHFYDDR [21], HFVSLCQK [23], IANISGDGQK [26], IPENFFEEESR [29], ISEWPIDDHFTYSR [30], KRNWEEAER [32], KYFWTGLR [34], MSGPLGPEEASPK [44], NNSLMWFDK [45], RGWHFYDDR [48], RHGETCYK [49], SDQALHSFSEAK [52], SHILSIR [53], SPDLQGSWQWSDR [55], TPDWYNPDR [57], TPLSYTHWR [58], TPVSTIIMPNEFQQDYDIR [59], VECEHGFGR [60], VFHRPWR [61], VIEEAVYFHQH [62], VQCSEQWIPFQNK [63], WVSQHR [64], YFWTGLR [65] |
| 176135 | | DGAICYKPTK [9], EEVWIGLK [12], FEQEYLNDLMK [18], FPVTFGEECLYMSAK [19], GNCEVSSVEGTLCK [20], GWHFYDDR [21], HMATTQDEVHTK [25], IANISGDGQK [26], IPENFFEEESR [29], ISEWPIDDHFTYSR [30], LHLAGFSSVR [37], NNSLMWFDK [45], RNWEEAER [51], SDQALHSFSEAK [52], SPDLQGSWQWSDR [55], TPDWYNPDR [57], TPLSYTHWR [58], VECEHGFGR [60], VFHRPWR [61], VQCSEQWIPFQNK [63], WVSQHR [64], YFWTGLR [65] |
| 207419 | | AFSSDLISIHSLADVEVVVTK [5], CLGLDITK [7], DVDSCGEYNWATVGGRRR [11], EEVWIGLK [12], FEQEYLNDLMK [18], FPVTFGEECLYMSAK [19], HMATTQDEVHTK [25], IPENFFEEESR [29], RGWHFYDDR [48], RHGETCYK [49], SHILSIR [53], TLTWHSAK [56] |

TABLE 2c-continued

Pancreatic cancer 1D gel

| MW (Da) | Subfractionation | Tryptics identified [SEQ ID No] |
|---|---|---|
| 261976 | | AFSSDLISIHSLADVEVVVTK [5], DGAICYKPTK [9], DGHGTAISNASDVWKK [10], DVDSCGEYNWATVGGRRR [11], EEVWIGLK [12], EFIYLRPFACDTK [13], FEQEYLNDLMK [18], FPVTFGEECLYMSAK [19], GWHFYDDR [21], HMATTQDEVHTK [25], IPENFFEEESR [29], ISEWPIDDHFTYSR [30], LHLAGFSSVR [37], RGWHFYDDR [48], SPDLQGSWQWSDR [55], TPLSYTHWR [58], TPVSTIIMPNEFQQDYDIR [59], VFHRPWR [61], VIEEAVYFHQH [62], YFWTGLR [65] |

For OGTA076, the detected level obtained upon analyzing tissue from subjects having colorectal cancer, kidney cancer, liver cancer, lung cancer, lymphoid leukaemia (particularly chronic lymphocytic leukaemia), ovarian cancer or pancreatic cancer relative to the detected level obtained upon analyzing tissue from subjects free from colorectal cancer, kidney cancer, liver cancer, lung cancer, lymphoid leukaemia (particularly chronic lymphocytic leukaemia), ovarian cancer and pancreatic cancer will depend upon the particular analytical protocol and detection technique that is used. Accordingly, the present invention contemplates that each laboratory will establish a reference range in subjects free from colorectal cancer, kidney cancer, liver cancer, lung cancer, lymphoid leukaemia (particularly chronic lymphocytic leukaemia), ovarian cancer and pancreatic cancer according to the analytical protocol and detection technique in use, as is conventional in the diagnostic art. Preferably, at least one control positive tissue sample from a subject known to have colorectal cancer, kidney cancer, liver cancer, lung cancer, lymphoid leukaemia (particularly chronic lymphocytic leukaemia), ovarian cancer or pancreatic cancer or at least one control negative tissue sample from a subject known to be free from colorectal cancer, kidney cancer, liver cancer, lung cancer, lymphoid leukaemia (particularly chronic lymphocytic leukaemia), ovarian cancer and pancreatic cancer (and more preferably both positive and negative control samples) are included in each batch of test samples analysed.

OGTA076 can be used for detection, prognosis, diagnosis, or monitoring of colorectal cancer, kidney cancer, liver cancer, lung cancer, lymphoid leukaemia (particularly chronic lymphocytic leukaemia), ovarian cancer or pancreatic cancer or for drug development. In one embodiment of the invention, tissue from a subject (e.g. a subject suspected of having colorectal cancer, kidney cancer, liver cancer, lung cancer, lymphoid leukaemia (particularly chronic lymphocytic leukaemia), ovarian cancer or pancreatic cancer) is analysed by 1D gel electrophoresis or iTRAQ for detection of OGTA076. An increased abundance of OGTA076 in the tissue from the subject relative to tissue from a subject or subjects free from colorectal cancer, kidney cancer, liver cancer, lung cancer, lymphoid leukaemia (particularly chronic lymphocytic leukaemia), ovarian cancer and pancreatic cancer (e.g. a control sample) or a previously determined reference range indicates the presence of colorectal cancer, kidney cancer, liver cancer, lung cancer, lymphoid leukaemia (particularly chronic lymphocytic leukaemia), ovarian cancer or pancreatic cancer.

In relation to fragments, epitope containing fragments, immunogenic fragments or antigenic fragments of OGTA076:

for colorectal cancer applications, these may comprise the sequences identified as tryptic sequences in the 3$^{rd}$ column of Table 1a or the 3$^{rd}$ column of Table 2a;

for kidney cancer applications, these may comprise the sequences identified as tryptic sequences in the 3$^{rd}$ column of Table 1b;

for liver cancer applications, these may comprise the sequences identified as tryptic sequences in the 3$^{rd}$ column of Table 1c;

for non-small cell lung cancer applications, these may comprise the sequences identified as tryptic sequences in the 3$^{rd}$ column of Table 1d;

for small cell lung cancer applications, these may comprise the sequences identified as tryptic sequences in the 3$^{rd}$ column of Table 1e;

for ovarian cancer applications, these may comprise the sequences identified as tryptic sequences in the 3$^{rd}$ column of Table 1f;

for chronic lymphocytic leukaemia applications, these may comprise the sequences identified as tryptic sequences in the 3$^{rd}$ column of Table 2b;

for pancreatic cancer applications, these may comprise the sequences identified as tryptic sequences in the 3$^{rd}$ column of Table 2c.

As used herein, OGTA076 is "isolated" when it is present in a preparation that is substantially free of contaminating proteins, i.e. a preparation in which less than 10% (for example less than 5%, such as less than 1%) of the total protein present is contaminating protein(s). A contaminating protein is a protein having a significantly different amino acid sequence from that of isolated OGTA076, as determined by mass spectral analysis. As used herein, a "significantly different" sequence is one that permits the contaminating protein to be resolved from OGTA076 by mass spectral analysis, performed according to the Reference Protocols.

OGTA076 can be assayed by any method known to those skilled in the art, including but not limited to, the Preferred Technologies described herein, kinase assays, enzyme assays, binding assays and other functional assays, immunoassays, and western blotting. In one embodiment, OGTA076 is separated on a 1-D gel by virtue of its MW and visualized by staining the gel. In one embodiment, OGTA076 is stained with a fluorescent dye and imaged with a fluorescence scanner. Sypro Red (Molecular Probes, Inc., Eugene, Oreg.) is a suitable dye for this purpose. A preferred fluorescent dye is disclosed in U.S. application Ser. No. 09/412,168, filed on Oct. 5, 1999, which is incorporated herein by reference in its entirety. In another embodiment, OGTA076 is analysed using isobaric tags for relative and absolute quantification (iTRAQ).

Alternatively, OGTA076 can be detected in an immunoassay. In one embodiment, an immunoassay is performed by contacting a sample from a subject to be tested with an anti-OGTA076 antibody (or other affinity reagent) under conditions such that binding (e.g. immunospecific binding) can occur if OGTA076 is present, and detecting or measuring the amount of any binding (e.g. immunospecific binding) by the agent. OGTA076 binding agents can be produced by the methods and techniques taught herein.

OGTA076 may be detected by virtue of the detection of a fragment thereof e.g. an epitope containing (e.g. an immunogenic or antigenic) fragment thereof. Fragments may have a length of at least 10, more typically at least 20 amino acids e.g. at least 50 or 100 amino acids e.g. at least 200 or 500 amino acids e.g. at least 1000 or 1500 amino acids.

In one or more embodiments OGTA076 is differentially expressed in patients/subjects with colorectal cancer, kidney cancer, liver cancer, lung cancer, lymphoid leukaemia (particularly chronic lymphocytic leukaemia), ovarian cancer or pancreatic cancer. Differentially expressed is intended to refer to a higher or lower level of expression in a relevant sample in comparison to cancer free/healthy sample.

In one embodiment, binding of an affinity reagent (e.g. an antibody) in tissue sections can be used to detect aberrant OGTA076 localization or an aberrant level of OGTA076. In a specific embodiment, an antibody (or other affinity reagent) to OGTA076 can be used to assay a patient tissue (e.g. a colorectal, kidney, liver, lung, lymphoid, ovarian or pancreatic tissue) for the level of OGTA076 where an aberrant level of OGTA076 is indicative of colorectal cancer, kidney cancer, liver cancer, lung cancer, lymphoid leukaemia (particularly chronic lymphocytic leukaemia), ovarian cancer or pancreatic cancer. As used herein, an "aberrant level" means a level that is increased compared with the level in a subject free from colorectal cancer, kidney cancer, liver cancer, lung cancer, lymphoid leukaemia (particularly chronic lymphocytic leukaemia), ovarian cancer and pancreatic cancer or a reference level.

Any suitable immunoassay can be used, including, without limitation, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

For example, OGTA076 can be detected in a fluid sample (e.g. blood, urine, or saliva) by means of a two-step sandwich assay. In the first step, a capture reagent (e.g. an anti-OGTA076 antibody or other affinity reagent) is used to capture OGTA076. The capture reagent can optionally be immobilized on a solid phase. In the second step, a directly or indirectly labeled detection reagent is used to detect the captured OGTA076. In one embodiment, the detection reagent is a lectin. Any lectin can be used for this purpose that, for example binds to OGTA076 rather than to other isoforms that have the same core protein as OGTA076 or to other proteins that share the antigenic determinant recognized by the antibody. In a preferred embodiment, the chosen lectin binds OGTA076 with at least 2-fold greater affinity, more preferably at least 5-fold greater affinity, still more preferably at least 10-fold greater affinity, than to said other isoforms that have the same core protein as OGTA076 or to said other proteins that share the antigenic determinant recognized by the affinity reagent. Based on the present description, a lectin that is suitable for detecting OGTA076 can readily be identified by methods well known in the art, for instance upon testing one or more lectins enumerated in Table I on pages 158-159 of Sumar et al., Lectins as Indicators of Disease-Associated Glycoforms, In: Gabius H-J & Gabius S (eds.), 1993, Lectins and Glycobiology, at pp. 158-174 (which is incorporated herein by reference in its entirety). In an alternative embodiment, the detection reagent is an antibody (or other affinity reagent), e.g. an antibody that specifically (e.g. immunospecifically) detects other post-translational modifications, such as an antibody that immunospecifically binds to phosphorylated amino acids. Examples of such antibodies include those that bind to phosphotyrosine (BD Transduction Laboratories, catalog nos.: P11230-050/P11230-150; P11120; P38820; P39020), those that bind to phosphoserine (Zymed Laboratories Inc., South San Francisco, Calif., catalog no. 61-8100) and those that bind to phosphothreonine (Zymed Laboratories Inc., South San Francisco, Calif., catalogue nos. 71-8200, 13-9200).

If desired, a gene encoding OGTA076, a related gene, or related nucleic acid sequences or subsequences, including complementary sequences, can also be used in hybridization assays. A nucleotide encoding OGTA076, or subsequences thereof comprising at least 8 nucleotides, for example at least 12 nucleotides, such as at least 15 nucleotides can be used as a hybridization probe. Hybridization assays can be used for detection, prognosis, diagnosis, or monitoring of conditions, disorders, or disease states, associated with aberrant expression of the gene encoding OGTA076, or for differential diagnosis of subjects with signs or symptoms suggestive of colorectal cancer, kidney cancer, liver cancer, lung cancer, lymphoid leukaemia (particularly chronic lymphocytic leukaemia), ovarian cancer or pancreatic cancer. In particular, such a hybridization assay can be carried out by a method comprising contacting a subject's sample containing nucleic acid with a nucleic acid probe capable of hybridizing to a DNA or RNA that encodes OGTA076, under conditions such that hybridization can occur, and detecting or measuring any resulting hybridization.

Hence nucleic acid encoding OGTA076 (e.g. DNA or more suitably RNA) may be detected, for example, using a hybridizing agent capable of hybridizing to nucleic acid encoding OGTA076.

One such exemplary method comprises:
(a) contacting one or more oligonucleotide probes comprising 10 or more consecutive nucleotides complementary to a nucleotide sequence encoding OGTA076, with an RNA obtained from a biological sample from the subject or with cDNA copied from the RNA, wherein said contacting occurs under conditions that permit hybridization of the probe to the nucleotide sequence if present;
(b) detecting hybridization, if any, between the probe and the nucleotide sequence; and
(c) comparing the hybridization, if any, detected in step (b) with the hybridization detected in a control sample, or with a previously determined reference range.

The invention also provides diagnostic kits, comprising an anti-OGTA076 antibody (or other affinity reagent). In addition, such a kit may optionally comprise one or more of the following: (1) instructions for using the anti-OGTA076 affinity reagent for diagnosis, prognosis, therapeutic monitoring or any combination of these applications; (2) a labeled binding partner to the affinity reagent; (3) a solid phase (such as a reagent strip) upon which the anti-OGTA076 affinity reagent is immobilized; and (4) a label or insert indicating regulatory approval for diagnostic, prognostic or therapeutic use or any combination thereof. If no labeled binding partner to the affinity reagent is provided, the anti-OGTA076 affinity reagent itself can be labeled with a detectable marker, e.g. a chemiluminescent, enzymatic, fluorescent, or radioactive moiety.

The invention also provides a kit comprising a nucleic acid probe capable of hybridizing to nucleic acid, suitably RNA, encoding OGTA076. In a specific embodiment, a kit comprises in one or more containers a pair of primers (e.g. each in the size range of 6-30 nucleotides, more preferably 10-30 nucleotides and still more preferably 10-20 nucleotides) that under appropriate reaction conditions can prime amplification of at least a portion of a nucleic acid encoding OGTA076, such as by polymerase chain reaction (see, e.g. Innis et al., 1990, PCR Protocols, Academic Press, Inc., San Diego, Calif.), ligase chain reaction (see EP 320,308) use of Qβ replicase, cyclic probe reaction, or other methods known in the art.

A kit can optionally further comprise a predetermined amount of OGTA076 or a nucleic acid encoding OGTA076, e.g. for use as a standard or control.

Use in Clinical Studies

The diagnostic methods and compositions of the present invention can assist in monitoring a clinical study, e.g. to evaluate drugs for therapy of colorectal cancer, kidney cancer, liver cancer, lung cancer, lymphoid leukaemia (particularly chronic lymphocytic leukaemia), ovarian cancer or pancreatic cancer. In one embodiment, candidate molecules are tested for their ability to restore OGTA076 levels in a subject having colorectal cancer, kidney cancer, liver cancer, lung cancer, lymphoid leukaemia (particularly chronic lymphocytic leukaemia), ovarian cancer or pancreatic cancer to levels found in subjects free from colorectal cancer, kidney cancer, liver cancer, lung cancer, lymphoid leukaemia (particularly chronic lymphocytic leukaemia), ovarian cancer and pancreatic cancer or, in a treated subject, to preserve OGTA076 levels at or near non-colorectal cancer, non-kidney cancer, non-liver cancer, non-lung cancer, non-lymphoid leukaemia (particularly chronic lymphocytic leukaemia), non-ovarian cancer or non-pancreatic cancer values.

In another embodiment, the methods and compositions of the present invention are used to screen candidates for a clinical study to identify individuals having colorectal cancer, kidney cancer, liver cancer, lung cancer, lymphoid leukaemia (particularly chronic lymphocytic leukaemia), ovarian cancer or pancreatic cancer; such individuals can then be excluded from the study or can be placed in a separate cohort for treatment or analysis.

Production of Protein of the Invention and Corresponding Nucleic Acid

A DNA of the present invention can be obtained by isolation as a cDNA fragment from cDNA libraries using as starter materials commercial mRNAs and determining and identifying the nucleotide sequences thereof. That is, specifically, clones are randomly isolated from cDNA libraries, which are prepared according to Ohara et al's method (DNA Research Vol. 4, 53-59 (1997)). Next, through hybridization, duplicated clones (which appear repeatedly) are removed and then in vitro transcription and translation are carried out. Nucleotide sequences of both termini of clones, for which products of 50 kDa or more are confirmed, are determined. Furthermore, databases of known genes are searched for homology using the thus obtained terminal nucleotide sequences as queries. The entire nucleotide sequence of a clone revealed to be novel as a result is determined. In addition to the above screening method, the 5' and 3' terminal sequences of cDNA are related to a human genome sequence. Then an unknown long-chain gene is confirmed in a region between the sequences, and the full-length of the cDNA is analyzed. In this way, an unknown gene that is unable to be obtained by a conventional cloning method that depends on known genes can be systematically cloned.

Moreover, all of the regions of a human-derived gene containing a DNA of the present invention can also be prepared using a PCR method such as RACE while paying sufficient attention to prevent artificial errors from taking place in short fragments or obtained sequences. As described above, clones having DNA of the present invention can be obtained.

In another means for cloning DNA of the present invention, a synthetic DNA primer having an appropriate nucleotide sequence of a portion of a polypeptide of the present invention is produced, followed by amplification by the PCR method using an appropriate library. Alternatively, selection can be carried out by hybridization of the DNA of the present invention with a DNA that has been incorporated into an appropriate vector and labeled with a DNA fragment or a synthetic DNA encoding some or all of the regions of the polypeptide of the present invention. Hybridization can be carried out by, for example, the method described in Current Protocols in Molecular Biology (edited by Frederick M. Ausubel et al., 1987). DNA of the present invention may be any DNA, as long as they contain nucleotide sequences encoding the polypeptides of the present invention as described above. Such a DNA may be a cDNA identified and isolated from cDNA libraries or the like that are derived from colorectal, kidney, liver, lung, lymphoid, ovarian or pancreatic tissue. Such a DNA may also be a synthetic DNA or the like. Vectors for use in library construction may be any of bacteriophages, plasmids, cosmids, phagemids, or the like. Furthermore, by the use of a total RNA fraction or a mRNA fraction prepared from the above cells and/or tissues, amplification can be carried out by a direct reverse transcription coupled polymerase chain reaction (hereinafter abbreviated as "RT-PCR method").

DNA encoding the above polypeptide consisting of an amino acid sequence that is substantially identical to the amino acid sequence of OGTA076 or DNA encoding the above polypeptide consisting of an amino acid sequence derived from the amino acid sequence of OGTA076 by deletion, substitution, or addition of one or more amino acids composing a portion of the amino acid sequence can be easily produced by an appropriate combination of, for example, a site-directed mutagenesis method, a gene homologous recombination method, a primer elongation method, and the PCR method known by persons skilled in the art. In addition, at this time, a possible method for causing a polypeptide to have substantially equivalent biological activity is substitution of homologous amino acids (e.g. polar and nonpolar amino acids, hydrophobic and hydrophilic amino acids, positively-charged and negatively charged amino acids, and aromatic amino acids) among amino acids composing the polypeptide. Furthermore, to maintain substantially equivalent biological activity, amino acids within functional domains contained in the polypeptide of the present invention are preferably conserved.

Furthermore, examples of DNA of the present invention include DNA comprising a nucleotide sequence that encodes the amino acid sequence of OGTA076 and DNA hybridizing under stringent conditions to the DNA and encoding a polypeptide (protein) having biological activity (function) equivalent to the function of the polypeptide consisting of the amino acid sequence of OGTA076. Under such conditions, an example of such DNA capable of hybridizing to DNA comprising the nucleotide sequence that encodes the amino acid sequence of OGTA076 is DNA comprising a nucleotide sequence that has a degree of overall mean homology with the entire nucleotide sequence of the DNA, such as approximately 80% or more, preferably approximately 90% or more, and more preferably approximately 95% or more. Hybridization can be carried out according to a method known in the art such as a method described in Current Protocols in Molecular Biology (edited by Frederick M. Ausubel et al., 1987) or a method according thereto. Here, "stringent conditions" are, for example, conditions of approximately "1*SSC, 0.1% SDS, and 37° C., more stringent conditions of approximately "0.5*SSC, 0.1% SDS, and 42° C., or even more stringent conditions of approximately "0.2*SSC, 0.1% SDS, and 65° C. With more stringent hybridization conditions, the isolation of a DNA having high homology with a probe sequence can be expected. The above combinations of SSC, SDS, and temperature conditions are given for illustrative purposes. Stringency similar to the above can be achieved by persons skilled in the art using an appropriate combination of the above factors or other factors (for example, probe concentration, probe length, and reaction time for hybridization) for determination of hybridization stringency.

A cloned DNA of the present invention can be directly used or used, if desired, after digestion with a restriction enzyme or addition of a linker, depending on purposes. The DNA may have ATG as a translation initiation codon at the 5' terminal side and have TAA, TGA, or TAG as a translation termination codon at the 3' terminal side. These translation initiation and translation termination codons can also be added using an appropriate synthetic DNA adapter.

Where it is provided for use with the methods of the invention OGTA076 may, for example be provided in isolated form. In one embodiment the OGTA076 polypeptide has been purified to at least to some extent. OGTA076 polypeptide may be provided in substantially pure form, that is to say free, to a substantial extent, from other proteins. OGTA076 polypeptide can also be produced using recombinant methods, synthetically produced or produced by a combination of these methods. OGTA076 can be easily prepared by any method known by persons skilled in the art, which involves producing an expression vector containing a DNA of the present invention or a gene containing a DNA of the present invention, culturing a transformant transformed using the expression vector, generating and accumulating a polypeptide of the present invention or a recombinant protein containing the polypeptide, and then collecting the resultant.

Recombinant OGTA076 polypeptide may be prepared by processes well known in the art from genetically engineered host cells comprising expression systems. Accordingly, the present invention also relates to expression systems which comprise an OGTA076 polypeptide or nucleic acid, to host cells which are genetically engineered with such expression systems and to the production of OGTA076 polypeptide by recombinant techniques. For recombinant OGTA076 polypeptide production, host cells can be genetically engineered to incorporate expression systems or portions thereof for nucleic acids. Such incorporation can be performed using methods well known in the art, such as, calcium phosphate transfection, DEAD-dextran mediated transfection, transvection, microinjection, cationic lipid-mediated transfection, electroporation, transduction, scrape loading, ballistic introduction or infection (see e.g. Davis et al., Basic Methods in Molecular Biology, 1986 and Sambrook et al., Molecular Cloning: A Laboratory Manual, 2nd Ed., Cold Spring Harbour laboratory Press, Cold Spring Harbour, N.Y., 1989).

As host cells, for example, bacteria of the genus *Escherichia, Streptococci, Staphylococci, Streptomyces*, bacteria of the genus *Bacillus*, yeast, *Aspergillus* cells, insect cells, insects, and animal cells are used. Specific examples of bacteria of the genus *Escherichia*, which are used herein, include *Escherichia coli* K12 and DH1 (Proc. Natl. Acad. Sci. U.S.A., Vol. 60, 160 (1968)), JM103 (Nucleic Acids Research, Vol. 9, 309 (1981)), JA221 (Journal of Molecular Biology, Vol. 120, 517 (1978)), and HB101 (Journal of Molecular Biology, Vol. 41, 459 (1969)). As bacteria of the genus *Bacillus*, for example, *Bacillus subtilis* MI114 (Gene, Vol. 24, 255 (1983)) and 207-21 (Journal of Biochemistry, Vol. 95, 87 (1984)) are used. As yeast, for example, *Saccaromyces cerevisiae* AH22, AH22R-, NA87-11A, DKD-5D, and 20B-12, *Schizosaccaromyces pombe* NCYC1913 and NCYC2036, and *Pichia pastoris* are used. As insect cells, for example, *Drosophila* S2 and *Spodoptera* Sf9 cells are used. As animal cells, for example, COS-7 and Vero monkey cells, CHO Chinese hamster cells (hereinafter abbreviated as CHO cells), dhfr-gene-deficient CHO cells, mouse L cells, mouse AtT-20 cells, mouse myeloma cells, rat GH3 cells, human FL cells, COS, HeLa, C127, 3T3, HEK 293, BHK and Bowes melanoma cells are used.

Cell-free translation systems can also be employed to produce recombinant polypeptides (e.g. rabbit reticulocyte lysate, wheat germ lysate, SP6/T7 in vitro T&T and RTS 100 *E. Coli* HY transcription and translation kits from Roche Diagnostics Ltd., Lewes, UK and the TNT Quick coupled Transcription/Translation System from Promega UK, Southampton, UK).

The expression vector can be produced according to a method known in the art. For example, the vector can be produced by (1) excising a DNA fragment containing a DNA of the present invention or a gene containing a DNA of the present invention and (2) ligating the DNA fragment downstream of the promoter in an appropriate expression vector. A wide variety of expression systems can be used, such as and without limitation, chromosomal, episomal and virus-derived systems, e.g. plasmids derived from *Escherichia coli* (e.g. pBR322, pBR325, pUC18, and pUC118), plasmids derived from *Bacillus subtilis* (e.g. pUB110, pTP5, and pC194), from bacteriophage, from transposons, from yeast episomes (e.g. pSH19 and pSH15), from insertion elements, from yeast chromosomal elements, from viruses such as baculoviruses, papova viruses such as SV40, vaccinia viruses, adenoviruses, fowl pox viruses, pseudorabies viruses and retroviruses, and vectors derived from combinations thereof, such as those derived from plasmid and bacteriophage (such as [lambda] phage) genetic elements, such as cosmids and phagemids. The expression systems may contain control regions that regulate as well as engender expression. Promoters to be used in the present invention may be any promoters as long as they are appropriate for hosts to be used for gene expression. For example, when a host is *Escherichia coli*, a trp promoter, a lac promoter, a recA promoter, a pL promoter, an lpp promoter, and the like are preferred. When a host is *Bacillus subtilis*, an SPO1 promoter, an SPO2 promoter, a penP promoter, and the like are preferred. When a host is yeast, a PHO5 promoter, a PGK promoter, a GAP promoter, an ADH promoter, and the like are preferred. When an animal cell is used as a host, examples of promoters for use in this case include an SRa promoter, an SV40 promoter, an LTR promoter, a CMV promoter, and an HSV-TK promoter. Generally, any system or vector that is able to maintain, propagate or express a nucleic acid to produce a polypeptide in a host may be used.

The appropriate nucleic acid sequence may be inserted into an expression system by any variety of well known and routine techniques, such as those set forth in Sambrook et al., supra. Appropriate secretion signals may be incorporated into the OGTA076 polypeptide to allow secretion of the translated protein into the lumen of the endoplasmic reticulum, the periplasmic space or the extracellular environment. These signals may be endogenous to the OGTA076 polypeptide or they may be heterologous signals. Transformation of the host cells can be carried out according to methods known in the art. For example, the following documents can be referred to: Proc. Natl. Acad. Sci. U.S.A., Vol. 69, 2110 (1972); Gene, Vol. 17, 107 (1982); Molecular & General Genetics, Vol. 168, 111 (1979); Methods in Enzymology, Vol. 194, 182-187 (1991); Proc. Natl. Acad. Sci. U.S.A.), Vol. 75, 1929 (1978); Cell Technology, separate volume 8, New Cell Technology, Experimental Protocol. 263-267 (1995) (issued by Shujunsha); and Virology, Vol. 52, 456 (1973). The thus obtained transformant transformed with an expression vector containing a DNA of the present invention or a gene containing a DNA of the present invention can be cultured according to a method known in the art. For example, when hosts are bacteria of the genus *Escherichia*, the bacteria are generally cultured at approximately 15° C. to 43° C. for approximately 3 to 24 hours. If necessary, aeration or agitation can also be added. When hosts are bacteria of the genus *Bacillus*, the bacteria are generally cultured at approximately 30° C. to 40° C. for approximately 6 to 24 hours. If necessary, aeration or agitation can also be added. When transformants whose hosts are yeast are cultured, culture is generally carried out at approximately 20° C. to 35° C. for approximately 24 to 72 hours using media with pH adjusted to be approximately 5 to 8. If necessary, aeration or agitation can also be added. When transformants whose hosts are animal cells are cultured, the cells are generally cultured at approximately 30° C. to 40° C. for approximately 15 to 60 hours using media with the pH adjusted to be approximately 6 to 8. If necessary, aeration or agitation can also be added.

If an OGTA076 polypeptide is to be expressed for use in cell-based screening assays, it is preferred that the polypeptide be produced at the cell surface. In this event, the cells may be harvested prior to use in the screening assay. If the OGTA076 polypeptide is secreted into the medium, the medium can be recovered in order to isolate said polypeptide. If produced intracellularly, the cells must first be lysed before the OGTA076 polypeptide is recovered.

OGTA076 polypeptide can be recovered and purified from recombinant cell cultures or from other biological sources by well known methods including, ammonium sulphate or ethanol precipitation, acid extraction, anion or cation exchange chromatography, phosphocellulose chromatography, affinity chromatography, hydrophobic interaction chromatography, hydroxylapatite chromatography, molecular sieving chromatography, centrifugation methods, electrophoresis methods and lectin chromatography. In one embodiment, a combination of these methods is used. In another embodiment, high performance liquid chromatography is used. In a further embodiment, an antibody which specifically binds to an OGTA076 polypeptide can be used to deplete a sample comprising an OGTA076 polypeptide of said polypeptide or to purify said polypeptide.

To separate and purify a polypeptide or a protein of the present invention from the culture products, for example, after culture, microbial bodies or cells are collected by a known method, they are suspended in an appropriate buffer, the microbial bodies or the cells are disrupted by, for example, ultrasonic waves, lysozymes, and/or freeze-thawing, the resultant is then subjected to centrifugation or filtration, and then a crude extract of the protein can be obtained. The buffer may also contain a protein denaturation agent such as urea or guanidine hydrochloride or a surfactant such as Triton X-100™. When the protein is secreted in a culture solution, microbial bodies or cells and a supernatant are separated by a known method after the completion of culture and then the supernatant is collected. The protein contained in the thus obtained culture supernatant or the extract can be purified by an appropriate combination of known separation and purification methods. The thus obtained polypeptide (protein) of the present invention can be converted into a salt by a known method or a method according thereto. Conversely, when the polypeptide (protein) of the present invention is obtained in the form of a salt, it can be converted into a free protein or peptide or another salt by a known method or a method according thereto. Moreover, an appropriate protein modification enzyme such as trypsin or chymotrypsin is caused to act on a protein produced by a recombinant before or after purification, so that modification can be arbitrarily added or a polypeptide can be partially removed. The presence of a polypeptide (protein) of the present invention or a salt thereof can be measured by various binding assays, enzyme immunoassays using specific antibodies, and the like.

Techniques well known in the art may be used for refolding to regenerate native or active conformations of the OGTA076 polypeptide when the polypeptide has been denatured during isolation and or purification. In the context of the present invention, OGTA076 polypeptide can be obtained from a biological sample from any source, such as and without limitation, a blood sample or tissue sample, e.g. a colorectal, kidney, liver, lung, lymphoid, ovarian or pancreatic tissue sample.

OGTA076 polypeptide may be in the form of a "mature protein" or may be part of a larger protein such as a fusion protein. It is often advantageous to include an additional amino acid sequence which contains secretory or leader sequences, a pre-, pro- or prepro-protein sequence, or a sequence which aids in purification such as an affinity tag, for example, but without limitation, multiple histidine residues, a FLAG tag, HA tag or myc tag.

An additional sequence that may provide stability during recombinant production may also be used. Such sequences may be optionally removed as required by incorporating a cleavable sequence as an additional sequence or part thereof. Thus, an OGTA076 polypeptide may be fused to other moieties including other polypeptides or proteins (for example, glutathione S-transferase and protein A). Such a fusion protein can be cleaved using an appropriate protease, and then separated into each protein. Such additional sequences and affinity tags are well known in the art. In addition to the above, features known in the art, such as an enhancer, a splicing signal, a polyA addition signal, a selection marker, and an SV40 replication origin can be added to an expression vector, if desired.

Production of Affinity Reagents to OGTA076

According to those in the art, there are three main types of immunoaffinity reagent-monoclonal antibodies, phage display antibodies and smaller antibody-derived molecules such as Affibodies, Domain Antibodies (dAbs), Nanobodies or UniBodies. In general in applications according to the present invention where the use of antibodies is stated, other affinity reagents (e.g. Affibodies, domain antibodies, Nanobodies or UniBodies) may be employed. Such substances may be said to be capable of immunospecific binding to OGTA076. Where appropriate the term "affinity agent" shall be construed to embrace immunoaffinity reagents and other substances capable of specific binding to OGTA076 including but not limited to ligands, lectins, streptavidins, antibody mimetics and synthetic binding agents.

Production of Antibodies to OGTA076

According to the invention OGTA076, an OGTA076 analog, an OGTA076-related protein or a fragment or derivative of any of the foregoing may be used as an immunogen to generate antibodies which immunospecifically bind such an immunogen. Such immunogens can be isolated by any convenient means, including the methods described above. The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3$^{rd}$ Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites" (e.g. fragments, subsequences, complementarity determining regions (CDRs)) that retain capacity to bind antigen, including (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody." Antibodies of the invention include, but are not limited to polyclonal, monoclonal, bispecific, humanized or chimeric antibodies, single chain antibodies, Fab fragments and F(ab')$_2$ fragments, fragments produced by a Fab expression library, anti-idiotypic (anti-Id) antibodies, and epitope-binding fragments of any of the above. The immunoglobulin molecules of the invention can be of any class (e.g. IgG, IgE, IgM, IgD and IgA) or subclass of immunoglobulin molecule.

The term "specifically binds" (or "immunospecifically binds") is not intended to indicate that an antibody binds exclusively to its intended target. Rather, an antibody "specifically binds" if its affinity for its intended target is typically about 5-fold greater when compared to its affinity for a non-target molecule. Suitably there is no significant cross-reaction or cross-binding with undesired substances, especially naturally occurring proteins or tissues of a healthy person or animal. In one embodiment the affinity of the antibody will be at least about 5 fold, for example 10 fold, such as 25-fold, particularly 50-fold, and especially 100-fold or more, greater for a target molecule than its affinity for a non-target molecule. In some embodiments, specific binding between an antibody or other binding agent and an antigen means a binding affinity of at least $10^6$ M$^{-1}$. Antibodies bind with affinities of at least about $10^7$ M$^{-1}$, for example between about $10^8$ M$^{-1}$ to about $10^9$ M$^{-1}$, about $10^9$ M$^{-1}$ to about $10^{10}$ M$^{-1}$, or about $10^{10}$ M$^{-1}$ to about $10^{11}$ M$^{-1}$ may be particularly suitable for use in the invention.

Affinity is calculated as $K_d = k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labeled ligand at various concentrations (c). The data are graphed using the Scatchard equation: $r/c = K(n-r)$:

where
r=moles of bound ligand/mole of receptor at equilibrium;
c=free ligand concentration at equilibrium;
K=equilibrium association constant; and
n=number of ligand binding sites per receptor molecule By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g. U.S. Pat. No. 6,316,409). The affinity of a targeting agent for its target molecule is preferably at least about $1 \times 10^{-6}$ moles/liter, is more preferably at least about $1 \times 10^{-7}$ moles/liter, is even more preferably at least about $1 \times 10^{-8}$ moles/liter, is yet even more preferably at least about $1 \times 10^{-9}$ moles/liter, and is most preferably at least about $1 \times 10^{-10}$ moles/liter. Antibody affinity measurement by Scatchard analysis is well known in the art. See, e.g. van Erp et al., *J. Immunoassay* 12: 425-43, 1991; Nelson and Griswold, *Comput. Methods Programs Biomed.* 27: 65-8, 1988.

In one embodiment, antibodies that recognize gene products of genes encoding OGTA076 are publicly available. In another embodiment, methods known to those skilled in the art are used to produce antibodies that recognize OGTA076, an OGTA076 analog, an OGTA076-related polypeptide, or a fragment or derivative of any of the foregoing. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In one embodiment of the invention, antibodies to a specific domain of OGTA076 are produced. In a specific embodiment, hydrophilic fragments of OGTA076 are used as immunogens for antibody production.

In the production of antibodies, screening for the desired antibody can be accomplished by techniques known in the art, e.g. ELISA (enzyme-linked immunosorbent assay). For example, to select antibodies which recognize a specific domain of OGTA076, one may assay generated hybridomas for a product which binds to an OGTA076 fragment containing such domain. For selection of an antibody that specifically binds a first OGTA076 homolog but which does not specifically bind to (or binds less avidly to) a second OGTA076 homolog, one can select on the basis of positive binding to the first OGTA076 homolog and a lack of binding to (or reduced binding to) the second OGTA076 homolog. Similarly, for selection of an antibody that specifically binds OGTA076 but which does not specifically bind to (or binds less avidly to) a different isoform of the same protein (such as a different glycoform having the same core peptide as OGTA076), one can select on the basis of positive binding to OGTA076 and a lack of binding to (or reduced binding to) the different isoform (e.g. a different glycoform). Thus, the present invention provides an antibody (preferably a monoclonal antibody) that binds with greater affinity (for example at least 2-fold, such as at least 5-fold, particularly at least 10-fold greater affinity) to OGTA076 than to a different isoform or isoforms (e.g. glycoforms) of OGTA076.

Polyclonal antibodies which may be used in the methods of the invention are heterogeneous populations of antibody molecules derived from the sera of immunized animals. Unfractionated immune serum can also be used. Various procedures known in the art may be used for the production of polyclonal antibodies to OGTA076, a fragment of OGTA076, an OGTA076-related polypeptide, or a fragment of an OGTA076-related polypeptide. For example, one way is to purify polypeptides of interest or to synthesize the polypeptides of interest using, e.g. solid phase peptide synthesis methods well known in the art. See, e.g. *Guide to Protein Purification*, Murray P. Deutcher, ed., *Meth. Enzymol.* Vol 182 (1990); Solid Phase Peptide Synthesis, Greg B. Fields ed., *Meth. Enzymol.* Vol 289 (1997); Kiso et al., *Chem. Pharm. Bull.* (Tokyo) 38: 1192-99, 1990; Mostafavi et al., Biomed. Pept. Proteins Nucleic Acids 1: 255-60, 1995; Fujiwara et al., *Chem. Pharm. Bull.* (Tokyo) 44: 1326-31, 1996. The selected polypeptides may then be used to immunize by injection various host animals, including but not limited to rabbits, mice, rats, etc., to generate polyclonal or monoclonal antibodies. The Preferred Technology described herein in Example 1 provides isolated OGTA076 suitable for such immunization. If OGTA076 is purified by gel electrophoresis, OGTA076 can be used for immunization with or without prior extraction from the polyacrylamide gel. Various adjuvants (i.e. immunostimulants) may be used to enhance the immunological response, depending on the host species, including, but not limited to, complete or incomplete Freund's adjuvant, a mineral gel such as aluminum hydroxide, surface active substance such as lysolecithin, pluronic polyol, a polyanion, a peptide, an oil emulsion, keyhole limpet hemocyanin, dinitrophenol, and an adjuvant such as BCG (bacille Calmette-Guerin) or *corynebacterium parvum*. Additional adjuvants are also well known in the art.

For preparation of monoclonal antibodies (mAbs) directed toward OGTA076, a fragment of OGTA076, an OGTA076-related polypeptide, or a fragment of an OGTA076-related polypeptide, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mAbs of the invention may be cultivated in vitro or in vivo. In an additional embodiment of the invention, monoclonal antibodies can be produced in germ-free animals utilizing known technology (PCT/US90/02545, incorporated herein by reference).

The monoclonal antibodies include but are not limited to human monoclonal antibodies and chimeric monoclonal antibodies (e.g. human-mouse chimeras). A chimeric antibody is a molecule in which different portions are derived from different animal species, such as those having a human immunoglobulin constant region and a variable region derived from a murine mAb. (See, e.g. Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g. Queen, U.S. Pat. No. 5,585,089, which is incorporated herein by reference in its entirety.)

Chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, Bio/Techniques 4:214; U.S. Pat. No. 5,225,539; Jones et al., 1986, Nature 321:552-525; Verhoeyan et al. (1988) Science 239: 1534; and Beidler et al., 1988, J. Immunol. 141:4053-4060.

Completely human antibodies are particularly desirable for therapeutic treatment of human subjects. Such antibodies can be produced using transgenic mice which are incapable of expressing endogenous immunoglobulin heavy and light chain genes, but which can express human heavy and light chain genes. The transgenic mice are immunized in the normal fashion with a selected antigen, e.g. all or a portion of OGTA076. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g. U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection". In this approach a selected non-human monoclonal antibody, e.g. a mouse antibody, is used to guide the selection of a completely human antibody recognizing the same epitope. (Jespers et al. (1994) Bio/technology 12:899-903).

The antibodies of the present invention can also be generated by the use of phage display technology to produce and screen libraries of polypeptides for binding to a selected target. See, e.g. Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g. U.S. Pat. No. 6,057,098, which is hereby incorporated in its entirety, including all tables, figures, and claims. In particular, such phage can be utilized to display antigen binding domains expressed from a repertoire or combinatorial antibody library (e.g. human or murine). Phage expressing an antigen binding domain that binds the antigen of interest can be selected or identified with antigen, e.g. using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g. as described in detail below. For example, techniques to recombinantly produce Fab, Fab' and F(ab')$_2$ fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988).

The invention further provides for the use of bispecific antibodies, which can be made by methods known in the art. Traditional production of full length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., 1991, EMBO J. 10:3655-3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details for generating bispecific antibodies see, for example, Suresh et al., Methods in Enzymology, 1986, 121: 210.

The invention provides functionally active fragments, derivatives or analogs of the anti-OGTA076 immunoglobulin molecules. Functionally active means that the fragment, derivative or analog is able to elicit anti-anti-idiotype antibodies (i.e., tertiary antibodies) that recognize the same antigen that is recognized by the antibody from which the fragment, derivative or analog is derived. Specifically, in a preferred embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')$_2$ fragments and Fab fragments. Antibody fragments which recognize specific epitopes may be generated by known techniques. F(ab')$_2$ fragments consist of the variable region, the light chain constant region and the CH1 domain of the heavy chain and are generated by pepsin digestion of the antibody molecule. Fab fragments are generated by reducing the disulfide bridges of the F(ab')$_2$ fragments. The invention also provides heavy chain and light chain dimers of the antibodies of the invention, or any minimal fragment thereof such as Fvs or single chain antibodies (SCAs) (e.g. as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al., 1988, Science 242:1038-1041).

In other embodiments, the invention provides fusion proteins of the immunoglobulins of the invention (or functionally active fragments thereof), for example in which the immunoglobulin is fused via a covalent bond (e.g. a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogs and derivatives that are modified, i.e., by the covalent attachment of any type of molecule as long as such covalent attachment does not impair immunospecific binding. For example, but not by way of limitation, the derivatives and analogs of the immunoglobulins include those that have been further modified, e.g. by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analog or derivative may contain one or more non-classical amino acids.

The foregoing antibodies can be used in methods known in the art relating to the localization and activity of OGTA076, e.g. for imaging this protein, measuring levels thereof in appropriate physiological samples, in diagnostic methods, etc.

Production of Affibodies to OGTA076

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, Nat Biotechnol 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of Affibody-Fc chimeras produced in Escherichia coli, J Immunol Methods 2002; 261:199-211) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

Labelled Affibodies may also be useful in imaging applications for determining abundance of Isoforms.

Production of Domain Antibodies to OGTA076

References to antibodies herein embrace references to Domain Antibodies. Domain Antibodies (dAbs) are the smallest functional binding units of antibodies, corresponding to the variable regions of either the heavy ($V_H$) or light ($V_L$) chains of human antibodies. Domain Antibodies have a molecular weight of approximately 13 kDa. Domantis has developed a series of large and highly functional libraries of fully human $V_H$ and $V_L$ dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; US Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Production of Nanobodies to OGTA076

Nanobodies are antibody-derived therapeutic proteins that contain the unique structural and functional properties of naturally-occurring heavy-chain antibodies. These heavy-chain antibodies contain a single variable domain (VHH) and two constant domains ($C_H2$ and $C_H3$). Importantly, the cloned and isolated VHH domain is a perfectly stable polypeptide harbouring the full antigen-binding capacity of the original heavy-chain antibody. Nanobodies have a high homology with the VH domains of human antibodies and can be further humanized without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see e.g. WO 04/041867, which is herein incorporated by reference in its entirety) and are easy to manufacture. Other advantages of Nanobodies include recognising uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. E. coli (see e.g. U.S. Pat. No. 6,765,087, which is herein incorporated by reference in its entirety), moulds (for example Aspergillus or Thichoderma) and yeast (for example Saccharomyces, Kluyveromyces, Hansenula or Pichia) (see e.g. U.S. Pat. No. 6,838,254, which is herein incorporated by reference in its entirety). The production process is scalable and multikilogram quantities of Nanobodies have been produced. Because Nanobodies exhibit a superior stability compared with conventional antibodies, they can be formulated as a long ready-to-use solution.

The Nanoclone method (see e.g. WO 06/079372, which is herein incorporated by reference in its entirety) is a proprietary method for generating Nanobodies against a desired target, based on automated high-throughput selection of B-cells.

Production of UniBodies to OGTA076

UniBody is a new proprietary antibody technology that creates a stable, smaller antibody format with an anticipated longer therapeutic window than current small antibody formats. IgG4 antibodies are considered inert and thus do not interact with the immune system. Genmab modified fully human IgG4 antibodies by eliminating the hinge region of the antibody. Unlike the full size IgG4 antibody, the half molecule fragment is very stable and is termed a UniBody. Halving the IgG4 molecule left only one area on the UniBody that can bind to disease targets and the UniBody therefore binds univalently to only one site on target cells. This univalent binding does not stimulate cancer cells to grow like bivalent antibodies might and opens the door for treatment of some types of cancer which ordinary antibodies cannot treat.

The UniBody is about half the size of a regular IgG4 antibody. This small size can be a great benefit when treating some forms of cancer, allowing for better distribution of the molecule over larger solid tumors and potentially increasing efficacy.

Fabs typically do not have a very long half-life. UniBodies, however, were cleared at a similar rate to whole IgG4 antibodies and were able to bind as well as whole antibodies and antibody fragments in pre-clinical studies. Other antibodies primarily work by killing the targeted cells whereas UniBodies only inhibit or silence the cells.

Further details of UniBodies may be obtained by reference to patent WO2007/059782, which is herein incorporated by reference in its entirety.

Expression of Affinity Reagents
Expression of Antibodies

The antibodies of the invention can be produced by any method known in the art for the synthesis of antibodies, in particular, by chemical synthesis or by recombinant expression, and are preferably produced by recombinant expression techniques.

Recombinant expression of antibodies, or fragments, derivatives or analogs thereof, requires construction of a nucleic acid that encodes the antibody. If the nucleotide sequence of the antibody is known, a nucleic acid encoding the antibody may be assembled from chemically synthesized oligonucleotides (e.g. as described in Kutmeier et al., 1994, BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody may be obtained by cloning the antibody. If a clone containing the nucleic acid encoding the particular antibody is not available, but the sequence of the antibody molecule is known, a nucleic acid encoding the antibody may be obtained from a suitable source (e.g. an antibody cDNA library, or cDNA library generated from any tissue or cells expressing the antibody) by PCR amplification using synthetic primers hybridizable to the 3' and 5' ends of the sequence or by cloning using an oligonucleotide probe specific for the particular gene sequence.

If an antibody molecule that specifically recognizes a particular antigen is not available (or a source for a cDNA library for cloning a nucleic acid encoding such an antibody), antibodies specific for a particular antigen may be generated by any method known in the art, for example, by immunizing an animal, such as a rabbit, to generate polyclonal antibodies or, more preferably, by generating monoclonal antibodies. Alternatively, a clone encoding at least the Fab portion of the antibody may be obtained by screening Fab expression libraries (e.g. as described in Huse et al., 1989, *Science* 246:1275-1281) for clones of Fab fragments that bind the specific antigen or by screening antibody libraries (See, e.g. Clackson et al., 1991, Nature 352:624; Hane et al., 1997 Proc. Natl. Acad. Sci. USA 94:4937).

Once a nucleic acid encoding at least the variable domain of the antibody molecule is obtained, it may be introduced into a vector containing the nucleotide sequence encoding the constant region of the antibody molecule (see, e.g. PCT Publication WO 86/05807; PCT Publication WO 89/01036; and U.S. Pat. No. 5,122,464). Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydyl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, J. Biol. Chem. 253: 6551), PCT based methods, etc.

In addition, techniques developed for the production of "chimeric antibodies" (Morrison et al., 1984, Proc. Natl. Acad. Sci. 81:851-855; Neuberger et al., 1984, *Nature* 312: 604-608; Takeda et al., 1985, Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g. humanized antibodies.

Once a nucleic acid encoding an antibody molecule of the invention has been obtained, the vector for the production of the antibody molecule may be produced by recombinant DNA technology using techniques well known in the art. Thus, methods for preparing the protein of the invention by expressing nucleic acid containing the antibody molecule sequences are described herein. Methods which are well known to those skilled in the art can be used to construct expression vectors containing an antibody molecule coding sequences and appropriate transcriptional and translational control signals. These methods include, for example, in vitro recombinant DNA techniques, synthetic techniques, and in vivo genetic recombination. See, for example, the techniques described in Sambrook et al. (1990, Molecular Cloning, A Laboratory Manual, $2^{nd}$ Ed., Cold Spring Harbor Laboratory, Cold Spring Harbor, N.Y.) and Ausubel et al. (eds., 1998, Current Protocols in Molecular Biology, John Wiley & Sons, NY).

The expression vector is transferred to a host cell by conventional techniques and the transfected cells are then cultured by conventional techniques to produce an antibody of the invention.

The host cells used to express a recombinant antibody of the invention may be either bacterial cells such as *Escherichia coli*, or, preferably, eukaryotic cells, especially for the expression of whole recombinant antibody molecule. In particular, mammalian cells such as Chinese hamster ovary cells (CHO), in conjunction with a vector such as the major intermediate early gene promoter element from human cytomegalovirus are an effective expression system for antibodies (Foecking et al., 1986, Gene 45:101; Cockett et al., 1990, Bio/Technology 8:2).

A variety of host-expression vector systems may be utilized to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g. *E. coli, B. subtilis*) transformed with recombinant bacteriophage DNA, plasmid DNA or cosmid DNA expression vectors containing antibody coding sequences; yeast (e.g. *Saccharomyces, Pichia*) transformed with recombinant yeast expression vectors containing antibody coding sequences; insect cell systems infected with recombinant virus expression vectors (e.g. baculovirus) containing the antibody coding sequences; plant cell systems infected with recombinant virus expression vectors (e.g. cauliflower mosaic virus, CaMV; tobacco mosaic virus, TMV) or transformed with recombinant plasmid expression vectors (e.g. Ti plasmid) containing antibody coding sequences; or mammalian cell systems (e.g. COS, CHO, BHK, 293, 3T3 cells) harboring recombinant expression constructs containing promoters derived from the genome of mammalian cells (e.g. metallothionein promoter) or from mammalian viruses (e.g. the adenovirus late promoter; the vaccinia virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g. an adenovirus expression system) may be utilized.

As discussed above, a host cell strain may be chosen which modulates the expression of the inserted sequences, or modifies and processes the gene product in the specific fashion desired. Such modifications (e.g. glycosylation) and processing (e.g. cleavage) of protein products may be important for the function of the protein.

For long-term, high-yield production of recombinant antibodies, stable expression is preferred. For example, cell lines that stably express an antibody of interest can be produced by transfecting the cells with an expression vector comprising the nucleotide sequence of the antibody and the nucleotide sequence of a selectable (e.g. neomycin or hygromycin), and selecting for expression of the selectable marker. Such engineered cell lines may be particularly useful in screening and evaluation of compounds that interact directly or indirectly with the antibody molecule.

The expression levels of the antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once the antibody molecule of the invention has been recombinantly expressed, it may be purified by any method known in the art for purification of an antibody molecule, for example, by chromatography (e.g. ion exchange chromatography, affinity chromatography such as with protein A or specific antigen, and sizing column chromatography), centrifugation, differential solubility, or by any other standard technique for the purification of proteins.

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitriloacetic acid-agarose columns and histidine-tagged proteins are selectively eluted with imidazole-containing buffers.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) is present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g. in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

For therapeutic applications, antibodies (particularly monoclonal antibodies) may suitably be human or humanized animal (e.g. mouse) antibodies. Animal antibodies may be raised in animals using the human protein (e.g. OGTA076) as immunogen. Humanization typically involves grafting CDRs identified thereby into human framework regions. Normally some subsequent retromutation to optimize the conformation of chains is required. Such processes are known to persons skilled in the art.

Expression of Affibodies

The construction of affibodies has been described elsewhere (Ronnmark J, Gronlund H, Uhle'n, M., Nygren P. A°, Human immunoglobulin A (IgA)-specific ligands from combinatorial engineering of protein A, 2002, Eur. J. Biochem. 269, 2647-2655), including the construction of Affibody phage display libraries (Nord, K., Nilsson, J., Nilsson, B., Uhle'n, M. & Nygren, P. A, A combinatorial library of an a-helical bacterial receptor domain, 1995, Protein Eng. 8, 601-608. Nord, K., Gunneriusson, E., Ringdahl, J., Stahl, S., Uhle'n, M. & Nygren, P. A, Binding proteins selected from combinatorial libraries of an a-helical bacterial receptor domain, 1997, Nat. Biotechnol. 15, 772-777.)

The biosensor analyses to investigate the optimal Affibody variants using biosensor binding studies has also been described elsewhere (Ronnmark J, Gronlund H, Uhle'n, M., Nygren P. A, Human immunoglobulin A (IgA)-specific ligands from combinatorial engineering of protein A, 2002, Eur. J. Biochem. 269, 2647-2655).

Affinity Reagent Modifications

In one embodiment, anti-OGTA076 affinity reagents such as antibodies or fragments thereof are conjugated to a diagnostic moiety (such as a detectable label) or a therapeutic moiety. The antibodies can be used for diagnosis or to determine the efficacy of a given treatment regimen. Detection can be facilitated by coupling the antibody to a detectable substance (label). Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics according to the present invention. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc. $^{68}$Ga may also be employed.

Anti-OGTA076 antibodies or fragments thereof as well as other affinity reagents can be conjugated to a therapeutic agent or drug moiety to modify a given biological response. An exemplary therapeutic agent to which the affinity reagent may be conjugated is a cytotoxic moiety. The therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g. angiostatin or endostatin; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Techniques for conjugating such therapeutic moiety to antibodies are well known, see, e.g. Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

An antibody with or without a therapeutic moiety conjugated to it can be used as a therapeutic that is administered alone or in combination with cytotoxic factor(s) and/or cytokine(s).

The invention also provides for fully human, or humanized antibodies that induce antibody-directed cell-mediated cytotoxicity (ADCC). A fully human antibody is one in which the protein sequences are encoded by naturally occurring human immunoglobulin sequences, either from isolated antibody-producing human B-lymphocytes, or from transgenic murine B-lymphocytes of mice in which the murine immunoglobulin coding chromosomal regions have been replaced by orthologous human sequences. Transgenic antibodies of the latter type include, but are not restricted to, HuMab (Medarex, Inc, CA) and Xenomouse (Abgenix Inc., CA). A humanized antibody is one in which the constant region of a non-human antibody molecule of appropriate antigen specificity, is replaced by the constant region of a human antibody, for example of the IgG subtype, with appropriate effector functions (Morrison et al., 1984, Proc. Natl. Acad. Sci. 81:851-855; Neuberger et al., 1984, Nature 312:604-608; Takeda et al., 1985, Nature 314:452-454). Appropriate effector functions include ADCC, which is a natural process by which fully-human antibodies or humanized antibodies, when bound to targets on the surface of cancer cells, switch on the cell killing properties of lymphocytes that are part of the normal immune system. These active lymphocytes, called Natural Killer (NK) cells, use a cytotoxic process to destroy living cells to which the antibodies are bound. ADCC activity may be detected and quantified by measuring release of Europium (Eu3+) from Eu3+ labelled, living cells in the presence of an antigen-specific antibody and peripheral blood mononuclear cells extracted from an immunocompetent, living human subject. The ADCC process is described in detail in Janeway Jr. C. A. et al., Immunobiology, 5th ed., 2001, Garland Publishing, ISBN 0-8153-3642-X; Pier G. B. et al., Immunology, Infection, and Immunity, 2004, p 246-5; Albanell J. et al., Advances in Experimental Medicine and Biology, 2003, 532:p 2153-68 and Weng, W.-K. et al., Journal of Clinical Oncology, 2003, 21:p 3940-3947. Suitable methods for the detection and quantification of ADCC can be found in Blomberg et al., Journal of Immunological Methods. 1986, 86:p 225-9; Blomberg et al., Journal of Immunological Methods. 1986, 21; 92:p 117-23 and Patel & Boyd, Journal of Immunological Methods. 1995, 184:p 29-38.

ADCC typically involves activation of NK cells and is dependent on the recognition of antibody-coated cells by Fc receptors on the surface of the NK cell. The Fc receptors recognize the Fc (crystalline) portion of antibodies such as IgG, bound specifically to the surface of a target cell. The Fc receptor that triggers activation of the NK cell is called CD16 or FcγRIIIa. Once the FcγRIIIa receptor is bound to the IgG Fc, the NK cell releases cytokines such as IFN-γ, and cytotoxic granules containing perforin and granzymes that enter the target cell and promote cell death by triggering apoptosis.

The induction of antibody-dependent cellular cytotoxicity (ADCC) by an antibody can be enhanced by modifications that alter interactions between the antibody constant region (Fc) and various receptors that are present on the surface of cells of the immune system. Such modifications include the reduction or absence of alpha-1,6-linked fucose moieties in the complex oligosaccharide chains that are normally added to the Fc of antibodies during natural or recombinant synthesis in mammalian cells. In one embodiment, non-fucosylated anti-OGTA076 affinity reagents such as antibodies or fragments thereof are produced for the purpose of enhancing their ability to induce the ADCC response.

Techniques for reducing or ablating alpha 1,6-linked fucose moieties in the oligosaccharide chains of the Fc are well established. In one example, the recombinant antibody is synthesized in a cell line that is impaired in its ability to add fucose in an alpha 1,6 linkage to the innermost N-acetylglucosamine of the N-linked biantennary complex-type Fc oligosaccharides. Such cell lines include, but are not limited to, the rat hybridoma YB2/0, which expresses a reduced level of the alpha 1,6-fucosyltransferase gene, FUT8. For example, the antibody is synthesized in a cell line that is incapable of adding alpha 1,6-linked fucosyl moieties to complex oligosaccharide chains, due to the deletion of both copies of the FUT8 gene. Such cell lines include, but are not limited to, FUT8-/- CHO/DG44 cell lines. Techniques for synthesizing partially fucosylated, or non-fucosylated antibodies and affinity reagents are described in Shinkawa et al., J. Biol. Chem. 278:3466-34735 (2003); Yamane-Ohnuki et al., Biotechnology and Bioengineering 87: 614-22 (2004) and in WO00/61739 A1, WO02/31140 A1 and WO03/085107 A1. In a second example, the fucosylation of a recombinant antibody is reduced or abolished by synthesis in a cell line that has been genetically engineered to overexpress a glycoprotein-modifying glycosyl transferase at a level that maximizes the production of complex N-linked oligosaccharides carrying bisecting N-acetylglucosamine. For example, the antibody is synthesized in a Chinese Hamster Ovary cell line expressing the enzyme N-acetyl glucosamine transferase III (GnT III). Cell lines stably transfected with suitable glycoprotein-modifying glycosyl transferases, and methods of synthesizing antibodies using these cells are described in WO9954342.

A non-fucosylated antibody or affinity reagent can be used as a therapeutic that is administered alone or in combination with cytotoxic factor(s) and/or cytokine(s).

In a further modification, the amino acid sequences of the antibody Fc are altered in a way that enhances ADCC activation, without affecting ligand affinity. Examples of such modifications are described in Lazar et al., Proceedings of the National Academy of Sciences 2006, 103:p 4005-4010; WO03074679 and WO2007039818. In these examples, substitution of amino acids in the antibody Fc, such as aspartate for serine at position 239, and isoleucine for glutamate at position 332, altered the binding affinity of an antibody for Fc receptors, leading to an increase in ADCC activation.

An antibody reagent with enhanced ADCC activation due to amino acid substitutions can be used as a therapeutic that is administered alone or in combination with cytotoxic factor(s) and/or cytokine(s).

Diagnosis of Colorectal Cancer, Kidney Cancer, Liver Cancer, Lung Cancer, Lymphoid Leukaemia (Particularly Chronic Lymphocytic Leukaemia), Ovarian Cancer or Pancreatic Cancer In accordance with the present invention, test samples of colorectal, kidney, liver, lung, lymphoid, ovarian or pancreatic tissue, serum, plasma or urine obtained from a subject suspected of having or known to have colorectal cancer, kidney cancer, liver cancer, lung cancer, lymphoid leukaemia (particularly chronic lymphocytic leukaemia), ovarian cancer or pancreatic cancer can be used for diagnosis or monitoring. In one embodiment, a change in the abundance of OGTA076 in a test sample relative to a control sample (from a subject or subjects free from colorectal cancer, kidney cancer, liver cancer, lung cancer, lymphoid leukaemia (particularly chronic lymphocytic leukaemia), ovarian cancer and pancreatic cancer) or a previously determined reference range indicates the presence of colorectal cancer, kidney cancer, liver cancer, lung cancer, lymphoid leukaemia (particularly chronic lymphocytic leukaemia), ovarian cancer or pancreatic cancer. In another embodiment, the relative abundance of OGTA076 in a test sample compared to a control sample or a previously determined reference range indicates a subtype of colorectal cancer, kidney cancer, liver cancer, lung cancer, lymphoid leukaemia (particularly chronic lymphocytic leukaemia), ovarian cancer or pancreatic cancer (e.g. familial or sporadic colorectal cancer, fibrolamellar hepatocellular carcinoma, squamous cell lung carcinoma, T-cell chronic lymphocytic leukaemia, malignant papillary serous adenocarcinoma or endocrine tumours of the pancreas). In yet another embodiment, the relative abundance of OGTA076 in a test sample relative to a control sample or a previously determined reference range indicates the degree or severity of colorectal cancer, kidney cancer, liver cancer, lung cancer, lymphoid leukaemia (particularly chronic lymphocytic leukaemia), ovarian cancer or pancreatic cancer (e.g. the likelihood for metastasis). In any of the aforesaid methods, detection of OGTA076 may optionally be combined with detection of one or more of additional biomarkers for colorectal cancer, kidney cancer, liver cancer, lung cancer, lymphoid leukaemia (particularly chronic lymphocytic leukaemia), ovarian cancer or pancreatic cancer. Any suitable method in the art can be employed to measure the level of OGTA076, including but not limited to the Preferred Technologies described herein, kinase assays, immunoassays to detect and/or visualize the OGTA076 (e.g. Western blot, immunoprecipitation followed by sodium dodecyl sulfate polyacrylamide gel electrophoresis, immunocytochemistry, etc.). In a further embodiment, a change in the abundance of mRNA encoding OGTA076 in a test sample relative to a control sample or a previously determined reference range indicates the presence of colorectal cancer, kidney cancer, liver cancer, lung cancer, lymphoid leukaemia (particularly chronic lymphocytic leukaemia), ovarian cancer or pancreatic cancer. Any suitable hybridization assay can be used to detect OGTA076 expression by detecting and/or visualizing mRNA encoding the OGTA076 (e.g. Northern assays, dot blots, in situ hybridization, etc.).

In another embodiment of the invention, labeled antibodies (or other affinity reagents), derivatives and analogs thereof, which specifically bind to OGTA076 can be used for diagnostic purposes to detect, diagnose, or monitor colorectal cancer, kidney cancer, liver cancer, lung cancer, lymphoid leukaemia (particularly chronic lymphocytic leukaemia), ovarian cancer or pancreatic cancer. Preferably, colorectal cancer, kidney cancer, liver cancer, lung cancer, lymphoid leukaemia (particularly chronic lymphocytic leukaemia), ovarian cancer or pancreatic cancer is detected in an animal, more preferably in a mammal and most preferably in a human.

Screening Assays

The invention provides methods for identifying agents (e.g. candidate compounds or test compounds) that bind to OGTA076 or have a stimulatory or inhibitory effect on the expression or activity of OGTA076. The invention also provides methods of identifying agents, candidate compounds or test compounds that bind to an OGTA076-related polypeptide or an OGTA076 fusion protein or have a stimulatory or inhibitory effect on the expression or activity of an OGTA076-related polypeptide or an OGTA076 fusion protein. Examples of agents, candidate compounds or test compounds include, but are not limited to, nucleic acids (e.g. DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233, each of which is incorporated herein in its entirety by reference.

Libraries of compounds may be presented, e.g. presented in solution (e.g. Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310), each of which is incorporated herein in its entirety by reference.

In one embodiment, agents that interact with (i.e. bind to) OGTA076, an OGTA076 fragment (e.g. a functionally active fragment), an OGTA076-related polypeptide, a fragment of an OGTA076-related polypeptide, or an OGTA076 fusion protein are identified in a cell-based assay system. In accordance with this embodiment, cells expressing OGTA076, a fragment of an OGTA076, an OGTA076-related polypeptide, a fragment of the OGTA076-related polypeptide, or an OGTA076 fusion protein are contacted with a candidate compound or a control compound and the ability of the candidate compound to interact with the OGTA076 is determined. If desired, this assay may be used to screen a plurality (e.g. a library) of candidate compounds. The cell, for example, can be of prokaryotic origin (e.g. E. coli) or eukaryotic origin (e.g. yeast or mammalian). Further, the cells can express OGTA076, a fragment of OGTA076, an OGTA076-related polypeptide, a fragment of the OGTA076-related polypeptide, or an OGTA076 fusion protein endogenously or be genetically engineered to express OGTA076, a fragment of OGTA076, an OGTA076-related polypeptide, a fragment of the OGTA076-related polypeptide, or an OGTA076 fusion protein. In certain instances, OGTA076, a fragment of OGTA076, an OGTA076-related polypeptide, a fragment of the OGTA076-related polypeptide, or an OGTA076 fusion protein or the candidate compound is labeled, for example with a radioactive label (such as $^{32}P$, $^{35}S$, and $^{125}I$) or a fluorescent label (such as fluorescein isothiocyanate, rhodamine, phycoerythrin, phycocyanin, allophycocyanin, o-phthaldehyde or fluorescamine) to enable detection of an interaction between OGTA076 and a candidate compound. The ability of the candidate compound to interact directly or indirectly with OGTA076, a fragment of an OGTA076, an OGTA076-related polypeptide, a fragment of an OGTA076-related polypeptide, or an OGTA076 fusion protein can be determined by methods known to those of skill in the art. For example, the interaction between a candidate compound and OGTA076, an OGTA076-related polypeptide, a fragment of an OGTA076-related polypeptide, or an OGTA076 fusion protein can be determined by flow cytometry, a scintillation assay, immunoprecipitation or western blot analysis.

In another embodiment, agents that interact with (i.e. bind to) OGTA076, an OGTA076 fragment (e.g. a functionally active fragment), an OGTA076-related polypeptide, a fragment of an OGTA076-related polypeptide, or an OGTA076 fusion protein are identified in a cell-free assay system. In accordance with this embodiment, a native or recombinant OGTA076 or fragment thereof, or a native or recombinant OGTA076-related polypeptide or fragment thereof, or an OGTA076-fusion protein or fragment thereof, is contacted with a candidate compound or a control compound and the ability of the candidate compound to interact with OGTA076 or OGTA076-related polypeptide, or OGTA076 fusion protein is determined. If desired, this assay may be used to screen a plurality (e.g. a library) of candidate compounds. For example, OGTA076, an OGTA076 fragment, an OGTA076-related polypeptide, a fragment of an OGTA076-related polypeptide, or an OGTA076-fusion protein is first immobilized, by, for example, contacting OGTA076, an OGTA076 fragment, an OGTA076-related polypeptide, a fragment of an OGTA076-related polypeptide, or an OGTA076 fusion protein with an immobilized antibody (or other affinity reagent) which specifically recognizes and binds it, or by contacting a purified preparation of OGTA076, an OGTA076 fragment, an OGTA076-related polypeptide, fragment of an OGTA076-related polypeptide, or an OGTA076 fusion protein with a surface designed to bind proteins. OGTA076, an OGTA076 fragment, an OGTA076-related polypeptide, a fragment of an OGTA076-related polypeptide, or an OGTA076 fusion protein may be partially or completely purified (e.g. partially or completely free of other polypeptides) or part of a cell lysate. Further, OGTA076, an OGTA076 fragment, an OGTA076-related polypeptide, or a fragment of an OGTA076-related polypeptide may be a fusion protein comprising OGTA076 or a biologically active portion thereof, or OGTA076-related polypeptide and a domain such as glutathionine-S-transferase. Alternatively, OGTA076, an OGTA076 fragment, an OGTA076-related polypeptide, a fragment of an OGTA076- related polypeptide or an OGTA076 fusion protein can be biotinylated using techniques well known to those of skill in the art (e.g. biotinylation kit, Pierce Chemicals; Rockford, Ill.). The ability of the candidate compound to interact with OGTA076, an OGTA076 fragment, an OGTA076-related polypeptide, a fragment of an OGTA076-related polypeptide, or an OGTA076 fusion protein can be determined by methods known to those of skill in the art.

In another embodiment, a cell-based assay system is used to identify agents that bind to or modulate the activity of a protein, such as an enzyme, or a biologically active portion thereof, which is responsible for the production or degradation of OGTA076 or is responsible for the post-translational modification of OGTA076. In a primary screen, a plurality (e.g. a library) of compounds are contacted with cells that naturally or recombinantly express: (i) OGTA076, an isoform of OGTA076, an OGTA076 homolog, an OGTA076-related polypeptide, an OGTA076 fusion protein, or a biologically active fragment of any of the foregoing; and (ii) a protein that is responsible for processing of OGTA076, an OGTA076 isoform, an OGTA076 homolog, an OGTA076-related polypeptide, an OGTA076 fusion protein, or a fragment in order to identify compounds that modulate the production, degradation, or post-translational modification of OGTA076, an OGTA076 isoform, an OGTA076 homolog, an OGTA076-related polypeptide, an OGTA076 fusion protein or fragment. If desired, compounds identified in the primary screen can then be assayed in a secondary screen against cells naturally or recombinantly expressing OGTA076. The ability of the candidate compound to modulate the production, degradation or post-translational modification of OGTA076, isoform, homolog, OGTA076-related polypeptide, or OGTA076 fusion protein can be determined by methods known to those of skill in the art, including without limitation, flow cytometry, a scintillation assay, immunoprecipitation and western blot analysis.

In another embodiment, agents that competitively interact with (i.e. bind to) OGTA076, an OGTA076 fragment, an OGTA076-related polypeptide, a fragment of an OGTA076-related polypeptide, or an OGTA076 fusion protein are identified in a competitive binding assay. In accordance with this embodiment, cells expressing OGTA076, an OGTA076 fragment, an OGTA076-related polypeptide, a fragment of an OGTA076-related polypeptide, or an OGTA076 fusion protein are contacted with a candidate compound and a compound known to interact with OGTA076, an OGTA076 fragment, an OGTA076-related polypeptide, a fragment of an OGTA076-related polypeptide or an OGTA076 fusion protein; the ability of the candidate compound to preferentially interact with OGTA076, an OGTA076 fragment, an OGTA076-related polypeptide, a fragment of an OGTA076-related polypeptide, or an OGTA076 fusion protein is then determined. Alternatively, agents that preferentially interact with (i.e. bind to) OGTA076, an OGTA076 fragment, an OGTA076-related polypeptide or fragment of an OGTA076-related polypeptide are identified in a cell-free assay system by contacting OGTA076, an OGTA076 fragment, an OGTA076-related polypeptide, a fragment of an OGTA076-related polypeptide, or an OGTA076 fusion protein with a candidate compound and a compound known to interact with OGTA076, an OGTA076-related polypeptide or an OGTA076 fusion protein. As stated above, the ability of the candidate compound to interact with OGTA076, an OGTA076 fragment, an OGTA076-related polypeptide, a fragment of an OGTA076-related polypeptide, or an OGTA076 fusion protein can be determined by methods known to those of skill in the art. These assays, whether cell-based or cell-free, can be used to screen a plurality (e.g. a library) of candidate compounds.

In another embodiment, agents that modulate (i.e. upregulate or downregulate) the expression or activity of OGTA076 or an OGTA076-related polypeptide are identified by contacting cells (e.g. cells of prokaryotic origin or eukaryotic origin) expressing OGTA076 or an OGTA076-related polypeptide with a candidate compound or a control compound (e.g. phosphate buffered saline (PBS)) and determining the expression of OGTA076, OGTA076-related polypeptide, or OGTA076 fusion protein, mRNA encoding OGTA076, or mRNA encoding the OGTA076-related polypeptide. The level of expression of OGTA076, OGTA076-related polypeptide, mRNA encoding OGTA076, or mRNA encoding the OGTA076-related polypeptide in the presence of the candidate compound is compared to the level of expression of OGTA076, OGTA076-related polypeptide, mRNA encoding OGTA076, or mRNA encoding the OGTA076-related polypeptide in the absence of the candidate compound (e.g. in the presence of a control compound). The candidate compound can then be identified as a modulator of the expression of OGTA076, or the OGTA076-related polypeptide based on this comparison. For example, when expression of OGTA076 or mRNA is significantly greater in the presence of the candidate compound than in its absence, the candidate compound is identified as a stimulator of expression of OGTA076 or mRNA. Alternatively, when expression of OGTA076 or mRNA is significantly less in the presence of the candidate compound than in its absence, the candidate compound is identified as an inhibitor of the expression of OGTA076 or mRNA. The level of expression of OGTA076 or the mRNA that encodes it can be determined by methods known to those of skill in the art. For example, mRNA expression can be assessed by Northern blot analysis or RT-PCR, and protein levels can be assessed by western blot analysis.

In another embodiment, agents that modulate the activity of OGTA076 or an OGTA076-related polypeptide are identified by contacting a preparation containing OGTA076 or OGTA076-related polypeptide or cells (e.g. prokaryotic or eukaryotic cells) expressing OGTA076 or OGTA076-related polypeptide with a test compound or a control compound and determining the ability of the test compound to modulate (e.g. stimulate or inhibit) the activity of OGTA076 or OGTA076-related polypeptide. The activity of OGTA076 or an OGTA076-related polypeptide can be assessed by detecting induction of a cellular signal transduction pathway of OGTA076 or OGTA076-related polypeptide (e.g. intracellular $Ca^{2+}$, diacylglycerol, IP3, etc.), detecting catalytic or enzymatic activity of the target on a suitable substrate, detecting the induction of a reporter gene (e.g. a regulatory element that is responsive to OGTA076 or an OGTA076-related polypeptide and is operably linked to a nucleic acid encoding a detectable marker, e.g. luciferase), or detecting a cellular response, for example, cellular differentiation, or cell proliferation. Based on the present description, techniques known to those of skill in the art can be used for measuring these activities (see, e.g. U.S. Pat. No. 5,401,639, which is incorporated herein by reference). The candidate compound can then be identified as a modulator of the activity of OGTA076 or an OGTA076-related polypeptide by comparing the effects of the candidate compound to the control compound. Suitable control compounds include phosphate buffered saline (PBS) and normal saline (NS).

In another embodiment, agents that modulate (i.e. upregulate or downregulate) the expression, activity or both the expression and activity of OGTA076 or an OGTA076-related polypeptide are identified in an animal model. Examples of suitable animals include, but are not limited to, mice, rats, rabbits, monkeys, guinea pigs, dogs and cats. Preferably, the animal used represent a model of colorectal cancer, kidney cancer, liver cancer, lung cancer, lymphoid leukaemia (particularly chronic lymphocytic leukaemia), ovarian cancer or pancreatic cancer (e.g. xenografts of human colorectal cancer cell lines such as MDA-MB-345 in oestrogen-deprived SCID mice, Eccles et al. 1994 Cell Biophysics 24/25, 279; xenografts of renal cell cancer cell lines such as LABAZ1 in immune compromised mice, Zisman et al, Cancer Research 63, 4952-4959, Aug. 15, 2003; xenografts of hepatocellular carcinoma cell lines such as MHCC97 in nude mice, Tian et al., Br J 5 Cancer 1999 November; 81(5):814-21; xenografts of non small cell lung cancer cell lines such as A549 and H460 and xenografts of small cell lung cancer cell lines such as NCI-H345; xenografts of chronic lymphocytic leukaemia cell lines such as WSU-CLL in SCID mice, Mohammad et al, Leukaemia. 1996 January; 10(1):130-7; xenografts of ovarian cancer cell lines such as IGROV1 in nude mice, Benard et al, Cancer Res. 1985 October; 45(10):4970-9 or xenografts of pancreatic cancer cell lines such as MIA PaCa-2 in nude mice, Marincola et al., J Surg Res 1989 December; 47(6): 520-9). These can be utilized to test compounds that modulate OGTA076 levels, since the pathology exhibited in these models is similar to that of colorectal cancer, kidney cancer, liver cancer, lung cancer, lymphoid leukaemia (particularly chronic lymphocytic leukaemia), ovarian cancer or pancreatic cancer. In accordance with this embodiment, the test compound or a control compound is administered (e.g. orally, rectally or parenterally such as intraperitoneally or intravenously) to a suitable animal and the effect on the expression, activity or both expression and activity of OGTA076 or OGTA076-related polypeptide is determined. Changes in the expression of OGTA076 or an OGTA076-related polypeptide can be assessed by the methods outlined above.

In yet another embodiment, OGTA076 or an OGTA076-related polypeptide is used as a "bait protein" in a two-hybrid assay or three hybrid assay to identify other proteins that bind to or interact with OGTA076 or an OGTA076-related polypeptide (see, e.g. U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and PCT Publication No. WO 94/10300). As those skilled in the art will appreciate, such binding proteins are also likely to be involved in the propagation of signals by OGTA076 as, for example, upstream or downstream elements of a signaling pathway involving OGTA076.

This invention further provides novel agents identified by the above-described screening assays and uses thereof for treatments as described herein. In addition, the invention also provides the use of an agent which interacts with, or modulates the activity of, OGTA076 in the manufacture of a medicament for the treatment of colorectal cancer, kidney cancer, liver cancer, lung cancer, lymphoid leukaemia (particularly chronic lymphocytic leukaemia), ovarian cancer or pancreatic cancer.

Therapeutic Use of OGTA076

The invention provides for treatment or prevention of various diseases and disorders by administration of a therapeutic compound. Such compounds include but are not limited to: OGTA076, OGTA076 analogs, OGTA076-related polypeptides and derivatives (including fragments) thereof; antibodies (or other affinity reagents) to the foregoing; nucleic acids encoding OGTA076, OGTA076 analogs, OGTA076-related polypeptides and fragments thereof; antisense nucleic acids to a gene encoding OGTA076 or an OGTA076-related polypeptide; and modulator (e.g. agonists and antagonists) of a gene encoding OGTA076 or an OGTA076-related polypeptide. An important feature of the present invention is the identification of genes encoding OGTA076 involved in colorectal cancer, kidney cancer, liver cancer, lung cancer, lymphoid leukaemia (particularly chronic lymphocytic leukaemia), ovarian cancer or pancreatic cancer. Colorectal cancer, kidney cancer, liver cancer, lung cancer, lymphoid leukaemia (particularly chronic lymphocytic leukaemia), ovarian cancer or pancreatic cancer can be treated (e.g. to ameliorate symptoms or to retard onset or progression) or prevented by administration of a therapeutic compound that reduces function or expression of OGTA076 in the serum or tissue of subjects having colorectal cancer, kidney cancer, liver cancer, lung cancer, lymphoid leukaemia (particularly chronic lymphocytic leukaemia), ovarian cancer or pancreatic cancer. Thus in one aspect the invention provides one or more of the aforementioned moieties for use in treatment or prophylaxis, for example in the treatment or prophylaxis of cancer, such as a cancer defined herein. The invention also extends to use of said moieties in the manufacture of a medicament for the treatment or prophylaxis of cancer, for example a cancer described herein and uses in a method of treating cancer, for example a cancer described herein.

In one embodiment, one or more antibodies (or other affinity reagents) each specifically binding to OGTA076 are administered alone or in combination with one or more additional therapeutic compounds or treatments.

In a further embodiment, a biological product such as an antibody (or other affinity reagent) is allogeneic to the subject to which it is administered. In another embodiment, a human OGTA076 or a human OGTA076-related polypeptide, a nucleotide sequence encoding a human OGTA076 or a human OGTA076-related polypeptide, or an antibody (or other affinity reagent) to a human OGTA076 or a human OGTA076-related polypeptide, is administered to a human subject for therapy (e.g. to ameliorate symptoms or to retard onset or progression) or prophylaxis.

Without being limited by theory, it is conceived that the therapeutic activity of antibodies (or other affinity reagents) which specifically bind to OGTA076 may be achieved through the phenomenon of Antibody-Dependent Cell-mediated Cytotoxicity (ADCC) (see e.g. Janeway Jr. C. A. et al., Immunobiology, 5th ed., 2001, Garland Publishing, ISBN 0-8153-3642-X; Pier G. B. et al., Immunology, Infection, and Immunity, 2004, p 246-5; Albanell J. et al., Advances in Experimental Medicine and Biology, 2003, 532:p 2153-68 and Weng, W.-K. et al., Journal of Clinical Oncology, 2003, 21:p 3940-3947).

Treatment and Prevention of Colorectal Cancer, Kidney Cancer, Liver Cancer, Lung Cancer, Lymphoid Leukaemia (Particularly Chronic Lymphocytic Leukaemia), Ovarian Cancer or Pancreatic Cancer Colorectal cancer, kidney cancer, liver cancer, lung cancer, lymphoid leukaemia (particularly chronic lymphocytic leukaemia), ovarian cancer or pancreatic cancer is treated or prevented by administration to a subject suspected of having or known to have colorectal cancer, kidney cancer, liver cancer, lung cancer, lymphoid leukaemia (particularly chronic lymphocytic leukaemia), ovarian cancer or pancreatic cancer or to be at risk of developing colorectal cancer, kidney cancer, liver cancer, lung cancer, lymphoid leukaemia (particularly chronic lymphocytic leukaemia), ovarian cancer or pancreatic cancer of a compound that modulates (i.e. increases or decreases) the level or activity (i.e. function) of OGTA076 that is differentially present in the serum or tissue of subjects having colorectal cancer, kidney cancer, liver cancer, lung cancer, lymphoid leukaemia (particularly chronic lymphocytic leukaemia), ovarian cancer or pancreatic cancer compared with serum or tissue of subjects free from colorectal cancer, kidney cancer, liver cancer, lung cancer, lymphoid leukaemia (particularly chronic lymphocytic leukaemia), ovarian cancer and pancreatic cancer. In one embodiment, colorectal cancer, kidney cancer, liver cancer, lung cancer, lymphoid leukaemia (particularly chronic lymphocytic leukaemia), ovarian cancer or pancreatic cancer is treated or prevented by administering to a subject suspected of having or known to have colorectal cancer, kidney cancer, liver cancer, lung cancer, lymphoid leukaemia (particularly chronic lymphocytic leukaemia), ovarian cancer or pancreatic cancer or to be at risk of developing colorectal cancer, kidney cancer, liver cancer, lung cancer, lymphoid leukaemia (particularly chronic lymphocytic leukaemia), ovarian cancer or pancreatic cancer a compound that upregulates (i.e. increases) the level or activity (i.e. function) of OGTA076 that are decreased in the serum or tissue of subjects having colorectal cancer, kidney cancer, liver cancer, lung cancer, lymphoid leukaemia (particularly chronic lymphocytic leukaemia), ovarian cancer or pancreatic cancer. Examples of such a compound include, but are not limited to, OGTA076 antisense oligonucleotides, ribozymes, antibodies (or other affinity reagents) directed against OGTA076, and compounds that inhibit the enzymatic activity of OGTA076. Other useful compounds e.g. OGTA076 antagonists and small molecule OGTA076 antagonists, can be identified using in vitro assays.

Colorectal cancer, kidney cancer, liver cancer, lung cancer, lymphoid leukaemia (particularly chronic lymphocytic leukaemia), ovarian cancer or pancreatic cancer is also treated or prevented by administration to a subject suspected of having or known to have colorectal cancer, kidney cancer, liver cancer, lung cancer, lymphoid leukaemia (particularly chronic lymphocytic leukaemia), ovarian cancer or pancreatic cancer or to be at risk of developing colorectal cancer, kidney cancer, liver cancer, lung cancer, lymphoid leukaemia (particularly chronic lymphocytic leukaemia), ovarian cancer or pancreatic cancer of a compound that downregulates the level or activity (i.e. function) of OGTA076 that are increased in the serum or tissue of subjects having colorectal cancer, kidney cancer, liver cancer, lung cancer, lymphoid leukaemia (particularly chronic lymphocytic leukaemia), ovarian cancer or pancreatic cancer. Examples of such a compound include but are not limited to: OGTA076, OGTA076 fragments and OGTA076-related polypeptides; nucleic acids encoding OGTA076, an OGTA076 fragment and an OGTA076-related polypeptide (e.g. for use in gene therapy); and, for those OGTA076 or OGTA076-related polypeptides with enzymatic activity, compounds or molecules known to modulate that enzymatic activity. Other compounds that can be used, e.g. OGTA076 agonists, can be identified using in in vitro assays.

In one embodiment, therapy or prophylaxis is tailored to the needs of an individual subject. Thus, in specific embodiments, compounds that promote the level or function of OGTA076 are therapeutically or prophylactically administered to a subject suspected of having or known to have colorectal cancer, kidney cancer, liver cancer, lung cancer, lymphoid leukaemia (particularly chronic lymphocytic leukaemia), ovarian cancer or pancreatic cancer, in whom the levels or functions of OGTA076 are absent or are decreased relative to a control or normal reference range. In further embodiments, compounds that promote the level or function of OGTA076 are therapeutically or prophylactically administered to a subject suspected of having or known to have colorectal cancer, kidney cancer, liver cancer, lung cancer, lymphoid leukaemia (particularly chronic lymphocytic leukaemia), ovarian cancer or pancreatic cancer in whom the levels or functions of OGTA076 are increased relative to a control or to a reference range. In further embodiments, compounds that decrease the level or function of OGTA076 are therapeutically or prophylactically administered to a subject suspected of having or known to have colorectal cancer, kidney cancer, liver cancer, lung cancer, lymphoid leukaemia (particularly chronic lymphocytic leukaemia), ovarian cancer or pancreatic cancer in whom the levels or functions of OGTA076 are increased relative to a control or to a reference range. In further embodiments, compounds that decrease the level or function of OGTA076 are therapeutically or prophylactically administered to a subject suspected of having or known to have colorectal cancer, kidney cancer, liver cancer, lung cancer, lymphoid leukaemia (particularly chronic lymphocytic leukaemia), ovarian cancer or pancreatic cancer in whom the levels or functions of OGTA076 are decreased relative to a control or to a reference range. The change in OGTA076 function or level due to the administration of such compounds can be readily detected, e.g. by obtaining a sample (e.g. blood or urine) and assaying in vitro the levels or activities of OGTA076, or the levels of mRNAs encoding OGTA076, or any combination of the foregoing. Such assays can be performed before and after the administration of the compound as described herein.

The compounds of the invention include but are not limited to any compound, e.g. a small organic molecule, protein, peptide, antibody (or other affinity reagent), nucleic acid, etc. that restores the OGTA076 profile towards normal. The compounds of the invention may be given in combination with any other chemotherapy drugs.

Vaccine Therapy

Another aspect of the invention is an immunogenic composition or a pharmaceutical composition, suitably a vaccine composition, comprising OGTA076 or an epitope containing fragment thereof, or nucleic acid encoding OGTA076 or a fragment thereof optionally together with an immunostimulant. The invention also extends to said composition(s) for use in treatment or prophylaxis, for example for the treatment or prophylaxis of cancer, such as a cancer described herein. The invention further extends to use of said compostions for the manufacture of a medicament for the treatment or prophylaxis of cancer, for example a cancer described herein and the use of the composition(s) in treating same.

There is also provided a method of raising an immune response which comprises administering to a subject such compositions and a method for treating or preventing colorectal cancer, kidney cancer, liver cancer, lung cancer, lymphoid leukaemia (particularly chronic lymphocytic leukaemia), ovarian cancer or pancreatic cancer which comprises administering to a subject in need thereof a therapeutically effective amount of such compositions and such compositions for use in preventing or treating colorectal cancer, kidney cancer, liver cancer, lung cancer, lymphoid leukaemia (particularly chronic lymphocytic leukaemia), ovarian cancer or pancreatic cancer.

Thus, OGTA076 may be useful as antigenic material, and may be used in the production of vaccines for treatment or prophylaxis of colorectal cancer, kidney cancer, liver cancer, lung cancer, lymphoid leukaemia (particularly chronic lymphocytic leukaemia), ovarian cancer or pancreatic cancer. Such material can be "antigenic" and/or "immunogenic". Generally, "antigenic" is taken to mean that the protein is capable of being used to raise antibodies (or other affinity reagents) or indeed is capable of inducing an antibody response in a subject or experimental animal. "Immunogenic" is taken to mean that the protein is capable of eliciting an immune response, for example a protective immune response in a subject or experimental animal. Thus, in the latter case, the protein may be capable of not only generating an antibody response but, in addition, non-antibody based immune responses. "Immunogenic" also embraces whether the protein may elicit an immune-like response in an in-vitro setting e.g. a T-cell proliferation assay.

The skilled person will appreciate that homologues or derivatives of OGTA076 will also find use as antigenic/immunogenic material. Thus, for instance proteins which include one or more additions, deletions, substitutions or the like are encompassed by the present invention. In addition, it may be possible to replace one amino acid with another of similar "type". For instance, replacing one hydrophobic amino acid with another. One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein as described herein is less important than that the homologue or derivative should retain its antigenicity and/or immunogenicity. However, suitably, homologues or derivatives having at least 60% similarity (as discussed above) with the proteins or polypeptides described herein are provided. In one embodiment, homologues or derivatives having at least 70% similarity, for example at least 80% similarity are provided, such as homologues or derivatives having at least 90% or even 95% similarity. Suitably, homologues or derivatives have at least 60% sequence identity with the proteins or polypeptides described herein. In one embodiment homologues or derivatives have at least 70% identity, more preferably at least 80% identity. Most preferably, homologues or derivatives have at least 90% or even 95% identity.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

It is well known that it is possible to screen an antigenic protein or polypeptide to identify epitopic regions, i.e. those regions which are responsible for the protein or polypeptide's antigenicity or immunogenicity. Methods well known to the skilled person can be used to test fragments and/or homologues and/or derivatives for antigenicity. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties of the protein from which it is derived.

What is important for homologues, derivatives and fragments is that they possess at least a degree of the antigenicity/immunogenicity of the protein or polypeptide from which they are derived. Thus, in an additional aspect of the invention, there is provided antigenic/or immunogenic fragments of OGTA076, or of homologues or derivatives thereof.

OGTA076, or antigenic fragments thereof, can be provided alone, as a purified or isolated preparation. They may be provided as part of a mixture with one or more other proteins of the invention, or antigenic fragments thereof. In a further aspect, therefore, the invention provides an antigen composition comprising OGTA076 and/or one or more antigenic fragments thereof. Such a composition can be used for the detection and/or diagnosis of colorectal cancer, kidney cancer, liver cancer, lung cancer, lymphoid leukaemia (particularly chronic lymphocytic leukaemia), ovarian cancer or pancreatic cancer.

Vaccine compositions according to the invention may be either a prophylactic or therapeutic vaccine composition.

The vaccine compositions of the invention can include one or more adjuvants (immunostimulants). Examples well-known in the art include inorganic gels, such as aluminium hydroxide, and water-in-oil emulsions, such as incomplete Freund's adjuvant. Other useful adjuvants will be well known to the skilled person.

Suitable adjuvants for use in vaccine compositions for the treatment of cancer include: 3De-O-acylated monophosphoryl lipid A (known as 3D-MPL or simply MPL see WO92/116556), a saponin, for example QS21 or QS7, and TLR4 agonists such as a CpG containing molecule, for example as disclosed in WO95/26204.

The adjuvants employed may be a combination of components, for example MPL and QS21 or MPL, QS21 and a CpG containing moiety.

Adjuvants may be formulated as oil-in-water emulsions or liposomal formulations.

Such preparations may include other vehicles.

In another embodiment, a preparation of oligonucleotides comprising 10 or more consecutive nucleotides complementary to a nucleotide sequence encoding OGTA076 or an OGTA076 peptide fragments is used as vaccines for the treatment of colorectal cancer, kidney cancer, liver cancer, lung cancer, lymphoid leukaemia (particularly chronic lymphocytic leukaemia), ovarian cancer or pancreatic cancer. Such preparations may include adjuvants or other vehicles.

Inhibition of OGTA076 to Treat Colorectal Cancer, Kidney Cancer, Liver Cancer, Lung Cancer, Lymphoid Leukaemia (Particularly Chronic Lymphocytic Leukaemia), Ovarian Cancer or Pancreatic Cancer In one embodiment of the invention, colorectal cancer, kidney cancer, liver cancer, lung cancer, lymphoid leukaemia (particularly chronic lymphocytic leukaemia), ovarian cancer or pancreatic cancer is treated or prevented by administration of a compound that antagonizes (inhibits) the level(s) and/or function(s) of OGTA076 which are elevated in the serum or tissue of subjects having colorectal cancer, kidney cancer, liver cancer, lung cancer, lymphoid leukaemia (particularly chronic lymphocytic leukaemia), ovarian cancer or pancreatic cancer as compared with serum or tissue of subjects free from colorectal cancer, kidney cancer, liver cancer, lung cancer, lymphoid leukaemia (particularly chronic lymphocytic leukaemia), ovarian cancer and pancreatic cancer.

Compounds useful for this purpose include but are not limited to anti-OGTA076 antibodies (or other affinity reagents, and fragments and derivatives containing the binding region thereof), OGTA076 antisense or ribozyme nucleic acids, and nucleic acids encoding dysfunctional OGTA076 that are used to "knockout" endogenous OGTA076 function by homologous recombination (see, e.g. Capecchi, 1989, *Science* 244:1288-1292). Other compounds that inhibit OGTA076 function can be identified by use of known in vitro assays, e.g. assays for the ability of a test compound to inhibit binding of OGTA076 to another protein or a binding partner, or to inhibit a known OGTA076 function. Preferably such inhibition is assayed in vitro or in cell culture, but genetic assays may also be employed. The Preferred Technologies can also be used to detect levels of OGTA076 before and after the administration of the compound. Preferably, suitable in vitro or in vivo assays are utilized to determine the effect of a specific compound and whether its administration is indicated for treatment of the affected tissue, as described in more detail below.

In a specific embodiment, a compound that inhibits OGTA076 function (activity) is administered therapeutically or prophylactically to a subject in whom an increased serum or tissue level or functional activity of OGTA076 (e.g. greater than the normal level or desired level) is detected as compared with serum or tissue of subjects free from colorectal cancer, kidney cancer, liver cancer, lung cancer, lymphoid leukaemia (particularly chronic lymphocytic leukaemia), ovarian cancer and pancreatic cancer or a predetermined reference range. Methods standard in the art can be employed to measure the increase in OGTA076 level or function, as outlined above. Preferred OGTA076 inhibitor compositions include small molecules, i.e. molecules of 1000 daltons or less. Such small molecules can be identified by the screening methods described herein.

Assays for Therapeutic or Prophylactic Compounds

The present invention also provides assays for use in drug discovery in order to identify or verify the efficacy of compounds for treatment or prevention of colorectal cancer, kidney cancer, liver cancer, lung cancer, lymphoid leukaemia (particularly chronic lymphocytic leukaemia), ovarian cancer or pancreatic cancer.

Thus there is provided a method of screening for compounds that modulate the activity of OGTA076, the method comprising: (a) contacting OGTA076 or a biologically active portion thereof with a candidate compound; and (b) determining whether activity of OGTA076 is thereby modulated. Such a process may comprise (a) contacting OGTA076 or a biologically active portion thereof with a candidate compound in a sample; and (b) comparing the activity of OGTA076 or a biologically active portion thereof in said sample after contact with said candidate compound with the activity of OGTA076 or a biologically active portion thereof in said sample before contact with said candidate compound, or with a reference level of activity.

The method of screening may be a method of screening for compounds that inhibit activity of OGTA076.

OGTA076 or a biologically active portion thereof may, for example be expressed on or by a cell. OGTA076 or a biologically active portion thereof may, for example, be isolated from cells which express it. OGTA076 or a biologically active portion thereof may, for example, be immobilised onto a solid phase.

There is also provided a method of screening for compounds that modulate the expression of OGTA076 or nucleic acid encoding OGTA076, the method comprising: (a) contacting cells expressing OGTA076 or nucleic acid encoding OGTA076 with a candidate compound; and (b) determining whether expression of OGTA076 or nucleic acid encoding OGTA076 is thereby modulated. Such a process may comprise (a) contacting cells expressing OGTA076 or nucleic acid encoding OGTA076 with a candidate compound in a sample; and (b) comparing the expression of OGTA076 or nucleic acid encoding OGTA076 by cells in said sample after contact with said candidate compound with the expression of OGTA076 or nucleic acid encoding OGTA076 of cells in said sample before contact with said candidate compound, or with a reference level of expression.

The method may be a method of screening for compounds that inhibit expression of OGTA076 or nucleic acid encoding OGTA076.

Other aspects of the invention include: a compound obtainable by an aforementioned screening method, a compound which modulates the activity or expression of OGTA076 or nucleic acid encoding OGTA076, for example a compound which inhibits the activity or expression of OGTA076 or nucleic acid encoding OGTA076.

Such a compound is provided for use in treating or preventing colorectal cancer, kidney cancer, liver cancer, lung cancer, lymphoid leukaemia (particularly chronic lymphocytic leukaemia), ovarian cancer or pancreatic cancer. There is also provided a method for treating or preventing colorectal cancer, kidney cancer, liver cancer, lung cancer, lymphoid leukaemia (particularly chronic lymphocytic leukaemia), ovarian cancer or pancreatic cancer which comprises administering to a subject in need thereof a therapeutically effective amount of such a compound.

Test compounds can be assayed for their ability to restore OGTA076 levels in a subject having colorectal cancer, kidney cancer, liver cancer, lung cancer, lymphoid leukaemia (particularly chronic lymphocytic leukaemia), ovarian cancer or pancreatic cancer towards levels found in subjects free from colorectal cancer, kidney cancer, liver cancer, lung cancer, lymphoid leukaemia (particularly chronic lymphocytic leukaemia), ovarian cancer and pancreatic cancer or to produce similar changes in experimental animal models of colorectal cancer, kidney cancer, liver cancer, lung cancer, lymphoid leukaemia (particularly chronic lymphocytic leukaemia), ovarian cancer or pancreatic cancer. Compounds able to restore OGTA076 levels in a subject having colorectal cancer, kidney cancer, liver cancer, lung cancer, lymphoid leukaemia (particularly chronic lymphocytic leukaemia), ovarian cancer or pancreatic cancer towards levels found in subjects free from colorectal cancer, kidney cancer, liver cancer, lung cancer, lymphoid leukaemia (particularly chronic lymphocytic leukaemia), ovarian cancer and pancreatic cancer or to produce similar changes in experimental animal models of colorectal cancer, kidney cancer, liver cancer, lung cancer, lymphoid leukaemia (particularly chronic lymphocytic leukaemia), ovarian cancer or pancreatic cancer can be used as lead compounds for further drug discovery, or used therapeutically. OGTA076 expression can be assayed by the Preferred Technologies, immunoassays, gel electrophoresis followed by visualization, detection of OGTA076 activity, or any other method taught herein or known to those skilled in the art. Such assays can be used to screen candidate drugs, in clinical monitoring or in drug development, where abundance of OGTA076 can serve as a surrogate marker for clinical disease.

In various specific embodiments, in vitro assays can be carried out with cells representative of cell types involved in a subject's disorder, to determine if a compound has a desired effect upon such cell types.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. Examples of animal models of colorectal cancer, kidney cancer, liver cancer, lung cancer, lymphoid leukaemia (particularly chronic lymphocytic leukaemia), ovarian cancer or pancreatic cancer include, but are not limited to xenografts of human colorectal cancer cell lines such as MDA-MB-345 in oestrogen-deprived SCID mice, Eccles et al. 1994 Cell Biophysics 24/25, 279; xenografts of renal cell cancer cell lines such as LABAZ1 in immune compromised mice, Zisman et al, Cancer Research 63, 4952-4959, Aug. 15, 2003; xenografts of hepatocellular carcinoma cell lines such as MHCC97 in nude mice, Tian et al., Br J 5 Cancer 1999 November; 81(5):814-21; xenografts of non small cell lung cancer cell lines such as A549 and H460 and xenografts of small cell lung cancer cell lines such as NCI-H345; xenografts of chronic lymphocytic leukaemia cell lines such as WSU-CLL in SCID mice, Mohammad et al, Leukaemia. 1996 January; 10(1):130-7; xenografts of ovarian cancer cell lines such as IGROV1 in nude mice, Benard et al, Cancer Res. 1985 October; 45(10): 4970-9 or xenografts of pancreatic cancer cell lines such as MIA PaCa-2 in nude mice, Marincola et al., J Surg Res 1989 December; 47(6):520-9. These can be utilized to test compounds that modulate OGTA076 levels, since the pathology exhibited in these models is similar to that of colorectal cancer, kidney cancer, liver cancer, lung cancer, lymphoid leukaemia (particularly chronic lymphocytic leukaemia), ovarian cancer or pancreatic cancer. It is also apparent to the skilled artisan that based upon the present disclosure, transgenic animals can be produced with "knock-out" mutations of the gene or genes encoding OGTA076. A "knock-out" mutation of a gene is a mutation that causes the mutated gene to not be expressed, or expressed in an aberrant form or at a low level, such that the activity associated with the gene product is nearly or entirely absent. Preferably, the transgenic animal is a mammal; more preferably, the transgenic animal is a mouse.

In one embodiment, test compounds that modulate the expression of OGTA076 are identified in non-human animals (e.g. mice, rats, monkeys, rabbits, and guinea pigs), for example non-human animal models for colorectal cancer, kidney cancer, liver cancer, lung cancer, lymphoid leukaemia (particularly chronic lymphocytic leukaemia), ovarian cancer or pancreatic cancer, expressing OGTA076. In accordance with this embodiment, a test compound or a control compound is administered to the animals, and the effect of the test compound on expression of OGTA076 is determined. A test compound that alters the expression of OGTA076 can be identified by comparing the level of OGTA076 (or mRNA encoding the same) in an animal or group of animals treated with a test compound with the level of OGTA076 or mRNA in an animal or group of animals treated with a control compound. Techniques known to those of skill in the art can be used to determine the mRNA and protein levels, for example, in situ hybridization. The animals may or may not be sacrificed to assay the effects of a test compound.

In another embodiment, test compounds that modulate the activity of OGTA076 or a biologically active portion thereof are identified in non-human animals (e.g. mice, rats, monkeys, rabbits, and guinea pigs), for example non-human animal models for colorectal cancer, kidney cancer, liver cancer, lung cancer, lymphoid leukaemia (particularly chronic lymphocytic leukaemia), ovarian cancer or pancreatic cancer, expressing OGTA076. In accordance with this embodiment, a test compound or a control compound is administered to the animals, and the effect of a test compound on the activity of OGTA076 is determined. A test compound that alters the activity of OGTA076 can be identified by assaying animals treated with a control compound and animals treated with the test compound. The activity of OGTA076 can be assessed by detecting induction of a cellular second messenger of OGTA076 (e.g. intracellular $Ca^{2+}$, diacylglycerol, IP3, etc.), detecting catalytic or enzymatic activity of OGTA076 or binding partner thereof, detecting the induction of a reporter gene (e.g. a regulatory element that is responsive to OGTA076 operably linked to a nucleic acid encoding a detectable marker, such as luciferase or green fluorescent protein), or detecting a cellular response (e.g. cellular differentiation or cell proliferation). Techniques known to those of skill in the art can be utilized to detect changes in the activity of OGTA076 (see, e.g. U.S. Pat. No. 5,401,639, which is incorporated herein by reference).

In yet another embodiment, test compounds that modulate the level or expression of OGTA076 are identified in human subjects having colorectal cancer, kidney cancer, liver cancer, lung cancer, lymphoid leukaemia (particularly chronic lymphocytic leukaemia), ovarian cancer or pancreatic cancer, for example those having severe colorectal cancer, kidney cancer, liver cancer, lung cancer, lymphoid leukaemia (particularly chronic lymphocytic leukaemia), ovarian cancer or pancreatic cancer. In accordance with this embodiment, a test compound or a control compound is administered to the human subject, and the effect of a test compound on OGTA076 expression is determined by analyzing the expression of OGTA076 or the mRNA encoding the same in a biological sample (e.g. serum, plasma, or urine). A test compound that alters the expression of OGTA076 can be identified by comparing the level of OGTA076 or mRNA encoding the same in a subject or group of subjects treated with a control compound to that in a subject or group of subjects treated with a test compound. Alternatively, alterations in the expression of OGTA076 can be identified by comparing the level of OGTA076 or mRNA encoding the same in a subject or group of subjects before and after the administration of a test compound. Techniques known to those of skill in the art can be used to obtain the biological sample and analyze the mRNA or protein expression. For example, the Preferred Technologies described herein can be used to assess changes in the level of OGTA076.

In another embodiment, test compounds that modulate the activity of OGTA076 are identified in human subjects having colorectal cancer, kidney cancer, liver cancer, lung cancer, lymphoid leukaemia (particularly chronic lymphocytic leukaemia), ovarian cancer or pancreatic cancer (preferably those with severe colorectal cancer, kidney cancer, liver cancer, lung cancer, lymphoid leukaemia (particularly chronic lymphocytic leukaemia), ovarian cancer or pancreatic cancer). In this embodiment, a test compound or a control compound is administered to the human subject, and the effect of a test compound on the activity of OGTA076 is determined. A test compound that alters the activity of OGTA076 can be identified by comparing biological samples from subjects treated with a control compound to samples from subjects treated with the test compound. Alternatively, alterations in the activity of OGTA076 can be identified by comparing the activity of OGTA076 in a subject or group of subjects before and after the administration of a test compound. The activity of OGTA076 can be assessed by detecting in a biological sample (e.g. serum, plasma, or urine) induction of a cellular signal transduction pathway of OGTA076 (e.g. intracellular $Ca^{2+}$, diacylglycerol, IP3, etc.), catalytic or enzymatic activity of OGTA076 or a binding partner thereof, or a cellular response, for example, cellular differentiation, or cell proliferation. Techniques known to those of skill in the art can be used to detect changes in the induction of a second messenger of OGTA076 or changes in a cellular response. For example, RT-PCR can be used to detect changes in the induction of a cellular second messenger.

In one embodiment, a test compound that changes the level or expression of OGTA076 towards levels detected in control subjects (e.g. humans free from colorectal cancer, kidney cancer, liver cancer, lung cancer, lymphoid leukaemia (particularly chronic lymphocytic leukaemia), ovarian cancer and pancreatic cancer) is selected for further testing or therapeutic use. In another embodiment, a test compound that changes the activity of OGTA076 towards the activity found in control subjects (e.g. humans free from colorectal cancer, kidney cancer, liver cancer, lung cancer, lymphoid leukaemia (particularly chronic lymphocytic leukaemia), ovarian cancer and pancreatic cancer) is selected for further testing or therapeutic use.

In another embodiment, test compounds that reduce the severity of one or more symptoms associated with colorectal cancer, kidney cancer, liver cancer, lung cancer, lymphoid leukaemia (particularly chronic lymphocytic leukaemia), ovarian cancer or pancreatic cancer are identified in human subjects having colorectal cancer, kidney cancer, liver cancer, lung cancer, lymphoid leukaemia (particularly chronic lymphocytic leukaemia), ovarian cancer or pancreatic cancer, for example subjects with severe colorectal cancer, kidney cancer, liver cancer, lung cancer, lymphoid leukaemia (particularly chronic lymphocytic leukaemia), ovarian cancer or pancreatic cancer. In accordance with this embodiment, a test compound or a control compound is administered to the subjects, and the effect of a test compound on one or more symptoms of colorectal cancer, kidney cancer, liver cancer, lung cancer, lymphoid leukaemia (particularly chronic lymphocytic leukaemia), ovarian cancer or pancreatic cancer is determined. A test compound that reduces one or more symptoms can be identified by comparing the subjects treated with a control compound to the subjects treated with the test compound. Techniques known to physicians familiar with colorectal cancer, kidney cancer, liver cancer, lung cancer, lymphoid leukaemia (particularly chronic lymphocytic leukaemia), ovarian cancer or pancreatic cancer can be used to determine whether a test compound reduces one or more symptoms associated with colorectal cancer, kidney cancer, liver cancer, lung cancer, lymphoid leukaemia (particularly chronic lymphocytic leukaemia), ovarian cancer or pancreatic cancer. For example, a test compound that reduces tumour burden in a subject having colorectal cancer, kidney cancer, liver cancer, lung cancer, lymphoid leukaemia (particularly chronic lymphocytic leukaemia), ovarian cancer or pancreatic cancer will be beneficial for subjects having colorectal cancer, kidney cancer, liver cancer, lung cancer, lymphoid leukaemia (particularly chronic lymphocytic leukaemia), ovarian cancer or pancreatic cancer.

In one embodiment, a test compound that reduces the severity of one or more symptoms associated with colorectal cancer, kidney cancer, liver cancer, lung cancer, lymphoid leukaemia (particularly chronic lymphocytic leukaemia), ovarian cancer or pancreatic cancer in a human having colorectal cancer, kidney cancer, liver cancer, lung cancer, lymphoid leukaemia (particularly chronic lymphocytic leukaemia), ovarian cancer or pancreatic cancer is selected for further testing or therapeutic use.

Therapeutic and Prophylactic Compositions and their Use

The invention provides methods of treatment (and prophylaxis) comprising administering to a subject an effective amount of a compound of the invention. In one aspect, the compound is substantially purified (e.g. substantially free from substances that limit its effect or produce undesired side-effects). The subject is for example an animal, including but not limited to animals such as cows, pigs, horses, chickens, cats, dogs, etc., such as a mammal, and particularly a human. In a specific embodiment, a non-human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g. encapsulation in liposomes, microparticles, microcapsules, recombinant cells capable of expressing the compound, receptor-mediated endocytosis (see, e.g. Wu and Wu, 1987, J. Biol. Chem. 262: 4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g. oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g. by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g. by injection, by means of a catheter, or by means of an implant, said implant being of a porous, non-porous, or gelatinous material, including membranes, such as sialastic membranes, or fibers. In one embodiment, administration can be by direct injection into colorectal, kidney, liver, lung, lymphoid, ovarian or pancreatic tissue or at the site (or former site) of a malignant tumor or neoplastic or pre-neoplastic tissue.

In another embodiment, the compound can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e. the colon, kidney, liver, lung, ovary or pancreas thus requiring only a fraction of the systemic dose (see, e.g. Goodson, in Medical Applications of Controlled Release, supra, vol. 2, pp. 115-138 (1984)).

Other controlled release systems are discussed in the review by Langer (1990, Science 249:1527-1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g. by use of a retroviral vector (see U.S. Pat. No. 4,980,286), or by direct injection, or by use of microparticle bombardment (e.g. a gene gun; Biolistic, Dupont), or coating with lipids or cell-surface receptors or transfecting agents, or by administering it in linkage to a homeobox-like peptide which is known to enter the nucleus (see e.g. Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water may be a suitable carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, for example in purified form, together with a suitable amount of carrier so as to provide the form for proper administration to the subject. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of colorectal cancer, kidney cancer, liver cancer, lung cancer, lymphoid leukaemia (particularly chronic lymphocytic leukaemia), ovarian cancer or pancreatic cancer can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 100 for example 10 such as 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Determining Abundance of OGTA076 by Imaging Technology

An advantage of determining abundance of OGTA076 by imaging technology may be that such a method is non-invasive (save that reagents may need to be administered) and there is no need to extract a sample from the subject.

Suitable imaging technologies include positron emission tomography (PET) and single photon emission computed tomography (SPECT). Visualisation of OGTA076 using such techniques requires incorporation or binding of a suitable label e.g. a radiotracer such as $^{18}$F, $^{11}$C or $^{123}$I (see e.g. NeuroRx—The Journal of the American Society for Experimental NeuroTherapeutics (2005) 2(2), 348-360 and idem pages 361-371 for further details of the techniques). Radiotracers or other labels may be incorporated into OGTA076 by administration to the subject (e.g. by injection) of a suitably labelled specific ligand. Alternatively they may be incorporated into a binding affinity reagent (e.g. antibody) specific for OGTA076 which may be administered to the subject (e.g. by injection). For discussion of use of Affibodies for imaging see e.g. Orlova A, Magnusson M, Eriksson T L, Nilsson M, Larsson B, Hoiden-Guthenberg I, Widstrom C, Carlsson J, Tolmachev V, Stahl S, Nilsson F Y, Tumor imaging using a picomolar affinity HER2 binding Affibody molecule, Cancer Res. 2006 Apr. 15; 66(8):4339-48).

Diagnosis and Treatment of Colorectal Cancer, Kidney Cancer, Liver Cancer, Lung Cancer, Lymphoid Leukaemia (Particularly Chronic Lymphocytic Leukaemia), Ovarian Cancer or Pancreatic Cancer Using Immunohistochemistry Immunohistochemistry is an excellent detection technique and may therefore be very useful in the diagnosis and treatment of colorectal cancer, kidney cancer, liver cancer, lung cancer, lymphoid leukaemia (particularly chronic lymphocytic leukaemia), ovarian cancer or pancreatic cancer. Immunohistochemistry may be used to detect, diagnose, or monitor colorectal cancer, kidney cancer, liver cancer, lung cancer, lymphoid leukaemia (particularly chronic lymphocytic leukaemia), ovarian cancer or pancreatic cancer through the localization of OGTA076 antigens in tissue sections by the use of labeled antibodies (or other affinity reagents), derivatives and analogs thereof, which specifically bind to OGTA076, as specific reagents through antigen-antibody interactions that are visualized by a marker such as fluorescent dye, enzyme, radioactive element or colloidal gold.

The advancement of monoclonal antibody technology has been of great significance in assuring the place of immunohistochemistry in the modern accurate microscopic diagnosis of human neoplasms. The identification of disseminated neoplastically transformed cells by immunohistochemistry allows for a clearer picture of cancer invasion and metastasis, as well as the evolution of the tumour cell associated immunophenotype towards increased malignancy. Future antineoplastic therapeutical approaches may include a variety of individualized immunotherapies, specific for the particular immunophenotypical pattern associated with each individual patient's neoplastic disease. For further discussion see e.g. Bodey B, The significance of immunohistochemistry in the diagnosis and therapy of neoplasms, Expert Opin Biol Ther. 2002 April; 2(4):371-93.

Preferred features of each aspect of the invention are as for each of the other aspects mutatis mutandis. The prior art documents mentioned herein are incorporated to the fullest extent permitted by law.

Example 1

Identification of Membrane Proteins Expressed in Colorectal Cancer, Chronic Lymphocytic Leukaemia and Pancreatic Cancer Blood and Tissue Samples Using 1D Gel Electrophoresis Using the following Reference Protocol, membrane proteins extracted from colorectal cancer, chronic lymphocytic leukaemia and pancreatic cancer tissue samples were separated by 1D gel and analysed.

1.1 Materials and Methods
1.1.1—Plasma Membrane Fractionation

The cells recovered from the epithelium of a colorectal cancer, chronic lymphocytic leukaemia or pancreatic cancer were lysed and submitted to centrifugation at 1000 G. The supernatant was taken, and it was subsequently centrifuged at 3000 G. Once again, the supernatant was taken, and it was then centrifuged at 100 000 G.

The resulting pellet was recovered and put on 15-60% sucrose gradient.

A Western blot was used to identify sub cellular markers, and the Plasma Membrane fractions were pooled.

The pooled solution was either run directly on 1D gels (see section 1.1.4 below), or further fractionated into heparin binding and nucleotide binding fractions as described below.

1.1.2—Plasma Membrane Heparin-Binding Fraction

The pooled solution from 1.1.1 above was applied to a Heparin column, eluted from column and run on 1D gels (see section 1.1.4 below).

1.1.3—Plasma Nucleotide-Binding Fraction

The pooled solution from 1.1.1 above was applied to a Cibacrom Blue 3GA column, eluted from column and run on 1D gels (see section 1.1.4 below).

1.1.4—1D Gel Technology

Protein or membrane pellets were solubilised in 1D sample buffer (1-2 µg/µl). The sample buffer and protein mixture was then heated to 95° C. for 3 min.

A 9-16% acrylamide gradient gel was cast with a stacking gel and a stacking comb according to the procedure described in Ausubel F. M. et al., eds., 1989, Current Protocols in Molecular Biology, Vol. II, Green Publishing Associates, Inc., and John Wiley & Sons, Inc., New York, section 10.2, incorporated herein by reference in its entirety.

30-50 micrograms of the protein mixtures obtained from detergent and the molecular weight standards (66, 45, 31, 21, 14 kDa) were added to the stacking gel wells using a 10 microliter pipette tip and the samples run at 40 mA for 5 hours.

The plates were then prised open, the gel placed in a tray of fixer (10% acetic acid, 40% ethanol, 50% water) and shaken overnight. Following this, the gel was primed by 30 minutes shaking in a primer solution (7.5% acetic acid (75 ml), 0.05% SDS (5 ml of 10%)). The gel was then incubated with a fluorescent dye (7.5% acetic acid, 0.06% OGS in-house dye (600 µl) with shaking for 3 hrs. Sypro Red (Molecular Probes, Inc., Eugene, Oreg.) is a suitable dye for this purpose. A preferred fluorescent dye is disclosed in U.S. application Ser. No. 09/412,168, filed on Oct. 5, 1999, which is incorporated herein by reference in its entirety.

A computer-readable output was produced by imaging the fluorescently stained gels with an Apollo 3 scanner (Oxford Glycosciences, Oxford, UK). This scanner is developed from the scanner described in WO 96/36882 and in the Ph.D. thesis of David A. Basiji, entitled "Development of a High-throughput Fluorescence Scanner Employing Internal Reflection Optics and Phase-sensitive Detection (Total Internal Reflection, Electrophoresis)", University of Washington (1997), Volume 58/12-B of Dissertation Abstracts International, page 6686, the contents of each of which are incorporated herein by reference. The latest embodiment of this instrument includes the following improvements: The gel is transported through the scanner on a precision lead-screw drive system. This is preferable to laying the glass plate on the belt-driven system that is defined in the Basiji thesis as it provides a reproducible means of accurately transporting the gel past the imaging optics.

The gel is secured into the scanner against three alignment stops that rigidly hold the glass plate in a known position. By doing this in conjunction with the above precision transport system and the fact that the gel is bound to the glass plate, the absolute position of the gel can be predicted and recorded. This ensures that accurate co-ordinates of each feature on the gel can be communicated to the cutting robot for excision. This cutting robot has an identical mounting arrangement for the glass plate to preserve the positional accuracy.

The carrier that holds the gel in place has integral fluorescent markers (Designated M1, M2, M3) that are used to correct the image geometry and are a quality control feature to confirm that the scanning has been performed correctly.

The optical components of the system have been inverted. The laser, mirror, waveguide and other optical components are now above the glass plate being scanned. The embodiment of the Basiji thesis has these underneath. The glass plate is therefore mounted onto the scanner gel side down, so that the optical path remains through the glass plate. By doing this, any particles of gel that may break away from the glass plate will fall onto the base of the instrument rather than into the optics.

In scanning the gels, they were removed from the stain, rinsed with water and allowed to air dry briefly and imaged on the Apollo 3. After imaging, the gels were sealed in polyethylene bags containing a small volume of staining solution, and then stored at 4° C.

Apparent molecular weights were calculated by interpolation from a set of known molecular weight markers run alongside the samples.

1.1.5—Recovery and Analysis of Selected Proteins

Proteins were robotically excised from the gels by the process described in U.S. Pat. No. 6,064,754, Sections 5.4 and 5.6, 5.7, 5.8 (incorporated herein by reference), as is applicable to 1D-electrophoresis, with modification to the robotic cutter as follows: the cutter begins at the top of the lane, and cuts a gel disc 1.7 mm in diameter from the left edge of the lane. The cutter then moves 2 mm to the right, and 0.7 mm down and cuts a further disc. This is then repeated. The cutter then moves back to a position directly underneath the first gel cut, but offset by 2.2 mm downwards, and the pattern of three diagonal cuts are repeated. This is continued for the whole length of the gel.

NOTE: If the lane is observed to broaden significantly then a correction can be made also sideways i.e. instead of returning to a position directly underneath a previous gel cut, the cut can be offset slightly to the left (on the left of the lane) and/or the right (on the right of the lane). The proteins contained within the gel fragments were processed to generate tryptic peptides; partial amino acid sequences of these peptides were determined by mass spectroscopy as described in WO98/53323 and application Ser. No. 09/094,996, filed Jun. 15, 1998.

Proteins were processed to generate tryptic digest peptides. Tryptic peptides were analyzed by mass spectrometry using a PerSeptive Biosystems Voyager—DETM STR Matrix-Assisted Laser Desorption Ionization Time-of-Flight (MALDI-TOF) mass spectrometer, and selected tryptic peptides were analyzed by tandem mass spectrometry (MS/MS) using a Micromass Quadrupole Time-of-Flight (Q-TOF) mass spectrometer (Micromass, Altrincham, U.K.) equipped with a Nanoflow™ electrospray Z-spray source. For partial amino acid sequencing and identification of OGTA076, uninterpreted tandem mass spectra of tryptic peptides were searched using the SEQUEST search program (Eng et al., 1994, J. Am. Soc. Mass Spectrom. 5:976-989), version v.C.1. Criteria for database identification included: the cleavage specificity of trypsin; the detection of a suite of a, b and y ions in peptides returned from the database, and a mass increment for all Cys residues to account for carbamidomethylation. The database searched was a database constructed of protein entries in the non-redundant database held by the National Centre for Biotechnology Information (NCBI) which is accessible at worldwide web ncbi.nlm.nih.gov. Following identification of proteins through spectral-spectral correlation using the SEQUEST program, masses detected in MALDI-TOF mass spectra were assigned to tryptic digest peptides within the proteins identified. In cases where no amino acid sequences could be identified through searching with uninterpreted MS/MS spectra of tryptic digest peptides using the SEQUEST program, tandem mass spectra of the peptides were interpreted manually, using methods known in the art. (In the case of interpretation of low-energy fragmentation mass spectra of peptide ions see Gaskell et al., 1992, Rapid Commun. Mass Spectrom. 6:658-662).

1.1.6—Discrimination of Colorectal Cancer, Chronic Lymphocytic Leukaemia or Pancreatic Cancer Associated Proteins The process to identify OGTA076 uses the peptide sequences obtained experimentally by mass spectrometry described above of naturally occurring human proteins to identify and organize coding exons in the published human genome sequence.

Recent dramatic advances in defining the chemical sequence of the human genome have led to the near completion of this immense task (Venter, J. C. et al. (2001). The sequence of the human genome. Science 16: 1304-51; International Human Genome Sequencing Consortium. (2001). Initial sequencing and analysis of the human genome Nature 409: 860-921). There is little doubt that this sequence information will have a substantial impact on our understanding of many biological processes, including molecular evolution, comparative genomics, pathogenic mechanisms and molecular medicine. For the full medical value inherent in the sequence of the human genome to be realised, the genome needs to be 'organised' and annotated. By this, is meant at least the following three things: (i) The assembly of the sequences of the individual portions of the genome into a coherent, continuous sequence for each chromosome. (ii) The unambiguous identification of those regions of each chromosome that contain genes. (iii) Determination of the fine structure of the genes and the properties of its mRNA and protein products. While the definition of a 'gene' is an increasingly complex issue (H Pearson: What is a gene? Nature (2006) 24: 399-401), what is of immediate interest for drug discovery and development is a catalogue of those genes that encode functional, expressed proteins. A subset of these genes will be involved in the molecular basis of most if not all pathologies. Therefore an important and immediate goal for the pharmaceutical industry is to identify all such genes in the human genome and describe their fine structure.

Processing and Integration of Peptide Masses, Peptide Signatures, ESTs and Public Domain Genomic Sequence Data to Form OGAP® Database Discrete genetic units (exons, transcripts and genes) were identified using the following sequential steps:

1. A 'virtual transcriptome' is generated, containing the tryptic peptides which map to the human genome by combining the gene identifications available from Ensembl and various gene prediction programs. This also incorporates SNP data (from dbSNP) and all alternate splicing of gene identifications. Known contaminants were also added to the virtual transcriptome.

2. All tandem spectra in the OGeS Mass Spectrometry Database are interpreted in order to produce a peptide that can be mapped to one in the virtual transcriptome. A set of automated spectral interpretation algorithms were used to produce the peptide identifications.

3. The set of all mass-matched peptides in the OGeS Mass Spectrometry Database is generated by searching all peptides from transcripts hit by the tandem peptides using a tolerance based on the mass accuracy of the mass spectrometer, typically 20 ppm.

4. All tandem and mass-matched peptides are combined in the form of "protein clusters". This is done using a recursive process which groups sequences into clusters based on common peptide hits. Biological sequences are considered to belong to the same cluster if they share one or more tandem or mass-matched peptide.

5. After initial filtering to screen out incorrectly identified peptides, the resulting clusters are then mapped on the human genome.
6. The protein clusters are then aggregated into regions that define preliminary gene boundaries using their proximity and the co-observation of peptides within protein clusters. Proximity is defined as the peptide being within 80,000 nucleotides on the same strand of the same chromosome. Various elimination rules, based on cluster observation scoring and multiple mapping to the genome are used to refine the output. The resulting 'confirmed genes' are those which best account for the peptides and masses observed by mass spectrometry in each cluster. Nominal co-ordinates for the gene are also an output of this stage.
7. The best set of transcripts for each confirmed gene are created from the protein clusters, peptides, ESTs, candidate exons and molecular weight of the original protein spot.
8. Each identified transcript was linked to the sample providing the observed peptides.
9. Use of an application for viewing and mining the data. The result of steps 1-8 was a database containing genes, each of which consisted of a number of exons and one or more transcripts. An application was written to display and search this integrated genome/proteome data. Any features (OMIM disease locus, InterPro etc.) that had been mapped to the same Golden Path co-ordinate system by Ensembl could be cross-referenced to these genes by coincidence of location and fine structure.

Results

The process was used to generate approximately 1 million peptide sequences to identify protein-coding genes and their exons resulted in the identification of protein sequences for 18083 genes across 67 different tissues and 57 diseases including 506 genes in bladder cancer, 4,713 genes in breast cancer, 766 genes in burkitt's lymphoma, 1,371 genes in cervical cancer, 2,424 genes in chronic lymphocytic leukaemia, 949 genes in colorectal cancer, 1,782 genes in hepatocellular carcinoma, 1,004 genes in kidney cancer, 978 genes in lung cancer, 1,764 genes in melanoma, 1,033 genes in ovarian cancer, 2,961 genes in pancreatic cancer and 3,307 genes in prostate cancer, illustrated here by OGTA076 isolated and identified from colorectal cancer, chronic lymphocytic leukaemia, kidney cancer, liver cancer, lung cancer, ovarian cancer and pancreatic cancer samples. Following comparison of the experimentally determined sequences with sequences in the OGAP® database, OGTA076 showed a high degree of specificity to colorectal cancer, chronic lymphocytic leukaemia, kidney cancer, liver cancer, lung cancer, ovarian cancer and pancreatic cancer indicative of the prognostic and diagnostic nature.

1.2 Results

These experiments identified OGTA076, in its three different isoforms, as further described herein. The full-length OGTA076 was detected in the plasma membrane of colorectal cancer, chronic lymphocytic leukaemia and pancreatic cancer samples and was not detected in the cytosol.

FIG. 2 shows the Protein Index for OGTA076. For each gene, the protein index uses the mass spectrometry data to assign a score to each disease, relative to the global database. The Protein Index can then be used to identify cancer specific genes with a high score in cancer indications and low/negligible scores in normal and other diseases. The index contains ~1 million peptides sequenced via mass spectrometry from 56 diseases. For each gene, this yields a score for each disease and subcellular location. The results are summarized below:

Protein Index Report for OGTA076

Indications Positive:
Colorectal cancer
Chronic lymphocytic leukaemia
Kidney cancer
Liver cancer
Lung cancer
Ovarian cancer
Pancreatic cancer
Disease Controls Acute monocytic leukaemia
Acute T-cell leukaemia
Alzheimer's Disease
Arthritis
Asthma
Atherosclerosis
B-cell non-Hodgkin's lymphoma
Bladder carcinoma
Breast cancer
Breast diseases, benign
Burkitt's lymphoma
Bursitis
Cancer, unspecified
Cervical cancer
Chronic lymphocytic leukaemia
Chronic obstructive pulmonary disease
Colorectal cancer
Dementia, vascular
Depression
Diabetes and Obesity
Diverticulitis
Dyslipidaemia
Emphysema
Focal apocrine metaplasia
Gastric cancer
Gaucher disease
Glioblastoma
Hepatoblastoma
Hypertension
Lactational foci
Kidney cancer
Leukaemia, unspecified
Liver cancer
Liver cirrhosis
Lung cancer
Lymphoma, histiocytic
Melanoma
Metabolic syndrome X
Migraine, acute
Multiple sclerosis
Neuroblastoma
Normal
Obesity
Osteoarthritis
Osteosarcoma
Ovarian cancer
Pancreatic cancer
Prostate cancer
Prostatic diseases, benign
Prostatitis
Retinoblastoma
Schizophrenia
Skin ulcer
Smoker
Teratocarcinoma Subcellular Location Birbeck Granules
Cell surface digest
Chromatin Fraction
Crude Cell Membrane
Cytosol
Golgi/Mitochondrial
Membrane
Membrane Glycoprotein Binding Fraction -continued Mitochondria
Nucleus
Peroxisomes
Plasma Membrane
Secreted
Soluble Fraction
Supernatant
Whole Cell FIG. 2 shows the Protein Index for OGTA076 is high in colorectal cancer, medium in chronic lymphocytic leukaemia, medium in kidney cancer, low in liver cancer, high in lung cancer, medium in ovarian cancer and low in pancreatic cancer plasma membrane and very low in normal plasma membrane and membrane. OGTA076 was not detected in any other diseases. This indicates that OGTA076 is potentially a good marker for colorectal cancer, kidney cancer, liver cancer, lung cancer, chronic lymphocytic leukaemia, ovarian cancer and pancreatic cancer.

Example 2

Identification of Membrane Proteins Expressed in Colorectal Cancer, Kidney Cancer, Liver Cancer, Lung Cancer or Ovarian Cancer Blood and Tissue Samples Using the following Reference Protocol, membrane proteins extracted from colorectal cancer, kidney cancer, liver cancer, lung cancer and ovarian cancer tissue and normal adjacent colorectal, kidney, liver, lung and ovarian tissue samples were digested, labelled with Isotope Tagging for Absolute & Relative Quantitation reagents (iTRAQ; Applied Biosystems, Foster City, Calif., USA) and resulting peptides sequenced by tandem mass spectrometry.

2.1 Materials and Methods
2.1.1—Plasma Membrane Fractionation

The cells recovered from a colorectal cancer, kidney cancer, liver cancer, lung cancer or ovarian cancer or normal adjacent colorectal, kidney, liver, lung or ovarian tissue were lysed and submitted to centrifugation at 1000 G. The supernatant was taken, and it was subsequently centrifuged at 3000 G. Once again, the supernatant was taken, and it was then centrifuged at 100 000 G.

The resulting pellet was recovered and put on 15-60% sucrose gradient.

A Western blot was used to identify sub cellular markers, and the Plasma Membrane fractions were pooled.

The pooled solution was then analysed directly by iTRAQ (see section 2.1.2 below).

2.1.2—iTRAQ Methodology

Membrane protein pellets from colorectal cancer, kidney cancer, liver cancer, lung cancer or ovarian cancer and normal adjacent colorectal, kidney, liver, lung or ovarian tissue were solubilised in sample buffer (2-4 μg/μl in 0.5% SDS) by the addition of buffer and then heating to 95° C. for 3 min.

To a volume of each protein solution equating to 50 μg, 150 μl of 0.5M triethylammonium bicarbonate (TEAB) solution was added. To each sample, 3 μl of 50 mM tris-(2-carboxyethyl)phosphine was added and the mixture was incubated at 60° C. for 1 hour. 1 μl of cysteine blocking reagent, 200 mM methyl methanethiosulphonate (MMTS) in isopropanol, was then added. After incubation at room temperature for 10 minutes, 15 μl of 1 μg/μl trypsin was added to each sample followed by incubation at 37° C. overnight.

The digested samples were dried under a vacuum and re-constituted with 30 μl of 0.5M TEAB solution. 70 μl ethanol was added to each of the four iTRAQ reagents (114/115/116/117) and one reagent added to each of the four samples analysed (two colorectal cancer, kidney cancer, liver cancer, lung cancer or ovarian cancer samples and two corresponding normal adjacent tissue samples) and left at room temperature for 1 hour. The specific reagent added to each sample was recorded. The four labeled samples were combined & vortexed.

The combined sample was reduced to dryness under a vacuum and de-salted by loading onto a C18 spin column, washing with aqueous solvent and then eluting with 70% acetonitrile. The sample fraction was again reduced to dryness and then re-dissolved in 40 μl of solvent A (97.9 water, 2% acetonitrile, 0.1% formic acid) prior to ion exchange fractionation.

2.1.3—Fractionation and Analysis of Labeled Peptides

The sample was fractionated by strong cation exchange chromatography using an Agilent 1200 chromatograph (Agilent, Santa Clara, Calif., USA). Samples were eluted off an Agilent Zorbax Bio-SCXII column (3.5 μm; 50×0.8 mm) using a 20 μl/min gradient of 0-100 mM sodium acetate over 20 minutes and then to 1M over 10 minutes. 1 minute fractions were collected over the 30 minute run.

Each fraction was analysed by liquid chromatography/mass spectrometry using an Agilent 1200 chromatograph fitted with a Zorbax 300SB-C18 (150 mm×75 μm) and an Agilent 6510 quadrupole-time-of-flight instrument (Agilent, Santa Clara, Calif., USA). Peptides were eluted with a 300 nl/min gradient increasing from 15% to 45% acetonitrile in 60 minutes. Data was acquired in auto MS/MS mode such that up to 3 precursor ions above the intensity threshold were selected and product ion spectra accumulated to facilitate the sequencing of the labeled peptides. Raw was processed to create peak lists using Spectrum Mill software (Agilent, Santa Clara, Calif., USA).

2.1.4—Amino Acid Sequence Analysis of Labeled Peptides

For partial amino acid sequencing and identification of OGTA076, uninterpreted tandem mass spectra of tryptic peptides were searched using the SEQUEST search program (Eng et al., 1994, J. Am. Soc. Mass Spectrom. 5:976-989). Criteria for database identification included: the cleavage specificity of trypsin; the detection of a suite of a, b and y ions in peptides returned from the database, and a mass increment for all cysteine residues to account for modification with methyl methanethiosulphonate and the addition of iTRAQ labels to free amines (N-terminus & lysine). The data was searched through IPI Human v3.23 (worldwide web ebi.ac.uk/IPI/IPIhuman.html).

2.1.5—Discrimination of Colorectal Cancer, Kidney Cancer, Liver Cancer, Lung Cancer or Ovarian Cancer Associated Proteins The process described in Example 1 section 1.1.6 was employed to discriminate the colorectal cancer, kidney cancer, liver cancer, lung cancer and ovarian cancer associated proteins in the experimental samples.

2.2 Results

These experiments identified OGTA076, in its three different isoforms, as further described herein. The full-length OGTA076 was detected in the plasma membrane of colorectal cancer, kidney cancer, liver cancer, lung cancer and ovarian cancer samples. The iTRAQ analysis showed that levels of OGTA076 in the cancer samples were higher than in the matched normal adjacent tissue samples.

FIG. 2 shows the Protein Index for OGTA076. See Example 1 section 1.2 for a description of the Protein Index for OGTA076.

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims form part may be used as a basis for priority in respect of any subsequent application. The claims of such subsequent application may be directed to any feature or combination of features described herein. They may take the form of product, composition, process, or use claims and may include, by way of example and without limitation, the following claims:

| Sequence | Seq. ID |
|---|---|
| MRTGWATPRRPAGLLMLLFWFFDLAEPSGRAANDPFTIVHGNTGKCIKPVYGWIVADDCDETEDKLWKWVS QHRLFHLHSQKCLGLDITKSVNELRMFSCDSSAMLWWKCEHHSLYGAARYRLALKDGHGTAISNASDVWKK GGSEESLCDQPYHEIYTRDGNSYGRPCEFPFLIDGTWHHDCILDEDHSGPWCATTLNYEYDRKWGICLKPE NGCEDNWEKNEQFGSCYQFNTQTALSWKEAYVSCQNQGADLLSINSAAELTYLKEKEGIAKIFWIGLNQLY SARGWEWSDHKPLNFLNWDPDRPSAPTIGGSSCARMDAESGLWQSFSCEAQLPYVCRKPLNNTVELTDVWT YSDTRCDAGWLPNNGFCYLLVNESNSWDKAHAKCKAFSSDLISIHSLADVEVVVTKLHNEDIKEEVWIGLK NINIPTLFQWSDGTEVTLTYWDENEPNVPYNKTPNCVSYLGELGQWKVQSCEEKLKYVCKRKGEKLNDASS DKMCPPDEGWKRHGETCYKIYEDEVPFGTNCNLTITSRFEQEYLNDLMKKYDKSLRKYFWTGLRDVDSCGE YNWATVGGRRRAVTFSNWNFLEPASPGGCVAMSTGKSVGKWEVKDCRSFKALSICKKMSGPLGPEEASPKP DDPCPEGWQSFPASLSCYKVFHAERIVRKRNWEEAERFCQALGAHLSSFSHVDEIKEFLHFLTDQFSGQHW LWIGLNKRSPDLQGSWQWSDRTPVSTIIMPNEFQQDYDIRDCAAVKVFHRPWRRGWHFYDDREFIYLRPFA CDTKLEWVCQIPKGRTPKTPDWYNPDRAGIHGPPLIIEGSEYWFVADLHLNYEEAVLYCASNHSFLATITS FVGLKAIKNKIANISGDGQKWWIRISEWPIDDHFTYSRYPWHRFPVTFGEECLYMSAKTWLIDLGKPTDCS TKLPFICEKYNVSSLEKYSPDSAAKVQCSEQWIPFQNKCFLKIKPVSLTFSQASDTCHSYGGTLPSVLSQI EQDFITSLLPDMEATLWIGLRWTAYEKINKWTDNRELTYSNFHPLLVSGRLRIPENFFEEESRYHCALILN LQKSPFTGTWNFTSCSERHFVSLCQKYSEVKSRQTLQNASETVKYLNNLYKIIPKTLTWHSAKRECLKSNM QLVSITDPYQQAFLSVQALLHNSSLWIGLFSQDDELNFGWSDGKRLHFSRWAETNGQLEDCVVLDTDGFWK TVDCNDNQPGAICYYSGNETEKEVKPVDSVKCPSPVLNTPWIPFQNCCYNFIITKNRHMATTQDEVHTKCQ KLNPKSHILSIRDEKENNFVLEQLLYFNYMASWVMLGITYRNNSLMWFDKTPLSYTHWRAGRPTIKNEKFL AGLSTDGFWDIQTFKVIEEAVYFHQHSILACKIEMVDYKEEHNTTLPQFMPYEDGIYSVIQKKVTWYEALN MCSQSGGHLASVHNQNGQLFLEDIVKRDGFPLWVGLSSHDGSESSFEWSDGSTFDYIPWKGQTSPGNCVLL DPKGTWKHEKCNSVKDGAICYKPTKSKKLSRLTYSSRCPAAKENGSRWIQYKGHCYKSDQALHSFSEAKKL CSKHDHSATIVSIKDEDENKFVSRLMRENNNITMRVWLGLSQHSVDQSWSWLDGSEVTFVKWENKSKSGVG RCSMLIASNETWKKVECEHGFGRVVCKVPLGPDYTAIAIIVATLSILVLMGGLIWFLFQRHRLHLAGFSSV RYAQGVNEDEIMLPSFHD | 1 |
| MRTGWATPRRPAGLLMLLFWFFDLAEPSGRAANDPFTIVHGNTGKCIKPVYGWIVADDCDETEDKLWKWVS QHRLFHLHSQKCLGLDITKSVNELRMFSCDSSAMLWWKCEHHSLYGAARYRLALKDGHGTAISNASDVWKK GGSEESLCDQPYHEIYTRDGNSYGRPCEFPFLIDGTWHHDCILDEDHSGPWCATTLNYEYDRKWGICLKPE NGCEDNWEKNEQFGSCYQFNTQTALSWKEAYVSCQNQGADLLSINSAAELTYLKEKEGIAKIFWIGLNQLY SARGWEWSDHKPLNFLNWDPDRPSAPTIGGSSCARMDAESGLWQSFSCEAQLPYVCRKPLNNTVELTDVWT YSDTRCDAGWLPNNGFCYLLVNESNSWDKAHAKCKAFSSDLISIHSLADVEVVVTKLHNEDIKEEVWIGLK NINIPTLFQWSDGTEVTLTYWDENEPNVPYNKTPNCVSYLGELGQWKVQSCEEKLKYVCKRKGEKLNDASS DKMCPPDEGWKRHGETCYKIYEDEVPFGTNCNLTITSRFEQEYLNDLMKKYDKSLRKYFWTGLRDVDSCGE YNWATVGGRRRAVTFSNWNFLEPASPGGCVAMSTGKSVGKWEVKDCRSFKALSICKKMSGPLGPEEASPKP DDPCPEGWQSFPASLSCYKVFHAERIVRKRNWEEAERFCQALGAHLSSFSHVDEIKEFLHFLTDQFSGQHW LWIGLNKRSPDLQGSWQWSDRTPVSTIIMPNEFQQDYDIRDCAAVKVFHRPWRRGWHFYDDREFIYLRPFA CDTKLEWVCQIPKGRTPKTPDWYNPDRAGIHGPPLIIEGSEYWFVADLHLNYEEAVLYCASNHSFLATITS FVGLKAIKNKIANISGDGQKWWIRISEWPIDDHFTYSRYPWHRFPVTFGEECLYMSAKTWLIDLGKPTDCS TKLPFICEKYNVSSLEKYSPDSAAKVQCSEQWIPFQNKCFLKIKPVSLTFSQASDTCHSYGGTLPSVLSQI EQDFITSLLPDMEATLWIGLRWTAYEKINKWTDNRELTYSNFHPLLVSGRLRIPENFFEEESRYHCALILN LQKSPFTGTWNFTSCSERHFVSLCQKYSEVKSRQTLQNASETVKYLNNLYKIIPKTLTWHSAKRECLKSNM QLVSITDPYQQAFLSVQALLHNSSLWIGLFSQDDELNFGWSDGKRLHFSRWAETNGQLEDCVVLDTDGFWK TVDCNDNQPGAICYYSGNETEKEVKPVDSVKCPSPVLNTPWIPFQNCCYNFIITKNRHMATTQDEVHTKCQ KLNPKSHILSIRDEKENNFVLEQLLYFNYMASWVMLGITYRNNSLMWFDKTPLSYTHWRAGRPTIKNEKFL AGLSTDGFWDIQTFKVIEEAVYFHQHSILACKIEMVDYKEEHNTTLPQFMPYEDGIYSVIQKKVTWYEALN MCSQSGGHLASVHNQNGQLFLEDIVKRDGFPLWVGLSSHDGSESSFEWSDGSTFDYIPWKGQTSPGNCVLL DPKGTWKHEKCNSVKDGAICYKPTKSKKLSRLTYSSRCPAAKENGSRWIQYKGHCYKSDQALHSFSEAKKL CSKHDHSATIVSIKDEDENKFVSRLMRENNNITMRVWLGLSQHSVDQSWSWLDGSEVTFVKWENKSKSGVG RCSMLIASNETWKKVECEHGFGRVVCKVPLDCPSSTWIQFQDSCYIFLQEAIKVESIEDVRNQCTDHGADM ISIHNEEENAFILDTLKKQWKGPDDILLGMFYDTDDASFKWFDNSNMTFDKWTDQDDDEDLVDTCAFLHIK TGEWKKGNCEVSSVEGTLCKTAIPYKRKYLSDNHILISALVIASTVILTVLGAIIWFLYKKHSDSRFTTVF STAPQSPYNEDCVLVVGEENEYPVQFD | 2 |
| MRTGWATPRRPAGLLMLLFWFFDLAEPSGRAANDPFTIVHGNTGKCIKPVYGWIVADDCDETEDKLWKWVS QHRLFHLHSQKCLGLDITKSVNELRMFSCDSSAMLWWKCEHHSLYGAARYRLALKDGHGTAISNASDVWKK GGSEESLCDQPYHEIYTRDGNSYGRPCEFPFLIDGTWHHDCILDEDHSGPWCATTLNYEYDRKWGICLKPE NGCEDNWEKNEQFGSCYQFNTQTALSWKEAYVSCQNQGADLLSINSAAELTYLKEKEGIAKIFWIGLNQLY SARGWEWSDHKPLNFLNWDPDRPSAPTIGGSSCARMDAESGLWQSFSCEAQLPYVCRKPLNNTVELTDVWT YSDTRCDAGWLPNNGFCYLLVNESNSWDKAHAKCKAFSSDLISIHSLADVEVVVTKLHNEDIKEEVWIGLK NINIPTLFQWSDGTEVTLTYWDENEPNVPYNKTPNCVSYLGELGQWKVQSCEEKLKYVCKRKGEKLNDASS DKMCPPDEGWKRHGETCYKIYEDEVPFGTNCNLTITSRFEQEYLNDLMKKYDKSLRKYFWTGLRDVDSCGE YNWATVGGRRRAVTFSNWNFLEPASPGGCVAMSTGKSVGKWEVKDCRSFKALSICKKMSGPLGPEEASPKP DDPCPEGWQSFPASLSCYKVFHAERIVRKRNWEEAERFCQALGAHLSSFSHVDEIKEFLHFLTDQFSGQHW LWIGLNKRSPDLQGSWQWSDRTPVSTIIMPNEFQQDYDIRDCAAVKVFHRPWRRGWHFYDDREFIYLRPFA | 3 |

| Sequence | Seq. ID |
|---|---|
| CDTKLEWVCQIPKGRTPKTPDWYNPDRAGIHGPPLIIEGSEYWFVADLHLNYEEAVLYCASNHSFLATITS FVGLKAIKNKIANISGDGQKWWIRISEWPIDDHFTYSRYPWHRFPVTFGEECLYMSAKTWLIDLGKPTDCS TKLPFICEKYNVSSLEKYSPDSAAKVQCSEQWIPFQNKCFLKIKPVSLTFSQASDTCHSYGGTLPSVLSQI EQDFITSLLPDMEATLWIGLRWTAYEKINKWTDNRELTYSNFHPLLVSGRLRIPENFFEEESRYHCALILN LQKSPFTGTWNFTSCSERHFVSLCQKYSEVKSRQTLQNASETVKYLNNLYKIIPKTLTWHSAKRECLKSNM QLVSITDPYQQAFLSVQALLHNSSLWIGLFSQDDELNFGWSDGKRLHFSRWAETNGQLEDCVVLDTDGFWK TVDCNDNQPGAICYYSGNETEKEVKPVDSVKCPSPVLNTPWIPFQNCCYNFIITKNRHMATTQDEVHTKCQ KLNPKSHILSIRDEKENNFVLEQLLYFNYMASWVMLGITYRNNSLMVFDKTPLSYTHWRAGRPTIKNEKFL AGLSTDGFWDIQTFKVIEEAVYFHQHSILACKIEMVDYKEEHNTTLPQFMPYEDGIYSVIQKKVTWYEALN MCSQSGGHLASVHNQGQLFLEDIVKRDGFPLWVGLSSHDGSESSFEWSDGSTFDYIPWKGQTSPGNCVLL DPKGTWKHEKCNSVKDGAICYKPTKSKKLSRLTYSSRCPAAKENGSRWIQYKGHCYKSDQALHSFSEAKKL CSKHDHSATIVSIKDEDENKFVSRLMRENNNITMRVWLGLSQHSVDCPSSTWIQFQDSCYIFLQEAIKVES IEDVRNQCTDHGADMISIHNEEENAFILDTLKKQWKGPDDILLGMFYDTDDASFKWFDNSNMTFDKWTDQD DDEDLVDTCAFLHIKTGEWKKGNCEVSSVEGTLCKTAIPYKRKYLSDNHILISALVIASTVILTVLGAIIW FLYKKHSDSRFTTVFSTAPQSPYNEDCVLVVGEENEYPVQFD | |
| AANDPFTIVHGNTGK | 4 |
| AFSSDLISIHSLADVEVVVTK | 5 |
| CEHHSLYGAAR | 6 |
| CLGLDITK | 7 |
| CSMLIASNETWKK | 8 |
| DGAICYKPTK | 9 |
| DGHGTAISNASDVWKK | 10 |
| DVDSCGEYNWATVGGRRR | 11 |
| EEVWIGLK | 12 |
| EFIYLRPFACDTK | 13 |
| EGIAK | 14 |
| ELTYSNFHPLLVSGR | 15 |
| ENNNITMR | 16 |
| EVKPVDSVK | 17 |
| FEQEYLNDLMK | 18 |
| FPVTFGEECLYMSAK | 19 |
| GNCEVSSVEGTLCK | 20 |
| GWHFYDDR | 21 |
| HDHSATIVSIK | 22 |
| HFVSLCQK | 23 |
| HGETCYK | 24 |
| HMATTQDEVHTK | 25 |
| IANISGDGQK | 26 |
| IEMVDYK | 27 |
| IIPK | 28 |
| IPENFFEEESR | 29 |
| ISEWPIDDHFTYSR | 30 |
| KGNCEVSSVEGTLCK | 31 |
| KRNWEEAER | 32 |
| KVECEHGFGR | 33 |

| Sequence | Seq. ID |
|---|---|
| KYFWTGLR | 34 |
| LALK | 35 |
| LFHLHSQK | 36 |
| LHLAGFSSVR | 37 |
| LHNEDIK | 38 |
| LNDASSDK | 39 |
| LNPK | 40 |
| LPFICEK | 41 |
| MCPPDEGWKR | 42 |
| MFSCDSSAMLWWK | 43 |
| MSGPLGPEEASPK | 44 |
| NNSLMWFDK | 45 |
| NWEEAER | 46 |
| QTLQNASETVK | 47 |
| RGWHFYDDR | 48 |
| RHGETCYK | 49 |
| RLHFSR | 50 |
| RNWEEAER | 51 |
| SDQALHSFSEAK | 52 |
| SHILSIR | 53 |
| SNFHPLLVSGR | 54 |
| SPDLQGSWQWSDR | 55 |
| TLTWHSAK | 56 |
| TPDWYNPDR | 57 |
| TPLSYTHWR | 58 |
| TPVSTIIMPNEFQQDYDIR | 59 |
| VECEHGFGR | 60 |
| VFHRPWR | 61 |
| VIEEAVYFHQH | 62 |
| VQCSEQWIPFQNK | 63 |
| WVSQHR | 64 |
| YFWTGLR | 65 |
| YLNNLYK | 66 |

The invention claimed is:

1. A method comprising administering to a patient having a cancer in which OGTA076 is overexpressed in cancer tissue as compared to healthy control tissue a composition comprising an antibody or an antigen-binding fragment thereof that specifically binds to OGTA076 isoforms as defined in SEQ ID NO: 1, SEQ ID NO: 2 or SEQ ID NO: 3, wherein said antigen-binding fragment is conjugated to a therapeutic moiety, and a pharmaceutically acceptable diluent or carrier, wherein the cancer is liver cancer, lung cancer, chronic lymphocytic leukaemia, ovarian cancer, or pancreatic cancer and the administering treats the patient with the cancer.

2. The method of claim 1, wherein said antibody is conjugated to a label.

3. The method according to claim 2, wherein said label is a detectable label or therapeutic moiety.

4. The method according to claim 3, wherein said therapeutic moiety is selected from the group consisting of a cytotoxic moiety and a radioactive isotope.

5. The method of claim 1, wherein said antibody is a monoclonal antibody, a humanized antibody, a bispecific antibody, or a non-fucosylated antibody.

6. The method of claim 1, wherein said antibody kills OGTA076 antigen expressing cells in the presence of human complement or in the presence of human immune effector cells by complement dependent cytotoxicity or antibody dependent cellular cytotoxicity.

7. The method according to claim 1, wherein said therapeutic moiety is selected from the group consisting of a cytotoxic moiety and a radioactive isotope.

8. The method of claim 1, wherein said antigen binding fragment is a fragment of a monoclonal antibody, a fragment of a humanized antibody, a fragment of a bispecific antibody, or a fragment of a non-fucosylated antibody.

* * * * *

SEQUENCE LISTING

<160> NUMBER OF SEQ ID NOS: 66

<210> SEQ ID NO 1
<211> LENGTH: 1722

```
<212> TYPE: PRT
<213> ORGANISM: Homo Sapiens
<220> FEATURE:
<221> NAME/KEY: MISC_FEATURE
<222> LOCATION: (1)..(1722)
<223> OTHER INFORMATION: Swissprot Accession No: O60449, Lymphocyte
      antigen 75 - Designated in application as OGT076 isoform a

<400> SEQUENCE: 1

Met Arg Thr Gly Trp Ala Thr Pro Arg Arg Pro Ala Gly Leu Leu Met
1               5                   10                  15

Leu Leu Phe Trp Phe Phe Asp Leu Ala Glu Pro Ser Gly Arg Ala Ala
            20                  25                  30

Asn Asp Pro Phe Thr Ile Val His Gly Asn Thr Gly Lys Cys Ile Lys
        35                  40                  45

Pro Val Tyr Gly Trp Ile Val Ala Asp Asp Cys Asp Glu Thr Glu Asp
    50                  55                  60

Lys Leu Trp Lys Trp Val Ser Gln His Arg Leu Phe His Leu His Ser
65                  70                  75                  80

Gln Lys Cys Leu Gly Leu Asp Ile Thr Lys Ser Val Asn Glu Leu Arg
                85                  90                  95

Met Phe Ser Cys Asp Ser Ser Ala Met Leu Trp Trp Lys Cys Glu His
            100                 105                 110

His Ser Leu Tyr Gly Ala Ala Arg Tyr Arg Leu Ala Leu Lys Asp Gly
        115                 120                 125

His Gly Thr Ala Ile Ser Asn Ala Ser Asp Val Trp Lys Lys Gly Gly
    130                 135                 140

Ser Glu Glu Ser Leu Cys Asp Gln Pro Tyr His Glu Ile Tyr Thr Arg
145                 150                 155                 160

Asp Gly Asn Ser Tyr Gly Arg Pro Cys Glu Phe Pro Phe Leu Ile Asp
                165                 170                 175

Gly Thr Trp His His Asp Cys Ile Leu Asp Glu Asp His Ser Gly Pro
            180                 185                 190

Trp Cys Ala Thr Thr Leu Asn Tyr Glu Tyr Asp Arg Lys Trp Gly Ile
        195                 200                 205

Cys Leu Lys Pro Glu Asn Gly Cys Glu Asp Asn Trp Glu Lys Asn Glu
    210                 215                 220

Gln Phe Gly Ser Cys Tyr Gln Phe Asn Thr Gln Thr Ala Leu Ser Trp
225                 230                 235                 240

Lys Glu Ala Tyr Val Ser Cys Gln Asn Gln Gly Ala Asp Leu Leu Ser
                245                 250                 255

Ile Asn Ser Ala Ala Glu Leu Thr Tyr Leu Lys Glu Lys Glu Gly Ile
            260                 265                 270

Ala Lys Ile Phe Trp Ile Gly Leu Asn Gln Leu Tyr Ser Ala Arg Gly
        275                 280                 285

Trp Glu Trp Ser Asp His Lys Pro Leu Asn Phe Leu Asn Trp Asp Pro
    290                 295                 300

Asp Arg Pro Ser Ala Pro Thr Ile Gly Gly Ser Ser Cys Ala Arg Met
305                 310                 315                 320

Asp Ala Glu Ser Gly Leu Trp Gln Ser Phe Ser Cys Glu Ala Gln Leu
                325                 330                 335

Pro Tyr Val Cys Arg Lys Pro Leu Asn Asn Thr Val Glu Leu Thr Asp
            340                 345                 350

Val Trp Thr Tyr Ser Asp Thr Arg Cys Asp Ala Gly Trp Leu Pro Asn
        355                 360                 365
```

```
Asn Gly Phe Cys Tyr Leu Leu Val Asn Glu Ser Asn Ser Trp Asp Lys
    370             375             380

Ala His Ala Lys Cys Lys Ala Phe Ser Ser Asp Leu Ile Ser Ile His
385             390             395                 400

Ser Leu Ala Asp Val Glu Val Val Thr Lys Leu His Asn Glu Asp
            405             410                 415

Ile Lys Glu Glu Val Trp Ile Gly Leu Lys Asn Ile Asn Ile Pro Thr
        420             425             430

Leu Phe Gln Trp Ser Asp Gly Thr Glu Val Thr Leu Thr Tyr Trp Asp
            435             440             445

Glu Asn Glu Pro Asn Val Pro Tyr Asn Lys Thr Pro Asn Cys Val Ser
450             455             460

Tyr Leu Gly Glu Leu Gly Gln Trp Lys Val Gln Ser Cys Glu Glu Lys
465             470             475                 480

Leu Lys Tyr Val Cys Lys Arg Lys Gly Glu Lys Leu Asn Asp Ala Ser
                485             490             495

Ser Asp Lys Met Cys Pro Pro Asp Glu Gly Trp Lys Arg His Gly Glu
            500             505             510

Thr Cys Tyr Lys Ile Tyr Glu Asp Glu Val Pro Phe Gly Thr Asn Cys
            515             520             525

Asn Leu Thr Ile Thr Ser Arg Phe Glu Gln Glu Tyr Leu Asn Asp Leu
530             535             540

Met Lys Lys Tyr Asp Lys Ser Leu Arg Lys Tyr Phe Trp Thr Gly Leu
545             550             555             560

Arg Asp Val Asp Ser Cys Gly Glu Tyr Asn Trp Ala Thr Val Gly Gly
                565             570             575

Arg Arg Arg Ala Val Thr Phe Ser Asn Trp Asn Phe Leu Glu Pro Ala
            580             585             590

Ser Pro Gly Gly Cys Val Ala Met Ser Thr Gly Lys Ser Val Gly Lys
            595             600             605

Trp Glu Val Lys Asp Cys Arg Ser Phe Lys Ala Leu Ser Ile Cys Lys
            610             615             620

Lys Met Ser Gly Pro Leu Gly Pro Glu Glu Ala Ser Pro Lys Pro Asp
625             630             635             640

Asp Pro Cys Pro Glu Gly Trp Gln Ser Phe Pro Ala Ser Leu Ser Cys
            645             650             655

Tyr Lys Val Phe His Ala Glu Arg Ile Val Arg Lys Arg Asn Trp Glu
            660             665             670

Glu Ala Glu Arg Phe Cys Gln Ala Leu Gly Ala His Leu Ser Ser Phe
        675             680             685

Ser His Val Asp Glu Ile Lys Glu Phe Leu His Phe Leu Thr Asp Gln
        690             695             700

Phe Ser Gly Gln His Trp Leu Trp Ile Gly Leu Asn Lys Arg Ser Pro
705             710             715             720

Asp Leu Gln Gly Ser Trp Gln Trp Ser Asp Arg Thr Pro Val Ser Thr
            725             730             735

Ile Ile Met Pro Asn Glu Phe Gln Gln Asp Tyr Asp Ile Arg Asp Cys
            740             745             750

Ala Ala Val Lys Val Phe His Arg Pro Trp Arg Arg Gly Trp His Phe
            755             760             765

Tyr Asp Asp Arg Glu Phe Ile Tyr Leu Arg Pro Phe Ala Cys Asp Thr
770             775             780

Lys Leu Glu Trp Val Cys Gln Ile Pro Lys Gly Arg Thr Pro Lys Thr
```

-continued

```
                785                 790                 795                 800
        Pro Asp Trp Tyr Asn Pro Asp Arg Ala Gly Ile His Gly Pro Pro Leu
                        805                 810                 815

Ile Ile Glu Gly Ser Glu Tyr Trp Phe Val Ala Asp Leu His Leu Asn
                        820                 825                 830

Tyr Glu Glu Ala Val Leu Tyr Cys Ala Ser Asn His Ser Phe Leu Ala
                        835                 840                 845

Thr Ile Thr Ser Phe Val Gly Leu Lys Ala Ile Lys Asn Lys Ile Ala
                        850                 855                 860

Asn Ile Ser Gly Asp Gly Gln Lys Trp Trp Ile Arg Ile Ser Glu Trp
        865                 870                 875                 880

Pro Ile Asp Asp His Phe Thr Tyr Ser Arg Tyr Pro Trp His Arg Phe
                        885                 890                 895

Pro Val Thr Phe Gly Glu Glu Cys Leu Tyr Met Ser Ala Lys Thr Trp
                        900                 905                 910

Leu Ile Asp Leu Gly Lys Pro Thr Asp Cys Ser Thr Lys Leu Pro Phe
                        915                 920                 925

Ile Cys Glu Lys Tyr Asn Val Ser Ser Leu Gly Lys Tyr Ser Pro Asp
                        930                 935                 940

Ser Ala Ala Lys Val Gln Cys Ser Glu Gln Trp Ile Pro Phe Gln Asn
        945                 950                 955                 960

Lys Cys Phe Leu Lys Ile Lys Pro Val Ser Leu Thr Phe Ser Gln Ala
                        965                 970                 975

Ser Asp Thr Cys His Ser Tyr Gly Gly Thr Leu Pro Ser Val Leu Ser
                        980                 985                 990

Gln Ile Glu Gln Asp Phe Ile Thr Ser Leu Leu Pro Asp Met Glu Ala
                        995                 1000                1005

Thr Leu Trp Ile Gly Leu Arg Trp Thr Ala Tyr Glu Lys Ile Asn
                        1010                1015                1020

Lys Trp Thr Asp Asn Arg Glu Leu Thr Tyr Ser Asn Phe His Pro
                        1025                1030                1035

Leu Leu Val Ser Gly Arg Leu Arg Ile Pro Glu Asn Phe Phe Glu
                        1040                1045                1050

Glu Glu Ser Arg Tyr His Cys Ala Leu Ile Leu Asn Leu Gln Lys
                        1055                1060                1065

Ser Pro Phe Thr Gly Thr Trp Asn Phe Thr Ser Cys Ser Glu Arg
                        1070                1075                1080

His Phe Val Ser Leu Cys Gln Lys Tyr Ser Glu Val Lys Ser Arg
                        1085                1090                1095

Gln Thr Leu Gln Asn Ala Ser Glu Thr Val Lys Tyr Leu Asn Asn
                        1100                1105                1110

Leu Tyr Lys Ile Ile Pro Lys Thr Leu Thr Trp His Ser Ala Lys
                        1115                1120                1125

Arg Glu Cys Leu Lys Ser Asn Met Gln Leu Val Ser Ile Thr Asp
                        1130                1135                1140

Pro Tyr Gln Gln Ala Phe Leu Ser Val Gln Ala Leu Leu His Asn
                        1145                1150                1155

Ser Ser Leu Trp Ile Gly Leu Phe Ser Gln Asp Asp Glu Leu Asn
                        1160                1165                1170

Phe Gly Trp Ser Asp Gly Lys Arg Leu His Phe Ser Arg Trp Ala
                        1175                1180                1185

Glu Thr Asn Gly Gln Leu Glu Asp Cys Val Val Leu Asp Thr Asp
                        1190                1195                1200
```

-continued

```
Gly Phe Trp Lys Thr Val Asp Cys Asn Asp Asn Gln Pro Gly Ala
1205                1210                1215

Ile Cys Tyr Tyr Ser Gly Asn Glu Thr Glu Lys Glu Val Lys Pro
1220                1225                1230

Val Asp Ser Val Lys Cys Pro Ser Pro Val Leu Asn Thr Pro Trp
1235                1240                1245

Ile Pro Phe Gln Asn Cys Cys Tyr Asn Phe Ile Ile Thr Lys Asn
1250                1255                1260

Arg His Met Ala Thr Thr Gln Asp Glu Val His Thr Lys Cys Gln
1265                1270                1275

Lys Leu Asn Pro Lys Ser His Ile Leu Ser Ile Arg Asp Glu Lys
1280                1285                1290

Glu Asn Asn Phe Val Leu Glu Gln Leu Leu Tyr Phe Asn Tyr Met
1295                1300                1305

Ala Ser Trp Val Met Leu Gly Ile Thr Tyr Arg Asn Asn Ser Leu
1310                1315                1320

Met Trp Phe Asp Lys Thr Pro Leu Ser Tyr Thr His Trp Arg Ala
1325                1330                1335

Gly Arg Pro Thr Ile Lys Asn Glu Lys Phe Leu Ala Gly Leu Ser
1340                1345                1350

Thr Asp Gly Phe Trp Asp Ile Gln Thr Phe Lys Val Ile Glu Glu
1355                1360                1365

Ala Val Tyr Phe His Gln His Ser Ile Leu Ala Cys Lys Ile Glu
1370                1375                1380

Met Val Asp Tyr Lys Glu Glu His Asn Thr Thr Leu Pro Gln Phe
1385                1390                1395

Met Pro Tyr Glu Asp Gly Ile Tyr Ser Val Ile Gln Lys Lys Val
1400                1405                1410

Thr Trp Tyr Glu Ala Leu Asn Met Cys Ser Gln Ser Gly Gly His
1415                1420                1425

Leu Ala Ser Val His Asn Gln Asn Gly Gln Leu Phe Leu Glu Asp
1430                1435                1440

Ile Val Lys Arg Asp Gly Phe Pro Leu Trp Val Gly Leu Ser Ser
1445                1450                1455

His Asp Gly Ser Glu Ser Ser Phe Glu Trp Ser Asp Gly Ser Thr
1460                1465                1470

Phe Asp Tyr Ile Pro Trp Lys Gly Gln Thr Ser Pro Gly Asn Cys
1475                1480                1485

Val Leu Leu Asp Pro Lys Gly Thr Trp Lys His Glu Lys Cys Asn
1490                1495                1500

Ser Val Lys Asp Gly Ala Ile Cys Tyr Lys Pro Thr Lys Ser Lys
1505                1510                1515

Lys Leu Ser Arg Leu Thr Tyr Ser Ser Arg Cys Pro Ala Ala Lys
1520                1525                1530

Glu Asn Gly Ser Arg Trp Ile Gln Tyr Lys Gly His Cys Tyr Lys
1535                1540                1545

Ser Asp Gln Ala Leu His Ser Phe Ser Glu Ala Lys Lys Leu Cys
1550                1555                1560

Ser Lys His Asp His Ser Ala Thr Ile Val Ser Ile Lys Asp Glu
1565                1570                1575

Asp Glu Asn Lys Phe Val Ser Arg Leu Met Arg Glu Asn Asn Asn
1580                1585                1590
```

```
Ile Thr Met Arg Val Trp Leu Gly Leu Ser Gln His Ser Val Asp
1595                1600                1605

Gln Ser Trp Ser Trp Leu Asp Gly Ser Glu Val Thr Phe Val Lys
    1610                1615                1620

Trp Glu Asn Lys Ser Lys Ser Gly Val Gly Arg Cys Ser Met Leu
1625                1630                1635

Ile Ala Ser Asn Glu Thr Trp Lys Lys Val Glu Cys Glu His Gly
    1640                1645                1650

Phe Gly Arg Val Val Cys Lys Val Pro Leu Gly Pro Asp Tyr Thr
1655                1660                1665

Ala Ile Ala Ile Ile Val Ala Thr Leu Ser Ile Leu Val Leu Met
    1670                1675                1680

Gly Gly Leu Ile Trp Phe Leu Phe Gln Arg His Arg Leu His Leu
1685                1690                1695

Ala Gly Phe Ser Ser Val Arg Tyr Ala Gln Gly Val Asn Glu Asp
    1700                1705                1710

Glu Ile Met Leu Pro Ser Phe His Asp
1715                1720

<210> SEQ ID NO 2
<211> LENGTH: 1873
<212> TYPE: PRT
<213> ORGANISM: Homo Sapiens
<220> FEATURE:
<221> NAME/KEY: MISC_FEATURE
<222> LOCATION: (1)..(1873)
<223> OTHER INFORMATION: Swissprot Accession No: O60449, Lymphocyte
      antigen 75 - Designated in application as OGT076 isoform b

<400> SEQUENCE: 2

Met Arg Thr Gly Trp Ala Thr Pro Arg Arg Pro Ala Gly Leu Leu Met
1               5                   10                  15

Leu Leu Phe Trp Phe Phe Asp Leu Ala Glu Pro Ser Gly Arg Ala Ala
                20                  25                  30

Asn Asp Pro Phe Thr Ile Val His Gly Asn Thr Gly Lys Cys Ile Lys
            35                  40                  45

Pro Val Tyr Gly Trp Ile Val Ala Asp Asp Cys Asp Glu Thr Glu Asp
        50                  55                  60

Lys Leu Trp Lys Trp Val Ser Gln His Arg Leu Phe His Leu His Ser
65                  70                  75                  80

Gln Lys Cys Leu Gly Leu Asp Ile Thr Lys Ser Val Asn Glu Leu Arg
                85                  90                  95

Met Phe Ser Cys Asp Ser Ser Ala Met Leu Trp Trp Lys Cys Glu His
            100                 105                 110

His Ser Leu Tyr Gly Ala Ala Arg Tyr Arg Leu Ala Leu Lys Asp Gly
        115                 120                 125

His Gly Thr Ala Ile Ser Asn Ala Ser Asp Val Trp Lys Lys Gly Gly
    130                 135                 140

Ser Glu Glu Ser Leu Cys Asp Gln Pro Tyr His Glu Ile Tyr Thr Arg
145                 150                 155                 160

Asp Gly Asn Ser Tyr Gly Arg Pro Cys Glu Phe Pro Phe Leu Ile Asp
                165                 170                 175

Gly Thr Trp His His Asp Cys Ile Leu Asp Glu Asp His Ser Gly Pro
            180                 185                 190

Trp Cys Ala Thr Thr Leu Asn Tyr Glu Tyr Asp Arg Lys Trp Gly Ile
        195                 200                 205
```

-continued

```
Cys Leu Lys Pro Glu Asn Gly Cys Glu Asp Asn Trp Glu Lys Asn Glu
    210                 215                 220
Gln Phe Gly Ser Cys Tyr Gln Phe Asn Thr Gln Thr Ala Leu Ser Trp
225                 230                 235                 240
Lys Glu Ala Tyr Val Ser Cys Gln Asn Gln Gly Ala Asp Leu Leu Ser
                245                 250                 255
Ile Asn Ser Ala Ala Glu Leu Thr Tyr Leu Lys Glu Lys Glu Gly Ile
            260                 265                 270
Ala Lys Ile Phe Trp Ile Gly Leu Asn Gln Leu Tyr Ser Ala Arg Gly
        275                 280                 285
Trp Glu Trp Ser Asp His Lys Pro Leu Asn Phe Leu Asn Trp Asp Pro
    290                 295                 300
Asp Arg Pro Ser Ala Pro Thr Ile Gly Gly Ser Ser Cys Ala Arg Met
305                 310                 315                 320
Asp Ala Glu Ser Gly Leu Trp Gln Ser Phe Ser Cys Glu Ala Gln Leu
                325                 330                 335
Pro Tyr Val Cys Arg Lys Pro Leu Asn Asn Thr Val Glu Leu Thr Asp
            340                 345                 350
Val Trp Thr Tyr Ser Asp Thr Arg Cys Asp Ala Gly Trp Leu Pro Asn
        355                 360                 365
Asn Gly Phe Cys Tyr Leu Leu Val Asn Glu Ser Asn Ser Trp Asp Lys
    370                 375                 380
Ala His Ala Lys Cys Lys Ala Phe Ser Ser Asp Leu Ile Ser Ile His
385                 390                 395                 400
Ser Leu Ala Asp Val Glu Val Val Val Thr Lys Leu His Asn Glu Asp
                405                 410                 415
Ile Lys Glu Glu Val Trp Ile Gly Leu Lys Asn Ile Asn Ile Pro Thr
            420                 425                 430
Leu Phe Gln Trp Ser Asp Gly Thr Glu Val Thr Leu Thr Tyr Trp Asp
        435                 440                 445
Glu Asn Glu Pro Asn Val Pro Tyr Asn Lys Thr Pro Asn Cys Val Ser
    450                 455                 460
Tyr Leu Gly Glu Leu Gly Gln Trp Lys Val Gln Ser Cys Glu Glu Lys
465                 470                 475                 480
Leu Lys Tyr Val Cys Lys Arg Lys Gly Glu Lys Leu Asn Asp Ala Ser
                485                 490                 495
Ser Asp Lys Met Cys Pro Pro Asp Glu Gly Trp Lys Arg His Gly Glu
            500                 505                 510
Thr Cys Tyr Lys Ile Tyr Glu Asp Glu Val Pro Phe Gly Thr Asn Cys
        515                 520                 525
Asn Leu Thr Ile Thr Ser Arg Phe Glu Gln Glu Tyr Leu Asn Asp Leu
    530                 535                 540
Met Lys Lys Tyr Asp Lys Ser Leu Arg Lys Tyr Phe Trp Thr Gly Leu
545                 550                 555                 560
Arg Asp Val Asp Ser Cys Gly Glu Tyr Asn Trp Ala Thr Val Gly Gly
                565                 570                 575
Arg Arg Arg Ala Val Thr Phe Ser Asn Trp Asn Phe Leu Glu Pro Ala
            580                 585                 590
Ser Pro Gly Gly Cys Val Ala Met Ser Thr Gly Lys Ser Val Gly Lys
        595                 600                 605
Trp Glu Val Lys Asp Cys Arg Ser Phe Lys Ala Leu Ser Ile Cys Lys
    610                 615                 620
Lys Met Ser Gly Pro Leu Gly Pro Glu Glu Ala Ser Pro Lys Pro Asp
```

```
               625                 630                 635                 640
Asp Pro Cys Pro Glu Gly Trp Gln Ser Phe Pro Ala Ser Leu Ser Cys
                    645                 650                 655

Tyr Lys Val Phe His Ala Glu Arg Ile Val Arg Lys Arg Asn Trp Glu
                    660                 665                 670

Glu Ala Glu Arg Phe Cys Gln Ala Leu Gly Ala His Leu Ser Ser Phe
                    675                 680                 685

Ser His Val Asp Glu Ile Lys Glu Phe Leu His Phe Leu Thr Asp Gln
                    690                 695                 700

Phe Ser Gly Gln His Trp Leu Trp Ile Gly Leu Asn Lys Arg Ser Pro
705                 710                 715                 720

Asp Leu Gln Gly Ser Trp Gln Trp Ser Asp Arg Thr Pro Val Ser Thr
                    725                 730                 735

Ile Ile Met Pro Asn Glu Phe Gln Gln Asp Tyr Asp Ile Arg Asp Cys
                    740                 745                 750

Ala Ala Val Lys Val Phe His Arg Pro Trp Arg Arg Gly Trp His Phe
                    755                 760                 765

Tyr Asp Asp Arg Glu Phe Ile Tyr Leu Arg Pro Phe Ala Cys Asp Thr
                    770                 775                 780

Lys Leu Glu Trp Val Cys Gln Ile Pro Lys Gly Arg Thr Pro Lys Thr
785                 790                 795                 800

Pro Asp Trp Tyr Asn Pro Asp Arg Ala Gly Ile His Gly Pro Pro Leu
                    805                 810                 815

Ile Ile Glu Gly Ser Glu Tyr Trp Phe Val Ala Asp Leu His Leu Asn
                    820                 825                 830

Tyr Glu Glu Ala Val Leu Tyr Cys Ala Ser Asn His Ser Phe Leu Ala
                    835                 840                 845

Thr Ile Thr Ser Phe Val Gly Leu Lys Ala Ile Lys Asn Lys Ile Ala
                    850                 855                 860

Asn Ile Ser Gly Asp Gly Gln Lys Trp Trp Ile Arg Ile Ser Glu Trp
865                 870                 875                 880

Pro Ile Asp Asp His Phe Thr Tyr Ser Arg Tyr Pro Trp His Arg Phe
                    885                 890                 895

Pro Val Thr Phe Gly Glu Glu Cys Leu Tyr Met Ser Ala Lys Thr Trp
                    900                 905                 910

Leu Ile Asp Leu Gly Lys Pro Thr Asp Cys Ser Thr Lys Leu Pro Phe
                    915                 920                 925

Ile Cys Glu Lys Tyr Asn Val Ser Ser Leu Lys Tyr Ser Pro Asp
930                 935                 940

Ser Ala Ala Lys Val Gln Cys Ser Glu Gln Trp Ile Pro Phe Gln Asn
945                 950                 955                 960

Lys Cys Phe Leu Lys Ile Lys Pro Val Ser Leu Thr Phe Ser Gln Ala
                    965                 970                 975

Ser Asp Thr Cys His Ser Tyr Gly Gly Thr Leu Pro Ser Val Leu Ser
                    980                 985                 990

Gln Ile Glu Gln Asp Phe Ile Thr Ser Leu Leu Pro Asp Met Glu Ala
                    995                 1000                1005

Thr Leu Trp Ile Gly Leu Arg Trp Thr Ala Tyr Glu Lys Ile Asn
            1010                1015                1020

Lys Trp Thr Asp Asn Arg Glu Leu Thr Tyr Ser Asn Phe His Pro
            1025                1030                1035

Leu Leu Val Ser Gly Arg Leu Arg Ile Pro Glu Asn Phe Phe Glu
            1040                1045                1050
```

```
Glu Glu Ser Arg Tyr His Cys Ala Leu Ile Leu Asn Leu Gln Lys
1055                1060                1065

Ser Pro Phe Thr Gly Thr Trp Asn Phe Thr Ser Cys Ser Glu Arg
1070                1075                1080

His Phe Val Ser Leu Cys Gln Lys Tyr Ser Glu Val Lys Ser Arg
        1085                1090                1095

Gln Thr Leu Gln Asn Ala Ser Glu Thr Val Lys Tyr Leu Asn Asn
1100                1105                1110

Leu Tyr Lys Ile Ile Pro Lys Thr Leu Thr Trp His Ser Ala Lys
1115                1120                1125

Arg Glu Cys Leu Lys Ser Asn Met Gln Leu Val Ser Ile Thr Asp
1130                1135                1140

Pro Tyr Gln Gln Ala Phe Leu Ser Val Gln Ala Leu Leu His Asn
1145                1150                1155

Ser Ser Leu Trp Ile Gly Leu Phe Ser Gln Asp Asp Glu Leu Asn
1160                1165                1170

Phe Gly Trp Ser Asp Gly Lys Arg Leu His Phe Ser Arg Trp Ala
1175                1180                1185

Glu Thr Asn Gly Gln Leu Glu Asp Cys Val Val Leu Asp Thr Asp
1190                1195                1200

Gly Phe Trp Lys Thr Val Asp Cys Asn Asp Asn Gln Pro Gly Ala
1205                1210                1215

Ile Cys Tyr Tyr Ser Gly Asn Glu Thr Glu Lys Glu Val Lys Pro
1220                1225                1230

Val Asp Ser Val Lys Cys Pro Ser Pro Val Leu Asn Thr Pro Trp
1235                1240                1245

Ile Pro Phe Gln Asn Cys Cys Tyr Asn Phe Ile Ile Thr Lys Asn
1250                1255                1260

Arg His Met Ala Thr Thr Gln Asp Glu Val His Thr Lys Cys Gln
1265                1270                1275

Lys Leu Asn Pro Lys Ser His Ile Leu Ser Ile Arg Asp Glu Lys
1280                1285                1290

Glu Asn Asn Phe Val Leu Glu Gln Leu Leu Tyr Phe Asn Tyr Met
1295                1300                1305

Ala Ser Trp Val Met Leu Gly Ile Thr Tyr Arg Asn Asn Ser Leu
1310                1315                1320

Met Trp Phe Asp Lys Thr Pro Leu Ser Tyr Thr His Trp Arg Ala
1325                1330                1335

Gly Arg Pro Thr Ile Lys Asn Glu Lys Phe Leu Ala Gly Leu Ser
1340                1345                1350

Thr Asp Gly Phe Trp Asp Ile Gln Thr Phe Lys Val Ile Glu Glu
1355                1360                1365

Ala Val Tyr Phe His Gln His Ser Ile Leu Ala Cys Lys Ile Glu
1370                1375                1380

Met Val Asp Tyr Lys Glu Glu His Asn Thr Thr Leu Pro Gln Phe
1385                1390                1395

Met Pro Tyr Glu Asp Gly Ile Tyr Ser Val Ile Gln Lys Lys Val
1400                1405                1410

Thr Trp Tyr Glu Ala Leu Asn Met Cys Ser Gln Ser Gly Gly His
1415                1420                1425

Leu Ala Ser Val His Asn Gln Asn Gly Gln Leu Phe Leu Glu Asp
1430                1435                1440
```

```
Ile Val Lys Arg Asp Gly Phe Pro Leu Trp Val Gly Leu Ser Ser
1445                1450                1455

His Asp Gly Ser Glu Ser Ser Phe Glu Trp Ser Asp Gly Ser Thr
1460                1465                1470

Phe Asp Tyr Ile Pro Trp Lys Gly Gln Thr Ser Pro Gly Asn Cys
1475                1480                1485

Val Leu Leu Asp Pro Lys Gly Thr Trp Lys His Glu Lys Cys Asn
1490                1495                1500

Ser Val Lys Asp Gly Ala Ile Cys Tyr Lys Pro Thr Lys Ser Lys
1505                1510                1515

Lys Leu Ser Arg Leu Thr Tyr Ser Ser Arg Cys Pro Ala Ala Lys
1520                1525                1530

Glu Asn Gly Ser Arg Trp Ile Gln Tyr Lys Gly His Cys Tyr Lys
1535                1540                1545

Ser Asp Gln Ala Leu His Ser Phe Ser Glu Ala Lys Lys Leu Cys
1550                1555                1560

Ser Lys His Asp His Ser Ala Thr Ile Val Ser Ile Lys Asp Glu
1565                1570                1575

Asp Glu Asn Lys Phe Val Ser Arg Leu Met Arg Glu Asn Asn Asn
1580                1585                1590

Ile Thr Met Arg Val Trp Leu Gly Leu Ser Gln His Ser Val Asp
1595                1600                1605

Gln Ser Trp Ser Trp Leu Asp Gly Ser Glu Val Thr Phe Val Lys
1610                1615                1620

Trp Glu Asn Lys Ser Lys Ser Gly Val Gly Arg Cys Ser Met Leu
1625                1630                1635

Ile Ala Ser Asn Glu Thr Trp Lys Lys Val Glu Cys Glu His Gly
1640                1645                1650

Phe Gly Arg Val Val Cys Lys Val Pro Leu Asp Cys Pro Ser Ser
1655                1660                1665

Thr Trp Ile Gln Phe Gln Asp Ser Cys Tyr Ile Phe Leu Gln Glu
1670                1675                1680

Ala Ile Lys Val Glu Ser Ile Glu Asp Val Arg Asn Gln Cys Thr
1685                1690                1695

Asp His Gly Ala Asp Met Ile Ser Ile His Asn Glu Glu Glu Asn
1700                1705                1710

Ala Phe Ile Leu Asp Thr Leu Lys Lys Gln Trp Lys Gly Pro Asp
1715                1720                1725

Asp Ile Leu Leu Gly Met Phe Tyr Asp Thr Asp Asp Ala Ser Phe
1730                1735                1740

Lys Trp Phe Asp Asn Ser Asn Met Thr Phe Asp Lys Trp Thr Asp
1745                1750                1755

Gln Asp Asp Asp Glu Asp Leu Val Asp Thr Cys Ala Phe Leu His
1760                1765                1770

Ile Lys Thr Gly Glu Trp Lys Lys Gly Asn Cys Glu Val Ser Ser
1775                1780                1785

Val Glu Gly Thr Leu Cys Lys Thr Ala Ile Pro Tyr Lys Arg Lys
1790                1795                1800

Tyr Leu Ser Asp Asn His Ile Leu Ile Ser Ala Leu Val Ile Ala
1805                1810                1815

Ser Thr Val Ile Leu Thr Val Leu Gly Ala Ile Ile Trp Phe Leu
1820                1825                1830

Tyr Lys Lys His Ser Asp Ser Arg Phe Thr Thr Val Phe Ser Thr
```

-continued

```
              1835                1840                1845

Ala Pro Gln Ser Pro Tyr Asn Glu Asp Cys Val Leu Val Val Gly
        1850                1855                1860

Glu Glu Asn Glu Tyr Pro Val Gln Phe Asp
        1865                1870

<210> SEQ ID NO 3
<211> LENGTH: 1817
<212> TYPE: PRT
<213> ORGANISM: Homo Sapiens
<220> FEATURE:
<221> NAME/KEY: MISC_FEATURE
<222> LOCATION: (1)..(1817)
<223> OTHER INFORMATION: Swissprot Accession No: O60449, Lymphocyte
      antigen 75 - Designated in application as OGT076 isoform c

<400> SEQUENCE: 3

Met Arg Thr Gly Trp Ala Thr Pro Arg Arg Pro Ala Gly Leu Leu Met
  1               5                  10                  15

Leu Leu Phe Trp Phe Phe Asp Leu Ala Glu Pro Ser Gly Arg Ala Ala
                 20                  25                  30

Asn Asp Pro Phe Thr Ile Val His Gly Asn Thr Gly Lys Cys Ile Lys
             35                  40                  45

Pro Val Tyr Gly Trp Ile Val Ala Asp Asp Cys Asp Glu Thr Glu Asp
         50                  55                  60

Lys Leu Trp Lys Trp Val Ser Gln His Arg Leu Phe His Leu His Ser
 65                  70                  75                  80

Gln Lys Cys Leu Gly Leu Asp Ile Thr Lys Ser Val Asn Glu Leu Arg
                 85                  90                  95

Met Phe Ser Cys Asp Ser Ser Ala Met Leu Trp Trp Lys Cys Glu His
            100                 105                 110

His Ser Leu Tyr Gly Ala Ala Arg Tyr Arg Leu Ala Leu Lys Asp Gly
        115                 120                 125

His Gly Thr Ala Ile Ser Asn Ala Ser Asp Val Trp Lys Lys Gly Gly
    130                 135                 140

Ser Glu Glu Ser Leu Cys Asp Gln Pro Tyr His Glu Ile Tyr Thr Arg
145                 150                 155                 160

Asp Gly Asn Ser Tyr Gly Arg Pro Cys Glu Phe Pro Phe Leu Ile Asp
                165                 170                 175

Gly Thr Trp His His Asp Cys Ile Leu Asp Glu Asp His Ser Gly Pro
            180                 185                 190

Trp Cys Ala Thr Thr Leu Asn Tyr Glu Tyr Asp Arg Lys Trp Gly Ile
        195                 200                 205

Cys Leu Lys Pro Glu Asn Gly Cys Glu Asp Asn Trp Glu Lys Asn Glu
    210                 215                 220

Gln Phe Gly Ser Cys Tyr Gln Phe Asn Thr Gln Thr Ala Leu Ser Trp
225                 230                 235                 240

Lys Glu Ala Tyr Val Ser Cys Gln Asn Gln Gly Ala Asp Leu Leu Ser
                245                 250                 255

Ile Asn Ser Ala Ala Glu Leu Thr Tyr Leu Lys Glu Lys Glu Gly Ile
            260                 265                 270

Ala Lys Ile Phe Trp Ile Gly Leu Asn Gln Leu Tyr Ser Ala Arg Gly
        275                 280                 285

Trp Glu Trp Ser Asp His Lys Pro Leu Asn Phe Leu Asn Trp Asp Pro
    290                 295                 300

Asp Arg Pro Ser Ala Pro Thr Ile Gly Gly Ser Ser Cys Ala Arg Met
```

```
305                 310                 315                 320
Asp Ala Glu Ser Gly Leu Trp Gln Ser Phe Ser Cys Glu Ala Gln Leu
                325                 330                 335

Pro Tyr Val Cys Arg Lys Pro Leu Asn Asn Thr Val Glu Leu Thr Asp
                340                 345                 350

Val Trp Thr Tyr Ser Asp Thr Arg Cys Asp Ala Gly Trp Leu Pro Asn
                355                 360                 365

Asn Gly Phe Cys Tyr Leu Leu Val Asn Glu Ser Asn Ser Trp Asp Lys
            370                 375                 380

Ala His Ala Lys Cys Lys Ala Phe Ser Ser Asp Leu Ile Ser Ile His
385                 390                 395                 400

Ser Leu Ala Asp Val Glu Val Val Thr Lys Leu His Asn Glu Asp
                405                 410                 415

Ile Lys Glu Glu Val Trp Ile Gly Leu Lys Asn Ile Asn Ile Pro Thr
                420                 425                 430

Leu Phe Gln Trp Ser Asp Gly Thr Glu Val Thr Leu Thr Tyr Trp Asp
            435                 440                 445

Glu Asn Glu Pro Asn Val Pro Tyr Asn Lys Thr Pro Asn Cys Val Ser
    450                 455                 460

Tyr Leu Gly Glu Leu Gly Gln Trp Lys Val Gln Ser Cys Glu Glu Lys
465                 470                 475                 480

Leu Lys Tyr Val Cys Lys Arg Lys Gly Glu Lys Leu Asn Asp Ala Ser
                485                 490                 495

Ser Asp Lys Met Cys Pro Pro Asp Glu Gly Trp Lys Arg His Gly Glu
                500                 505                 510

Thr Cys Tyr Lys Ile Tyr Glu Asp Glu Val Pro Phe Gly Thr Asn Cys
                515                 520                 525

Asn Leu Thr Ile Thr Ser Arg Phe Glu Gln Glu Tyr Leu Asn Asp Leu
            530                 535                 540

Met Lys Lys Tyr Asp Lys Ser Leu Arg Lys Tyr Phe Trp Thr Gly Leu
545                 550                 555                 560

Arg Asp Val Asp Ser Cys Gly Glu Tyr Asn Trp Ala Thr Val Gly Gly
                565                 570                 575

Arg Arg Arg Ala Val Thr Phe Ser Asn Trp Asn Phe Leu Glu Pro Ala
                580                 585                 590

Ser Pro Gly Gly Cys Val Ala Met Ser Thr Gly Lys Ser Val Gly Lys
            595                 600                 605

Trp Glu Val Lys Asp Cys Arg Ser Phe Lys Ala Leu Ser Ile Cys Lys
    610                 615                 620

Lys Met Ser Gly Pro Leu Gly Pro Glu Glu Ala Ser Pro Lys Pro Asp
625                 630                 635                 640

Asp Pro Cys Pro Glu Gly Trp Gln Ser Phe Pro Ala Ser Leu Ser Cys
                645                 650                 655

Tyr Lys Val Phe His Ala Glu Arg Ile Val Arg Lys Arg Asn Trp Glu
                660                 665                 670

Glu Ala Glu Arg Phe Cys Gln Ala Leu Gly Ala His Leu Ser Ser Phe
                675                 680                 685

Ser His Val Asp Glu Ile Lys Glu Phe Leu His Phe Leu Thr Asp Gln
            690                 695                 700

Phe Ser Gly Gln His Trp Leu Trp Ile Gly Leu Asn Lys Arg Ser Pro
705                 710                 715                 720

Asp Leu Gln Gly Ser Trp Gln Trp Ser Asp Arg Thr Pro Val Ser Thr
                725                 730                 735
```

```
Ile Ile Met Pro Asn Glu Phe Gln Gln Asp Tyr Asp Ile Arg Asp Cys
            740                 745                 750

Ala Ala Val Lys Val Phe His Arg Pro Trp Arg Arg Gly Trp His Phe
            755                 760                 765

Tyr Asp Asp Arg Glu Phe Ile Tyr Leu Arg Pro Phe Ala Cys Asp Thr
            770                 775                 780

Lys Leu Glu Trp Val Cys Gln Ile Pro Lys Gly Arg Thr Pro Lys Thr
785                 790                 795                 800

Pro Asp Trp Tyr Asn Pro Asp Arg Ala Gly Ile His Gly Pro Pro Leu
                805                 810                 815

Ile Ile Glu Gly Ser Glu Tyr Trp Phe Val Ala Asp Leu His Leu Asn
            820                 825                 830

Tyr Glu Glu Ala Val Leu Tyr Cys Ala Ser Asn His Ser Phe Leu Ala
            835                 840                 845

Thr Ile Thr Ser Phe Val Gly Leu Lys Ala Ile Lys Asn Lys Ile Ala
            850                 855                 860

Asn Ile Ser Gly Asp Gly Gln Lys Trp Trp Ile Arg Ile Ser Glu Trp
865                 870                 875                 880

Pro Ile Asp Asp His Phe Thr Tyr Ser Arg Tyr Pro Trp His Arg Phe
                885                 890                 895

Pro Val Thr Phe Gly Glu Glu Cys Leu Tyr Met Ser Ala Lys Thr Trp
                900                 905                 910

Leu Ile Asp Leu Gly Lys Pro Thr Asp Cys Ser Thr Lys Leu Pro Phe
                915                 920                 925

Ile Cys Glu Lys Tyr Asn Val Ser Ser Leu Glu Lys Tyr Ser Pro Asp
            930                 935                 940

Ser Ala Ala Lys Val Gln Cys Ser Glu Gln Trp Ile Pro Phe Gln Asn
945                 950                 955                 960

Lys Cys Phe Leu Lys Ile Lys Pro Val Ser Leu Thr Phe Ser Gln Ala
                965                 970                 975

Ser Asp Thr Cys His Ser Tyr Gly Gly Thr Leu Pro Ser Val Leu Ser
            980                 985                 990

Gln Ile Glu Gln Asp Phe Ile Thr Ser Leu Leu Pro Asp Met Glu Ala
            995                 1000                1005

Thr Leu Trp Ile Gly Leu Arg Trp Thr Ala Tyr Glu Lys Ile Asn
            1010                1015                1020

Lys Trp Thr Asp Asn Arg Glu Leu Thr Tyr Ser Asn Phe His Pro
            1025                1030                1035

Leu Leu Val Ser Gly Arg Leu Arg Ile Pro Glu Asn Phe Phe Glu
            1040                1045                1050

Glu Glu Ser Arg Tyr His Cys Ala Leu Ile Leu Asn Leu Gln Lys
            1055                1060                1065

Ser Pro Phe Thr Gly Thr Trp Asn Phe Thr Ser Cys Ser Glu Arg
            1070                1075                1080

His Phe Val Ser Leu Cys Gln Lys Tyr Ser Glu Val Lys Ser Arg
            1085                1090                1095

Gln Thr Leu Gln Asn Ala Ser Glu Thr Val Lys Tyr Leu Asn Asn
            1100                1105                1110

Leu Tyr Lys Ile Ile Pro Lys Thr Leu Thr Trp His Ser Ala Lys
            1115                1120                1125

Arg Glu Cys Leu Lys Ser Asn Met Gln Leu Val Ser Ile Thr Asp
            1130                1135                1140
```

-continued

```
Pro Tyr Gln Gln Ala Phe Leu Ser Val Gln Ala Leu Leu His Asn
    1145              1150                1155

Ser Ser Leu Trp Ile Gly Leu Phe Ser Gln Asp Asp Glu Leu Asn
    1160              1165                1170

Phe Gly Trp Ser Asp Gly Lys Arg Leu His Phe Ser Arg Trp Ala
    1175              1180                1185

Glu Thr Asn Gly Gln Leu Glu Asp Cys Val Val Leu Asp Thr Asp
    1190              1195                1200

Gly Phe Trp Lys Thr Val Asp Cys Asn Asp Asn Gln Pro Gly Ala
    1205              1210                1215

Ile Cys Tyr Tyr Ser Gly Asn Glu Thr Glu Lys Glu Val Lys Pro
    1220              1225                1230

Val Asp Ser Val Lys Cys Pro Ser Pro Val Leu Asn Thr Pro Trp
    1235              1240                1245

Ile Pro Phe Gln Asn Cys Cys Tyr Asn Phe Ile Ile Thr Lys Asn
    1250              1255                1260

Arg His Met Ala Thr Thr Gln Asp Glu Val His Thr Lys Cys Gln
    1265              1270                1275

Lys Leu Asn Pro Lys Ser His Ile Leu Ser Ile Arg Asp Glu Lys
    1280              1285                1290

Glu Asn Asn Phe Val Leu Glu Gln Leu Leu Tyr Phe Asn Tyr Met
    1295              1300                1305

Ala Ser Trp Val Met Leu Gly Ile Thr Tyr Arg Asn Asn Ser Leu
    1310              1315                1320

Met Trp Phe Asp Lys Thr Pro Leu Ser Tyr Thr His Trp Arg Ala
    1325              1330                1335

Gly Arg Pro Thr Ile Lys Asn Glu Lys Phe Leu Ala Gly Leu Ser
    1340              1345                1350

Thr Asp Gly Phe Trp Asp Ile Gln Thr Phe Lys Val Ile Glu Glu
    1355              1360                1365

Ala Val Tyr Phe His Gln His Ser Ile Leu Ala Cys Lys Ile Glu
    1370              1375                1380

Met Val Asp Tyr Lys Glu Glu His Asn Thr Thr Leu Pro Gln Phe
    1385              1390                1395

Met Pro Tyr Glu Asp Gly Ile Tyr Ser Val Ile Gln Lys Lys Val
    1400              1405                1410

Thr Trp Tyr Glu Ala Leu Asn Met Cys Ser Gln Ser Gly Gly His
    1415              1420                1425

Leu Ala Ser Val His Asn Gln Asn Gly Gln Leu Phe Leu Glu Asp
    1430              1435                1440

Ile Val Lys Arg Asp Gly Phe Pro Leu Trp Val Gly Leu Ser Ser
    1445              1450                1455

His Asp Gly Ser Glu Ser Ser Phe Glu Trp Ser Asp Gly Ser Thr
    1460              1465                1470

Phe Asp Tyr Ile Pro Trp Lys Gly Gln Thr Ser Pro Gly Asn Cys
    1475              1480                1485

Val Leu Leu Asp Pro Lys Gly Thr Trp Lys His Glu Lys Cys Asn
    1490              1495                1500

Ser Val Lys Asp Gly Ala Ile Cys Tyr Lys Pro Thr Lys Ser Lys
    1505              1510                1515

Lys Leu Ser Arg Leu Thr Tyr Ser Ser Arg Cys Pro Ala Ala Lys
    1520              1525                1530

Glu Asn Gly Ser Arg Trp Ile Gln Tyr Lys Gly His Cys Tyr Lys
```

```
           1535                1540                1545

Ser Asp Gln Ala Leu His Ser Phe Ser Glu Ala Lys Lys Leu Cys
    1550                1555                1560

Ser Lys His Asp His Ser Ala Thr Ile Val Ser Ile Lys Asp Glu
    1565                1570                1575

Asp Glu Asn Lys Phe Val Ser Arg Leu Met Arg Glu Asn Asn Asn
    1580                1585                1590

Ile Thr Met Arg Val Trp Leu Gly Leu Ser Gln His Ser Val Asp
    1595                1600                1605

Cys Pro Ser Ser Thr Trp Ile Gln Phe Gln Asp Ser Cys Tyr Ile
    1610                1615                1620

Phe Leu Gln Glu Ala Ile Lys Val Glu Ser Ile Glu Asp Val Arg
    1625                1630                1635

Asn Gln Cys Thr Asp His Gly Ala Asp Met Ile Ser Ile His Asn
    1640                1645                1650

Glu Glu Glu Asn Ala Phe Ile Leu Asp Thr Leu Lys Lys Gln Trp
    1655                1660                1665

Lys Gly Pro Asp Asp Ile Leu Leu Gly Met Phe Tyr Asp Thr Asp
    1670                1675                1680

Asp Ala Ser Phe Lys Trp Phe Asp Asn Ser Asn Met Thr Phe Asp
    1685                1690                1695

Lys Trp Thr Asp Gln Asp Asp Asp Glu Asp Leu Val Asp Thr Cys
    1700                1705                1710

Ala Phe Leu His Ile Lys Thr Gly Glu Trp Lys Lys Gly Asn Cys
    1715                1720                1725

Glu Val Ser Ser Val Glu Gly Thr Leu Cys Lys Thr Ala Ile Pro
    1730                1735                1740

Tyr Lys Arg Lys Tyr Leu Ser Asp Asn His Ile Leu Ile Ser Ala
    1745                1750                1755

Leu Val Ile Ala Ser Thr Val Ile Leu Thr Val Leu Gly Ala Ile
    1760                1765                1770

Ile Trp Phe Leu Tyr Lys Lys His Ser Asp Ser Arg Phe Thr Thr
    1775                1780                1785

Val Phe Ser Thr Ala Pro Gln Ser Pro Tyr Asn Glu Asp Cys Val
    1790                1795                1800

Leu Val Val Gly Glu Glu Asn Glu Tyr Pro Val Gln Phe Asp
    1805                1810                1815

<210> SEQ ID NO 4
<211> LENGTH: 15
<212> TYPE: PRT
<213> ORGANISM: Homo Sapiens

<400> SEQUENCE: 4

Ala Ala Asn Asp Pro Phe Thr Ile Val His Gly Asn Thr Gly Lys
1               5                   10                  15

<210> SEQ ID NO 5
<211> LENGTH: 21
<212> TYPE: PRT
<213> ORGANISM: Homo Sapiens

<400> SEQUENCE: 5

Ala Phe Ser Ser Asp Leu Ile Ser Ile His Ser Leu Ala Asp Val Glu
1               5                   10                  15

Val Val Val Thr Lys
```

```
<210> SEQ ID NO 6
<211> LENGTH: 11
<212> TYPE: PRT
<213> ORGANISM: Homo Sapiens

<400> SEQUENCE: 6

Cys Glu His His Ser Leu Tyr Gly Ala Ala Arg
1               5                   10

<210> SEQ ID NO 7
<211> LENGTH: 8
<212> TYPE: PRT
<213> ORGANISM: Homo Sapiens

<400> SEQUENCE: 7

Cys Leu Gly Leu Asp Ile Thr Lys
1               5

<210> SEQ ID NO 8
<211> LENGTH: 13
<212> TYPE: PRT
<213> ORGANISM: Homo Sapiens

<400> SEQUENCE: 8

Cys Ser Met Leu Ile Ala Ser Asn Glu Thr Trp Lys Lys
1               5                   10

<210> SEQ ID NO 9
<211> LENGTH: 10
<212> TYPE: PRT
<213> ORGANISM: Homo Sapiens

<400> SEQUENCE: 9

Asp Gly Ala Ile Cys Tyr Lys Pro Thr Lys
1               5                   10

<210> SEQ ID NO 10
<211> LENGTH: 16
<212> TYPE: PRT
<213> ORGANISM: Homo Sapiens

<400> SEQUENCE: 10

Asp Gly His Gly Thr Ala Ile Ser Asn Ala Ser Asp Val Trp Lys Lys
1               5                   10                  15

<210> SEQ ID NO 11
<211> LENGTH: 18
<212> TYPE: PRT
<213> ORGANISM: Homo Sapiens

<400> SEQUENCE: 11

Asp Val Asp Ser Cys Gly Glu Tyr Asn Trp Ala Thr Val Gly Gly Arg
1               5                   10                  15

Arg Arg

<210> SEQ ID NO 12
<211> LENGTH: 8
<212> TYPE: PRT
<213> ORGANISM: Homo Sapiens

<400> SEQUENCE: 12

Glu Glu Val Trp Ile Gly Leu Lys
```

```
<210> SEQ ID NO 13
<211> LENGTH: 13
<212> TYPE: PRT
<213> ORGANISM: Homo Sapiens

<400> SEQUENCE: 13

Glu Phe Ile Tyr Leu Arg Pro Phe Ala Cys Asp Thr Lys
1               5                   10

<210> SEQ ID NO 14
<211> LENGTH: 5
<212> TYPE: PRT
<213> ORGANISM: Homo Sapiens

<400> SEQUENCE: 14

Glu Gly Ile Ala Lys
1               5

<210> SEQ ID NO 15
<211> LENGTH: 15
<212> TYPE: PRT
<213> ORGANISM: Homo Sapiens

<400> SEQUENCE: 15

Glu Leu Thr Tyr Ser Asn Phe His Pro Leu Leu Val Ser Gly Arg
1               5                   10                  15

<210> SEQ ID NO 16
<211> LENGTH: 8
<212> TYPE: PRT
<213> ORGANISM: Homo Sapiens

<400> SEQUENCE: 16

Glu Asn Asn Asn Ile Thr Met Arg
1               5

<210> SEQ ID NO 17
<211> LENGTH: 9
<212> TYPE: PRT
<213> ORGANISM: Homo Sapiens

<400> SEQUENCE: 17

Glu Val Lys Pro Val Asp Ser Val Lys
1               5

<210> SEQ ID NO 18
<211> LENGTH: 11
<212> TYPE: PRT
<213> ORGANISM: Homo Sapiens

<400> SEQUENCE: 18

Phe Glu Gln Glu Tyr Leu Asn Asp Leu Met Lys
1               5                   10

<210> SEQ ID NO 19
<211> LENGTH: 15
<212> TYPE: PRT
<213> ORGANISM: Homo Sapiens

<400> SEQUENCE: 19

Phe Pro Val Thr Phe Gly Glu Glu Cys Leu Tyr Met Ser Ala Lys
1               5                   10                  15
```

```
<210> SEQ ID NO 20
<211> LENGTH: 14
<212> TYPE: PRT
<213> ORGANISM: Homo Sapiens

<400> SEQUENCE: 20

Gly Asn Cys Glu Val Ser Ser Val Glu Gly Thr Leu Cys Lys
1               5                   10

<210> SEQ ID NO 21
<211> LENGTH: 8
<212> TYPE: PRT
<213> ORGANISM: Homo Sapiens

<400> SEQUENCE: 21

Gly Trp His Phe Tyr Asp Asp Arg
1               5

<210> SEQ ID NO 22
<211> LENGTH: 11
<212> TYPE: PRT
<213> ORGANISM: Homo Sapiens

<400> SEQUENCE: 22

His Asp His Ser Ala Thr Ile Val Ser Ile Lys
1               5                   10

<210> SEQ ID NO 23
<211> LENGTH: 8
<212> TYPE: PRT
<213> ORGANISM: Homo Sapiens

<400> SEQUENCE: 23

His Phe Val Ser Leu Cys Gln Lys
1               5

<210> SEQ ID NO 24
<211> LENGTH: 7
<212> TYPE: PRT
<213> ORGANISM: Homo Sapiens

<400> SEQUENCE: 24

His Gly Glu Thr Cys Tyr Lys
1               5

<210> SEQ ID NO 25
<211> LENGTH: 12
<212> TYPE: PRT
<213> ORGANISM: Homo Sapiens

<400> SEQUENCE: 25

His Met Ala Thr Thr Gln Asp Glu Val His Thr Lys
1               5                   10

<210> SEQ ID NO 26
<211> LENGTH: 10
<212> TYPE: PRT
<213> ORGANISM: Homo Sapiens

<400> SEQUENCE: 26

Ile Ala Asn Ile Ser Gly Asp Gly Gln Lys
1               5                   10

<210> SEQ ID NO 27
```

```
<211> LENGTH: 7
<212> TYPE: PRT
<213> ORGANISM: Homo Sapiens

<400> SEQUENCE: 27

Ile Glu Met Val Asp Tyr Lys
1               5

<210> SEQ ID NO 28
<211> LENGTH: 4
<212> TYPE: PRT
<213> ORGANISM: Homo Sapiens

<400> SEQUENCE: 28

Ile Ile Pro Lys
1

<210> SEQ ID NO 29
<211> LENGTH: 11
<212> TYPE: PRT
<213> ORGANISM: Homo Sapiens

<400> SEQUENCE: 29

Ile Pro Glu Asn Phe Phe Glu Glu Glu Ser Arg
1               5                   10

<210> SEQ ID NO 30
<211> LENGTH: 14
<212> TYPE: PRT
<213> ORGANISM: Homo Sapiens

<400> SEQUENCE: 30

Ile Ser Glu Trp Pro Ile Asp Asp His Phe Thr Tyr Ser Arg
1               5                   10

<210> SEQ ID NO 31
<211> LENGTH: 15
<212> TYPE: PRT
<213> ORGANISM: Homo Sapiens

<400> SEQUENCE: 31

Lys Gly Asn Cys Glu Val Ser Ser Val Glu Gly Thr Leu Cys Lys
1               5                   10                  15

<210> SEQ ID NO 32
<211> LENGTH: 9
<212> TYPE: PRT
<213> ORGANISM: Homo Sapiens

<400> SEQUENCE: 32

Lys Arg Asn Trp Glu Glu Ala Glu Arg
1               5

<210> SEQ ID NO 33
<211> LENGTH: 10
<212> TYPE: PRT
<213> ORGANISM: Homo Sapiens

<400> SEQUENCE: 33

Lys Val Glu Cys Glu His Gly Phe Gly Arg
1               5                   10

<210> SEQ ID NO 34
<211> LENGTH: 8
<212> TYPE: PRT
```

<213> ORGANISM: Homo Sapiens

<400> SEQUENCE: 34

Lys Tyr Phe Trp Thr Gly Leu Arg
1               5

<210> SEQ ID NO 35
<211> LENGTH: 4
<212> TYPE: PRT
<213> ORGANISM: Homo Sapiens

<400> SEQUENCE: 35

Leu Ala Leu Lys
1

<210> SEQ ID NO 36
<211> LENGTH: 8
<212> TYPE: PRT
<213> ORGANISM: Homo Sapiens

<400> SEQUENCE: 36

Leu Phe His Leu His Ser Gln Lys
1               5

<210> SEQ ID NO 37
<211> LENGTH: 10
<212> TYPE: PRT
<213> ORGANISM: Homo Sapiens

<400> SEQUENCE: 37

Leu His Leu Ala Gly Phe Ser Ser Val Arg
1               5                   10

<210> SEQ ID NO 38
<211> LENGTH: 7
<212> TYPE: PRT
<213> ORGANISM: Homo Sapiens

<400> SEQUENCE: 38

Leu His Asn Glu Asp Ile Lys
1               5

<210> SEQ ID NO 39
<211> LENGTH: 8
<212> TYPE: PRT
<213> ORGANISM: Homo Sapiens

<400> SEQUENCE: 39

Leu Asn Asp Ala Ser Ser Asp Lys
1               5

<210> SEQ ID NO 40
<211> LENGTH: 4
<212> TYPE: PRT
<213> ORGANISM: Homo Sapiens

<400> SEQUENCE: 40

Leu Asn Pro Lys
1

<210> SEQ ID NO 41
<211> LENGTH: 7
<212> TYPE: PRT
<213> ORGANISM: Homo Sapiens

```
<400> SEQUENCE: 41

Leu Pro Phe Ile Cys Glu Lys
1               5

<210> SEQ ID NO 42
<211> LENGTH: 10
<212> TYPE: PRT
<213> ORGANISM: Homo Sapiens

<400> SEQUENCE: 42

Met Cys Pro Pro Asp Glu Gly Trp Lys Arg
1               5                   10

<210> SEQ ID NO 43
<211> LENGTH: 13
<212> TYPE: PRT
<213> ORGANISM: Homo Sapiens

<400> SEQUENCE: 43

Met Phe Ser Cys Asp Ser Ser Ala Met Leu Trp Trp Lys
1               5                   10

<210> SEQ ID NO 44
<211> LENGTH: 13
<212> TYPE: PRT
<213> ORGANISM: Homo Sapiens

<400> SEQUENCE: 44

Met Ser Gly Pro Leu Gly Pro Glu Glu Ala Ser Pro Lys
1               5                   10

<210> SEQ ID NO 45
<211> LENGTH: 9
<212> TYPE: PRT
<213> ORGANISM: Homo Sapiens

<400> SEQUENCE: 45

Asn Asn Ser Leu Met Trp Phe Asp Lys
1               5

<210> SEQ ID NO 46
<211> LENGTH: 7
<212> TYPE: PRT
<213> ORGANISM: Homo Sapiens

<400> SEQUENCE: 46

Asn Trp Glu Glu Ala Glu Arg
1               5

<210> SEQ ID NO 47
<211> LENGTH: 11
<212> TYPE: PRT
<213> ORGANISM: Homo Sapiens

<400> SEQUENCE: 47

Gln Thr Leu Gln Asn Ala Ser Glu Thr Val Lys
1               5                   10

<210> SEQ ID NO 48
<211> LENGTH: 9
<212> TYPE: PRT
<213> ORGANISM: Homo Sapiens

<400> SEQUENCE: 48
```

Arg Gly Trp His Phe Tyr Asp Asp Arg
1               5

<210> SEQ ID NO 49
<211> LENGTH: 8
<212> TYPE: PRT
<213> ORGANISM: Homo Sapiens

<400> SEQUENCE: 49

Arg His Gly Glu Thr Cys Tyr Lys
1               5

<210> SEQ ID NO 50
<211> LENGTH: 6
<212> TYPE: PRT
<213> ORGANISM: Homo Sapiens

<400> SEQUENCE: 50

Arg Leu His Phe Ser Arg
1               5

<210> SEQ ID NO 51
<211> LENGTH: 8
<212> TYPE: PRT
<213> ORGANISM: Homo Sapiens

<400> SEQUENCE: 51

Arg Asn Trp Glu Glu Ala Glu Arg
1               5

<210> SEQ ID NO 52
<211> LENGTH: 12
<212> TYPE: PRT
<213> ORGANISM: Homo Sapiens

<400> SEQUENCE: 52

Ser Asp Gln Ala Leu His Ser Phe Ser Glu Ala Lys
1               5                   10

<210> SEQ ID NO 53
<211> LENGTH: 7
<212> TYPE: PRT
<213> ORGANISM: Homo Sapiens

<400> SEQUENCE: 53

Ser His Ile Leu Ser Ile Arg
1               5

<210> SEQ ID NO 54
<211> LENGTH: 11
<212> TYPE: PRT
<213> ORGANISM: Homo Sapiens

<400> SEQUENCE: 54

Ser Asn Phe His Pro Leu Leu Val Ser Gly Arg
1               5                   10

<210> SEQ ID NO 55
<211> LENGTH: 13
<212> TYPE: PRT
<213> ORGANISM: Homo Sapiens

<400> SEQUENCE: 55

Ser Pro Asp Leu Gln Gly Ser Trp Gln Trp Ser Asp Arg
1               5                   10

```
<210> SEQ ID NO 56
<211> LENGTH: 8
<212> TYPE: PRT
<213> ORGANISM: Homo Sapiens

<400> SEQUENCE: 56

Thr Leu Thr Trp His Ser Ala Lys
1               5

<210> SEQ ID NO 57
<211> LENGTH: 9
<212> TYPE: PRT
<213> ORGANISM: Homo Sapiens

<400> SEQUENCE: 57

Thr Pro Asp Trp Tyr Asn Pro Asp Arg
1               5

<210> SEQ ID NO 58
<211> LENGTH: 9
<212> TYPE: PRT
<213> ORGANISM: Homo Sapiens

<400> SEQUENCE: 58

Thr Pro Leu Ser Tyr Thr His Trp Arg
1               5

<210> SEQ ID NO 59
<211> LENGTH: 19
<212> TYPE: PRT
<213> ORGANISM: Homo Sapiens

<400> SEQUENCE: 59

Thr Pro Val Ser Thr Ile Ile Met Pro Asn Glu Phe Gln Gln Asp Tyr
1               5                   10                  15

Asp Ile Arg

<210> SEQ ID NO 60
<211> LENGTH: 9
<212> TYPE: PRT
<213> ORGANISM: Homo Sapiens

<400> SEQUENCE: 60

Val Glu Cys Glu His Gly Phe Gly Arg
1               5

<210> SEQ ID NO 61
<211> LENGTH: 7
<212> TYPE: PRT
<213> ORGANISM: Homo Sapiens

<400> SEQUENCE: 61

Val Phe His Arg Pro Trp Arg
1               5

<210> SEQ ID NO 62
<211> LENGTH: 11
<212> TYPE: PRT
<213> ORGANISM: Homo Sapiens

<400> SEQUENCE: 62

Val Ile Glu Glu Ala Val Tyr Phe His Gln His
1               5                   10
```

```
<210> SEQ ID NO 63
<211> LENGTH: 13
<212> TYPE: PRT
<213> ORGANISM: Homo Sapiens

<400> SEQUENCE: 63

Val Gln Cys Ser Glu Gln Trp Ile Pro Phe Gln Asn Lys
1               5                   10

<210> SEQ ID NO 64
<211> LENGTH: 6
<212> TYPE: PRT
<213> ORGANISM: Homo Sapiens

<400> SEQUENCE: 64

Trp Val Ser Gln His Arg
1               5

<210> SEQ ID NO 65
<211> LENGTH: 7
<212> TYPE: PRT
<213> ORGANISM: Homo Sapiens

<400> SEQUENCE: 65

Tyr Phe Trp Thr Gly Leu Arg
1               5

<210> SEQ ID NO 66
<211> LENGTH: 7
<212> TYPE: PRT
<213> ORGANISM: Homo Sapiens

<400> SEQUENCE: 66

Tyr Leu Asn Asn Leu Tyr Lys
1               5
```